US012678509B2

(12) United States Patent
Cosford et al.

(10) Patent No.: US 12,678,509 B2
(45) Date of Patent: Jul. 14, 2026

(54) INHIBITOR OF APOPTOSIS (IAP) PROTEIN ANTAGONISTS

(71) Applicant: Sanford Burnham Prebys Medical Discovery Institute, La Jolla, CA (US)

(72) Inventors: Nicholas David Peter Cosford, San Diego, CA (US); Dominik Heimann, Hamm (DE); Peter Teriete, San Diego, CA (US); Sumit Kumar Chanda, La Jolla, CA (US); Lars Pache, San Diego, CA (US); Nicole Bata, San Diego, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 974 days.

(21) Appl. No.: 17/773,749

(22) PCT Filed: Nov. 6, 2020

(86) PCT No.: PCT/US2020/059552
§ 371 (c)(1),
(2) Date: May 2, 2022

(87) PCT Pub. No.: WO2021/092500
PCT Pub. Date: May 14, 2021

(65) Prior Publication Data

US 2023/0115837 A1 Apr. 13, 2023

Related U.S. Application Data

(60) Provisional application No. 62/933,190, filed on Nov. 8, 2019.

(51) Int. Cl.
*A61K 47/55* (2017.01)
*A61P 31/18* (2006.01)
*A61P 35/00* (2006.01)

(52) U.S. Cl.
CPC .............. *A61K 47/55* (2017.08); *A61P 31/18* (2018.01); *A61P 35/00* (2018.01)

(58) Field of Classification Search
CPC ........... A61K 47/55; A61P 31/18; A61P 35/00
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 5,455,242 A | 10/1995 | Warshawsky et al. | |
| 5,457,196 A | 10/1995 | Warshawsky et al. | |
| 5,508,272 A | 4/1996 | Robl | |
| 5,635,502 A | 6/1997 | Flynn | |
| 7,244,851 B2 | 7/2007 | Cohen et al. | |
| 7,309,792 B2 | 12/2007 | Harran et al. | |
| 7,345,081 B2 | 3/2008 | Cohen et al. | |
| 7,419,975 B2 | 9/2008 | Palermo et al. | |
| 7,456,209 B2 | 11/2008 | Condon et al. | |
| 7,517,906 B2 | 4/2009 | Condon et al. | |
| 7,547,724 B2 | 6/2009 | Laurent et al. | |
| 7,674,787 B2 | 3/2010 | Wang et al. | |
| 9,546,174 B2 | 1/2017 | Cosford et al. | |
| 10,047,119 B2 | 8/2018 | Cosford et al. | |
| 10,300,074 B2 | 5/2019 | Pache et al. | |
| 10,544,188 B2 | 1/2020 | Cosford et al. | |
| 10,864,217 B2 | 12/2020 | Pache et al. | |
| 11,111,270 B2 | 9/2021 | Cosford et al. | |
| 11,912,786 B2 | 2/2024 | Cosford et al. | |
| 2008/0132485 A1 | 6/2008 | Wang et al. | |
| 2008/0269140 A1 | 10/2008 | Wang et al. | |
| 2009/0010941 A1 | 1/2009 | Stevenson et al. | |
| 2009/0123480 A1 | 5/2009 | Wang et al. | |
| 2010/0048545 A1 | 2/2010 | Jette et al. | |
| 2010/0190688 A1 | 7/2010 | Chao et al. | |
| 2010/0273812 A1 | 10/2010 | Wang et al. | |
| 2011/0046189 A1 | 2/2011 | Wang et al. | |
| 2014/0057924 A1* | 2/2014 | Wang | A61P 31/00 514/413 |
| 2017/0081362 A1 | 3/2017 | Cosford et al. | |
| 2020/0299309 A1* | 9/2020 | Dunham | A61P 31/18 |
| 2022/0119444 A1 | 4/2022 | Cosford et al. | |
| 2023/0295181 A1 | 9/2023 | Cosford et al. | |
| 2025/0129099 A1 | 4/2025 | Cosford et al. | |

FOREIGN PATENT DOCUMENTS

| | | |
|---|---|---|
| EP | 0629627 A2 | 12/1994 |
| JP | 2003519629 A | 6/2003 |
| JP | 2007522116 A | 8/2007 |
| JP | 2008505976 A | 2/2008 |
| JP | 2008545780 A | 12/2008 |
| JP | 2009536204 A | 10/2009 |

(Continued)

OTHER PUBLICATIONS

Cetraro, Cancers, 2022, 14, 1671 (Year: 2022).*
Thornber, Chemical Society Reviews, 4, 1979 (Year: 1979).*
Caron, et al. Preparation and utility of trihaloethyl imidates: useful reagents for the synthesis of amidines. J Org Chem 75(3):945-947 (2010).
U.S. Appl. No. 17/389,171 Office Action dated Jun. 23, 2023.
Badley et al. Altering cell death pathways as an approach to cure HIV infection. Cell Death Dis 4:e718 (2013).
Baldwin et al. Synthesis of potential β-turn bicyclic dipeptide mimetics. J Chem Soc Chem Commun 9:935-936 (1993).
Bosque et al. Induction of HIV-1 latency and reactivation in primary memory CD4+ T cells. Blood 113:58-65 (2009).
Cai et al. A potent and orally active antagonist (SM-406/AT-406) of multiple inhibitor of apoptosis proteins (IAPs) in clinical development for cancer treatment. J Med Chem 54(8):2714-2726 (2011).

(Continued)

*Primary Examiner* — Andrew D Kosar
*Assistant Examiner* — Phillip Matthew Rzeczycki
(74) *Attorney, Agent, or Firm* — WILSON SONSINI GOODRICH & ROSATI

(57) ABSTRACT

Provided herein are compounds that modulate the activity of inhibitor of apoptosis (IAPs) proteins, compositions comprising the compounds, and methods of using the compounds and compositions comprising the compounds.

15 Claims, 6 Drawing Sheets

(56) References Cited

FOREIGN PATENT DOCUMENTS

| | | | |
|---|---|---|---|
| JP | 2010523722 | A | 7/2010 |
| JP | 2011516581 | A | 5/2011 |
| JP | 2012529482 | A | 11/2012 |
| JP | 2013509429 | A | 3/2013 |
| JP | 2013516422 | A | 5/2013 |
| JP | 2016501223 | A | 1/2016 |
| JP | 2017522273 | A | 8/2017 |
| WO | WO-2004007529 | A2 | 1/2004 |
| WO | WO-2006017295 | A2 | 2/2006 |
| WO | WO-2006069063 | A1 | 6/2006 |
| WO | WO-2007041775 | A1 | 4/2007 |
| WO | WO-2007101347 | A1 | 9/2007 |
| WO | WO-2007130626 | A2 | 11/2007 |
| WO | WO-2008073305 | A1 | 6/2008 |
| WO | WO-2008128121 | A1 | 10/2008 |
| WO | WO-2008128171 | A2 | 10/2008 |
| WO | WO-2008134679 | A1 | 11/2008 |
| WO | WO-2008148202 | A1 | 12/2008 |
| WO | WO-2009060292 | A2 | 5/2009 |
| WO | WO-2009126947 | A2 | 10/2009 |
| WO | WO-2010031735 | A1 | 3/2010 |
| WO | WO-2010120476 | A2 | 10/2010 |
| WO | WO-2010142994 | A1 | 12/2010 |
| WO | WO-2011059763 | A2 | 5/2011 |
| WO | WO-2011067306 | A1 | 6/2011 |
| WO | WO-2011094150 | A1 | 8/2011 |
| WO | WO-2012125622 | A1 | 9/2012 |
| WO | WO-2013182662 | A1 | 12/2013 |
| WO | WO-2014085489 | A1 | 6/2014 |
| WO | WO-2015187998 | A2 | 12/2015 |
| WO | WO-2017143059 | A1 | 8/2017 |
| WO | WO-2020110056 | A1 | 6/2020 |
| WO | WO-2021092500 | A1 | 5/2021 |
| WO | WO-2021222614 | A1 | 11/2021 |
| WO | WO-2023081290 | A1 | 5/2023 |

OTHER PUBLICATIONS

Chiou et al. Highly efficient synthesis of azabicyclo[x.y.0]alkane amino acids and congeners by means of Rh-catalyzed cyclohydrocarbonylation. J Org Chem 72(6):1871-1882 (2007).

Claridge et al. Synthesis and analysis of Leu-enkephalin analogues containing reverse turn peptidomimetics. Bioorg Med Chem Lett 6(4):485-490 (1996).

Cohen et al. Antagonists of inhibitor of apoptosis proteins based on thiazole amide isosteres. Bioorg Med Chem Lett. 20(7):2229-2233 (2010).

Cohen et al. Orally bioavailable antagonists of inhibitor of apoptosis proteins based on an azabicyclooctane scaffold. J Med Chem 52(6):1723-1730 (2009).

Cornille et al. Electrochemical Cyclization of Dipeptides toward Novel Bicyclic, Reverse-Turn Peptidomimetics. 1. Synthesis and Conformational Analysis of 7,5-Bicyclic Systems. J Am Chem Soc 117(3):909-917 (1995).

Database Registry 2009 RN 1177797-11-3. Retrieved from STN International on Sep. 20, 2017 (1 pg.).

Finlay et al. Small-molecule IAP antagonists sensitize cancer cells to TRAIL-induced apoptosis: roles of XIAP and cIAPs. Mol Cancer Ther 13(1):5-15 (2014).

Flygare et al. Small-molecule pan-IAP antagonists: a patent review. Expert Opinion on Therapeutic Patents 20(2):251-267 (2010).

Gilley et al. New entry to convertible isocyanides for the Ugi reaction and its application to the stereo-controlled formal total synthesis of the proteasome inhibitor omuralide. J. Org. Lett. 9:3631-3634 (2007).

Gonzalez-Lopez et al. Design, synthesis and evaluation of monovalent Smac mimetics that bind to the BIR2 domain of the anti-apoptotic protein XIAP. Bioorg Med Chem Lett 21(14):4332-4336 (2011).

Griesbaum et al. Difunctional and heterocyclic products from the ozonolysis of conjugated C5-C8-cyclodienes. J Org Chem 55:6024-6027 (1990).

Huang et al. Fragment-based design of small molecule X-linked inhibitor of apoptosis protein inhibitors. J Med Chem 51(22):7111-7118 (2008).

Hyvl et al. Copper-Catalyzed Activation of Disulfides as a Key Step in the Synthesis of Benzothiazole Moieties. Eur. J. Org. Chem. 15:2849-2851 (2010).

Konig et al. Global analysis of host-pathogen interactions that regulate early-stage HIV-1 replication. Cell 135:49-60 (2008).

Li et al. A small molecule Smac mimic potentiates TRAIL- and TNFalpha-mediated cell death. Science 305(5689):1471-1474 (2004).

Ling et al. Theoretical studies on the interactions of XIAP-BIR3 domain with bicyclic and tricyclic core monovalent Smac mimetics. J Mol Graph Model 29(3):354-362 (2010).

Lu et al., SM-164: A novel, bivalent Smac mimetic that induces apoptosis and tumor regression by concurrent removal of the blockade of cIAP-1/2 and XIAP. Cancer Research 68(22):9384-9393 (2008).

Monfardini et al. Screening multicomponent reactions for X-linked inhibitor of apoptosis-baculoviral inhibitor of apoptosis protein repeats domain binder. J Med Chem 54(3):890-900 (2011).

Ndubaku et al. Antagonism of c-IAP and XIAP proteins is required for efficient induction of cell death by small-molecule IAP antagonists. ACS Chem Biol 4(7):577-566 (2009).

Nikolovska-Coleska et al. Development and optimization of a binding assay for the XIAP BIR3 domain using fluorescence polarization. Anal Biochem 332(2):261-273 (2004).

O'Doherty et al. A sensitive, quantitative assay for human immunodeficiency virus type 1 integration. J Virol 76:10942-10950 (2002).

Oost et al. Discovery of potent antagonists of the antiapoptotic protein XIAP for the treatment of cancer. J Med Chem 47(18):4417-4426 (2004).

Orzaez et al. Characterization of dequalinium as a XIAP antagonist that targets the BIR2 domain. Apoptosis 16(5):460-467 (2011).

Park et al. Non-peptidic small molecule inhibitors of XIAP. Bioorg Med Chem Lett. 15(3):771-775 (2005).

PCT/US2013/072064 International Search Report and Written Opinion dated Mar. 31, 2014.

PCT/US2020/059552 International Search Report and Written Opinion dated Feb. 12, 2021.

PCT/US2021/029957 International Search Report and Written Opinion dated Jun. 18, 2021.

Peng et al. Design and synthesis of a 1,5-diazabicyclo[6,3,0] dodecane amino acid derivative as a novel dipeptide reverse-turn mimetic. Tetrahedron Letters 47(27):4769-4770 (2006).

Peng et al. Potent, orally bioavailable diazabicyclic small-molecule mimetics of second mitochondria-derived activator of caspases. J Med Chem 51(24):8158-8162 (2008).

Robl et al. Dual metalloprotease inhibitors: mercaptoacetyl-based fused heterocyclic dipeptide mimetics as inhibitors of angiotensin-converting enzyme and neutral endopeptidase. J Med Chem 40(11):1570-1577 (1997).

Seneci et al. Rational design, synthesis and characterization of potent, non-peptidic Smac mimics/XIAP inhibitors as proapoptotic agents for cancer therapy. Bioorg Med Chem 17(16):5834-5856 (2009).

Slomczynska et al. Electrochemical Cyclization of Dipeptides To Form Novel Bicyclic, Reverse-Turn Peptidomimetics. 2. Synthesis and Conformational Analysis of 6,5-Bicyclic Systems. J Org Chem 61:1198-1204 (1996).

Stoszko et al., A broad drug arsenal to attack a strenuous latent HIV reservoir. Curr Opin Virol. 38:37-53 (2019).

Sun et al. Building functionalized peptidomimetics: use of electroauxiliaries for introducing N-acyliminium ions into peptides. J Am Chem Soc 128(42):13761-13771 (2006).

Sun et al. Cyclopeptide Smac mimetics as antagonists of IAP proteins. Bioorg Med Chem Lett 20(10):3043-3046 (2010).

Sun et al. Design, Synthesis and Characterization of A Potent, Non-Peptide, Cell-Permeable, Bivalent Smac Mimetic that Concur-

(56) References Cited

OTHER PUBLICATIONS rently Targets both the BIR2 and BIR3 Domains in XIAP. J Am Chem Soc 129(49):15279-15294 (2007).
Sun et al. Design, synthesis, and evaluation of potent, nonpeptidic mimetics of second mitochondria-derived activator of caspases. J Med Chem 52(3):593-596 (2009).
Sun et al., Potent and Selective Small-Molecule Inhibitors of cIAP1/2 Proteins Reveal That the Binding of Smac Mimetics to XIAP BIR3 Is Not Required for Their Effective Induction of Cell Death in Tumor Cells. ACS Chem. Biol. 9(4): 994-1002 (2014).
Sun et al., Potent Bivalent Smac Mimetics: Effect of the Linker on binding to Inhibitor of Apoptosis Proteins (IAPs) and Anticancer Activity. J Med Chem 54(9):3306-3318 (2011).
Sun et al. Structure-based design, synthesis, evaluation, and crystallographic studies of conformationally constrained Smac mimetics as inhibitors of the X-linked inhibitor of apoptosis protein (XIAP). J Med Chem 51(22):7169-7180 (2008).
Swingler et al. Apoptotic killing of HIV-1-infected macrophages is subverted by the viral envelope glycoprotein. PLoS Pathog 3(9):1281-1290 (2007).
Ueda et al. Efficient entry into 2-substituted tetrahydroquinoline systems through alkylative ring expansion: stereoselective formal synthesis of (+/−)-martinellic acid. J Org Chem 75:914-921 (2010).
U.S. Appl. No. 14/648,435 Office Action dated Feb. 4, 2016.
U.S. Appl. No. 14/648,435 Office Action dated May 23, 2016.
U.S. Appl. No. 15/363,935 Office Action dated Aug. 16, 2017.
U.S. Appl. No. 15/363,935 Office Action dated Dec. 12, 2017.
U.S. Appl. No. 16/031,837 Office Action dated Jul. 8, 2019.
U.S. Appl. No. 16/031,837 Office Action dated Mar. 14, 2019.
U.S. Appl. No. 16/740,240 Office Action dated Jan. 28, 2021.
Vamos et al. Expedient synthesis of highly potent antagonists of inhibitor of apoptosis proteins (IAPs) with unique selectivity for ML-IAP. ACS Chem Biol 8(4):725-732 (2013).
Wang. Design of small-molecule Smac mimetics as IAP antagonists. Curr Top Microbiol Immunol. 348:89-113 (2011).
Yang et al. Importance of Ligand Reorganization Free Energy in Protein-Ligand Binding-Affinity Prediction. J Am Chem Soc 131(38):13709-13721 (2009).
Zbieg et al., Amplification of anti-diastereoselectivity via Curtin-Hammett effects in ruthenium-catalyzed hydrohydroxyalkylation of 1,1-disubstituted allenes: diastereoselective formation of all-carbon quaternary centers. J Am. Chem. Soc. 133(4):1141-1144 (2011).
Zhang et al. A convenient and versatile synthesis of 6,5- and 7,5-fused bicyclic lactams as peptidomimetics. Tetrahedron Letters 42(30):4943-4945 (2001).
Zhang et al. Design, synthesis, and evaluation of tricyclic, conformationally constrained small-molecule mimetics of second mitochondria-derived activator of caspases. J Med Chem 51(23)7352-7355 (2008).
Zobel et al. Design, synthesis, and biological activity of a potent Smac mimetic that sensitizes cancer cells to apoptosis by antagonizing IAPs. ACS Chem Biol. 1(8):525-533 (2006).
U.S. Appl. No. 17/997,461 Office Action dated May 22, 2025.
U.S. Appl. No. 17/997,461 Office Action dated Nov. 19, 2025.

* cited by examiner

INHIBITOR OF APOPTOSIS (IAP) PROTEIN ANTAGONISTS

RELATED APPLICATIONS

This application is the U.S. National Stage application of International Application No. PCT/US2020/059552, filed on Nov. 6, 2020, which claims the benefit of U.S. Provisional Patent Application No. 62/933,190, filed on Nov. 8, 2019, each of which is herein incorporated by reference in its entirety.

STATEMENT AS TO FEDERALLY SPONSORED RESEARCH

This invention was made with government support under Contract number R01CA195227 and R01AI124843 awarded by the National Institutes of Health (NIH). The government has certain rights in the invention.

SUMMARY OF THE INVENTION

Described herein are compounds that modulate the activity of certain proteins involved in apoptotic pathways, or signaling pathways associated with inflammation and/or autoimmune diseases and/or cell division and/or angiogenesis. In some embodiments, the compounds described herein are antagonists of inhibitor of apoptosis (IAP) proteins. In some embodiments, the compounds described herein are pan-IAP antagonists. In some embodiments, the compounds described herein are useful for the treatment of cancer, inflammatory diseases, and/or autoimmune diseases as described herein.

In one aspect, provided herein are compounds having the structure of formula I, pharmaceutically acceptable salt, N-oxide, racemate, or stereoisomer thereof:

Formula (I)

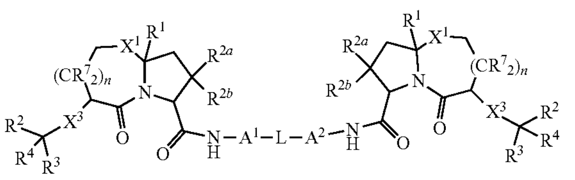

wherein, each $X^1$ is independently O, S, S(═O), or S(═O)$_2$;

each $R^1$, $R^3$ and $R^4$ is independently H, halogen, $C_1$-$C_6$alkyl, $C_3$-$C_6$cycloalkyl, $C_6$-$C_{10}$aryl, or 5- to 10-membered heteroaryl, wherein each alkyl, cycloalkyl, aryl, and heteroaryl is independently optionally substituted with one, two, or three $R^a$;

each $R^2$ is independently H, $C_1$-$C_6$alkyl, $C_3$-$C_6$cycloalkyl, —$C_1$-$C_6$alkyl-($C_3$-$C_6$cycloalkyl), or —$NR^5R^6$; wherein each alkyl and cycloalkyl is independently optionally substituted with one, two, or three $R^b$;

each $R^5$ and $R^6$ is independently H, $C_1$-$C_6$alkyl, or —$C_1$-$C_6$alkyl-($C_3$-$C_6$cycloalkyl);

each $R^7$ is independently H, halogen, $C_1$-$C_6$alkyl, or OH;

each n is independently 1 or 2;

each $X^3$ is independently —NHC(═O)—, —C(═O)NH—, —NHS(═O)$_2$—, —S(═O)$_2$NH—, —NHC(═O)NH—, —NH(C═O)O—, —O(C═O)NH—, —NHS(═O)$_2$NH—, —NHC($R^{1a}$)($R^{1b}$)—, or —C($R^{1a}$)($R^{1b}$)NH—;

A1 and A2 are independently $C_1$-$C_6$ alkylene, $C_3$-$C_{10}$ cycloalkylene, $C_5$-$C_{10}$ arylene, $C_2$-$C_{10}$ heterocycloalkylene, or 4- to 10-membered heteroarylene, wherein each alkylene, cycloalkylene, arylene, heterocycloalkylene, and heteroarylene is independently optionally substituted with one, two, or three $R^c$;

L is —$X^5$—$(CH_2)_{m1}$-$Q^1$-$(CH_2)_{n2}$—$X^5$—;

each $X^5$ is independently O, S, or absent;

each $n^1$ and $n^2$ is independently 0-5;

$Q^1$ is —$C_1$-$C_6$alkylene-, —$C_2$-$C_6$alkenylene-, —$C_2$-$C_6$alkynylene-, —C(O)NH—$C_1$-$C_6$ alkylene-NHC(O)—, —$SO_2$—, —$C_2$-$C_6$alkynylene-$C_6$-$C_{10}$ arylene-, —$C_2$-$C_6$alkynylene-$C_6$-$C_{10}$arylene-$C_2$-$C_6$alkynylene-, or —$C_6$-$C_{10}$arylene-$C_6$-$C_{10}$arylene-; wherein each alkylene, alkenylene, $C_2$-$C_6$alkynylene, and $C_6$-$C_{10}$arylene is independently optionally substituted with one, two, or three $R^d$;

each $R^{1a}$ and $R^{1b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl;

each $R^{2a}$ and $R^{2b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl; or $R^{1a}$ and $R^{2b}$ taken together form a $C_3$-$C_6$cycloalkyl or $C_2$-$C_5$heterocycloalkyl; and each $R^a$, $R^b$, $R^c$, and $R^d$ is independently halogen, OH, $NH_2$, CN, $C_1$-$C_6$alkoxy, $C_1$-$C_6$alkyl, $C_1$-$C_6$haloalkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl provided that the compound is not:

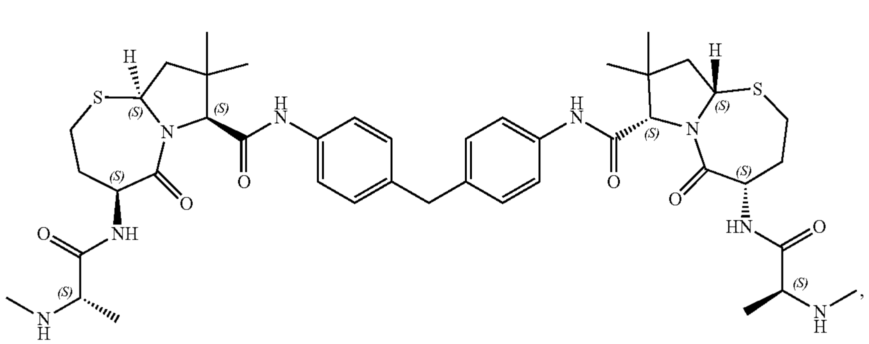

-continued
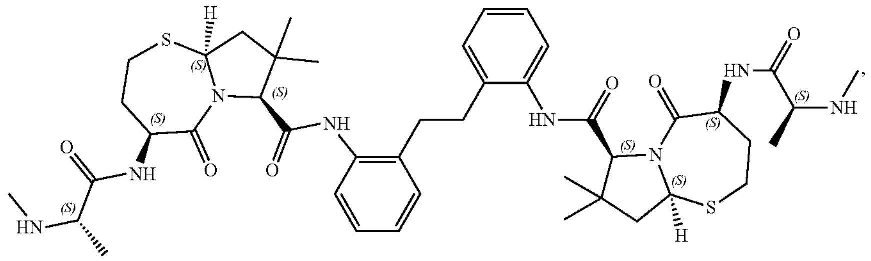
,
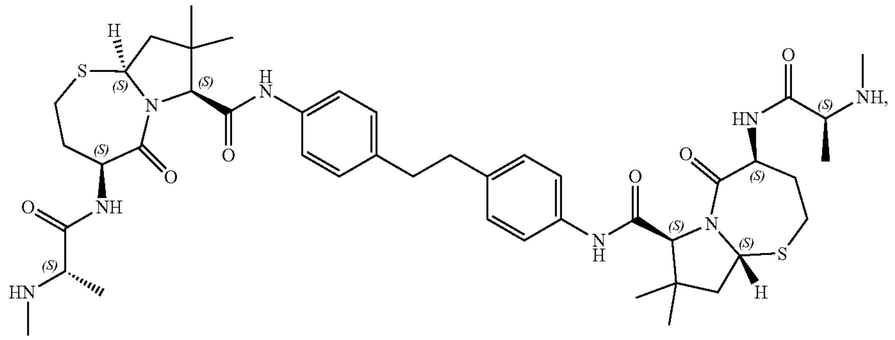
,
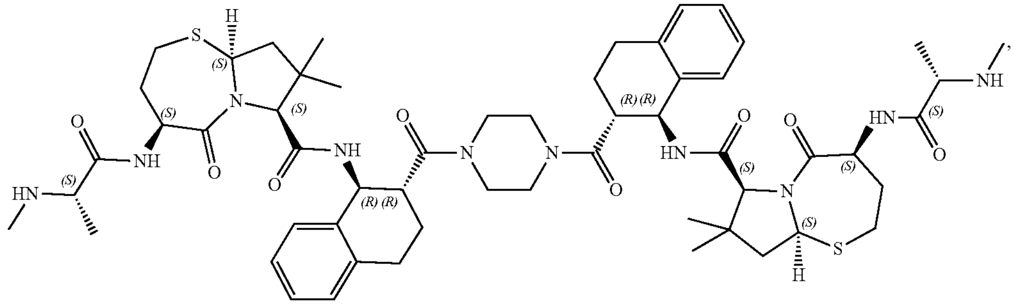
,
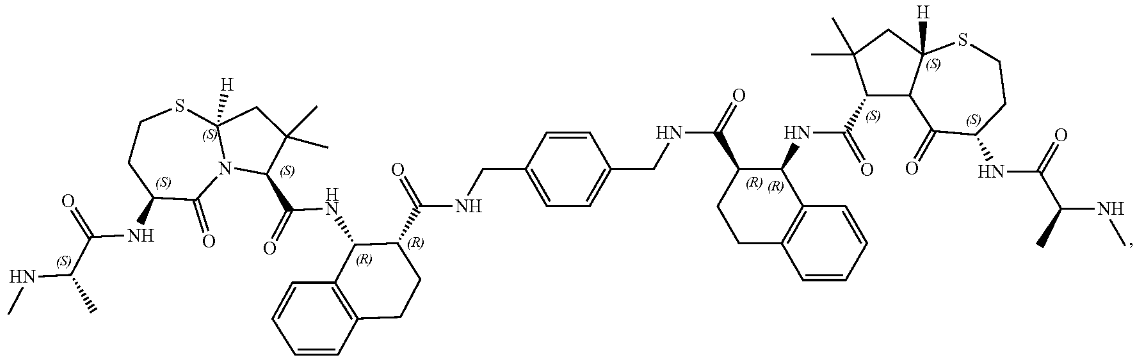
,
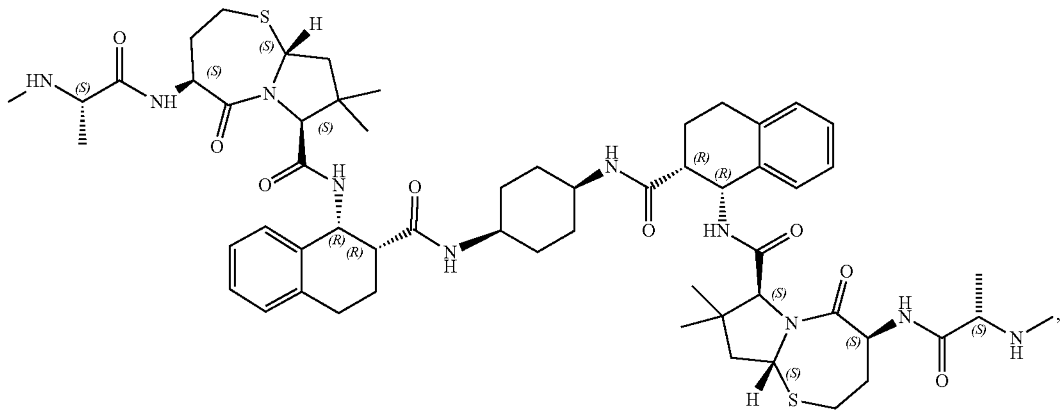
,

-continued
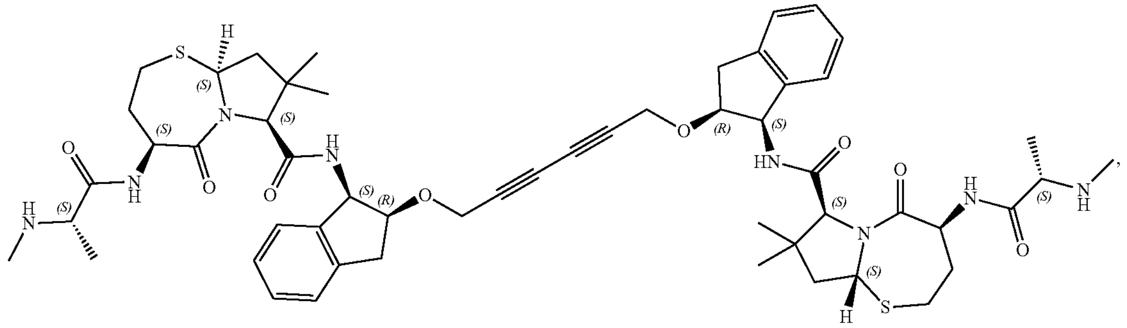
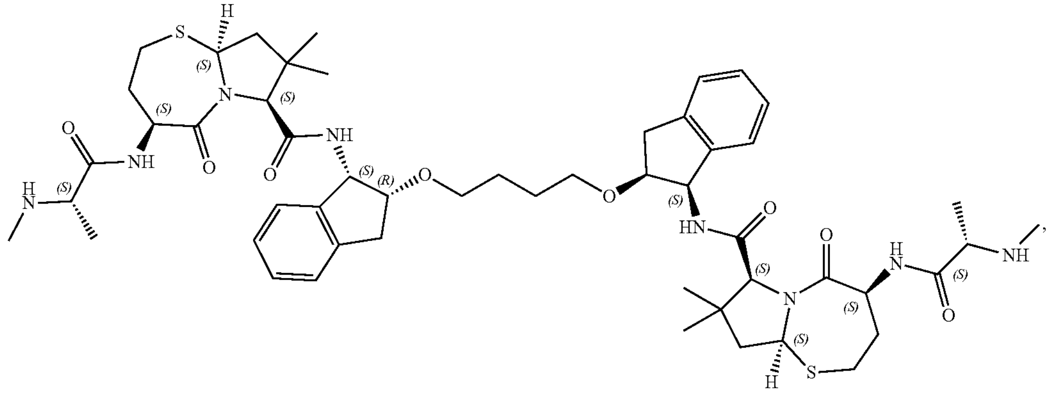
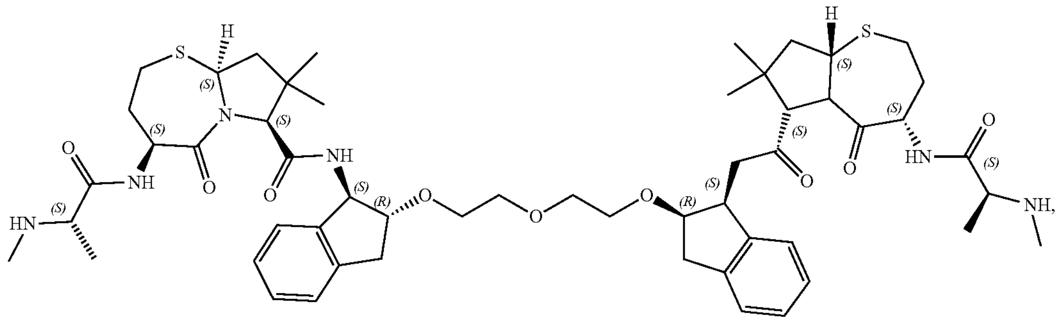
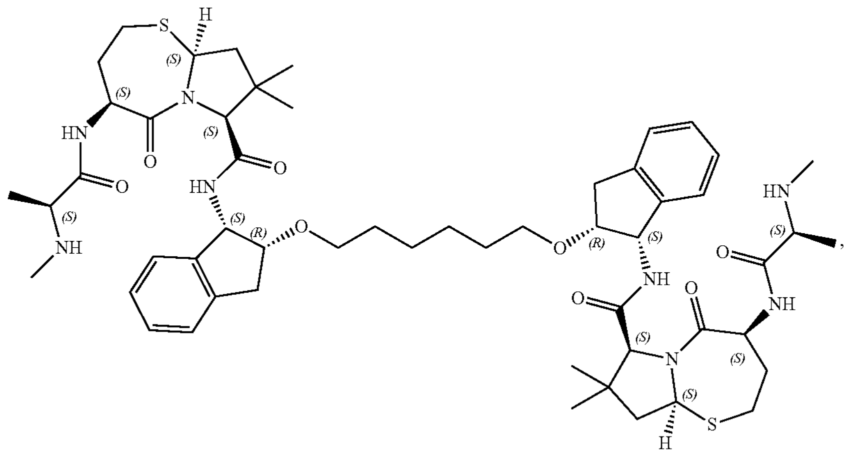

-continued
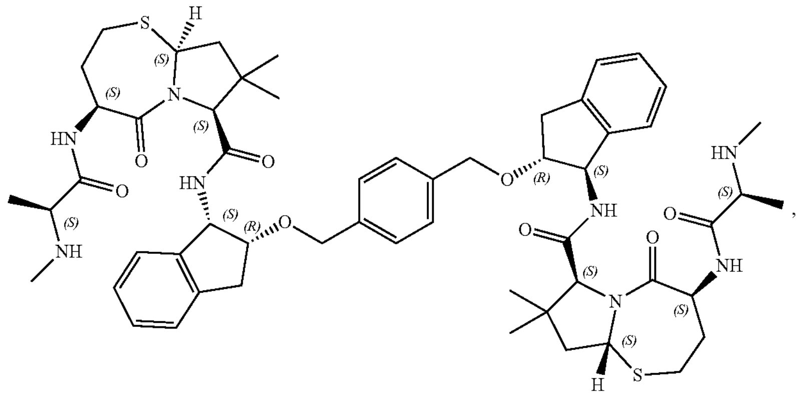
,
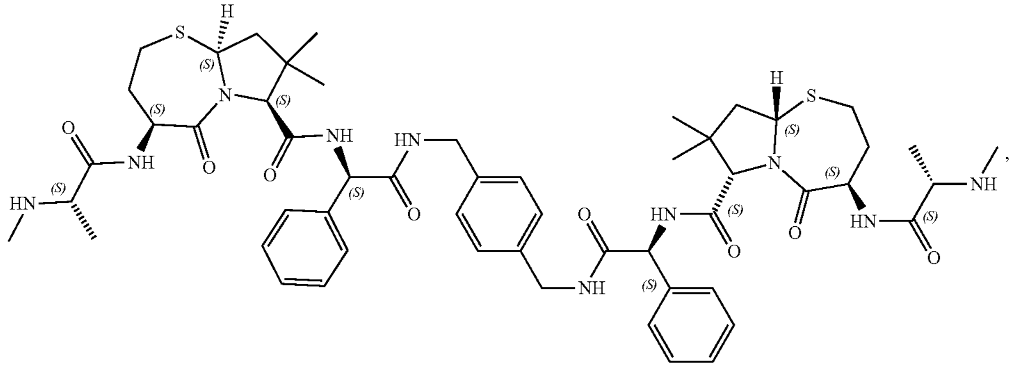
,
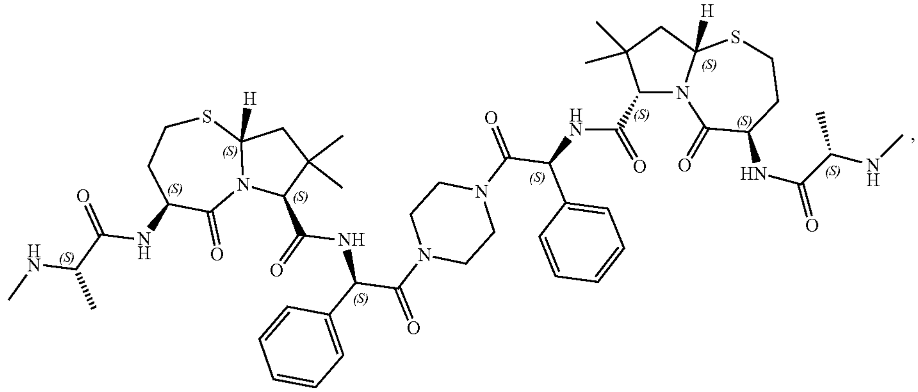
,
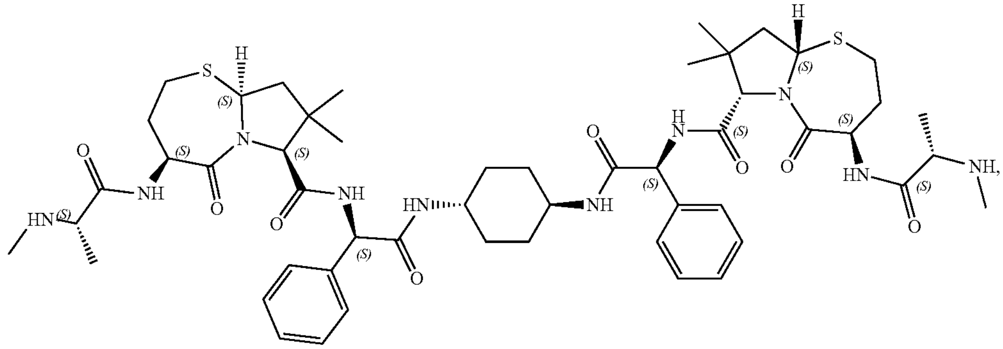
,

-continued
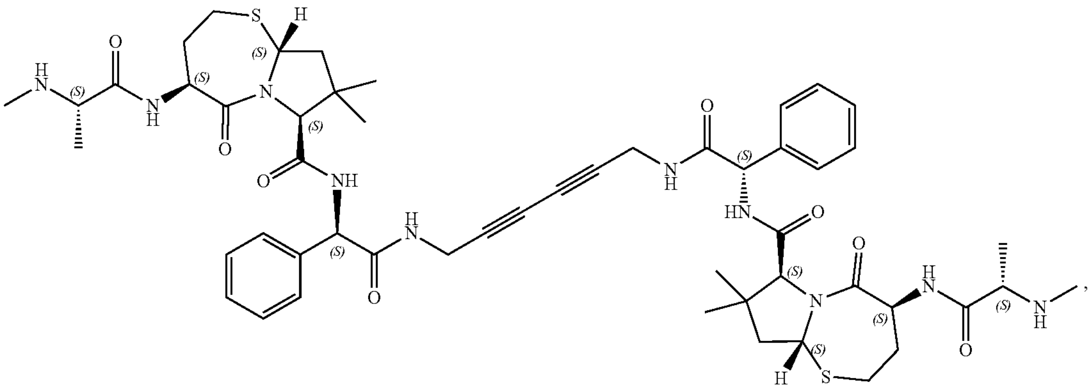
,
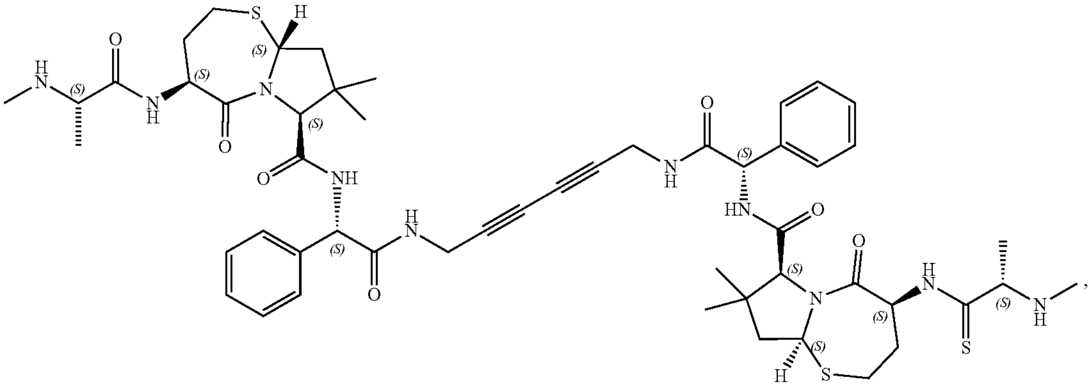
,
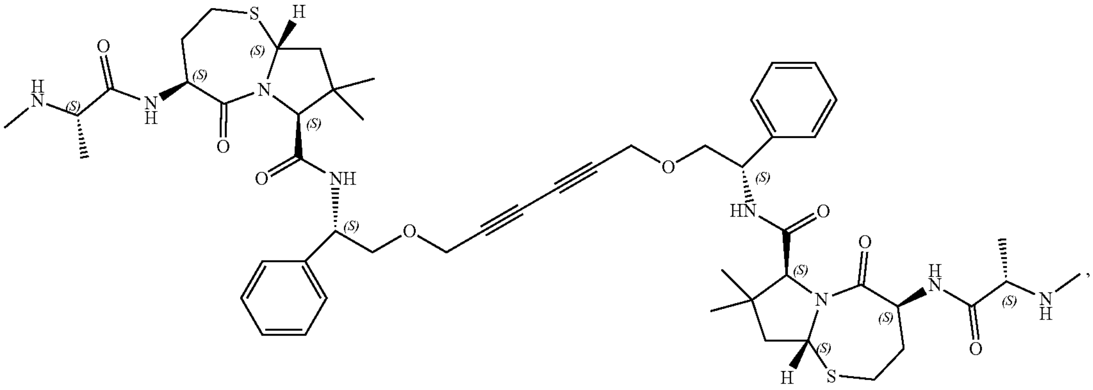
,
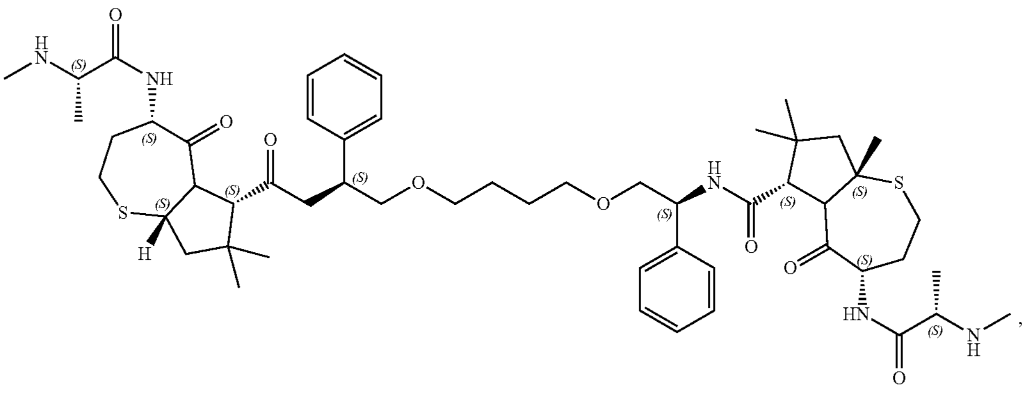
,

-continued
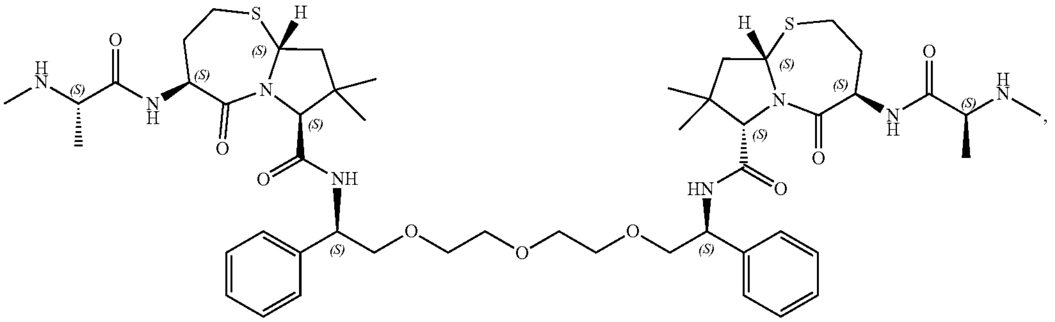
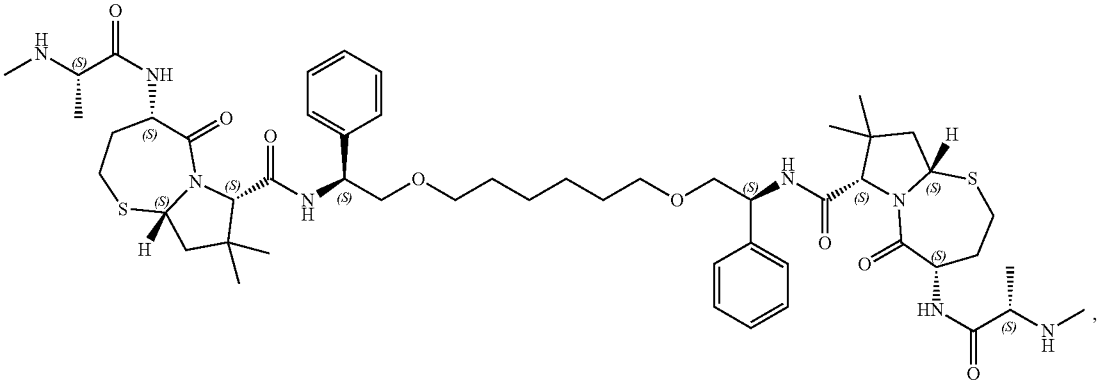
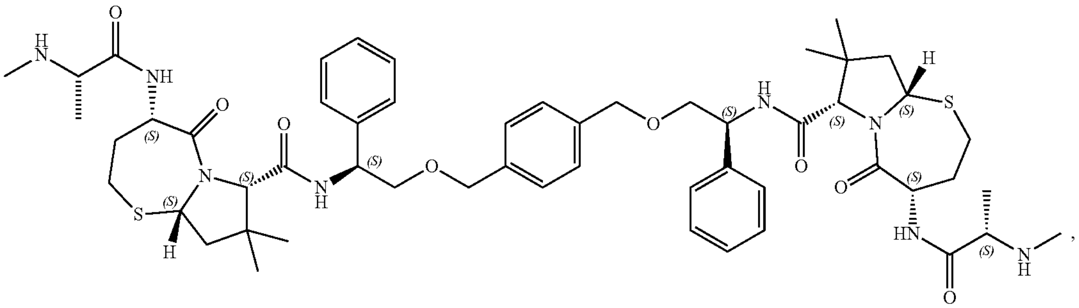
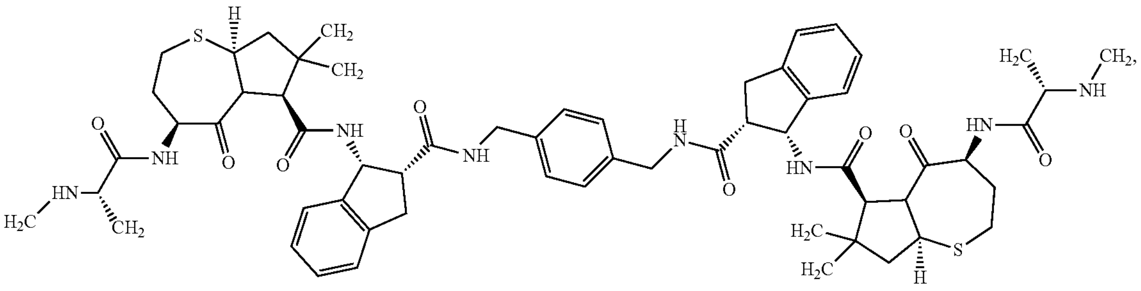
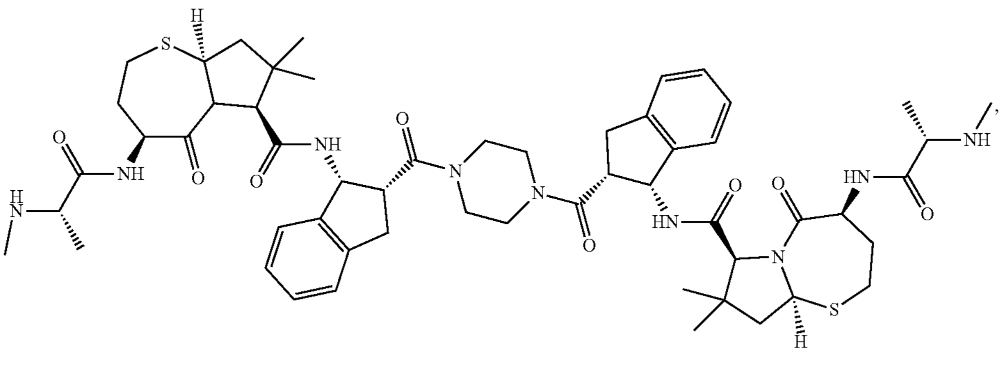

-continued
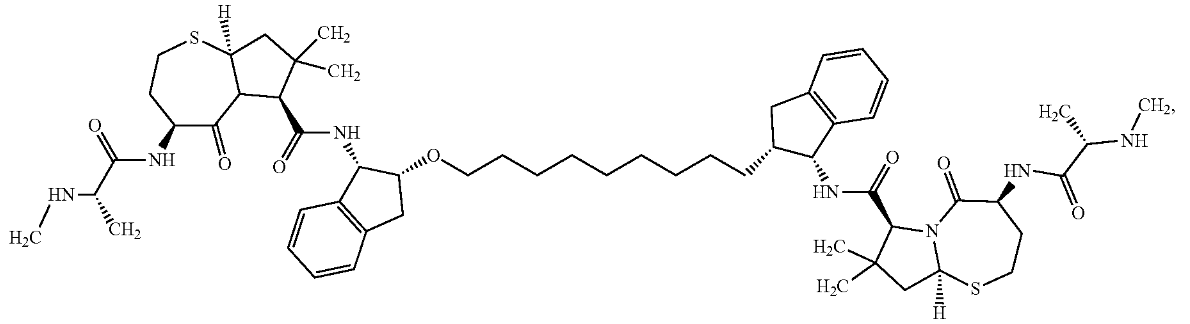
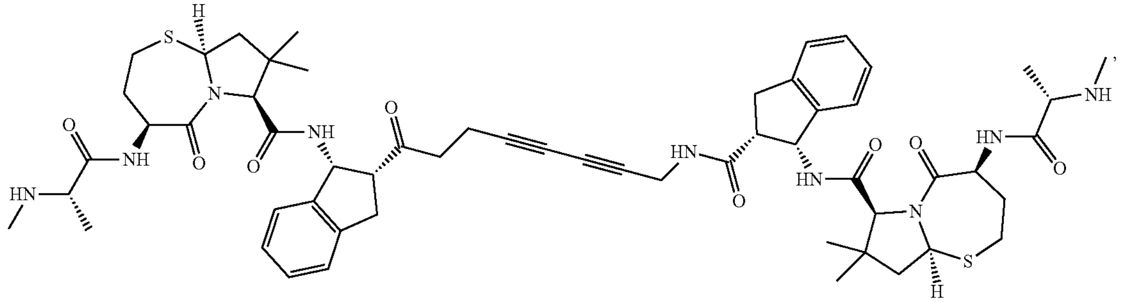
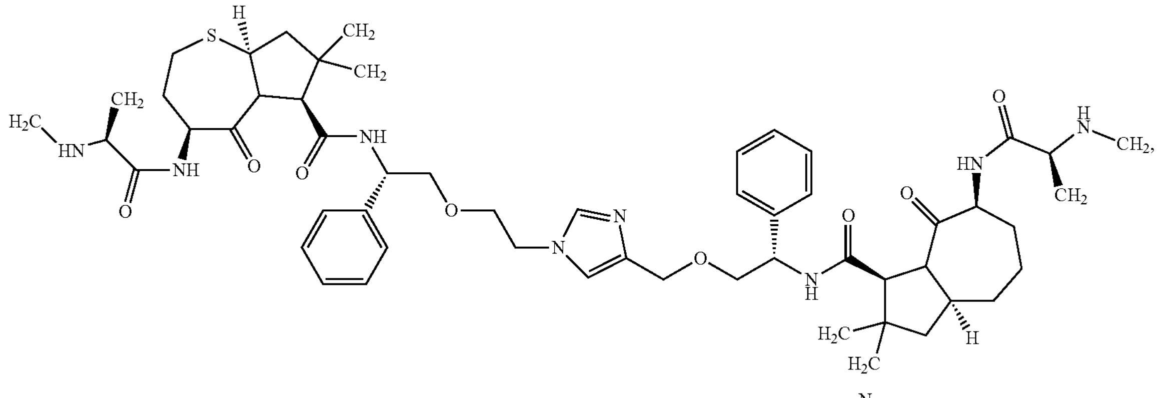
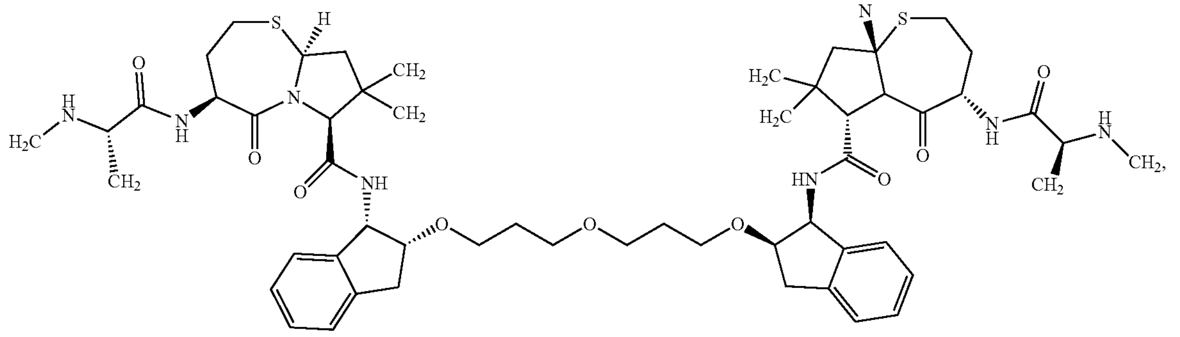

-continued
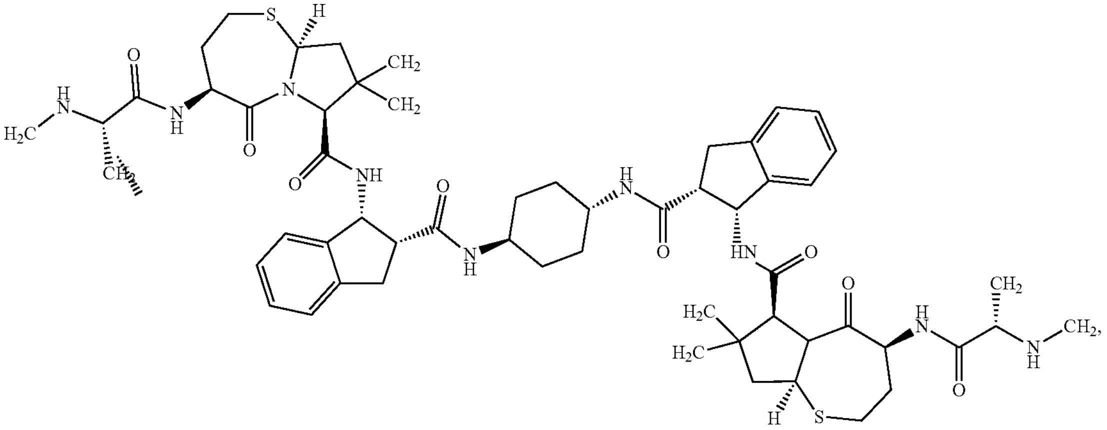
,
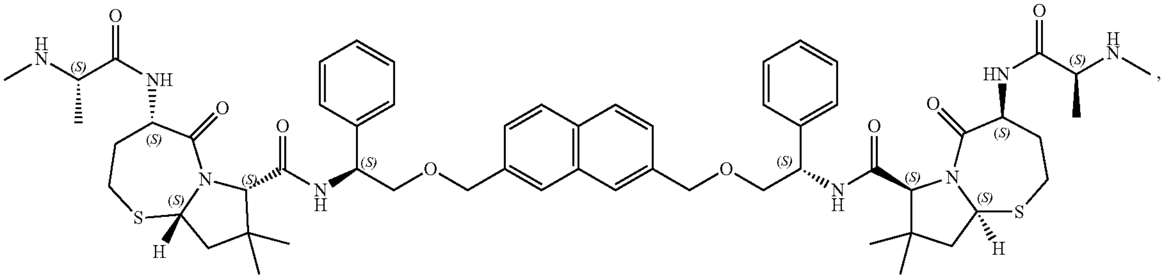
,
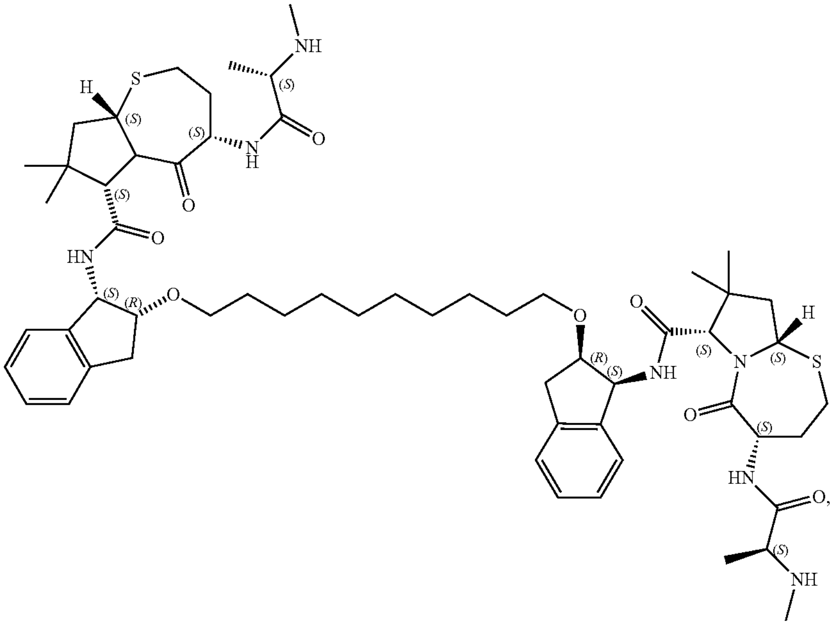
,
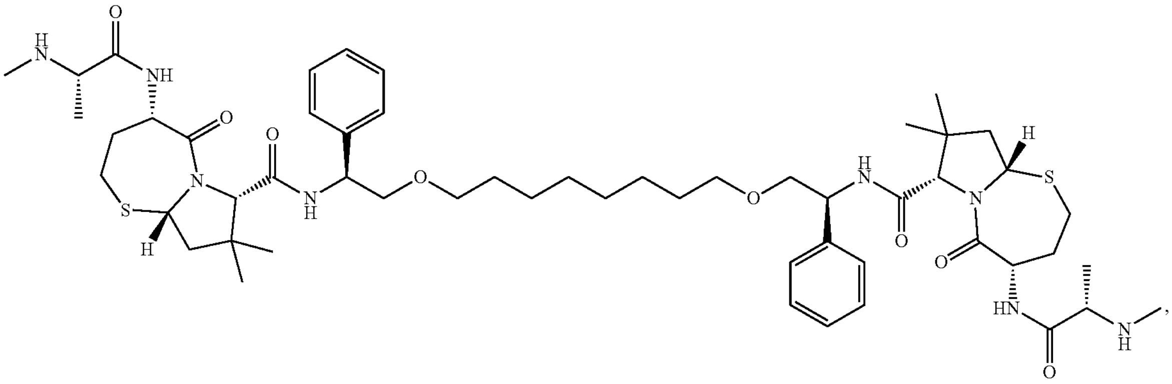
,

-continued
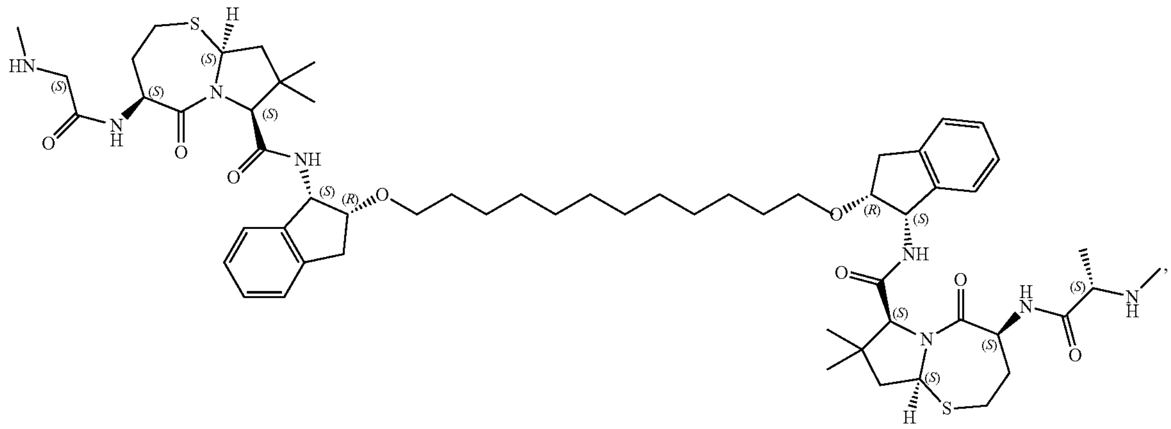
,
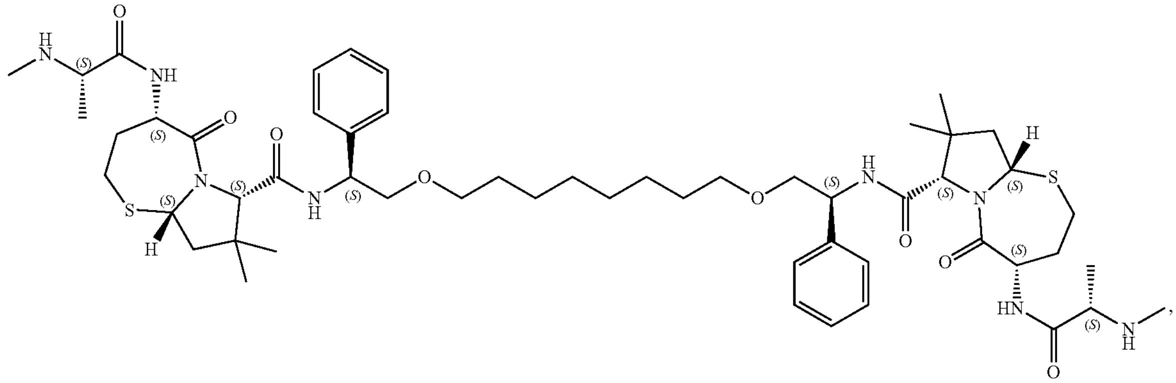
,
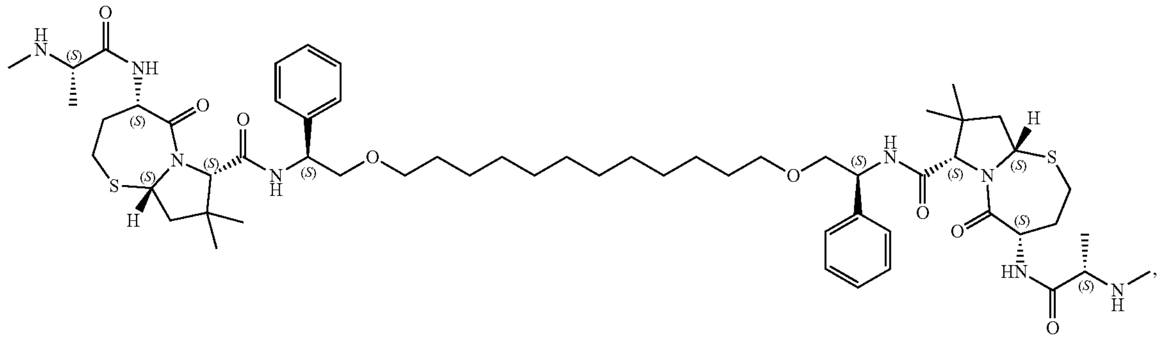
,
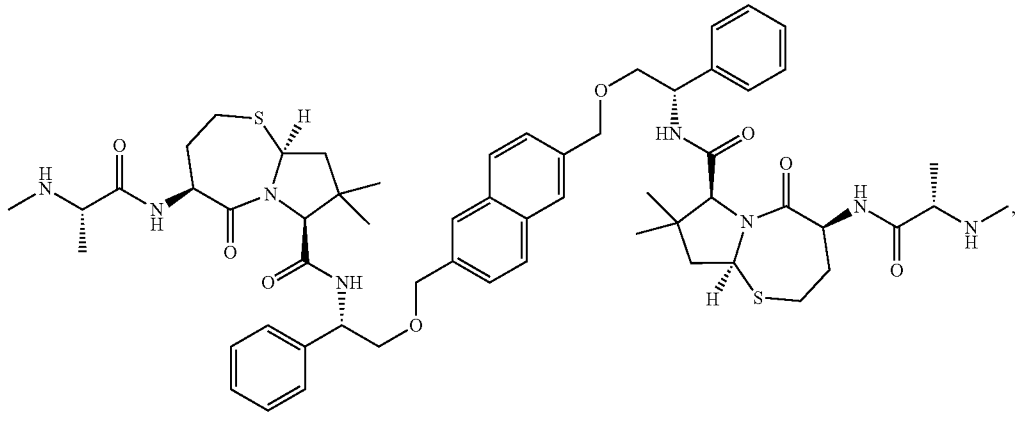
, or

-continued

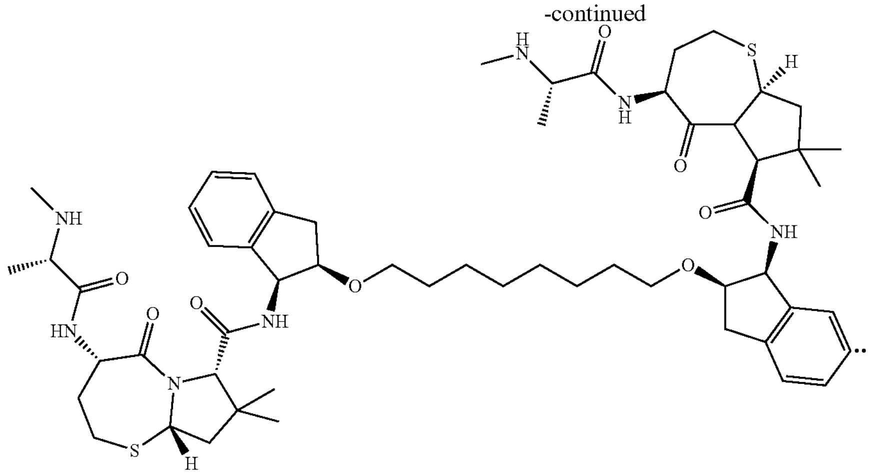

Also disclosed herein is a pharmaceutical composition comprising a compound disclosed herein, or pharmaceutically acceptable salt, N-oxide, racemate, or stereoisomer thereof, and a pharmaceutically acceptable carrier.

Also disclosed herein is a method of treating a hyperproliferative disorder in an individual in need thereof comprising administering a therapeutically effective amount of a compound disclosed herein, or pharmaceutically acceptable salt, N-oxide, racemate, or stereoisomer thereof, to the individual. In some embodiments of a method of treating a hyperproliferative disorder, the hyperproliferative disorder is a cancer or an autoimmune disease. In some embodiments of a method of treating a hyperproliferative disorder, the autoimmune disease is hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjogren's syndrome, systemic lupus erythematosus, type 1 diabetes, ulcerative colitis, or vitiligo.

Also disclosed herein is a method of treating cancer in an individual in need thereof comprising administering a therapeutically effective amount of a compound disclosed herein, or pharmaceutically acceptable salt, N-oxide, racemate, or stereoisomer thereof, to the individual. In some embodiments of a method of treating cancer, the cancer is a sarcoma, carcinoma, blastoma, myeloma, leukemia, lymphoma, or combinations thereof. In some embodiments of a method of treating cancer, the cancer is a skin cancer, lung cancer, breast cancer, prostate cancer, colorectal cancer, cervical cancer, uterine cancer, pancreatic cancer, liver cancer, or any combinations thereof. In some embodiments of a method of treating cancer, the cancer is acute myelogenous leukemia (AML). In some embodiments of a method of treating cancer, the cancer is renal cell carcinoma. In some embodiments of a method of treating cancer, the cancer is ovarian cancer. In some embodiments of a method of treating cancer, the cancer is prostate cancer. In some embodiments of a method of treating cancer, the cancer is renal cell carcinoma. In some embodiments of a method of treating cancer, the cancer is glioblastoma. In some embodiments of a method of treating cancer, the cancer is gastric carcinoma. In some embodiments of a method of treating cancer, the cancer is esophageal squamous cell carcinoma. In some embodiments of a method of treating cancer, the cancer is a lung cancer. In some embodiments of a method of treating cancer, the lung cancer is non-small cell lung carcinoma or small cell lung cancer. In some embodiments of a method of treating cancer, the cancer is multiple myeloma. In some embodiments of a method of treating cancer, the cancer is pancreatic cancer. In some embodiments of a method of treating cancer, the cancer is breast cancer.

Also disclosed herein is a method of treating a disease associated with unwanted angiogenesis in an individual in need thereof comprising administering a therapeutically effective amount of a compound disclosed herein, or pharmaceutically acceptable salt, N-oxide, racemate, or stereoisomer thereof, to the individual. In some embodiments of a method of treating a disease associated with unwanted angiogenesis, the disease associated with unwanted angiogenesis is macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma or hypertrophic scarring. In some embodiments of a method of treating a disease associated with unwanted angiogenesis, the disease associated with unwanted angiogenesis is cancer. In some embodiments of a method of treating a disease associated with unwanted angiogenesis, the cancer is a sarcoma, carcinoma, blastoma, myeloma, leukemia, lymphoma, or combinations thereof. In some embodiments of a method of treating a disease associated with unwanted angiogenesis, the cancer is Hodgkin lymphoma, non-Hodgkin lymphoma, myeloma, acute lymphocytic leukemia, chronic lymphocytic leukemia, acute myeloid leukemia, chronic myeloid leukemia, or other leukemia. In some embodiments of a method of treating a disease associated with unwanted angiogenesis, wherein the cancer is a skin cancer, lung cancer, breast cancer, prostate cancer, colorectal cancer, cervical cancer, uterine cancer, pancreatic cancer, liver cancer, or any combinations thereof. In some embodiments of a method of treating a disease associated with unwanted angiogenesis, the cancer is acute myelogenous leukemia (AML). In some embodiments of a method of treating a disease associated with unwanted angiogenesis, the cancer is renal cell carcinoma. In some embodiments of a method of treating a disease associated with unwanted angiogenesis, the cancer is ovarian cancer. In some embodiments of a method of treating a disease associated with unwanted angiogenesis, the cancer is prostate cancer. In some embodiments of a method of treating a disease associated with unwanted angiogenesis, the cancer is renal cell carcinoma. In some embodiments of a method of treating a disease associated with unwanted angiogenesis, the cancer is glioblastoma. In some embodiments of a method of treating a disease associated with unwanted angiogenesis, the cancer is gastric carcinoma. In some embodiments of a method of treating a disease associated with unwanted angiogenesis, the cancer is esophageal squamous cell carcinoma. In some embodiments of a method of treating a disease associated with unwanted angiogenesis, the cancer is a lung cancer. In some embodiments of a method of treating a disease associated with unwanted angiogenesis, the lung cancer is non-small cell lung carcinoma or small cell lung cancer. In some embodiments of a method of treating a disease associated with unwanted angiogenesis, the cancer is multiple myeloma. In some embodiments of a method of treating a disease associated with unwanted angiogenesis, the cancer is pancreatic cancer. In some embodiments of a method of treating a disease associated with unwanted angiogenesis, the cancer is breast cancer.

Also disclosed is a method of treating Human Immunodeficiency Virus (HIV) in a mammal comprising administering a therapeutically effective amount of a compound disclosed herein, or pharmaceutically acceptable salt, N-oxide, racemate, or stereoisomer thereof, to the individual.

Also disclosed is a method of reversing a latency of Human Immunodeficiency Virus (HW) in a mammal comprising administering a therapeutically effective amount of a compound disclosed herein, or pharmaceutically acceptable salt, N-oxide, racemate, or stereoisomer thereof, to the individual. In some embodiments of a method of reversing a latency of Human Immunodeficiency Virus (HIV), the latency of HW is reversed without activation of T cells. In some embodiments of a method of reversing a latency of Human Immunodeficiency Virus (HW), the method further comprises administering an additional latency reversal agent, a killer agent, CarT, immunotherapy, neutralizing antibodies, or other agents.

In some embodiments of a method of reversing a latency of Human Immunodeficiency Virus (HW), the additional latency reversal agent is a histone deacetylase inhibitor (HDACi), a bromodomain and extra terminal domain inhibitors (BETi), or a Protein Kinase C (PKC) agonist.

BRIEF DESCRIPTION OF THE DRAWINGS

FIG. 4 shows cIAP1 degradation, p100 cleavage, and the induction of GPF expression in the latently infected Jurkat 2D10 cell line upon treatment with Compound 18a.

DETAILED DESCRIPTION OF THE INVENTION

Provided herein are potent ML-IAP inhibitors available as either tools or potential drugs to treat cancer and other medical conditions. Genetic silencing of ML-IAP shows efficacy in various tumors as well as xenograft studies. By advancing the development of IAP antagonists, the survival of cancer patients including AML patients will be increased, giving new hope to the severely ill. This will lead to a major advancement in the treatment of cancers, in particular AML cancers.

AML is a diverse collection of hematological cancers characterized by the bone marrow's excessive production of immature myeloid blood cells. This acute proliferation of abnormal progenitors results in impairment of normal blood and bone marrow functions. The American Cancer Society estimated that there will be 11,000 deaths and 21,500 new incidences of AML in the U.S. in 2019. Leukemia is the fourth most common cancer among 17-34 year old age group, but AML is more fatal in older patients. AML is considered to be a "late effect" disease, and exposure to ionizing radiation and/or chemical agents has been implicated in the development of leukemias and other blood cancers. Leukemia is curable in approximately 30% of patients under age 60, but in older patients the cure rate is only about 10%. In fact, elderly patients unable to tolerate aggressive chemotherapies only survive an average of ~7 months. While the various AML subtypes have somewhat differing prognoses, more than 30% of all AML patients fail to enter complete remission upon standard chemotherapy regimens. Most patients that do respond initially will relapse within 5 years in the absence of a bone marrow transplant (BMT). Thus, the need for novel targets and drugs to treat AML is a significant unmet medical need. This is especially true in patient populations unable to tolerate aggressive chemotherapy, or where BMT is impossible or not recommended. The current standard of care (SOC) for AML has been the same for decades—the nucleoside derivative cytarabine ("ara-C") in combination with anthracyclines, usually daunorubicin, and these are used as frontline agents. Although many patients will enter remission, almost all will relapse, and consequently there is a critical need for new therapies.

Figure 1:
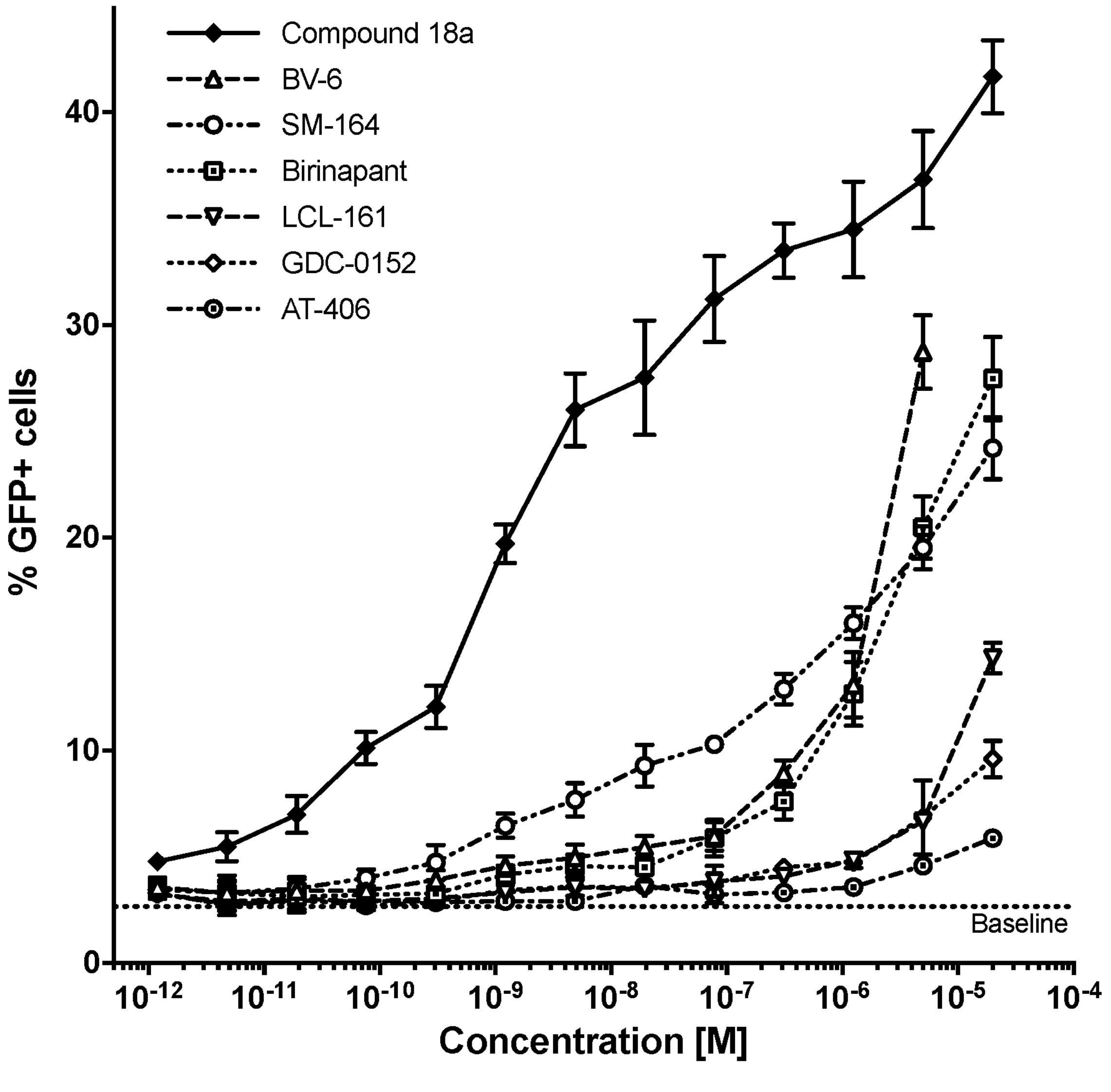
FIG. 1 illustrates comparative data of Compound 18a and various known compounds in their potency and efficacy in HIV latency reversal in latently infected cell line 2D10.

Apoptosis, a form of programmed cell death, is often dysregulated in malignant cells, and the evasion of apoptosis is a hallmark of cancer. As cancer cells divide and proliferate, normal control of cell death is impaired and tumor formation occurs. The IAP protein family is involved in blocking and attenuating programmed cell death pathways, predominantly through modulation of the caspase cascade (FIG. 1). IAP proteins are often upregulated in cancers and are believed to underlie the resistance of many malignant cells to chemotherapeutics. Ablation or antagonism of IAP proteins is therefore an attractive therapeutic strategy for the treatment of cancer.

Proteins and genes are ascribed to the IAP family if they possess a baculovirus IAP protein repeat (BIR) domain. Of the eight IAP proteins, five also contain a RING E3 ligase domain, with cIAP1 and cIAP2 also containing a caspase recruitment domain (CARD). The prototypical IAP family member is XIAP, which is a potent binder and inhibitor of caspase-3, one of the proteases that effects apoptosis. Another highly relevant member of the IAP protein family is ML-IAP, also known as Livin or KIAP, which was first identified as a member of the IAP protein family due to its single BIR domain (49, 50). The ML-IAP BIR domain is also responsible for apoptosis inhibition, and small molecule antagonists have significant potential for development as therapeutic agents. The RING domain of ML-IAP has been shown to function as an E3 ligase, facilitating the ubiquitination and subsequent degradation of itself and, more importantly, the natural caspase antagonist that modulates apoptotic signaling—the second mitochondria-derived activator of caspases (SMAC). Thus, inhibition of ML-IAP leads to a direct increase of SMAC and a re-sensitization of cells to apoptotic stimuli. Importantly, both protein and mRNA levels of ML-IAP are low to undetectable in most adult tissues but are highly expressed in a number of cancers including hematologic malignancies.

AML cells have been shown to overexpress multiple antiapoptotic proteins, including Bcl2 and IAP protein family members, and it is believed this may underlie their resistance to therapies and eventual relapse. IAP protein family members can be potential therapeutic targets for AML, and the expression levels of IAP proteins have been shown to be prognostic. Provided herein is a new series of highly potent, bivalent IAP antagonists with single agent malignant cell-killing activity in culture. IAP antagonists can also be effective against AML.

Aberrant and uncontrolled cell growth due to apoptosis suppression is a hallmark of cancer cells. Cancer cells often display aberrant upregulation of pathways which inhibit apoptosis, allowing the cancer cells to proliferate. One such pathway which is upregulated in cancer cells is the inhibitor of apoptosis (IAP) pathway. The members of the IAP family are functionally and structurally related proteins, which inhibit apoptosis. IAPB share a baculovirus IAP repeat (BIR) domain, each having one to three copies. Eight members of the IAP protein family have currently been identified, in both baculovirus and humans. Five human members of the IAP protein family include: XIAP, cIAP1 (also, BIRC2), cIAP2 (also, BIRC3), NAIP, and survivin. In certain instances, XIAP inhibits apoptosis by binding to and inhibiting the activity of caspase-9, caspase-3 and caspase 7.

Alterations in IAP proteins are found in many types of human cancer and are associated with chemoresistance, disease progression and poor prognosis. When the IAP pathway is upregulated, the IAP proteins bind to and prevent initiator and effector caspases from cleaving downstream cellular proteins.

The proteolytic action of caspases is required to allow the cell death cascade to progress normally. Accordingly, provided herein are compounds that bind the upregulated IAP proteins. The compounds provided herein, in some embodiments, bind to IAP proteins and prevent them from suppressing caspase action, thereby allowing the cell death cascade to progress normally. In other words, provided herein are compounds that inhibit the action of IAP proteins, thereby inducing apoptosis in cells.

One protein implicated in binding with IAPB is SMAC. SMAC is a mitochondrial protein that negatively regulates apoptosis, also known as programmed cell death. When a cell is primed for apoptosis by the final execution step of caspase activation, SMAC binds to IAP, which prevents IAP from binding to, and deactivating caspases. Thus, SMAC promotes apoptosis by activating caspases.

In some embodiments, the compounds described herein are nonpeptidic second mitochondria-derived activator of caspase (SMAC) mimetics and induce apoptosis (e.g., in cancer cells). In some embodiments, the compounds described herein are IAP antagonists.

In certain instances, IAP proteins not only regulate caspases and apoptosis, but also modulate inflammatory signaling and immunity, mitogenic kinase signaling, proliferation and mitosis, as well as cell invasion and metastasis. Inhibitor of apoptosis (IAP) proteins have emerged as regulators of innate immune signaling downstream of Pattern Recognition Receptors (PRRs) such as Toll-like receptor 4 (TLR4), Nucleotide-Binding Oligomerization Domain 1 (NOD1) and NOD2 receptors, and Retinoic Acid-Inducible Gene (RIG)-I Receptor. In certain instances, Cellular Inhibitor of Apoptosis Protein-1 (cIAP1; also Baculoviral IAP Repeat Containing 2 or BIRC2), Cellular Inhibitor of Apoptosis Protein-2 (cIAP2; also, Baculoviral IAP Repeat Containing 3 or BIRC3), and X-linked Inhibitor of Apoptosis (XIAP) facilitate ubiquitin-dependent signaling activated by these PRRs and mediate activation of nuclear factor-kappa B (NF-κB) transcription factors as well as the MAP kinases p38 and JNK. Accordingly, the compounds described herein are also useful in the treatment of non-neoplastic diseases and/or inflammatory diseases and/or autoimmune diseases.

Recent advances in combinatorial antiretroviral therapy (ART) have allowed individuals infected with human immunodeficiency virus (HW) to live long and otherwise normal lives. However, antiretroviral therapy only targets actively replicating HIV and not the dormant, replication competent HW that resides in certain types of cells. These dormant HW viruses can reactivate and trigger new rounds of viral replication upon discontinuation of antiretroviral therapy. In addition to targeting actively replicating HW, a strategy for improving HW treatment is to also target the dormant, replication competent HW virus residing in latently infected cells, which are cells that are infected with HW but are not actively producing HW. These latently infected cells are not undergoing active virus replication and the viral genome has been integrated into the host DNA in such a manner that the virus DNA is indistinguishable from the host's DNA. Latently infected cells are not recognized by the immune system and are not susceptible to antiretroviral therapy (ART). Thus, the dormant virus and latently infected cells can remain hidden and persist indefinitely. One approach for targeting latently infected cells is to develop new therapeutic agents or drugs that can reverse latency in infected cells by inducing active HW replication. Once the dormant HW virus is "awakened", the infected cells become susceptible to immune system clearance or the effects of additional treatments such as killer agents to eliminate infected cells. Concurrent treatment with antiretroviral drugs will prevent the spread of the reactivated virus and suppress new rounds of HIV infection. The combination of therapeutic agents that can reverse the latency of HIV-infected cells and drugs to eradicate the awakened HW virus is termed the "shock and kill" or "kick and kill" approach. IAP inhibition has been implicated in the reversal of HIV latency. The IAP antagonists may be used alone or in combination with other therapeutic agents, such as those that are used to treat HIV. In some embodiments, other therapeutic agents that could be used in combination with IAP antagonists include therapeutic agents that activate HIV transcription in latently infected cells, therapeutic agents that inhibit active HIV replication, or any combination thereof. In some embodiments, the additional therapeutic agents that inhibit active HW replication include antiretroviral therapy drugs. In some embodiments, the pharmaceutical compositions are described comprising IAP antagonists, alone or in combination with one or more additional therapeutics agents that are useful for the treatment of HW in a mammal. In some embodiments, the mammal is a human.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Oxo" refers to =O.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to, ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged, spirocyclic ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Deuteroalkyl" refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atoms. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Haloalkyl" refers to an alkyl radical, as defined above, that is substituted by one or more halogen atoms. In some embodiments, the alkyl is substituted with one, two, or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, or —$CH(CH_3)OCH_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl comprises 1 or 2 heteroatoms selected from nitrogen and oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —$CF_3$, —OH, —OMe, —$NH_2$, or —$NO_2$. In some embodiments, a heterocycloalkyl is optionally substituted with oxo, halogen, methyl, ethyl, —CN, —$CF_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, —OMe, —$NH_2$, or —$NO_2$. In some embodiments, a heteroaryl is optionally substituted with halogen, methyl, ethyl, —CN, —$CF_3$, —OH, or —OMe. In some embodiments, the heteroaryl is optionally substituted with halogen.

An "effective amount" or "therapeutically effective amount" refers to an amount of a compound administered to a subject (e.g. a mammal, such as a human), either as a single dose or as part of a series of doses, which is effective to produce a desired therapeutic effect.

"Treatment" of a subject (e.g. a mammal, such as a human) includes any type of intervention used in an attempt to alter the natural course of the subject. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

As used herein, “subject”, “individual” and “patient” are used interchangeably. None of the terms imply that a medical professional is required for the administration of the compounds disclosed herein.

Compounds

Some embodiments relate to a compound having the structure of Formula (I), pharmaceutically acceptable salt, N-oxide, racemate, or stereoisomer thereof:

Formula (I)

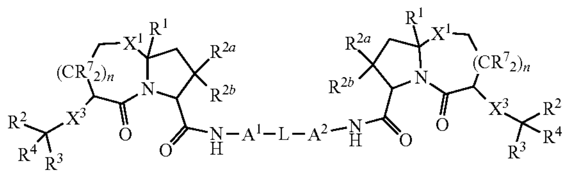

wherein, each $X^1$ is independently O, S, S(=O), or $S(=O)_2$;

each $R^1$, $R^3$ and $R^4$ is independently H, halogen, $C_1$-$C_6$alkyl, $C_3$-$C_6$cycloalkyl, $C_6$-$C_{10}$aryl, or 5- to 10-membered heteroaryl, wherein each alkyl, cycloalkyl, aryl, and heteroaryl is independently optionally substituted with one, two, or three $R^a$;

each $R^2$ is independently H, $C_1$-$C_6$alkyl, $C_3$-$C_6$cycloalkyl, —$C_1$-$C_6$alkyl-($C_3$-$C_6$cycloalkyl), or —$NR^5R^6$;

wherein each alkyl and cycloalkyl is independently optionally substituted with one, two, or three $R^b$;

each $R^5$ and $R^6$ is independently H, $C_1$-$C_6$alkyl, or —$C_1$-$C_6$alkyl-($C_3$-$C_6$cycloalkyl);

each $R^7$ is independently H, halogen, $C_1$-$C_6$alkyl, or OH;

each n is independently 1 or 2;

each $X^3$ is independently —NHC(=O)—, —C(=O)NH—, —NHS(=O)$_2$—, —S(=O)$_2$NH—, —NHC(=O)NH—, —NH(C=O)O—, —O(C=O)NH—, —NHS(=O)$_2$NH—, —NHC($R^{1a}$)($R^{1b}$)—, or —C($R^{1a}$)($R^{1b}$)NH—.

$A^1$ and $A^2$ are independently $C_1$-$C_6$ alkylene, $C_3$-$C_{10}$ cycloalkylene, $C_5$-$C_{10}$ arylene, $C_2$-$C_{10}$ heterocycloalkylene, or 4- to 10-membered heteroarylene, wherein each alkylene, cycloalkylene, arylene, heterocycloalkylene, and heteroarylene is independently optionally substituted with one, two, or three $R^c$;

L is —$X^5$—$(CH_2)_{n1}$-$Q^1$-$(CH_2)_{n2}$—$X^5$—;

each $X^5$ is independently O, S, or absent;

each $n^1$ and $n^2$ is independently 0-5;

$Q^1$ is —$C_1$-$C_6$alkylene-, —$C_2$-$C_6$alkenylene-, —$C_2$-$C_6$alkynylene-, —C(O)NH—$C_1$-$C_6$ alkylene-NHC(O)—, —$C_2$-$C_6$alkynylene-$C_6$-$C_{10}$ arylene-, —$C_2$-$C_6$alkynylene-$C_6$-$C_{10}$arylene-$C_2$-$C_6$alkynylene-, or —$C_6$-$C_{10}$arylene-$C_6$-$C_{10}$arylene-; wherein each alkylene, alkenylene, $C_2$-$C_6$alkynylene, and $C_6$-$C_{10}$arylene is independently optionally substituted with one, two, or three $R^d$;

each $R^{1a}$ and $R^{1b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl;

each $R^{2a}$ and $R^{2b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl; or $R^{2a}$ and $R^{2b}$ taken together form a $C_3$-$C_6$cycloalkyl or $C_2$-$C_5$heterocycloalkyl; and each $R^a$, $R^b$, $R^c$, and $R^d$ is independently halogen, OH, $NH_2$, CN, $C_1$-$C_6$alkoxy, $C_1$-$C_6$alkyl, $C_1$-$C_6$haloalkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl.

Some embodiments relate to a compound having the structure of Formula (I), pharmaceutically acceptable salt, N-oxide, racemate, or stereoisomer thereof:

Formula (I)

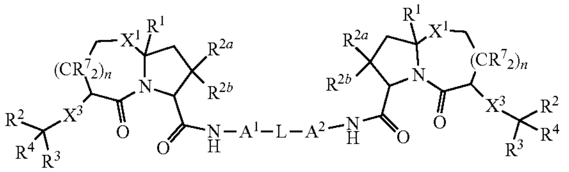

wherein, each $X^1$ is independently O, S, S(=O), or $S(=O)_2$;

each $R^1$, $R^3$ and $R^4$ is independently H, halogen, $C_1$-$C_6$alkyl, $C_3$-$C_6$cycloalkyl, $C_6$-$C_{10}$aryl, or 5- to 10-membered heteroaryl, wherein each alkyl, cycloalkyl, aryl, and heteroaryl is independently optionally substituted with one, two, or three $R^a$;

each $R^2$ is independently H, $C_1$-$C_6$alkyl, $C_3$-$C_6$cycloalkyl, —$C_1$-$C_6$alkyl-($C_3$-$C_6$cycloalkyl), or —$NR^5R^6$; wherein each alkyl and cycloalkyl is independently optionally substituted with one, two, or three $R^b$;

each $R^5$ and $R^6$ is independently H, $C_1$-$C_6$alkyl, or —$C_1$-$C_6$alkyl-($C_3$-$C_6$cycloalkyl);

each $R^7$ is independently H, halogen, $C_1$-$C_6$alkyl, or OH;

each n is independently 1 or 2;

each $X^3$ is independently —NHC(=O)—, —C(=O)NH—, —NHS(=O)$_2$—, —S(=O)$_2$NH—, —NHC(=O)NH—, —NH(C=O)O—, —O(C=O)NH—, —NHS(=O)$_2$NH—, —NHC($R^{1a}$)($R^{1b}$)—, or —C($R^{1a}$)($R^{1b}$)NH—;

$A^1$ and $A^2$ are independently $C_1$-$C_6$ alkylene, $C_3$-$C_{10}$ cycloalkylene, $C_5$-$C_{10}$ arylene, $C_2$-$C_{10}$ heterocycloalkylene, or 4- to 10-membered heteroarylene, wherein each alkylene, cycloalkylene, arylene, heterocycloalkylene, and heteroarylene is independently optionally substituted with one, two, or three $R^c$;

L is —$X^5$—$(CH_2)_{n1}$-$Q^1$-$(CH_2)_{n2}$—$X^5$—;

each $X^5$ is independently O, S, or absent;

each $n^1$ and $n^2$ is independently 0-5;

$Q^1$ is —$C_1$-$C_6$alkylene-, —$C_2$-$C_6$alkenylene-, —$C_2$-$C_6$alkynylene-, —C(O)NH—$C_1$-$C_6$ alkylene-NHC(O)—, —$SO_2$—, —$C_2$-$C_6$alkynylene-$C_6$-$C_{10}$ arylene-, —$C_2$-$C_6$alkynylene-$C_6$-$C_{10}$arylene-$C_2$-$C_6$alkynylene-, or —$C_6$-$C_{10}$arylene-$C_6$-$C_{10}$arylene-; wherein each alkylene, alkenylene, $C_2$-$C_6$alkynylene, and $C_6$-$C_{10}$arylene is independently optionally substituted with one, two, or three $R^d$;

each $R^{1a}$ and $R^{1b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl;

each $R^{2a}$ and $R^{2b}$ is independently H, OH, $NH_2$, CN, $C_1$-$C_6$alkoxy, $C_1$-$C_6$alkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl; or $R^{2a}$ and $R^{2b}$ taken together form a $C_3$-$C_6$cycloalkyl or $C_2$-$C_5$heterocycloalkyl; and each $R^a$, $R^b$, $R^c$, and $R^d$ is independently halogen, OH, $NH_2$, CN, $C_1$-$C_6$alkoxy, $C_1$-$C_6$alkyl, $C_1$-$C_6$haloalkyl, $C_2$-$C_6$alkene, $C_2$-$C_6$alkynyl, $C_1$-$C_6$heteroalkyl, $C_3$-$C_6$cycloalkyl, $C_2$-$C_5$heterocycloalkyl, $C_6$-$C_{10}$aryl, or 5- to 10-membered heteroaryl;

with the proviso that the compound is not:

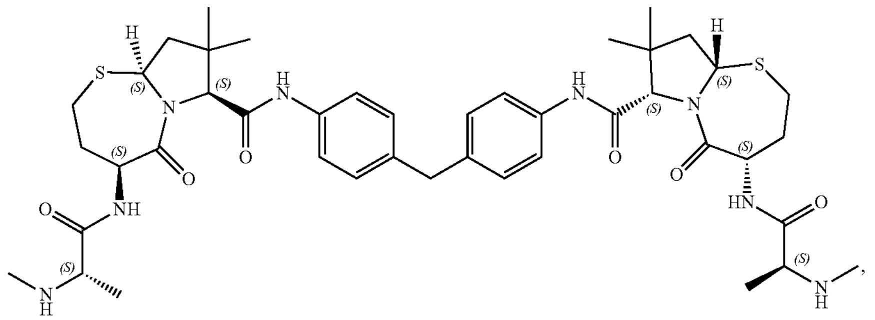
,
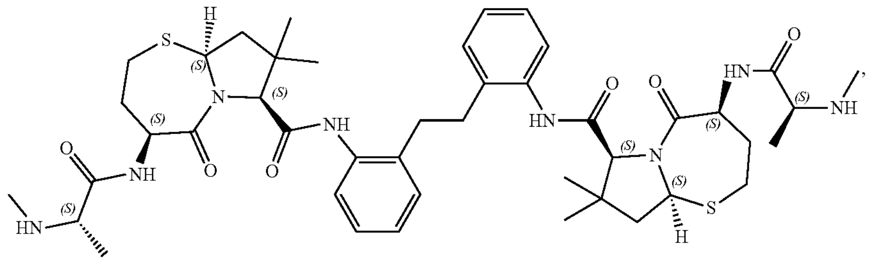
,
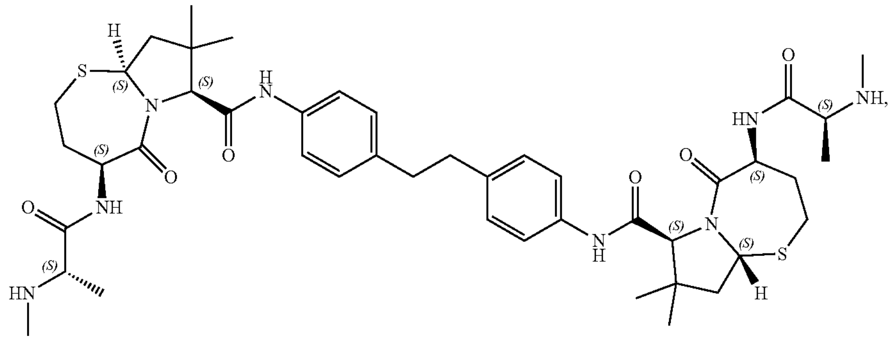
,
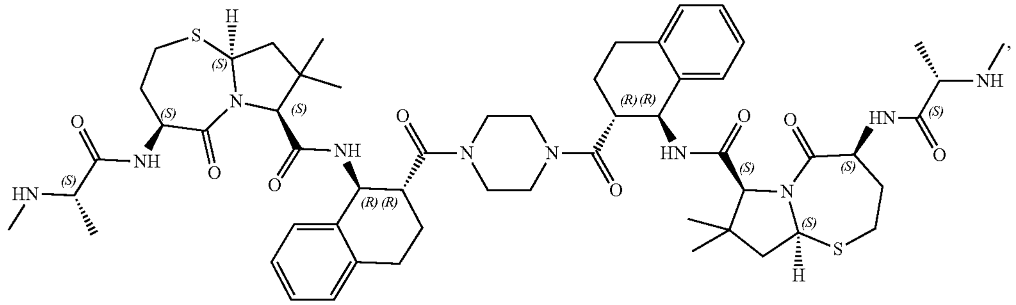
,
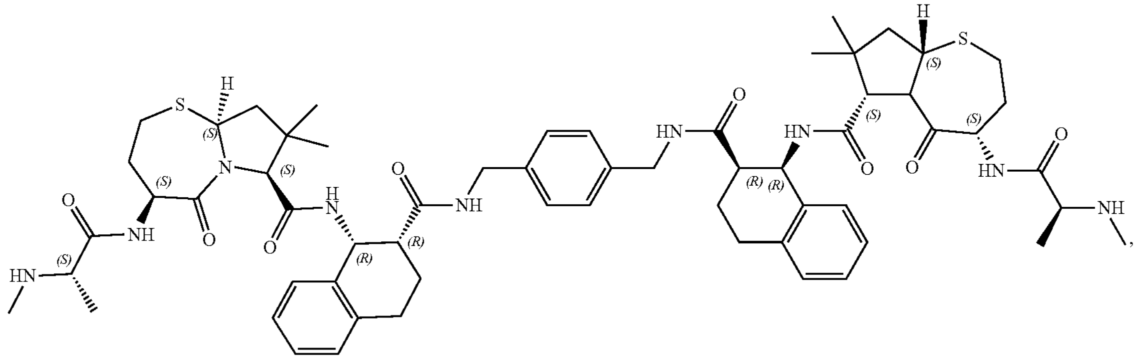
,

-continued
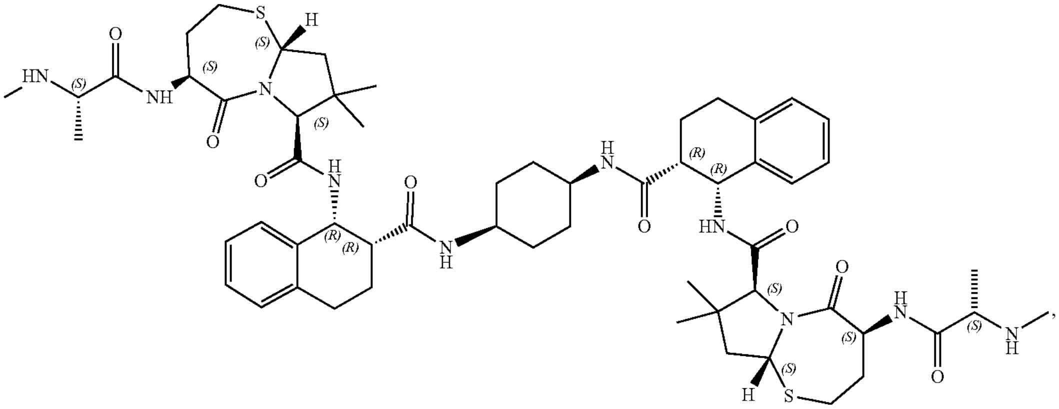
,
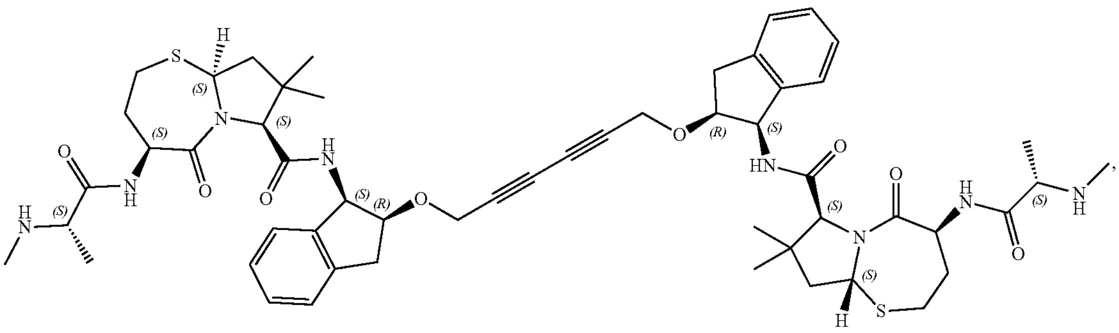
,
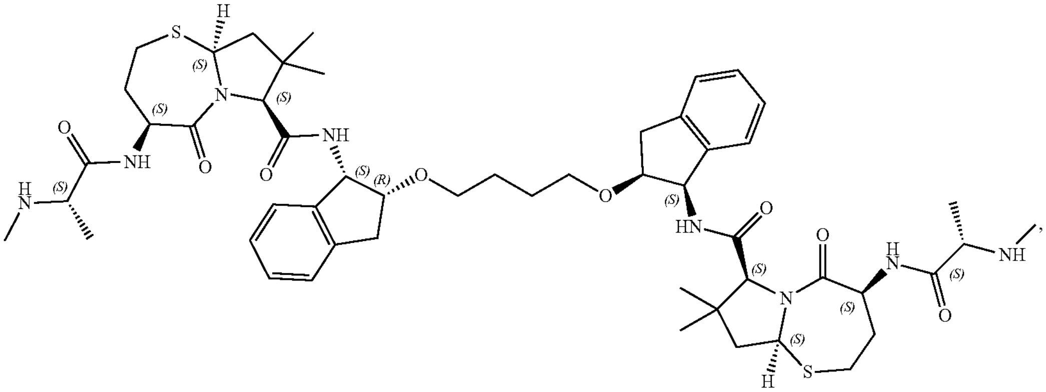
,
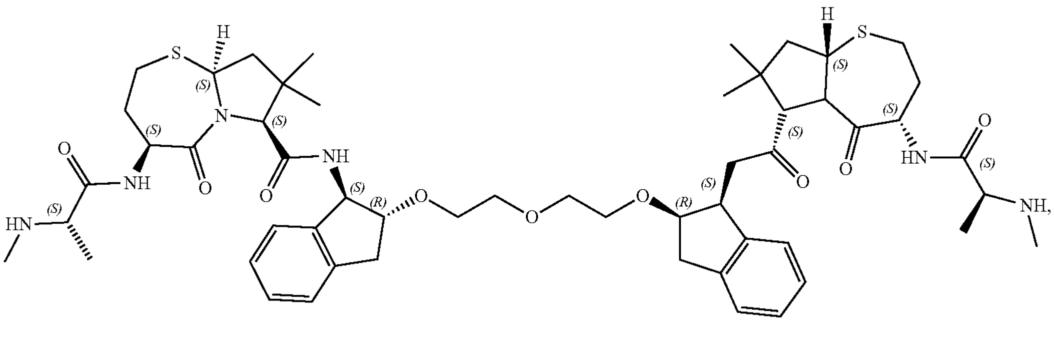
,

-continued
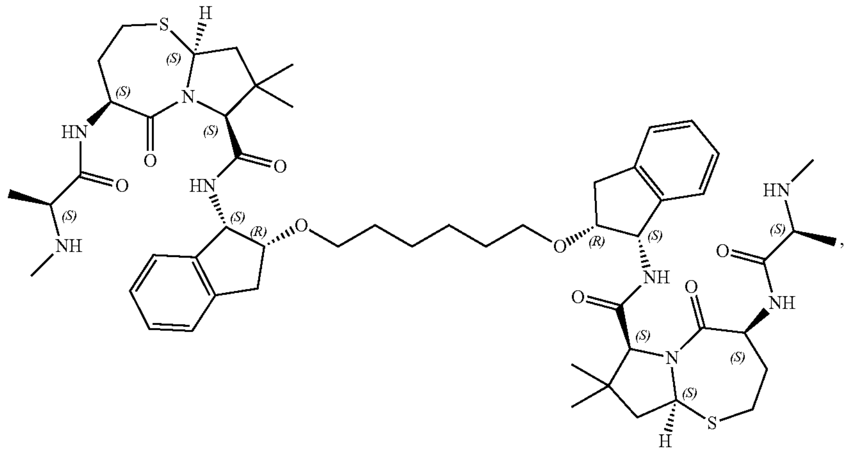
,
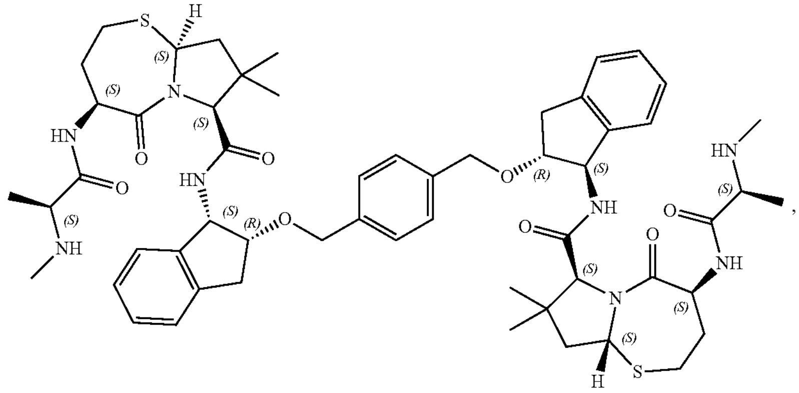
,
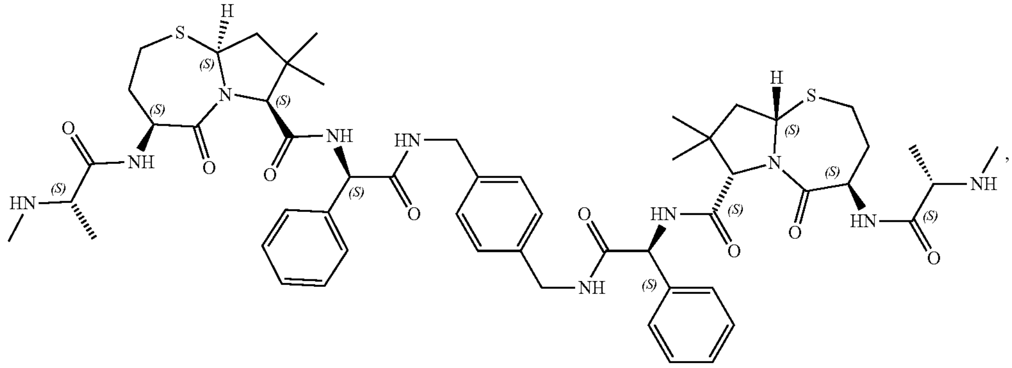
,
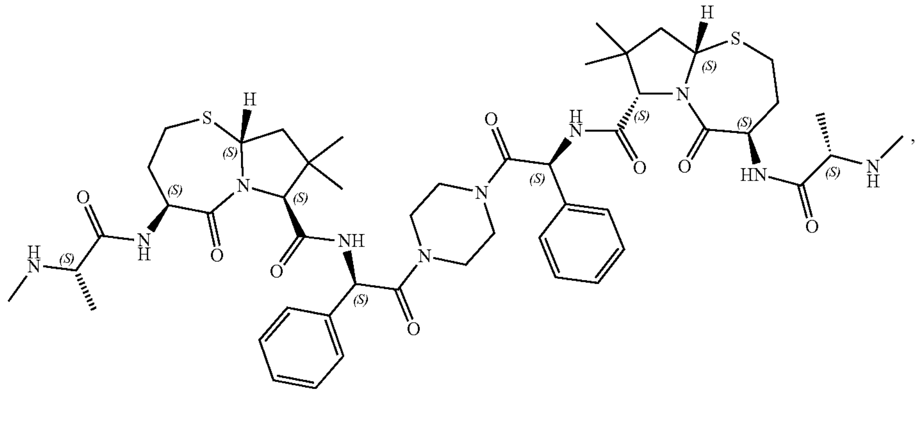
,

-continued
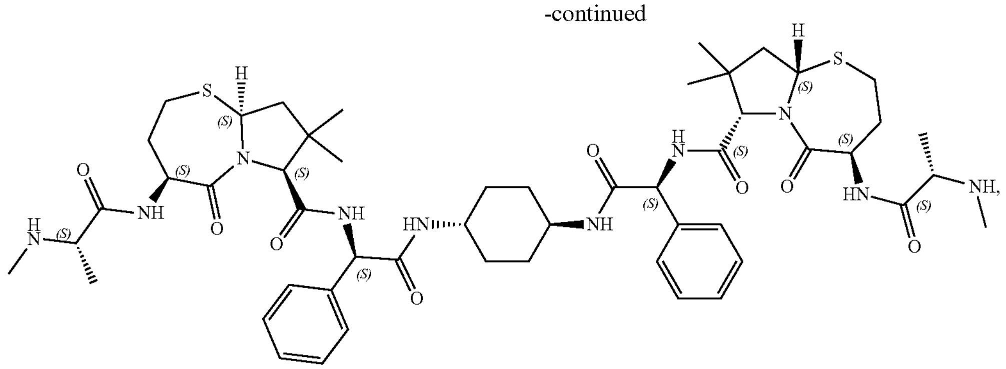
,
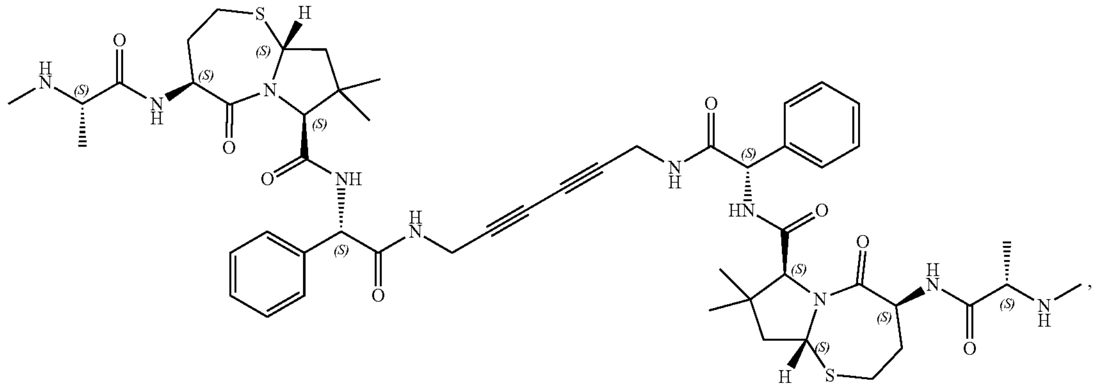
,
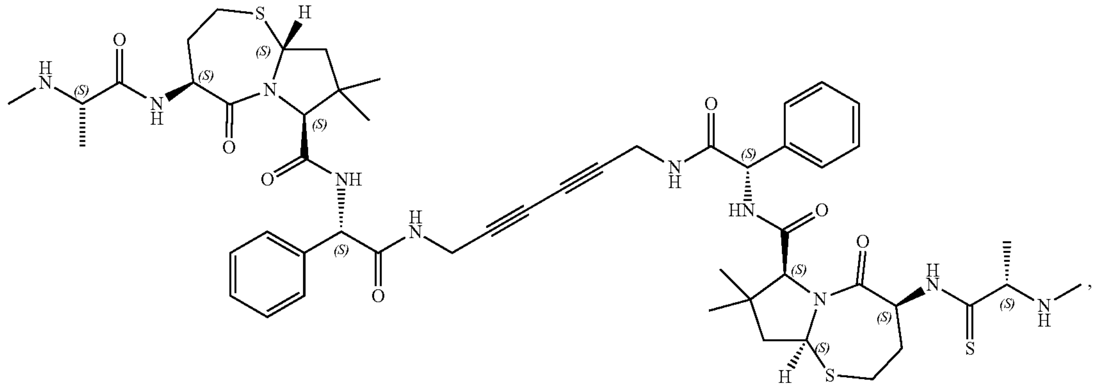
,
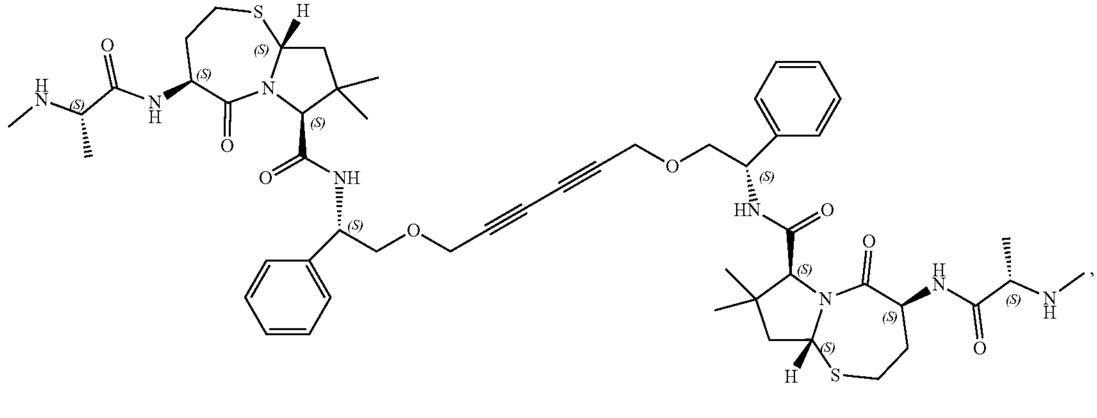
,

-continued
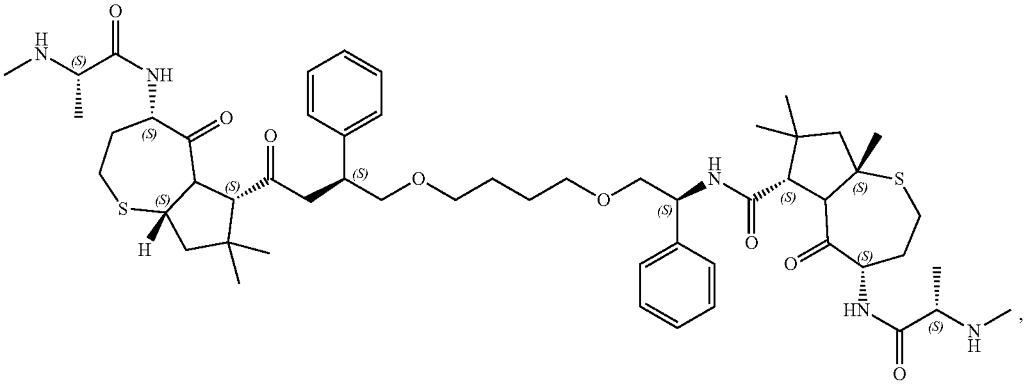
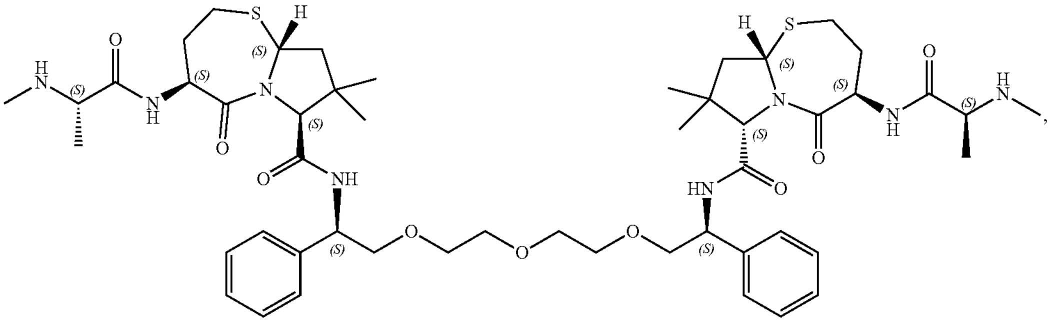
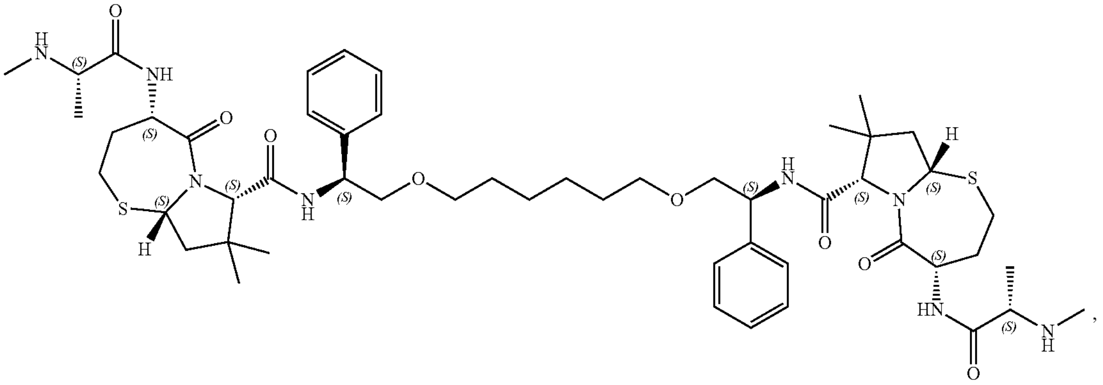
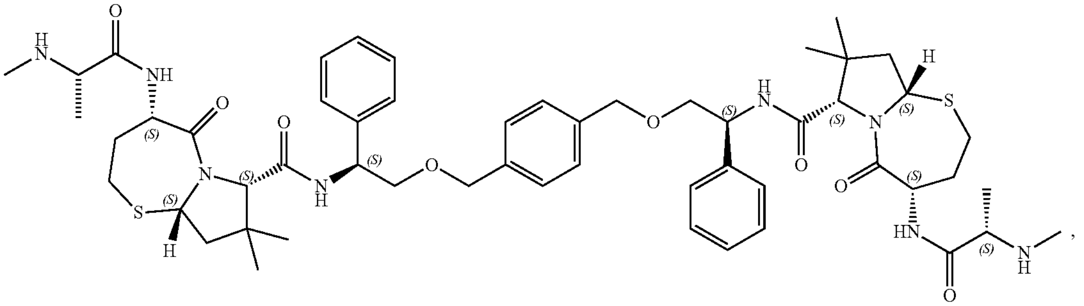

-continued
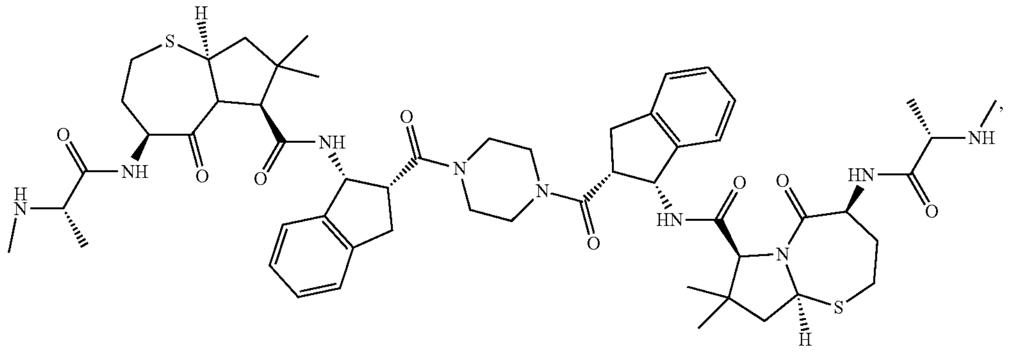
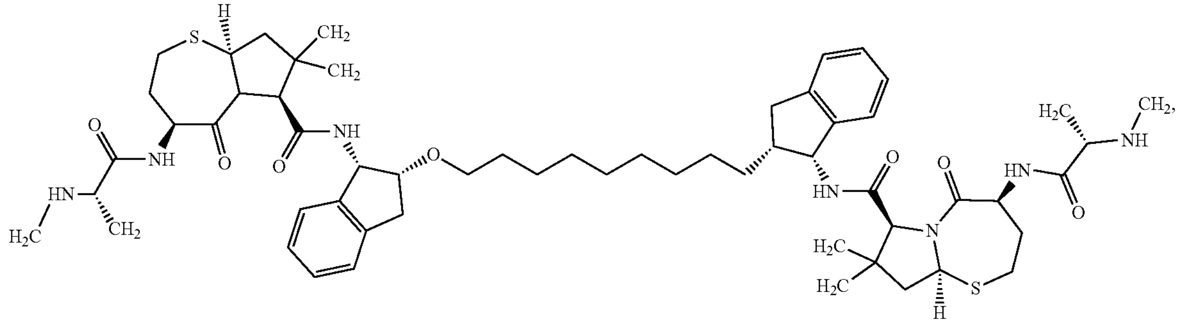
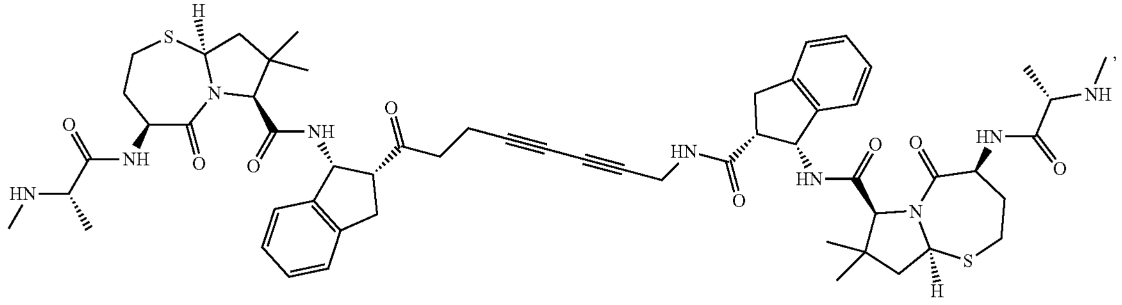
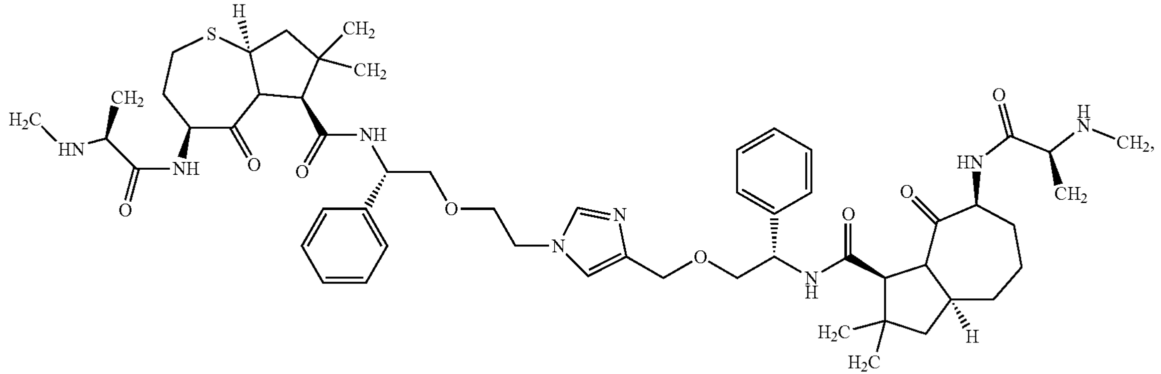
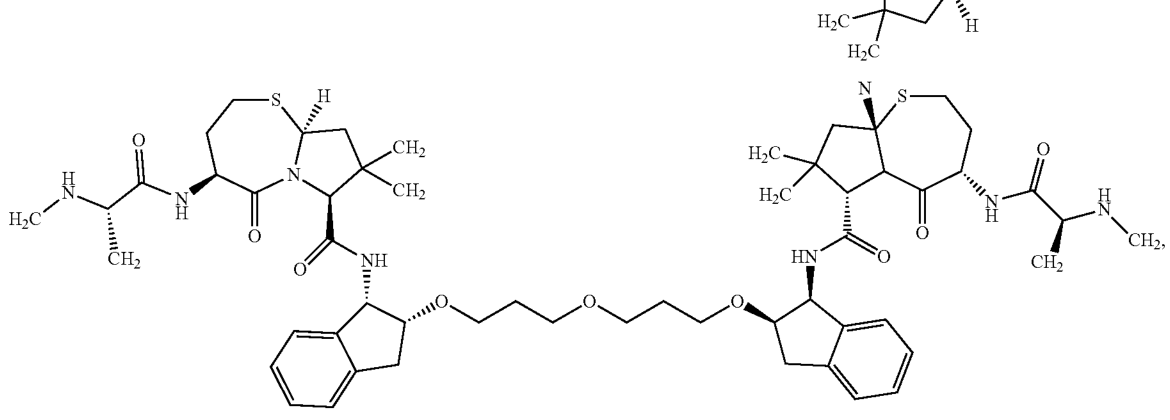

-continued
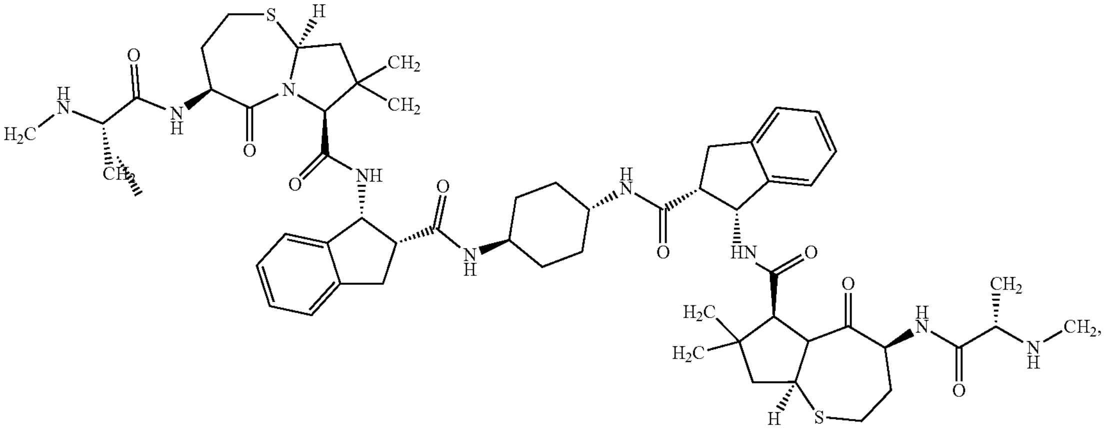
,
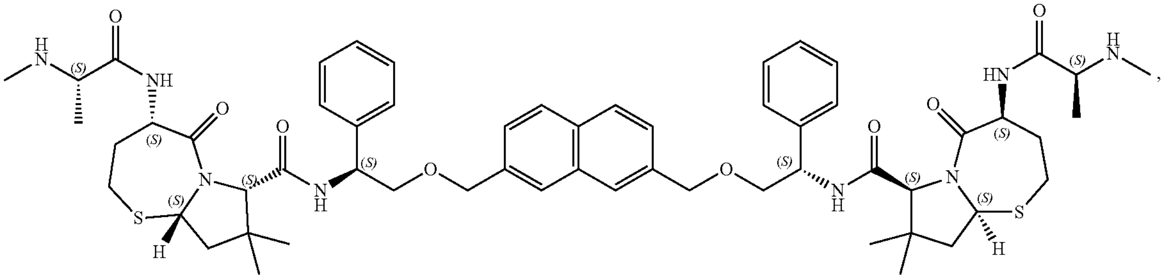
,
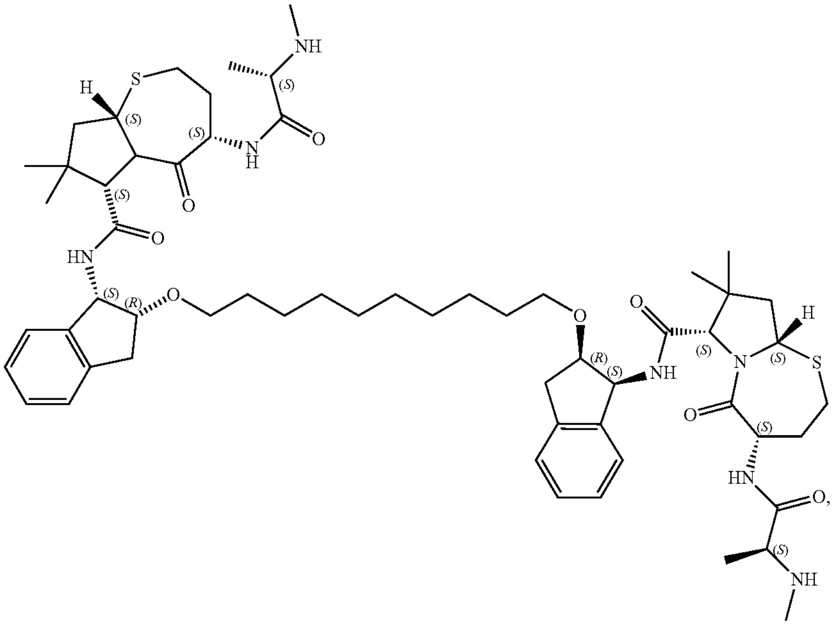
,
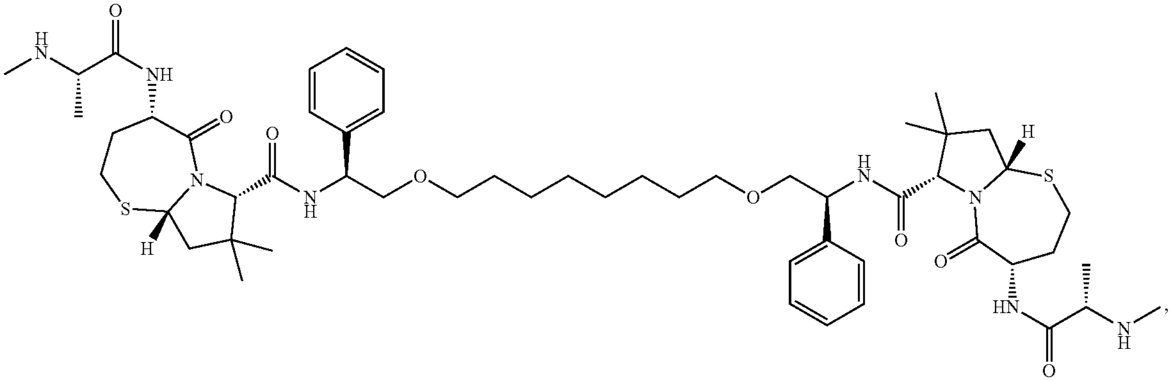
,

-continued
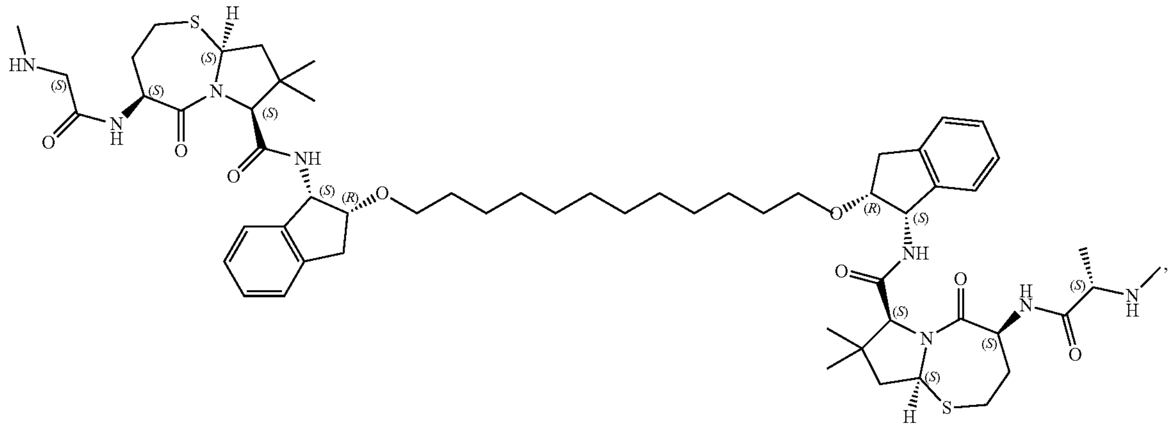
,
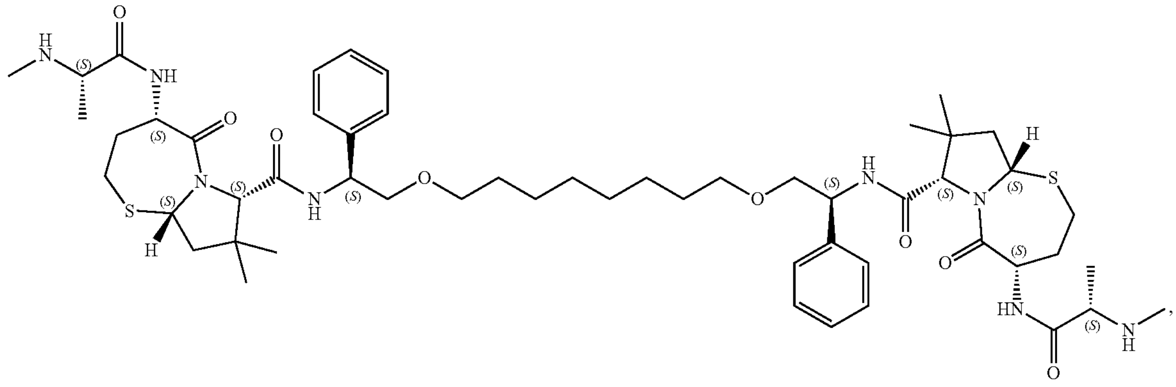
,
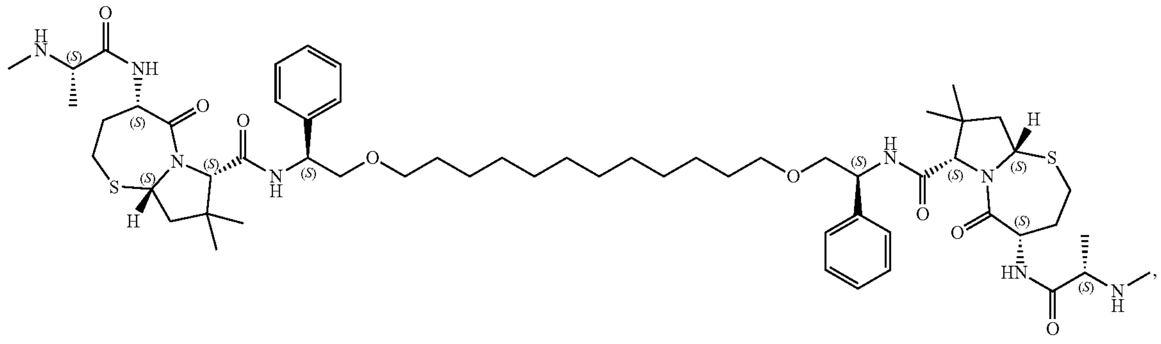
,
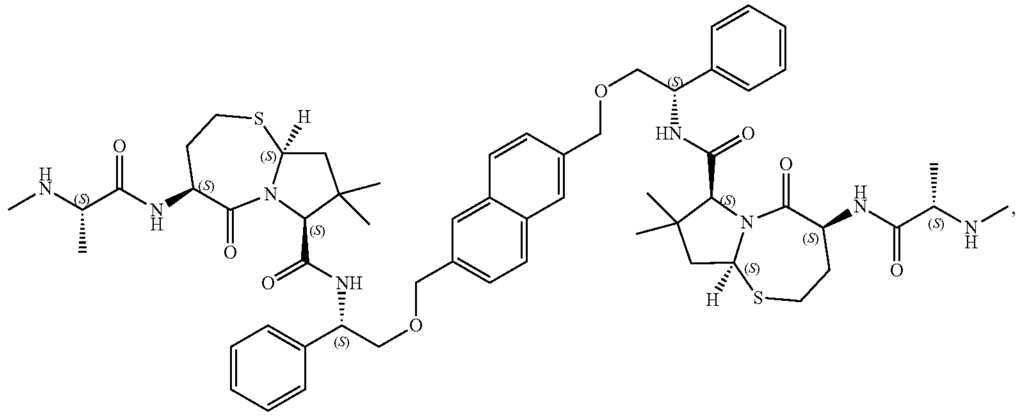
, or

-continued

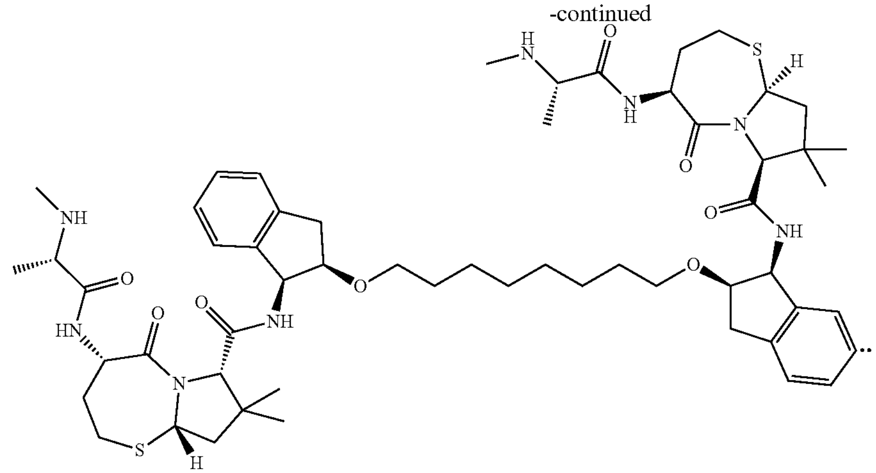

In some embodiments of a compound of Formula (I), each n is 1. In some embodiments of a compound of Formula (I), each n is 2.

In some embodiments of a compound of Formula (I), each $R^7$ is independently H or OH. In some embodiments of a compound of Formula (I), each $R^7$ is H.

In some embodiments, the compounds described herein or pharmaceutically acceptable salt, N-oxide, racemate, or stereoisomer thereof, has the structure of Formula II:

Formula II

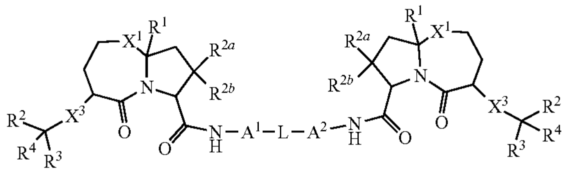

In some embodiments, the compounds described herein or pharmaceutically acceptable salt, N-oxide, racemate, or stereoisomer thereof, has the structure of Formula III:

Formula III

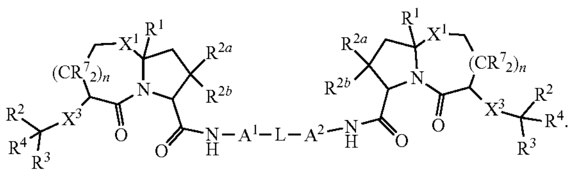

In some embodiments of a compound of Formula (I), (II), or (III), each $X^1$ is S, S(═O), or S(═O)$_2$. In some embodiments of a compound of Formula (I), (II), or (III), each $X^1$ is S. In some embodiments of a compound of Formula (I), (II), or (III), each $X^1$ is O. In some embodiments of a compound of Formula (I), (II), or (III), each $X^1$ is S(═O)$_2$.

In some embodiments of a compound of Formula (I), (II), or (III), each $R^{2a}$ and $R^{2b}$ is independently H, OH, $C_1$-$C_6$alkyl, or $C_2$-$C_6$alkene; or $R^{2a}$ and $R^{2b}$ taken together form a $C_3$-$C_6$cycloalkyl.

In some embodiments of a compound of Formula (I), (II), or (III), each $R^{2a}$ and $R^{2b}$ is independently OH or $C_2$-$C_6$alkene; or $R^{2a}$ and $R^{2b}$ taken together form a $C_3$-$C_6$cycloalkyl. In some embodiments of a compound of Formula (I), (II), or (III), each $R^{2a}$ or $R^{2b}$ is independently H or OH. In some embodiments of a compound of Formula (I), (II), or (III), Rea is OH. In some embodiments of a compound of Formula (I), (II), or (III), $R^{2b}$ is H. In some embodiments of a compound of Formula (I), (II), or (III), Rea is H and $R^{2b}$ is OH. In some embodiments of a compound of Formula (I), (II), or (III), Rea is OH and $R^{2b}$ is H. In some embodiments of a compound of Formula (I), (II), or (III), each $R^{2a}$ and $R^{2b}$ is independently $C_1$-$C_6$alkyl or $C_2$-$C_6$alkene. In some embodiments of a compound of Formula (I), (II), or (III), each $R^{2a}$ and $R^{2b}$ is independently $C_1$-$C_6$alkyl. In some embodiments of a compound of Formula (I), (II), or (III), each $R^{2a}$ and $R^{2b}$ is independently $C_2$-$C_6$alkenyl. In some embodiments of a compound of Formula (I), (II), or (III), each $R^{2a}$ and $R^{2b}$ is independently $C_2$-$C_3$alkenyl. In some embodiments of a compound of Formula (I), (II), or (III), $R^{2a}$ and $R^{2b}$ taken together form a $C_3$-$C_6$cycloalkyl. In some embodiments of a compound of Formula (I), (II), or (III), $R^{2a}$ and $R^{2b}$ taken together form a $C_3$-$C_5$cycloalkyl. In some embodiments of a compound of Formula (I), (II), or (III), $R^{2a}$ and $R^{2b}$ taken together form a $C_5$cycloalkyl. In some embodiments of a compound of Formula (I), (II), or (III), Rea and $R^{2b}$ taken together form a cyclopropyl, cyclobutyl, cyclopentyl, cyclopentenyl, cyclohexyl, or cyclohexenyl. In some embodiments of a compound of Formula (I), (II), or (III), $R^{2a}$ and $R^{2b}$ taken together form a cyclopentyl or cyclopentenyl.

In some embodiments of a compound of Formula (I), (II), or (III), each $X^3$ is independently —NHC(═O)— or —C(═O)NH—. In some embodiments of a compound of Formula (I), (II), or (III), each $X^3$ is —NHC(═O)—. In some embodiments of a compound of Formula (I), (II), or (III), each $X^3$ is —C(═O)NH—. In some embodiments of a compound of Formula (I), (II), or (III), each $X^3$ is —NHS(═O)$_2$—. In some embodiments of a compound of Formula (I), (II), or (III), each $X^3$ is —S(═O)$_2$NH—. In some embodiments of a compound of Formula (I), (II), or (III), each $X^3$ is —NHC(═O)NH—. In some embodiments of a compound of Formula (I), (II), or (III), each $X^3$ is —NH(C═O)O—. In some embodiments of a compound of Formula (I), (II), or (III), each $X^3$ is —O(C═O)NH—. In some embodiments of a compound of Formula (I), (II), or (III), each $X^3$ is —NHS(═O)$_2$NH—. In some embodiments of a compound of Formula (I), (II), or (III), each $X^3$ is —NHC($R^{1a}$)($R^{1b}$)— or —C($R^{1a}$)($R^{1b}$)NH—.

In some embodiments of a compound of Formula (I), (II), or (III), each $R^{1a}$ and $R^{1b}$ is independently H, OH, or $C_1$-$C_6$alkyl. In some embodiments of a compound of Formula (I), (II), or (III), each $R^{1a}$ and $R^{1b}$ is H.

In some embodiments of a compound of Formula (I), (II), or (III), each $R^1$ is independently H or $C_1$-$C_3$alkyl. In some embodiments of a compound of Formula (I), (II), or (III), each $R^1$ is H. In some embodiments of a compound of Formula (I), (II), or (III), each $R^1$ is independently $C_1$-$C_6$alkyl independently optionally substituted with one, two, or three $R^a$.

In some embodiments of a compound of Formula (I), (II), or (III), each $R^2$ is independently —$NR^5R^6$. In some embodiments of a compound of Formula (I), (II), or (III), each $R^5$ and $R^6$ is independently H or $C_1$-$C_6$alkyl. In some embodiments of a compound of Formula (I), (II), or (III), each $R^2$ is independently —$NH_2$ or —$NHCH_3$.

In some embodiments of a compound of Formula (I), (II), or (III), each $R^3$ is independently H or $C_1$-$C_3$alkyl. In some embodiments of a compound of Formula (I), (II), or (III), each $R^3$ is independently H or $CH_3$. In some embodiments of a compound of Formula (I), (II), or (III), each $R^3$ is independently H or $C_2$-$C_3$alkyl. In some embodiments of a compound of Formula (I), (II), or (III), $R^3$ is $CH_2CH_3$. In some embodiments of a compound of Formula (I), (II), or (III), each $R^3$ is H. In some embodiments of a compound of Formula (I), (II), or (III), each $R^3$ is independently $C_1$-$C_6$alkyl. In some embodiments of a compound of Formula (I), (II), or (III), each $R^3$ is independently $C_3$-$C_6$cycloalkyl.

In some embodiments of a compound of Formula (I), (II), or (III), each $R^4$ is independently H or $C_1$-$C_3$alkyl. In some embodiments of a compound of Formula (I), (II), or (III), each $R^4$ is independently H or $CH_3$. In some embodiments of a compound of Formula (I), (II), or (III), each $R^4$ is independently H or $C_2$-$C_3$alkyl. In some embodiments of a compound of Formula (I), (II), or (III), $R^4$ is $CH_2CH_3$. In some embodiments of a compound of Formula (I), (II), or (III), each $R^4$ is $CH_3$. In some embodiments of a compound of Formula (I), (II), or (III), each $R^4$ is H. In some embodiments of a compound of Formula (I), (II), or (III), each $R^4$ is independently $C_1$-$C_6$alkyl independently optionally substituted with one, two, or three $R^a$. In some embodiments of a compound of Formula (I), (II), or (III), each $R^4$ is independently $C_3$-$C_6$cycloalkyl independently optionally substituted with one, two, or three $R^a$. In some embodiments of a compound of Formula (I), (II), or (III), each $R^3$ is independently $C_1$-$C_3$alkyl and each $R^4$ is independently $C_1$-$C_3$alkyl. In some embodiments of a compound of Formula (I), (II), or (III), each $R^3$ is $CH_3$ and each $R^4$ is $CH_3$.

In some embodiments of a compound of Formula (I), (II), or (III), each

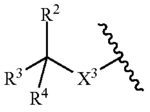

is independently

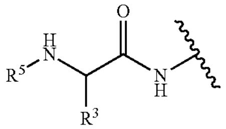

or

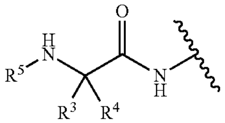

In some embodiments of a compound of Formula (I), (II), or (III), each

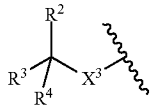

is independently

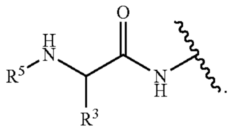

In some embodiments of a compound of Formula (I), (II), or (III), each

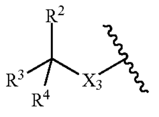

is

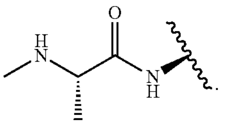

In some embodiments of a compound of Formula (I), (II), or (III), each

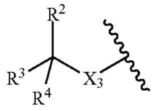

is

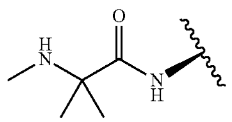

In some embodiments of a compound of Formula (I), (II), or (III), each

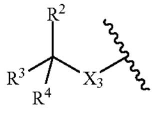

is

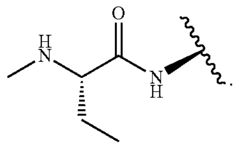

In some embodiments of a compound of Formula (I), (II), or (III), $A^1$ and $A^2$ are independently $C_1$-$C_6$ alkylene independently optionally substituted with one, two, or three $R^c$. In some embodiments of a compound of Formula (I), (II), or (III), $A^1$ and $A^2$ are independently $C_3$-$C_{10}$ cycloalkylene independently optionally substituted with one, two, or three $R^c$. In some embodiments of a compound of Formula (I), (II), or (III), $A^1$ and $A^2$ are independently $C_5$-$C_{10}$ arylene independently optionally substituted with one, two, or three $R^c$. In some embodiments of a compound of Formula (I), (II), or (III), $A^1$ and $A^2$ are independently 4-10 membered heterocycloalkylene independently optionally substituted with one, two, or three $R^c$. In some embodiments of a compound of Formula (I), (II), or (III), $A^1$ and $A^2$ are independently 4-10 membered heteroarylene independently optionally substituted with one, two, or three $R^c$. In some embodiments of a compound of Formula (I), (II), or (III), $A^1$ and $A^2$ are independently $C_1$-$C_6$ alkylene or $C_3$-$C_{10}$ cycloalkylene, wherein each alkylene and cycloalkylene is independently optionally substituted with one, two, or three $R^c$.

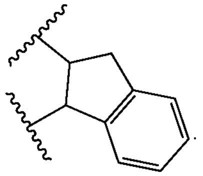 [SMILES: *C1Cc2ccccc2C1*]

In some embodiments of a compound of Formula (I), (II), or (III), $A^1$ and $A^2$ are

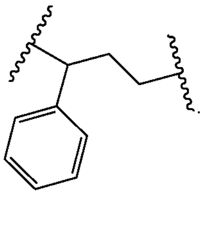 [SMILES: *CCC(*)c1ccccc1]

In some embodiments of a compound of Formula (I), (II), or (III), $A^1$ and $A^2$ are

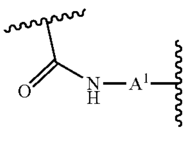

In some embodiments of a compound of Formula (I), (II), or (III), is

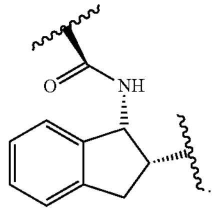

In some embodiments of a compound of Formula (I), (II), or (III), each $X^5$ is O. In some embodiments of a compound of Formula (I), (II), or (III), each $X^5$ is S. In some embodiments of a compound of Formula (I), (II), or (III), each $X^5$ is absent.

In some embodiments of a compound of Formula (I), (II), or (III), each $n^1$ and $n^2$ is independently 1-3. In some embodiments of a compound of Formula (I), (II), or (III), each $n^1$ and $n^2$ is independently 0-3. In some embodiments of a compound of Formula (I), (II), or (III), each $n^1$ and $n^2$ is independently 0-2. In some embodiments of a compound of Formula (I), (II), or (III), each $n^1$ and $n^2$ is independently 1-2. In some embodiments of a compound of Formula (I), (II), or (III), each $n^1$ and $n^2$ is 1. In some embodiments of a compound of Formula (I), (II), or (III), each $n^1$ and $n^2$ is 2. In some embodiments of a compound of Formula (I), (II), or (III), each $n^1$ and $n^2$ is 0.

In some embodiments of a compound of Formula (I), (II), or (III), $Q^1$ is —$C_1$-$C_6$alkylene-, —$C_2$-$C_6$alkynylene-, —$C_2$-$C_6$alkynylene-$C_6$-$C_{10}$ arylene-, —$C_2$-$C_6$alkynylene-$C_6$-$C_{10}$arylene-$C_2$-$C_6$alkynylene-, or —$C_6$-$C_{10}$arylene-$C_6$-$C_{10}$arylene-; wherein each alkylene, $C_2$-$C_6$alkynylene, and $C_6$-$C_{10}$arylene is independently optionally substituted with one, two, or three $R^d$. In some embodiments of a compound of Formula (I), (II), or (III), $Q^1$ is —$C_2$-$C_6$alkynylene- optionally substituted with one, two, or three $R^d$.

In some embodiments of a compound of Formula (I), (II), or (III), $Q^1$ is —$C_1$-$C_6$ alkylene. In some embodiments, $Q^1$ is —$C_2$-$C_6$alkenylene. In some embodiments of a compound of Formula (I), (II), or (III), $Q^1$ is —$C_2$-$C_6$ alkynylene. In some embodiments, $Q^1$ is —C(O)NH—$C_1$-$C_6$ alkylene-NHC(O)—. In some embodiments of a compound of Formula (I), (II), or (III), $Q^1$ is —$SO_2$—. In some embodiments of a compound of Formula (I), (II), or (III), $Q^1$ is —$C_2$-$C_6$ alkynyl-$C_6$-$C_{10}$arylene-. In some embodiments of a compound of Formula (I), (II), or (III), $Q^1$ is —$C_2$-$C_6$ alkynylene-$C_6$-$C_{10}$arylene-$C_2$-$C_6$ alkynylene. In some embodiments of a compound of Formula (I), (II), or (III), $Q^1$ is —$C_6$-$C_{10}$arylene-$C_6$-$C_{10}$arylene In some embodiments of a compound of Formula (I), (II), or (III), $Q^1$ is —$C_4$ alkylene-,

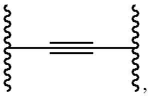,
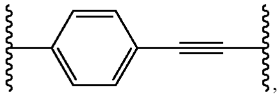,
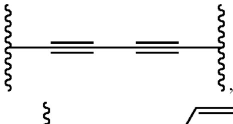,
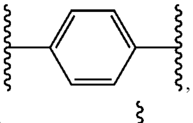,
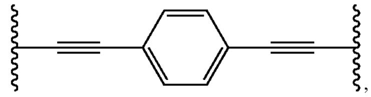,
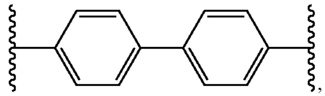,

-continued

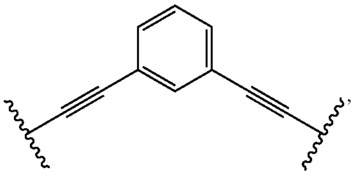

—C(O)NH—$(CH_2)_{1-3}$—NHC(O)—, or —$SO_2$—. In some embodiments of a compound of Formula (I), (II), or (III), $Q^1$ is

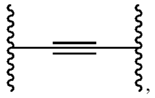
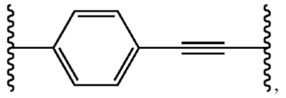
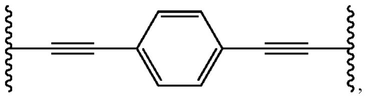
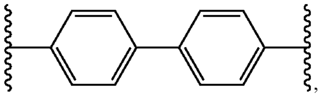
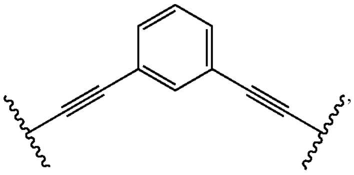

—C(O)NH—$(CH_2)_{1-3}$—NHC(O)—, or —$SO_2$—. In some embodiments of a compound of Formula (I), (II), or (III), $Q^1$ is

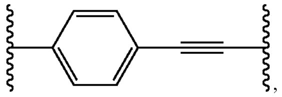
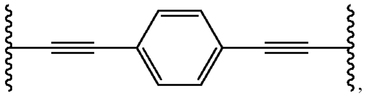
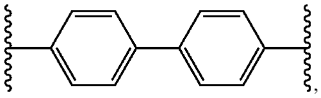
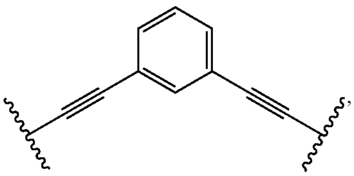

—C(O)NH—$(CH_2)_{1-3}$—NHC(O)—, or —$SO_2$—. In some embodiments of a compound of Formula (I), (II), or (III), $Q^1$ is —$C_4$ alkylene-. In some embodiments of a compound of Formula (I), (II), or (III), $Q^1$ is

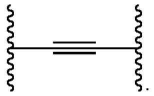

In some embodiments of a compound of Formula (I), (II), or (III), $Q^1$ is

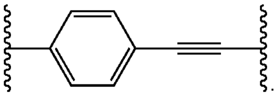 [SMILES: *C#Cc1ccc(*)cc1]

In some embodiments of a compound of Formula (I), (II), or (III), $Q^1$ is

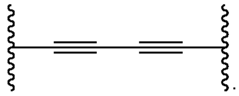

In some embodiments of a compound of Formula (I), (II), or (III), $Q^1$ is

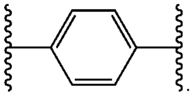 [SMILES: *c1ccc(*)cc1]

In some embodiments of a compound of Formula (I), (II), or (III), $Q^1$ is

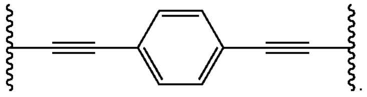 [SMILES: *C#Cc1ccc(C#C*)cc1]

In some embodiments of a compound of Formula (I), (II), or (III), $Q^1$ is

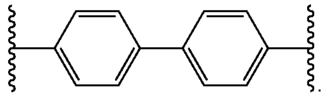 [SMILES: *c1ccc(-c2ccc(*)cc2)cc1]

In some embodiments of a compound of Formula (I), (II), or (III), $Q^1$ is

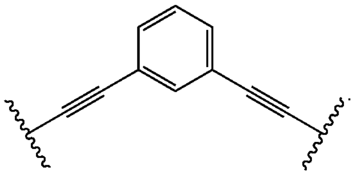 [SMILES: *C#Cc1cccc(C#C*)c1]

In some embodiments of a compound of Formula (I), (II), or (III), $Q^1$ is —C(O)NH—$(CH_2)_{1-3}$—NHC(O)—. In some embodiments of a compound of Formula (I), (II), or (III), $Q^1$ is —C(O)NH—$(CH_2)_2$—NHC(O)—. In some embodiments of a compound of Formula (I), (II), or (III), $Q^1$ is —$SO_2$—.

In some embodiments of a compound of Formula (I), (II), or (III), $Q^1$ is

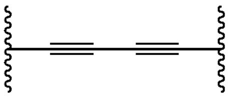 [SMILES: *C#CC#C*]

and $X^1$ is —O—. In some embodiments of a compound of Formula (I), (II), or (III),

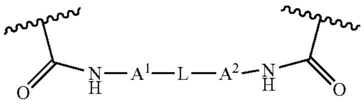

is

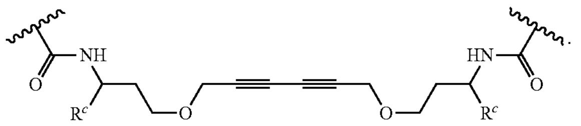

In some embodiments of a compound of Formula (I), (II), or (III), each $R^c$ is independently $C_6$aryl. In some embodiments of a compound of Formula (I), (II), or (III),

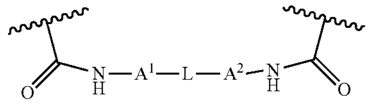

is

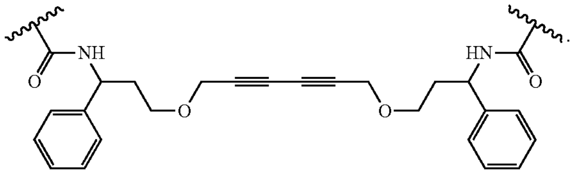

In some embodiments of a compound of Formula (I), (II), or (III), each W, $R^b$, W, and $R^d$ is independently halogen, OH, $NH_2$, CN, $C_1$-$C_6$alkoxy, $C_1$-$C_6$alkyl, $C_1$-$C_6$haloalkyl, $C_1$-$C_6$heteroalkyl, $C_3$-$C_6$cycloalkyl, or $C_2$-$C_5$heterocycloalkyl. In some embodiments of a compound of Formula (I), (II), or (III), each $R^a$, $R^b$, $R^c$, and $R^d$ is independently halogen, OH, $NH_2$, CN, $C_1$-$C_6$alkyl, or $C_1$-$C_6$haloalkyl. In some embodiments of a compound of Formula (I), (II), or (III), each W, $R^b$, $R^c$, and $R^d$ is independently halogen, $C_1$-$C_6$alkyl, or $C_1$-$C_6$haloalkyl.

In some embodiments of a compound of Formula (I), (II), or (III), the compound is not:

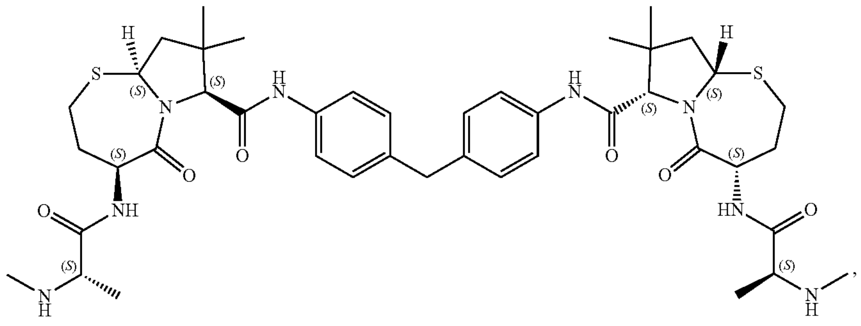

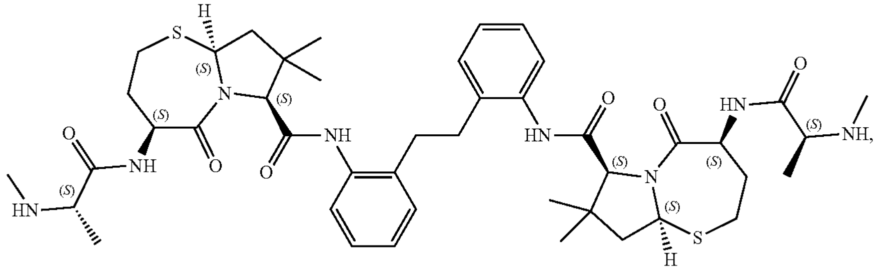

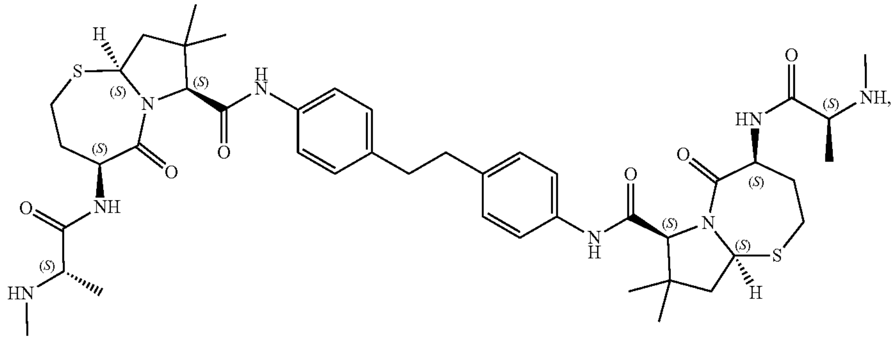

-continued
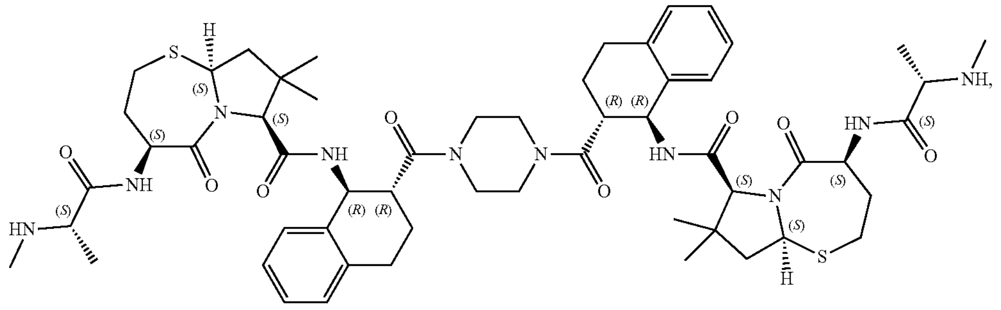
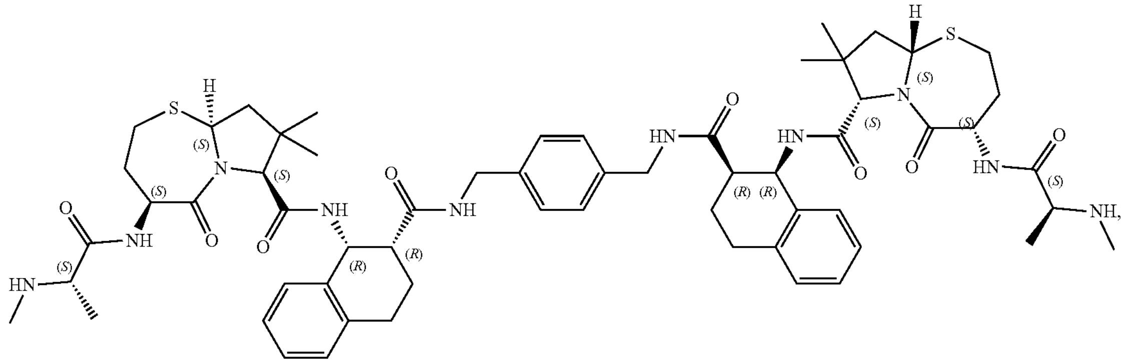
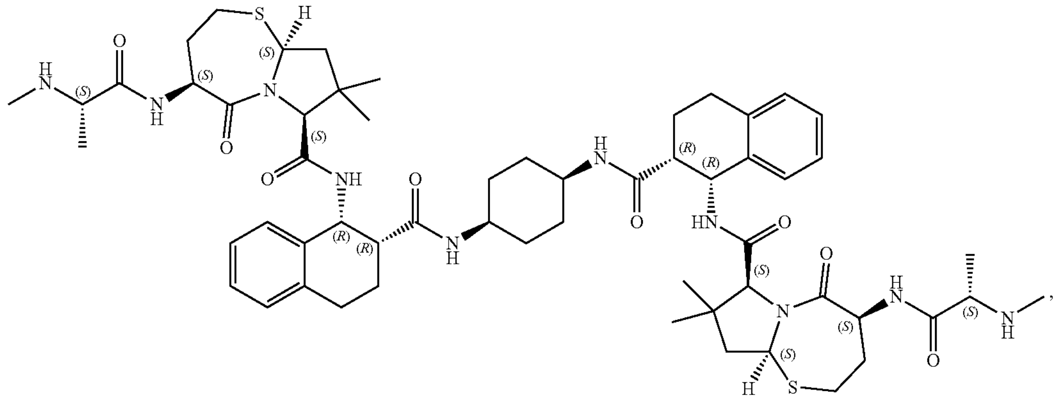
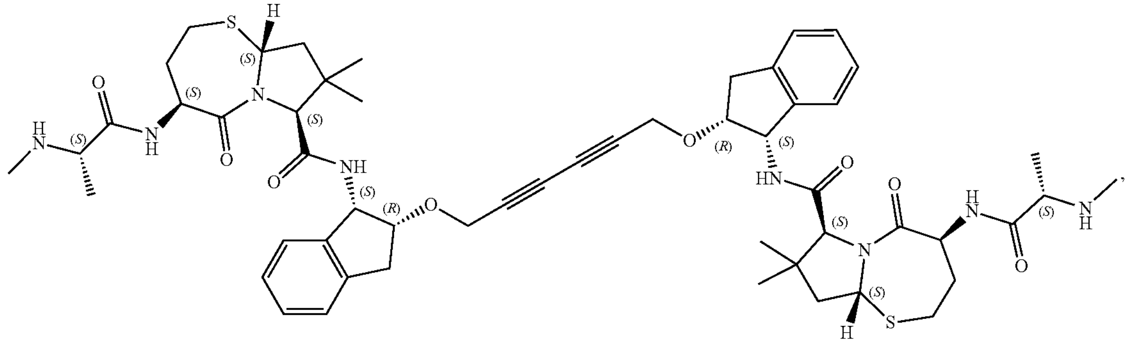

-continued
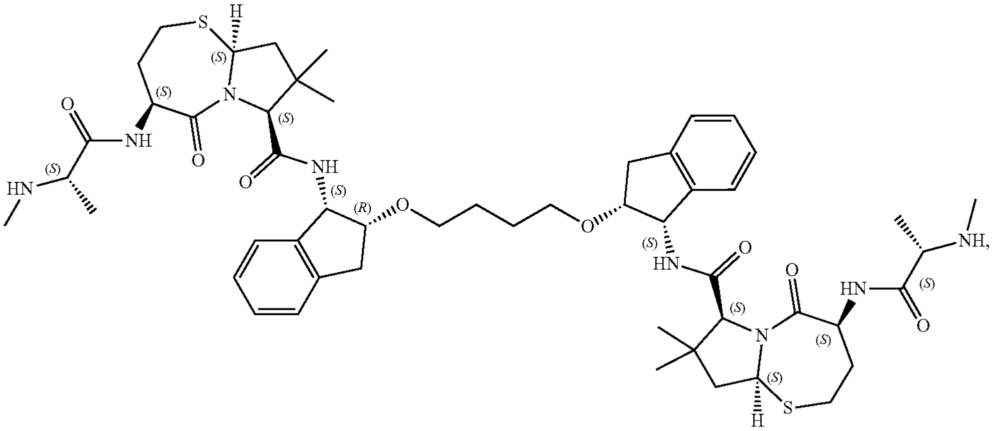
,
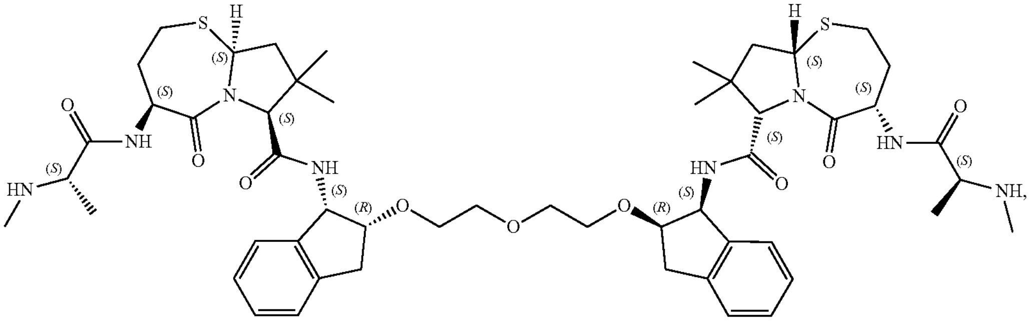
,
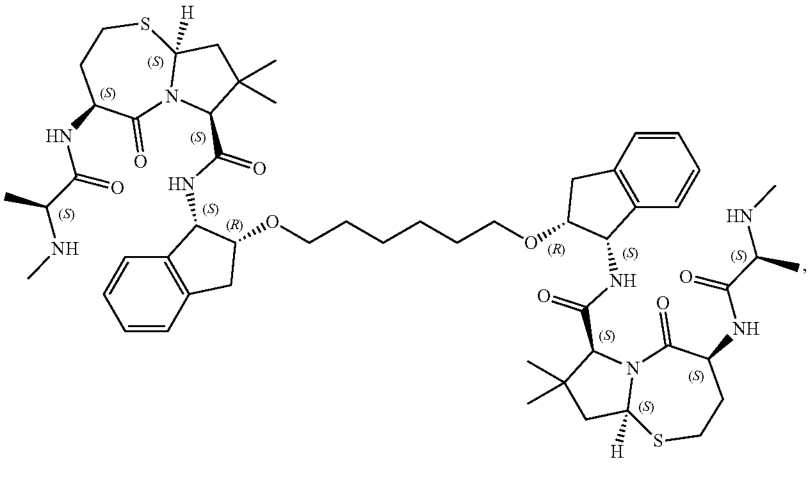
,
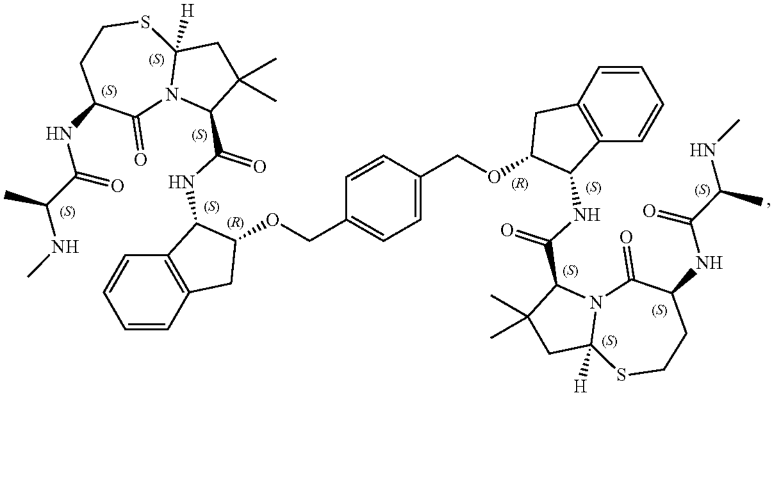
,

-continued
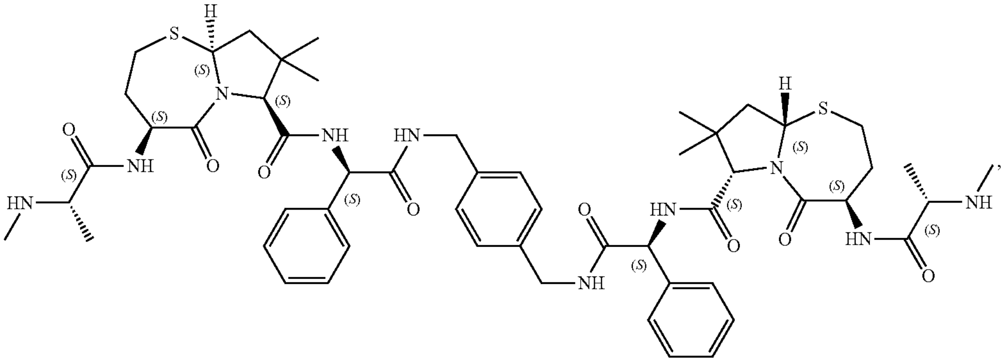
,
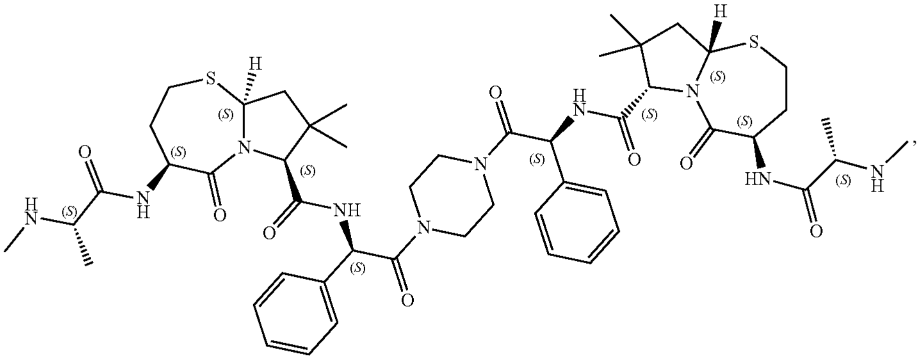
,
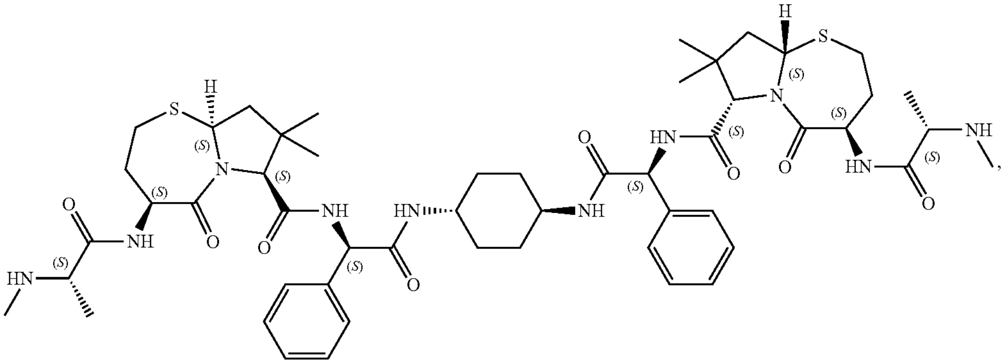
,
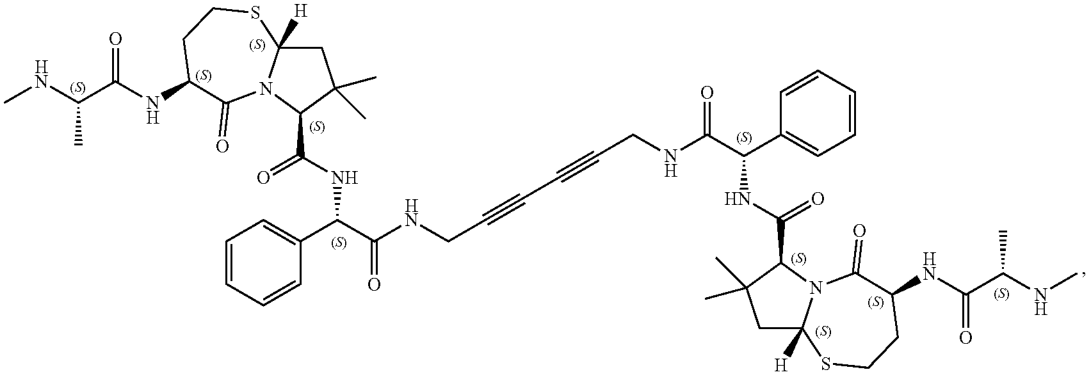
,

-continued
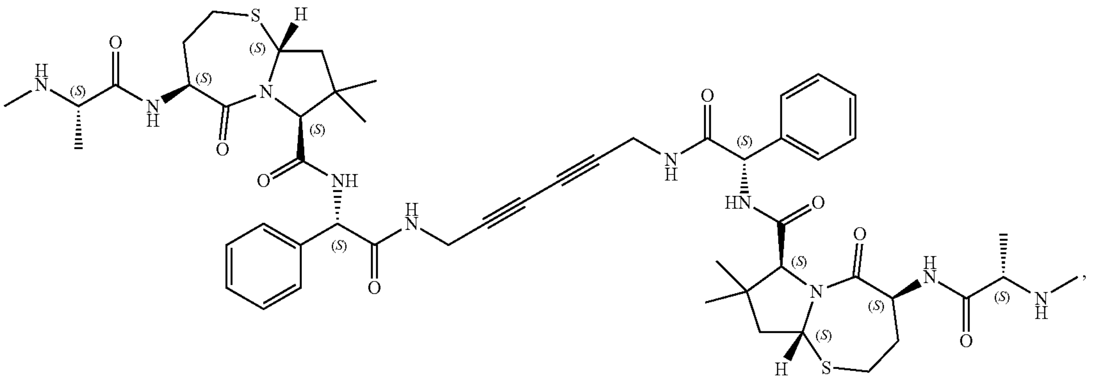
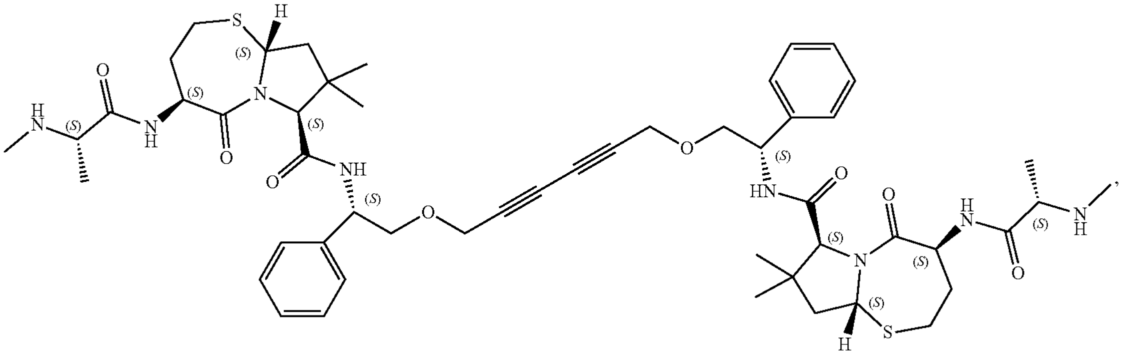
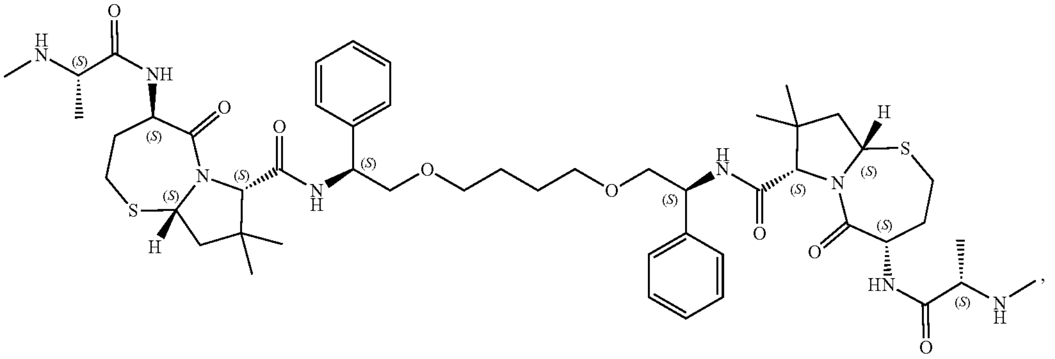
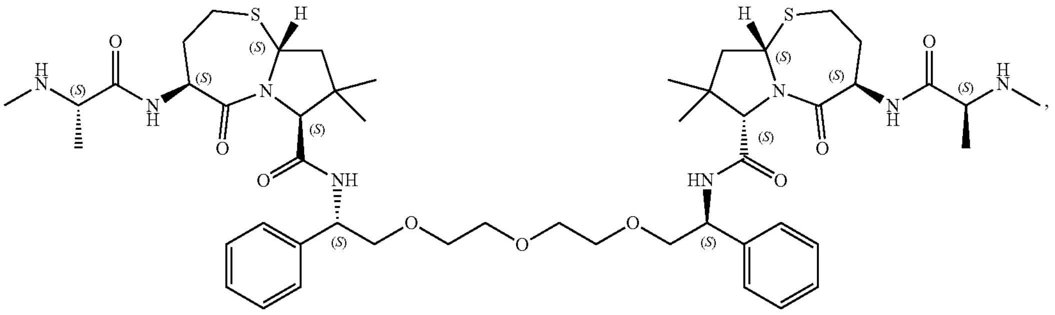

-continued
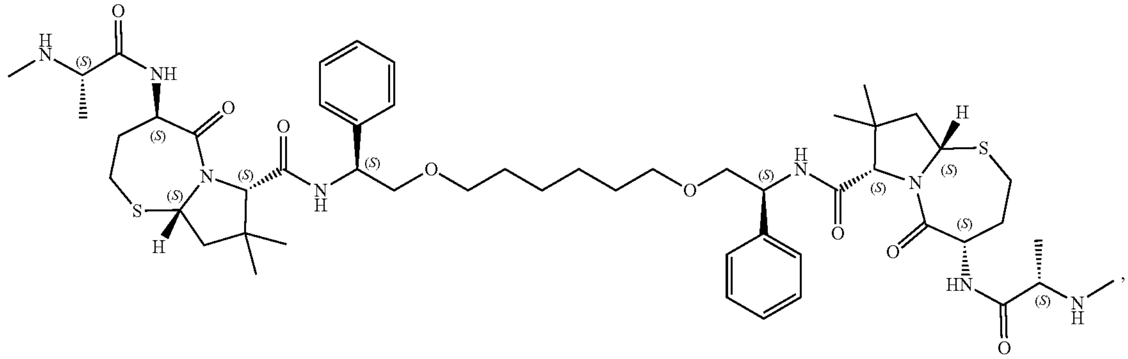
,
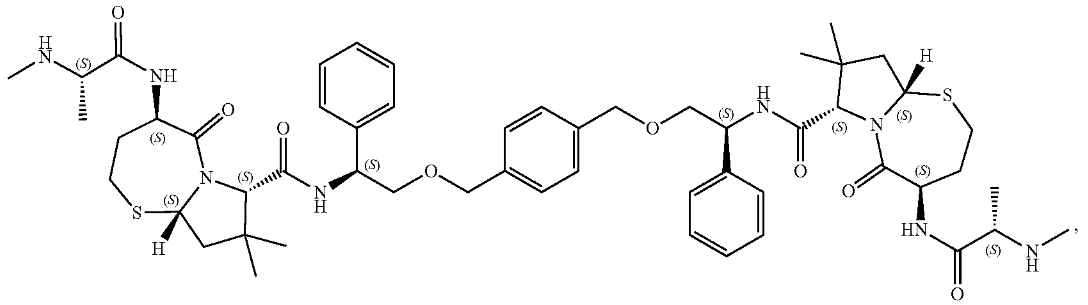
,
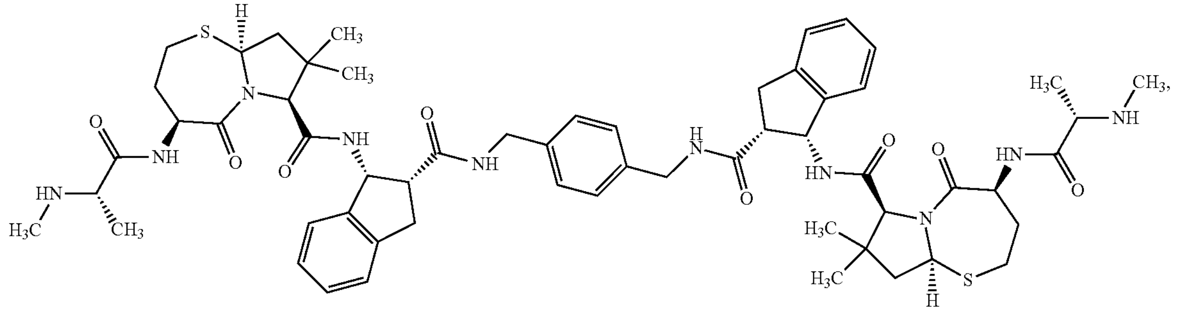
,
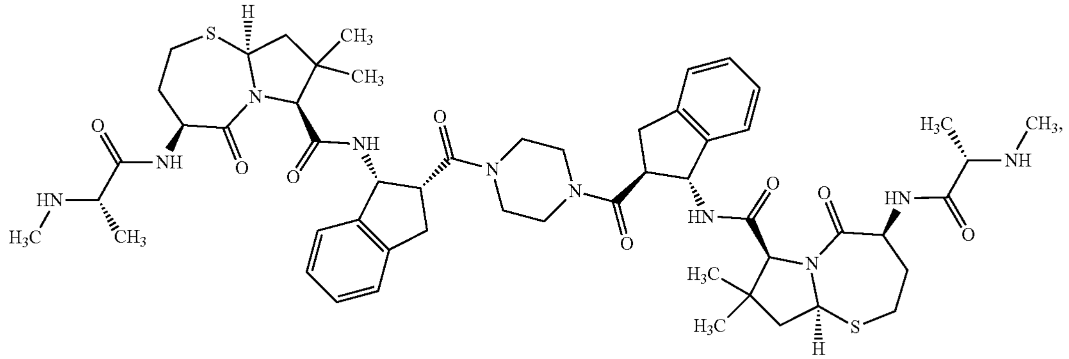
,
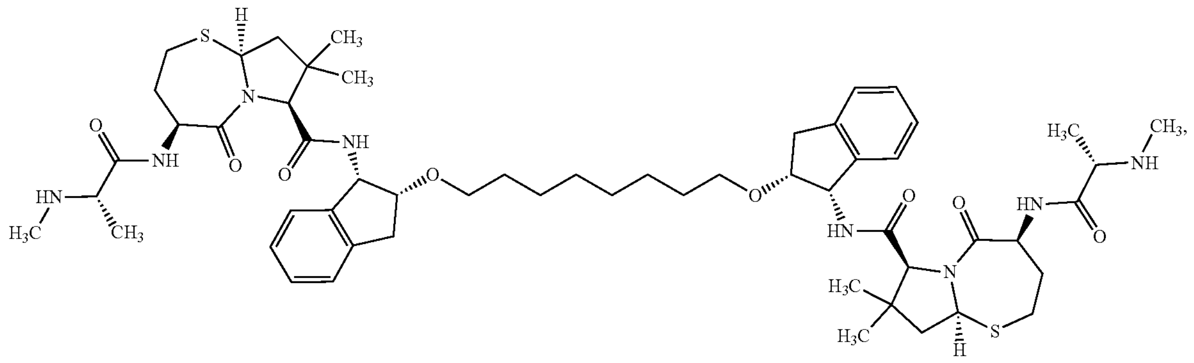
, -continued
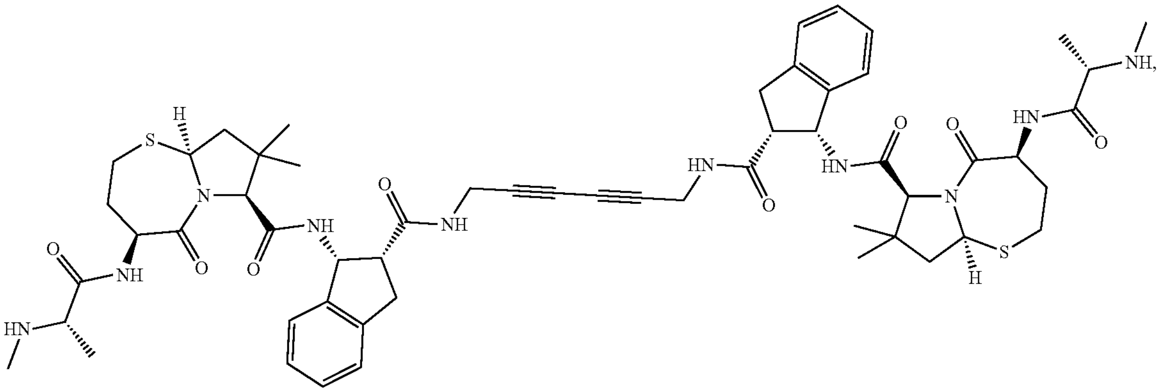
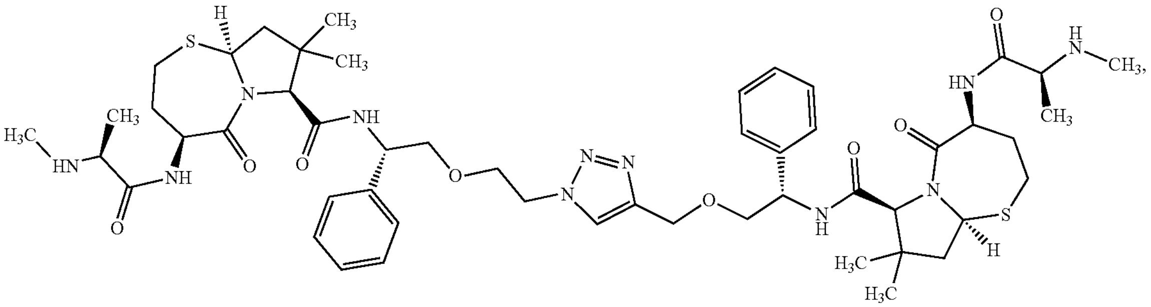
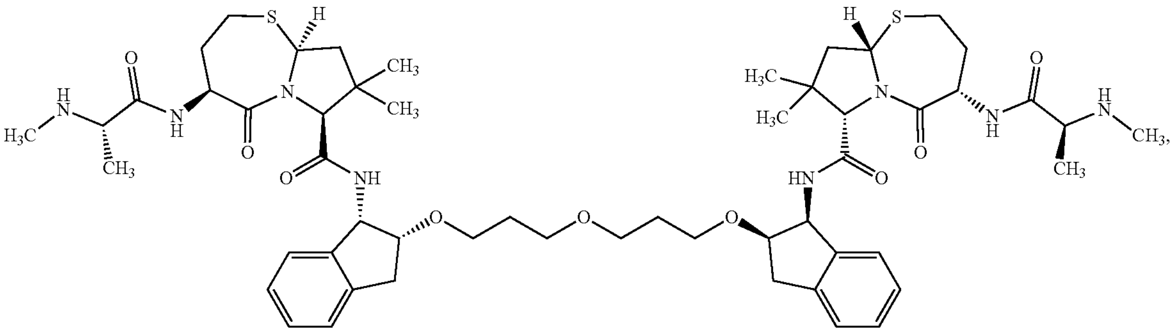
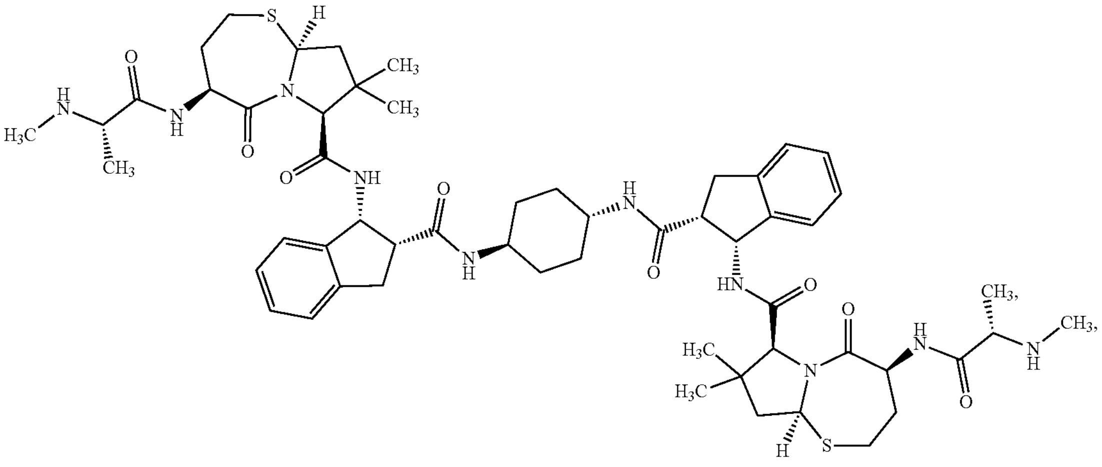

-continued
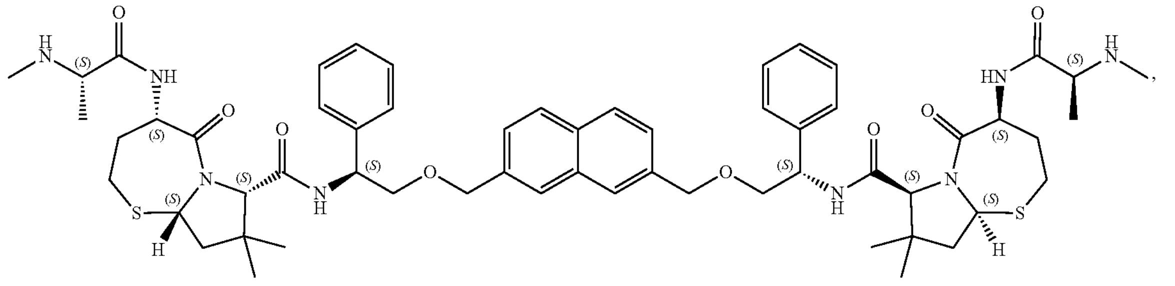
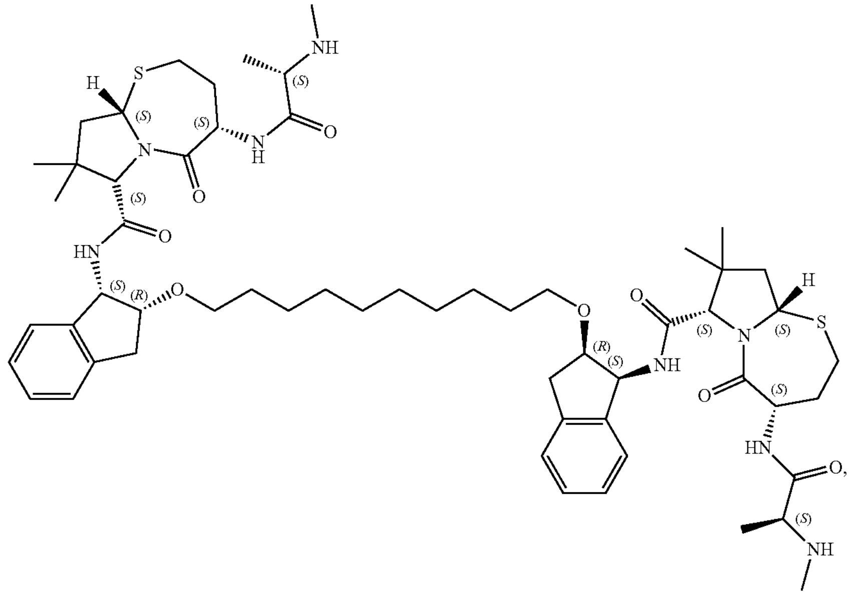
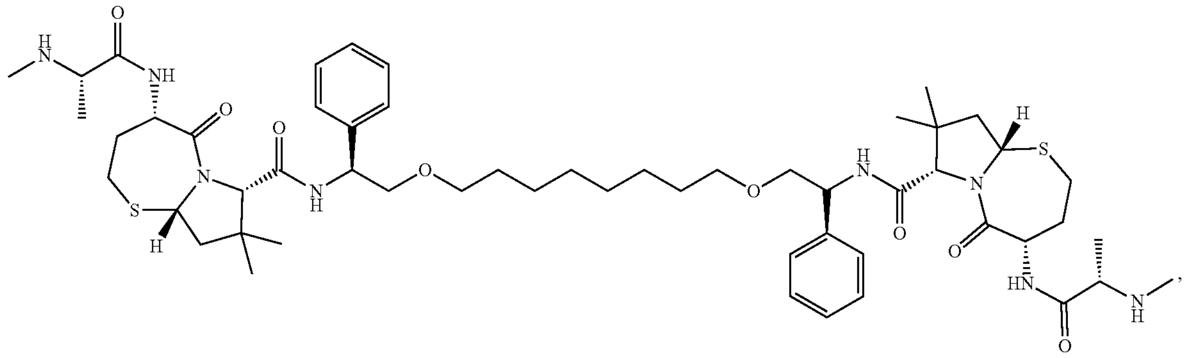
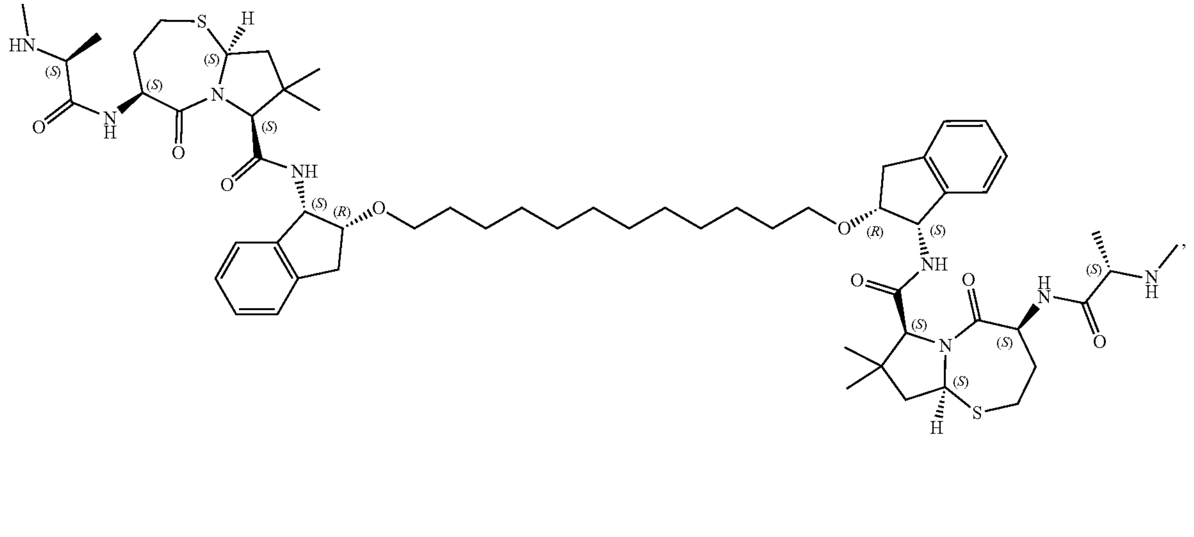

-continued
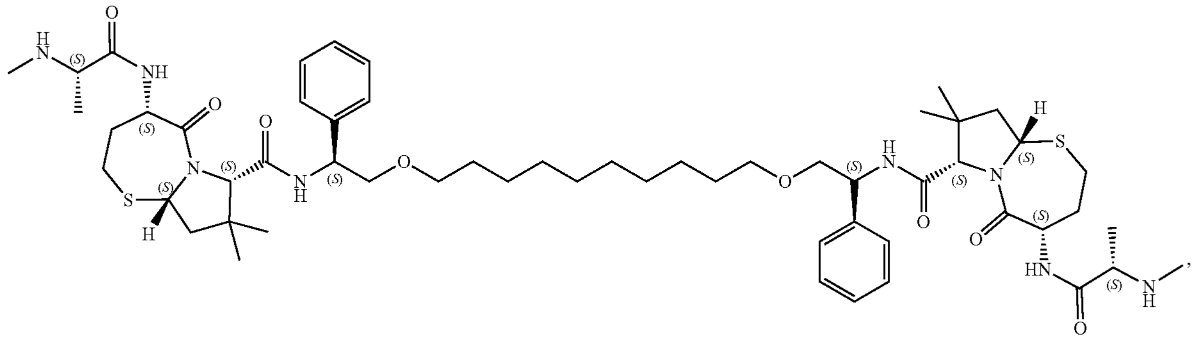
,
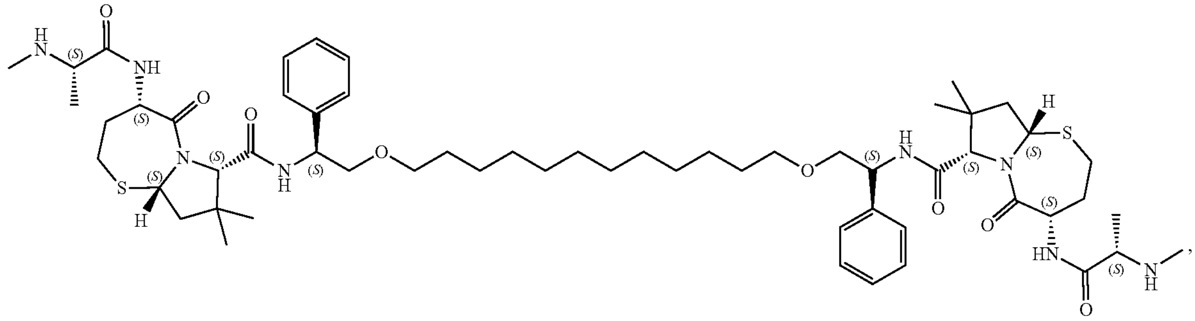
,
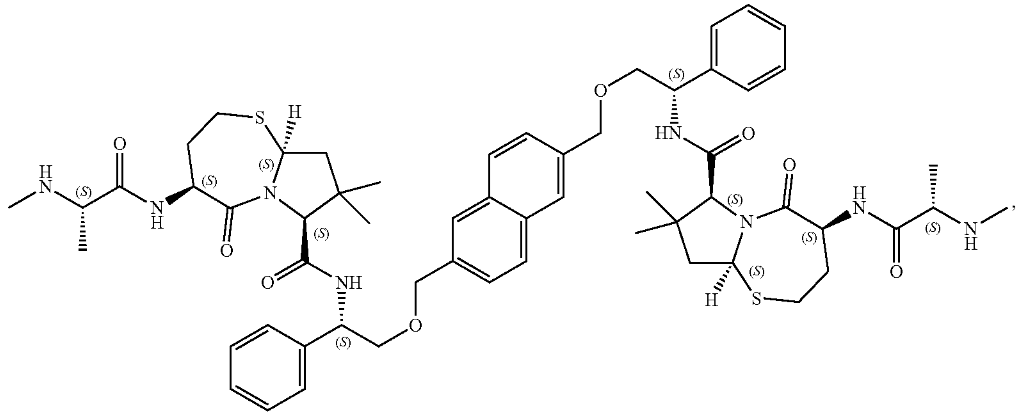
, or
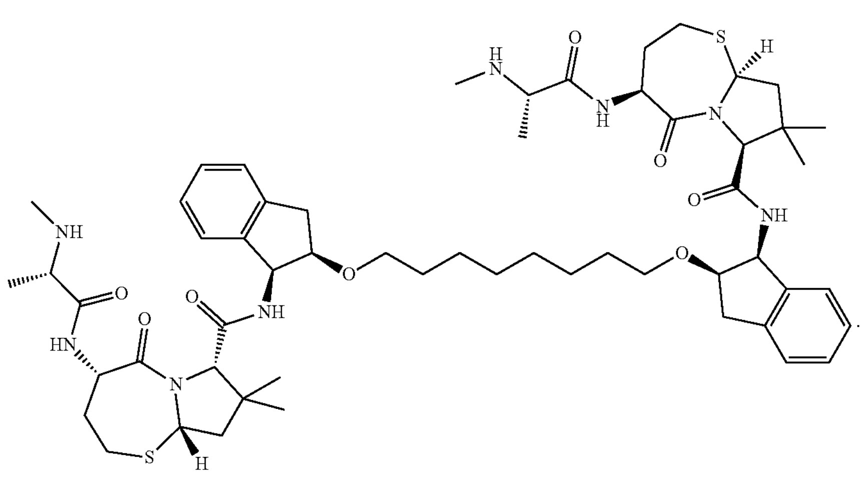
.

In some embodiments of a compound of Formula (I), (II), or (III), the compound is selected from table A.
TABLE A
| # | Structure |
|---|---|
| 18a | 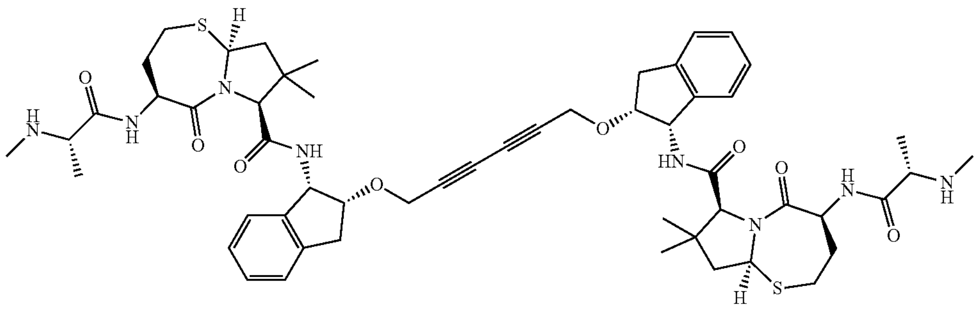 |
| 18b | 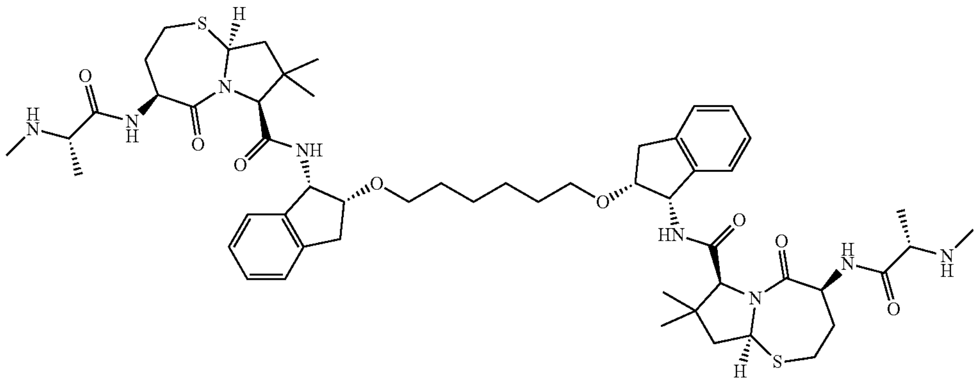 |
| 18c | 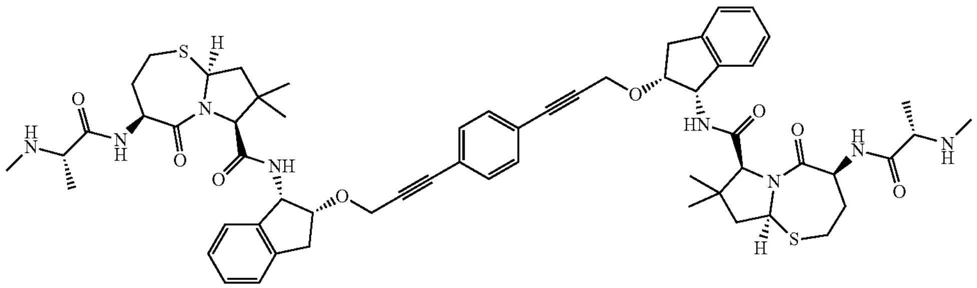 |
| 18d | 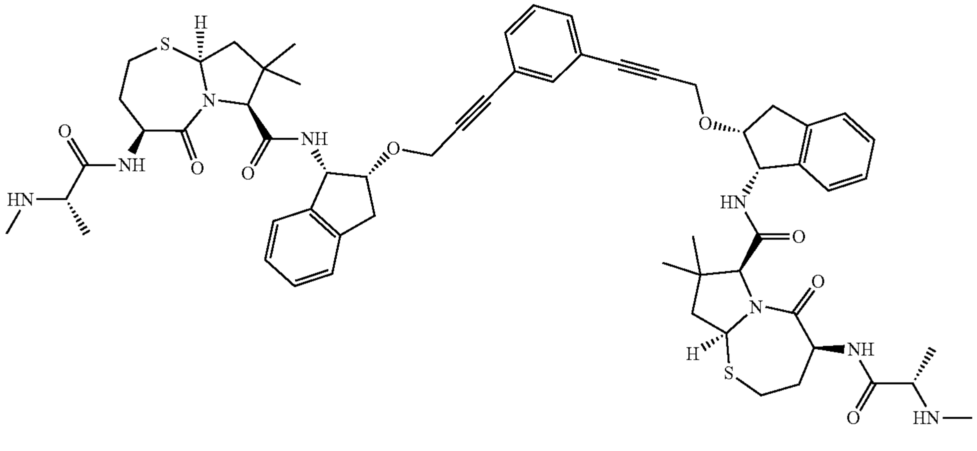 |

TABLE A-continued
| # | Structure |
| --- | --- |
| 18e | 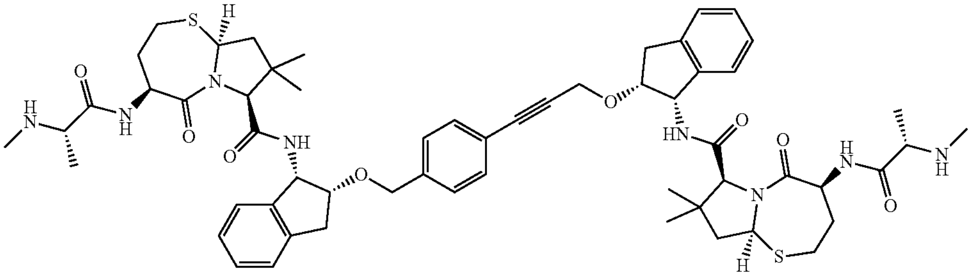 |
| 18f | 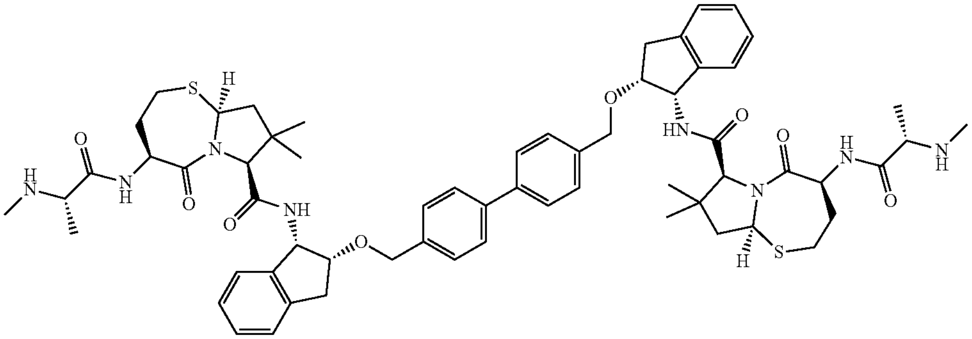 |
| 18g | 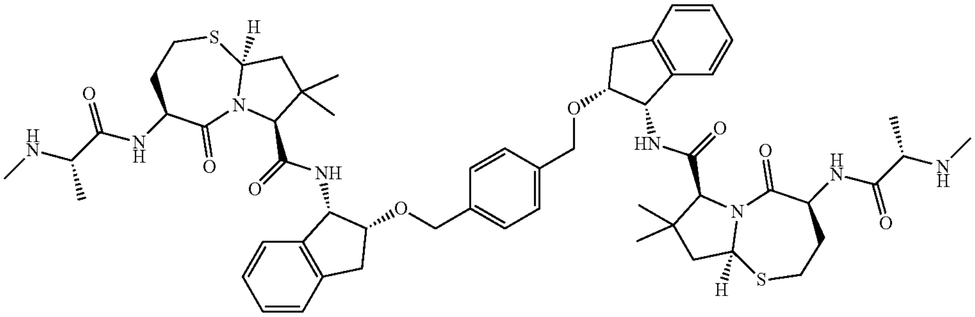 |
| 18h | 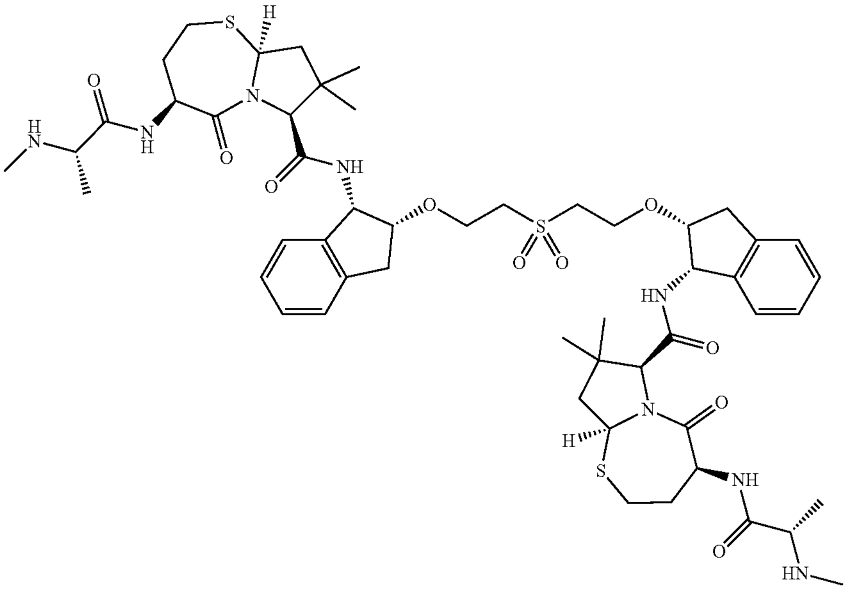 |

TABLE A-continued
| # | Structure |
| --- | --- |
| 18i | 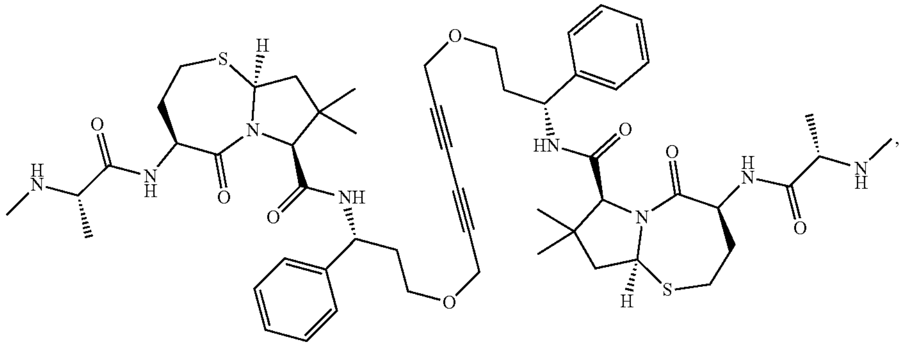 |
| 18j | 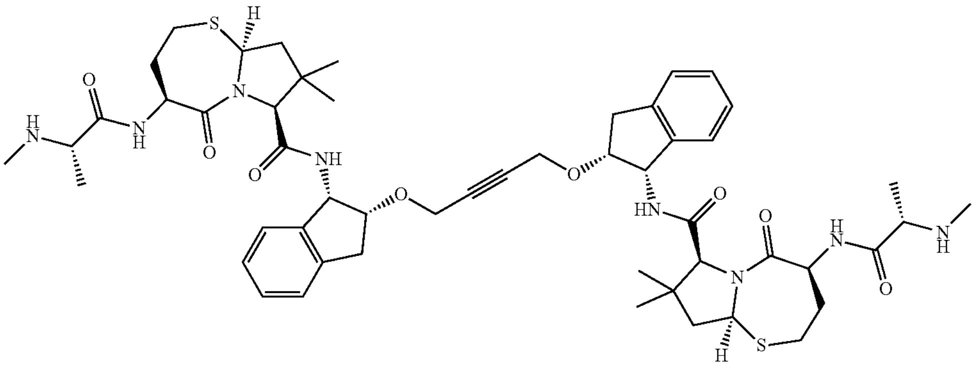 |
| 18k | 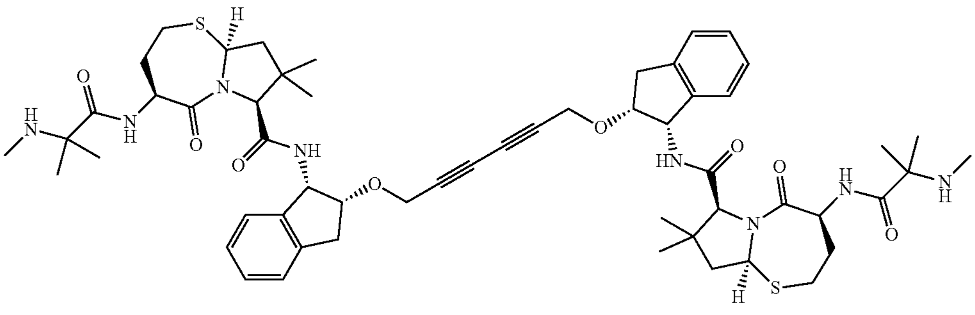 |
| 18l | 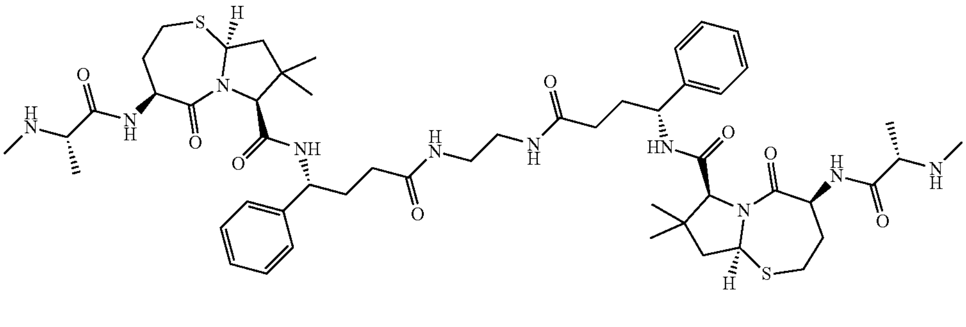 |

TABLE A-continued
| # | Structure |
|---|---|
| 18m | 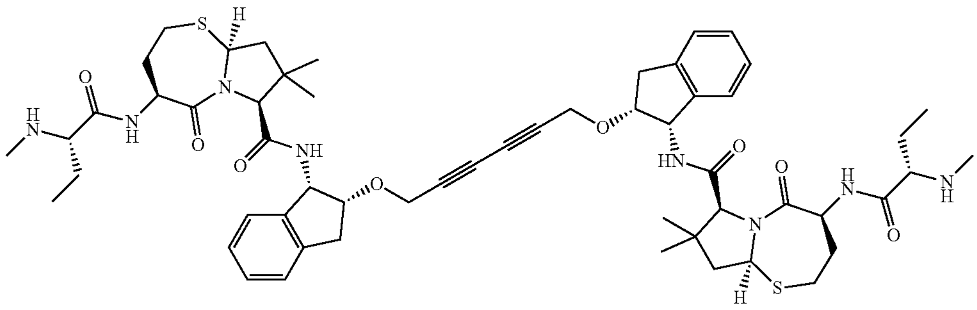 |
| 18n | 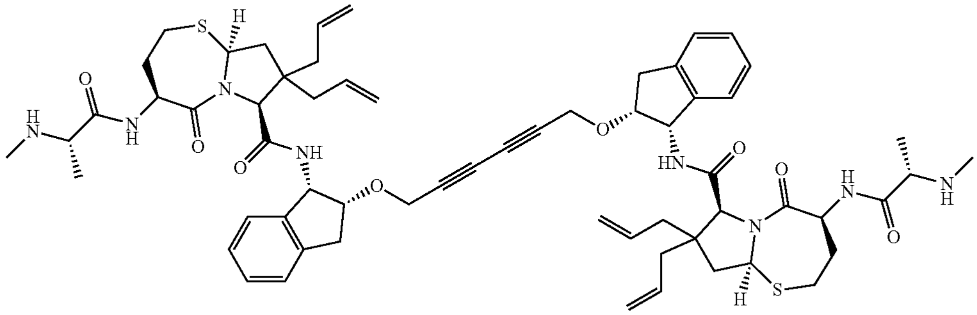 |
| 18o | 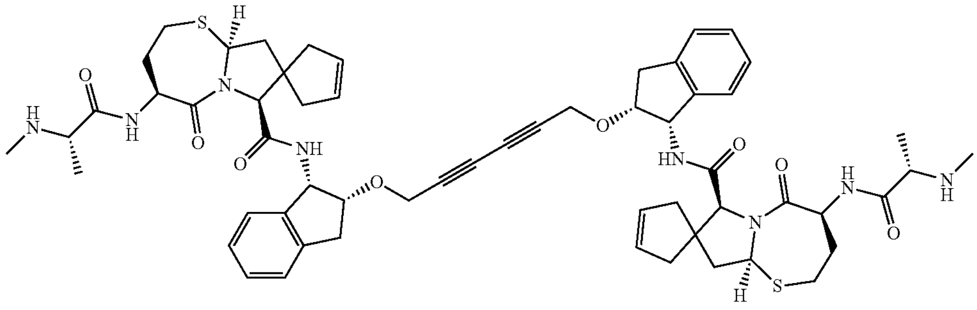 |
| 18p | 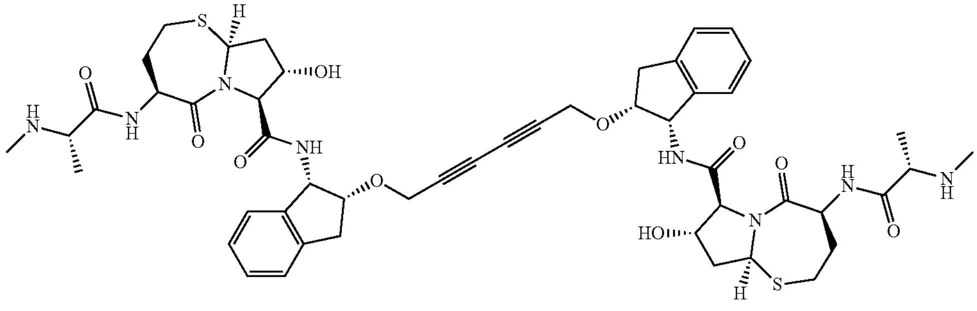 |
| 18q | 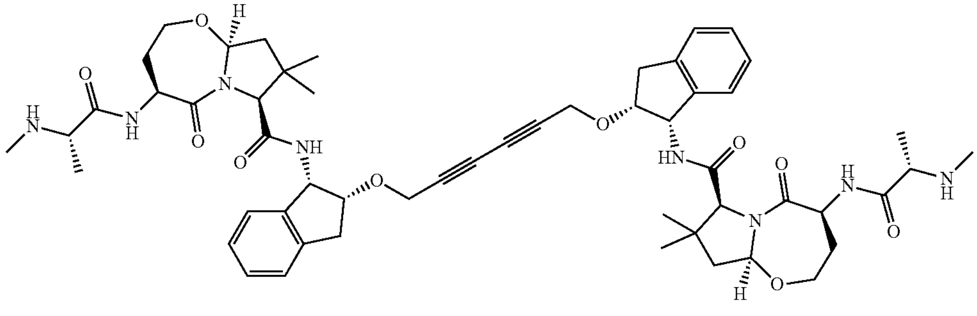 |

TABLE A-continued

| # | Structure |
|---|---|
| 18r | 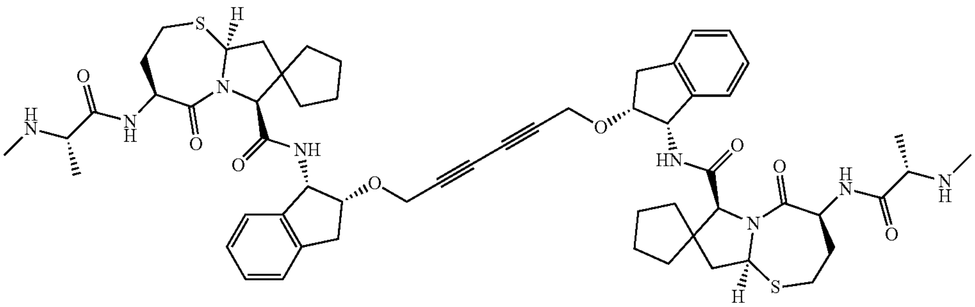 |

Any combination of the groups described above or below for the various variables is contemplated herein. Throughout the specification, groups and substituents thereof are chosen by one skilled in the field to provide stable moieties and compounds.

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., u isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^{+}(C_{1-4}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

Synthesis of Compounds of Formula I

A synthetic route to the bivalent compound of Formula (I) provides access to analogues in a highly stereospecific approach. As shown in Scheme 1, the intermediate VII can be prepared and then transformed in three steps to intermediate X (Scheme 2). Finally, the preparation of an exemplary compound of Formula (I) is completed using the chemistry shown in Scheme 3.

Scheme 1
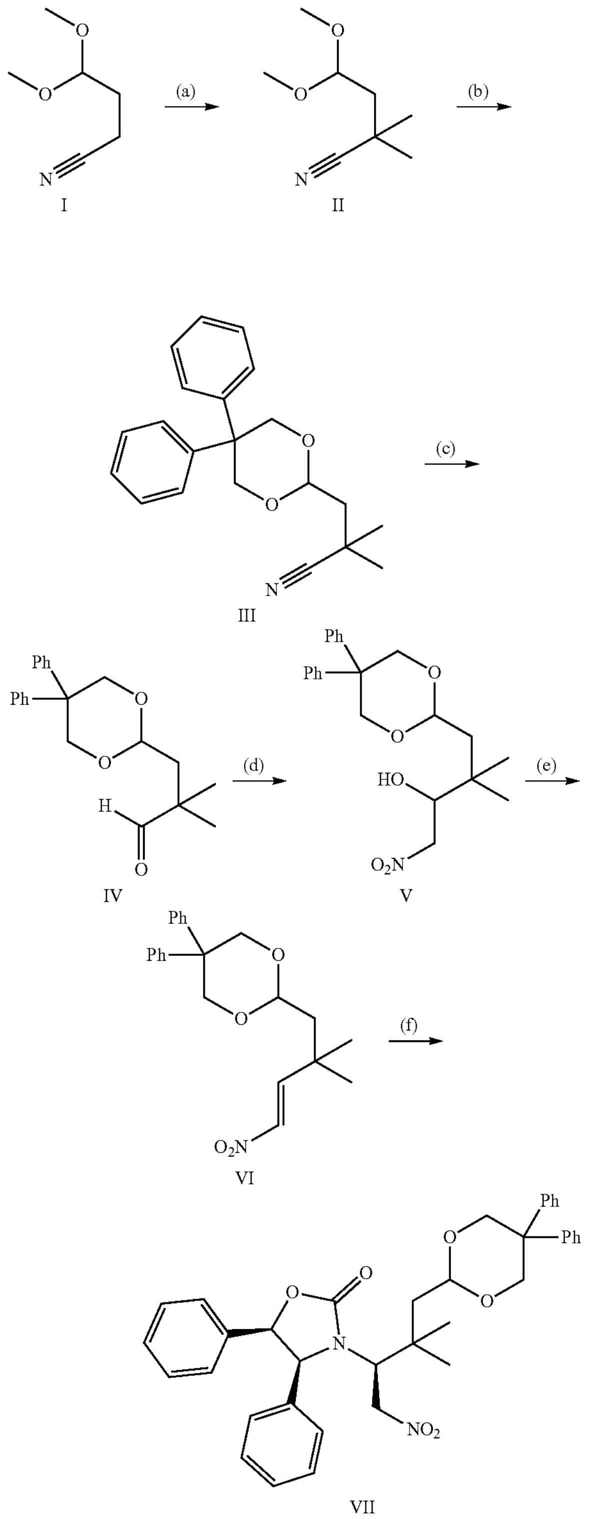
(a) LDA, MeI, THF, (90%)
(b) 2.2-diphenylpropane-1,3-diol, $CH_2Cl$, (76%)
(c) DABAL—H (60%)
(d) $CH_3NO_2$, $NEt_3$ (95%).
(e) MsCl, $NEt_3$, $CH_2Cl_2$, (75%)
(f) oxazolidin-2-one 24, t-BuOK, 18-crown-6 (70%).
Scheme 2
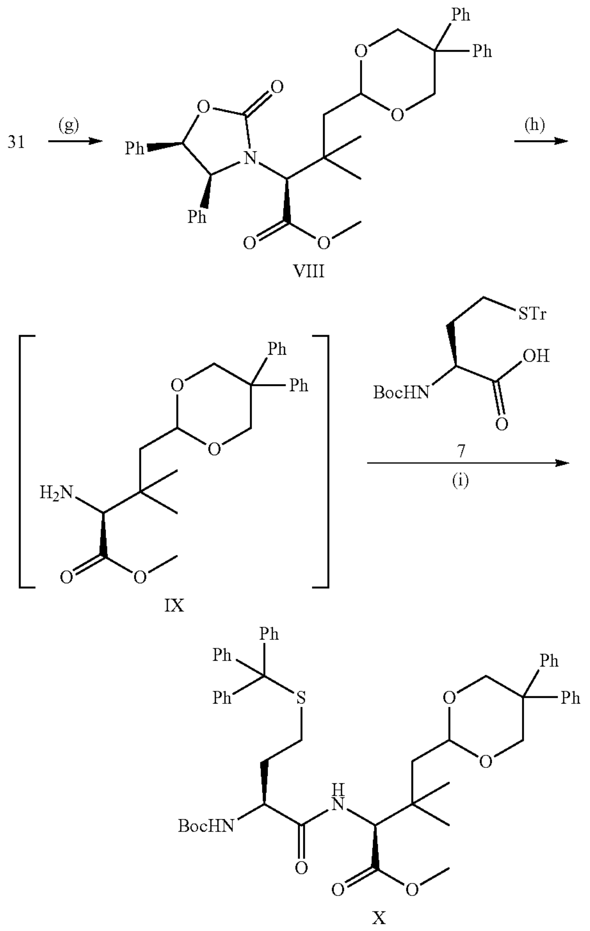
(g) 1. $NaNO_2$, $CH_3COOH$, DMSO 2. $K_2CO_3$, $CH_3I$, DMF (89% over 2 steps)
(h) Pd/C, MeOH.
(i) HOBt, NMM, EDC•HCl, THF (71% over 2 steps).

Scheme 3

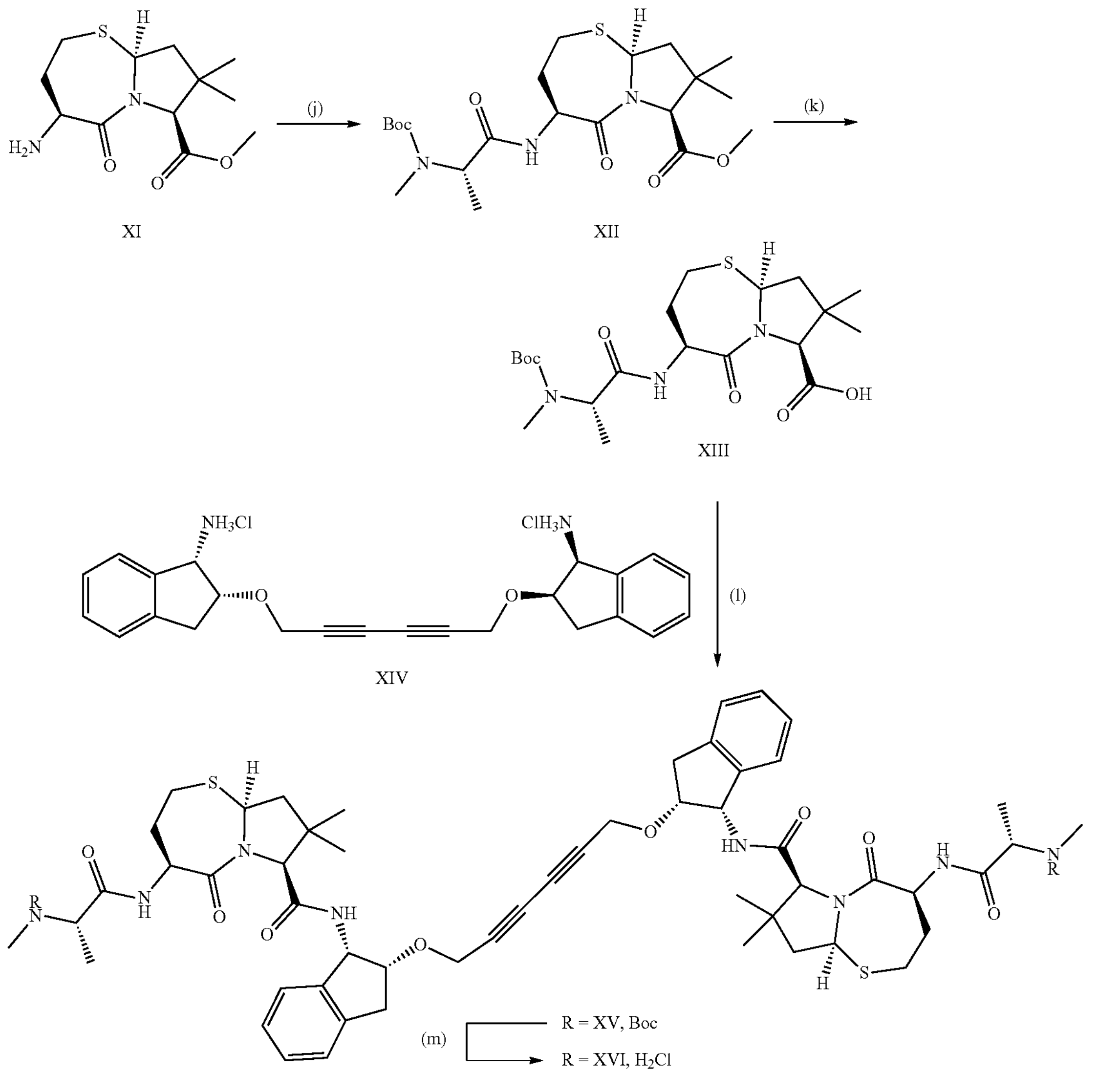

XI XII XIII XIV (j) 1. HCl in dioxane. 2. N-Boc-N-methyl-L-alanine, HOBt, NMM, EDC•HCl, DMF (77%)
(k) LiOH, $H_2O$, THF (69%)
(l) COMU ®, DIPEA, THF (69%) (m) HCl in dioxane (88%)

It will be understood that the reactions shown in Schemes 1-3 above are illustrative and are also applicable to synthesis of compounds of Formula II and III, and such disclosure is contemplated within the scope of embodiments described herein. Synthesis of compounds of Formula I, II, and III are also shown in further detail in the Chemistry Examples section.

Administration and Pharmaceutical Composition

In general, the compounds of this invention will be administered in a therapeutically effective amount by any of the accepted modes of administration for agents that serve similar utilities. Therapeutically effective amounts of compound of Formula I, II, or III may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound being utilized, the route and form of administration, and other factors.

In general, compounds of this invention will be administered as pharmaceutical compositions by any one of the following routes: oral, systemic (e.g., intranasal, suppository, intrapulmonary), or parenteral (e.g., intramuscular, intravenous, intrathecal, or intraperitoneal) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, liposomes, exosomes, nanoparticles, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I, II, or III in combination with at least one pharmaceutically acceptable excipient. Acceptable excipients are non-toxic, aid administration, and do not adversely affect the therapeutic benefit of the compound of Formula I, II, or III. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula I, II, or III based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In the case wherein the patient's status does improve, upon the doctor's discretion the administration of a compound described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

Combination Therapy

In some cases, a compound described herein is administered in combination with a second anti-cancer agent. Examples of anti-cancer agents for use in combination with a compound of Formula I, II, or III include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula I, II, or III include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula I, II, or III include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula I, II, or III include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula I, II, or III include but are not limited to *vinca* alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula I, II, or III include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomustine, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula I, II, or III include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible EGFR tyrosine kinase inhibitor compound include without limitation the following marketed drugs and drugs in development: Erbulozole (also known as R-55104), Dolastatin 10 (also known as DLS-10 and NSC-376128), Mivobulin isethionate (also known as $C_1$-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39·HCl), AC-7700 (Ajinomoto, also known as AVE-8062, AVE-8062A, CS-39-L-Ser·HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (*Asta Medica*), D-68836 (*Asta Medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some cases, a compound described herein (e.g., a compound of Formula I, II, or III) is administered in combination with TNF-alpha and/or TNF-related apoptosis-inducing ligand (TRAIL). TRAIL shows homology to other members of the TNF-alpha family of proteins. In some cases, a compound described herein (e.g., a compound of Formula I, II, or III) is administered in combination with a TNF-alpha modulator and/or a TNF-alpha analogue (e.g., lenalidomide, revlimid, CC-5013; CC-4047, ACTIMID. Tthalidomide and the like). In some cases, a compound described herein (e.g., a compound of Formula I, II, or III) is administered in combination with an adjuvant, hormone therapy, immunotherapy or any combination thereof.

In some cases, a compound described herein is administered in combination with antiretroviral therapy (ART). Examples of antiretroviral therapy (ART) for use in combination with a compound of Formula I, II, or III include Combivir, Kaletra, Aluvia, Trizivir, Epzicom, Kivexa, Triomune, Duovir-N, Truvada, Atripla, Complera, Eviplera, Stribild, Triumeq, Evotaz, Prezcobix, Rezolsta, Dutrebis, Genvoya, Odefsey, Descovy, Juluca, Symfi, Symfi Lo, Biktarvy, Cimduo, Symtuza, Delstrigo, and Dovato.

In some cases, a compound described herein is administered in combination with a latency reversal agent (LRA) with or without antiretroviral therapy (ART). Examples of latency reversal agent (LRA) for use in combination with a compound of Formula I, II, or III include histone deacetylase inhibitors (HDACi), bromodomain and extra terminal domain inhibitors (BETi), Protein Kinase C (PKC) agonists, activators of positive transcription elongation factor b (P-TEFb), Toll-like receptor (TLR) agonists, immune checkpoint inhibitors, tetraethylthiuram disulfide (Disulfiram), benzotriazole derivatives, quinolines, cytokines, methyltransferase inhibitors, and methylation inhibitors.

In some cases, a compound described herein is administered in combination with a killer agent, CarT, immunotherapy, neutralizing antibodies, or other agents. Additional latency reversal agents can be found in Stoszko et al., Curr Opin Virol. 2019 Jul. 16; 38:37-53 which is hereby incorporated by reference for such disclosures.

Methods of Use

Disclosed herein, in certain embodiments, are methods of inhibiting the activity of an inhibitor of apoptosis (IAP) protein in an individual in need thereof comprising administering a therapeutically effective amount of a compound disclosed herein to the individual. In some embodiments, the IAP protein is XIAP, cIAP-1, cIAP-2, ML-IAP, survivin, NAIP, apollon, ILP2, or any combinations thereof.

Provided herein are methods of treating a hyperproliferative disorder in an individual in need thereof comprising administration of a therapeutically effective amount of a compound of any one described herein, to the individual in need thereof.

In some of such embodiments, the hyperproliferative disorder is cancer or an autoimmune disease.

In some of such embodiments, the autoimmune disease is hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjogren's syndrome, systemic lupus erythematosus, type 1 diabetes, ulcerative colitis, or vitiligo.

Also provided herein are methods of treating cancer in an individual in need thereof comprising administration of a therapeutically effective amount of a compound of any one of Formula I, II, or III, to the individual in need thereof.

In some embodiments, the cancer is an epithelial cancer, a carcinoma, a neoplasm, a sarcoma, a chondrosarcoma, a blastoma, a cancer of the central nervous system, or a hematological cancer. In some embodiments, the cancer is an epithelial cancer or a carcinoma. In some embodiments, the cancer is a neoplasm or a sarcoma or a chondrosarcoma or a blastoma or a cancer of the central nervous system. In some embodiments, the cancer is a hematological cancer.

Also provided herein are methods of treating a disease associated with angiogenesis in an individual in need thereof comprising administration of a therapeutically effective amount of a compound of any one of Formula described herein to the individual in need thereof.

In some embodiments the disease associated with angiogenesis is macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma or hypertrophic scarring.

Also provided herein are methods of inhibiting the activity of inhibitor of apoptosis (IAP) proteins in an individual in need thereof comprising administration of a therapeutically effective amount of a compound of any one of Formula described herein to the individual in need thereof.

In some embodiments, the IAP protein is XIAP, cIAP-1, cIAP-2, ML-IAP, survivin, NAIP, apollon, or ILP2.

Also provided herein are methods of inducing apoptosis in a cell comprising contacting the cell with a therapeutically effective amount of a compound of any one of Formula described herein. In some of such embodiments the compound of any one of Formula described herein binds a XIAP BIR3 domain, thus antagonizing the action of IAPB.

In some embodiments, inhibiting the activity of an IAP protein induces apoptosis in a plurality of cells. In some embodiments, the cells are cancerous cells. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

In some embodiments, the cancer is a cancer of oral cavity and pharynx. In some embodiments, the cancer is a cancer of tongue, mouth, pharynx, or other oral cavity. In some embodiments, the cancer is a cancer of digestive system. In some embodiments, the cancer is esophagus cancer, stomach cancer, small intestine cancer, colon cancer, rectum cancer, anus cancer, anal canal cancer, anorectum cancer, liver cancer, intrahepatic bile duct cancer, gallbladder cancer, biliary cancer, pancreatic cancer, or cancers of other digestive organs. In some embodiments, the cancer is a cancer of the respiratory system. In some embodiments, the cancer is a larynx cancer, lung cancer, bronchus cancer, or cancers of other respiratory organs. In some embodiments, the cancer is a skin cancer. In some embodiments, the cancer is melanoma of the skin or a cancer of other nonepithelial skin.

In some embodiments, the cancer is a cancer of the genital system selected from uterine corpus, uterine cervix, uterine corpus, ovary, vulva, vagina, other female genital, prostate, testis, penis, and other male genital. In some embodiments, the cancer is a cancer of the urinary system selected from urinary bladder, kidney, renal pelvis, ureter, and other urinary organs. In some embodiments, the cancer is a cancer of the endocrine system selected from thyroid, other endocrine. In some embodiments, the cancer is a hematologic cancers. In some embodiments, the cancer is Hodgkin lymphoma, non-Hodgkin lymphoma, myeloma, acute lymphocytic leukemia, chronic lymphocytic leukemia, acute myeloid leukemia, chronic myeloid leukemia, or other leukemia.

In some embodiments, inhibiting the activity of an IAP protein treats a hyperproliferative disorder. In some embodiments, the hyperproliferative disorder is a cancer or an autoimmune disease. In some embodiments, the autoimmune disease is hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjogren's syndrome, systemic lupus erythematosus, type 1 diabetes, ulcerative colitis, or vitiligo. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

Disclosed herein, in certain embodiments, are methods of treating a cancer in an individual in need thereof comprising administering a therapeutically effective amount of a compound disclosed herein to the individual. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

Disclosed herein, in certain embodiments, are methods of treating a disease associated with unwanted angiogenesis in an individual in need thereof comprising administering a therapeutically effective amount of a compound disclosed herein to the individual. In some embodiments, the disease associated with unwanted angiogenesis is macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma or hypertrophic scarring. In some embodiments, the disease associated with unwanted angiogenesis is a cancer. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

Some embodiments relate to a method of reversing a latency of Human Immunodeficiency Virus (HW) in a mammal, wherein the method comprises administering a therapeutically effective amount of a compound described herein, or pharmaceutically acceptable salt, N-oxide, racemate, or stereoisomer thereof, to the individual. In some embodiments, the latency of HIV is reversed without activation of T cells.

CHEMISTRY EXAMPLES

The following examples are intended to illustrate but not limit the disclosed embodiments. All solvents were used as purchased from commercial sources or dried over 4 Å molecular sieves prior to use in the case of moisture sensitive reactions. Reactions conducted under microwave irradiation were performed in a CEM Discover microwave reactor using either CEM 10 mL reaction vessels or a ChemGlass heavy wall pressure vessel (100 mL, 38 mm×190 mm). Reaction progress was monitored by reverse-phase HPLC and/or thin-layer chromatography (TLC). High resolution mass spectrometry was performed using ESI-TOFMS, EI-MS (reference: perfluorokerosene) and APCI-MS. TLC was performed using silica gel 60 F254 pre-coated plates (0.25 mm). Flash chromatography was performed using silica gel (32-63 μm particle size) or aluminum oxide (activated, basic, —150 mesh size). All products were purified to homogeneity by TLC analysis (single spot, unless stated otherwise), using a UV lamp and/or iodine and/or CAM or basic $KMnO_4$ for detection purposes. NMR spectra were recorded on 400 MHz and 500 MHz spectrometers at ambient temperature. $^1H$ and $^{13}C$ NMR chemical shifts are reported as δ using residual solvent as an internal standard; CDCl3: 7.26, 77.16 ppm; $CD_3OD$: 3.31, 49.00 ppm; DMSO-d6: 2.50, 39.52 ppm, CD3CN: 1.94 (1H), 1.32 (13C) ppm. Abbreviations used: alanine (Ala), 1-hydroxybenzotriazole (HOBT), N-methylmorpholine (NMM), N-(3-dimethylaminopropyl)-N'-ethylcarbodiimide (EDC), palladium on carbon (Pd-C), dichloromethane (DCM), diethyl ether (Et2O), ethyl acetate (EtOAc), 2,2,2-trifluoroethanol (TFE), methanol (MeOH), homoserine (HSer), tetrahydrofuran (THF), trifluoroacetic acid (TFA), diisobutylaluminum hydride (DIBAL).

General Procedure A

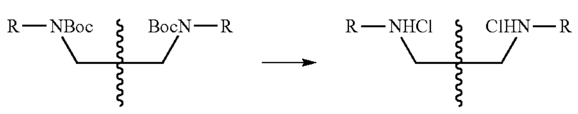

R = H or Alkyl

The boc protected compound was treated with HCl in dioxane (4 M, 40.0 eq.) and stirred at rt for 2 h. Upon completion, all volatiles were removed under reduced pressure. The residue was washed with diethyl ether over a fritted funnel and dried under reduced pressure.

General Procedure B

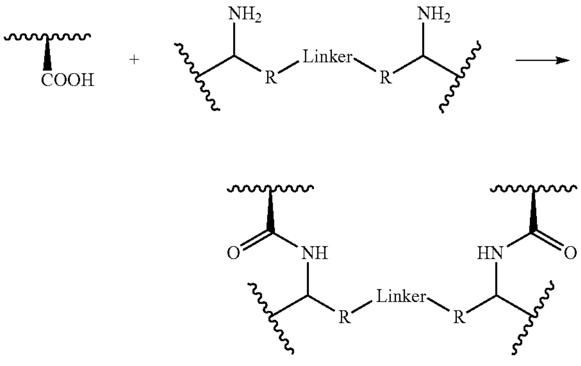

Under $N_2$ atmosphere, N-Ethyl-N-(propan-2-yl)propan-2-amine (5.00 eq.) and COMU® (2.50 eq.) were added to a solution of a carboxylic acid (2.10 eq.) dissolved in dry THF (287 eq.) and stirred at rt. After 45 minutes, the diamine dihydrochloride (1.00 eq) was added and stirring was continued for 20-23 h. Upon completion, ethyl acetate (30 mL) was added and washed with NaOH solution (1 M, 2×10 mL), HCl solution (1 M, 2×10 mL), water (10 mL) and brine (10 mL), dried ($Na_2SO4$) and concentrated in vacuo. The resulting residue was purified by fc (hexanes/ethyl acetate) to give 17a-m.

Synthetic Scheme for the Preparation of the (di)amine 6a Described Below

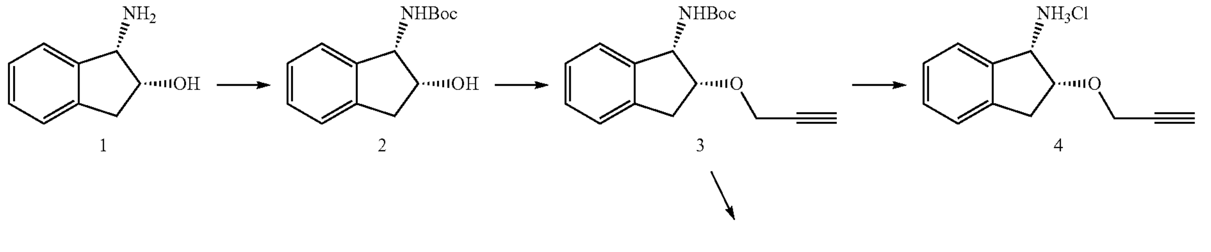

1 2 3 4

-continued

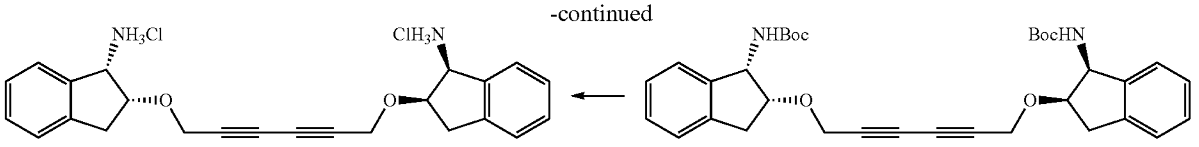

6a 5a

Example 1. Preparation of tert-Butyl (1S,2R)-2-hydroxy-2,3-dihydro-1H-inden-1-ylcarbamate (2)

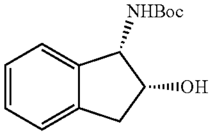 [SMILES: CC(C)(C)OC(=O)N[C@H]1c2ccccc2C[C@H]1O]

The compound 2 was prepared according to the established literature procedure; see Abdur-Rashid, K.; Guo, R.; Chen, X.; Jia, W. Application: WO 2008148202 A1.

Example 2. Preparation of tert-Butyl [(1S,2R)-2-(prop-2-yn-1-yloxy)-2,3-dihydro-1H-inden yl]carbamate (3)

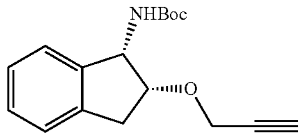 [SMILES: C#CCO[C@@H]1Cc2ccccc2[C@@H]1NC(=O)OC(C)(C)C]

Under $N_2$ atmosphere, the alcohol 2 (2.50 g, 10.0 mmol, 1.00 eq.) was dissolved in dry DMF (20.0 mL) and the solution was cooled to 0° C. Propargyl bromide in toluene (80%, 1.34 mL, 12.0 mmol, 1.20 eq.) was added. The resulting solution was treated in portions with powdered KOH (1.15 g, 420.6 mmol, 2.05 eq.) and stirring was continued at 0° C. After 1.5 h, water (40 mL) was added and the resulting mixture was extracted with ethyl acetate (4×40 mL). The combined organic layers were washed with water (2×40 mL) and brine (20 mL), dried ($Na_2SO_4$) and concentrated in vacuo. The residue was purified by fc (hexanes/ethyl acetate). Colorless solid, yield 2.29 g (79%). $^1$H NMR (400 MHz, $CDCl_3$): δ (ppm)=1.51 (s, 9H, $C(CH_3)_3$), 2.43 (t, 1H), 3.02 (dd, 1H), 3.09 (dd, 1H), 4.22 (dd, 2H), 4.48 (dq, 1H), 5.03-5.27 (m, 2H), 7.19-7.25 (m, 3H), 7.30-7.35 (m, 1H). LC-MS: m/z=287.90.

Example 3. Preparation of (1S,2R)-2-(Prop-2-yn-1-yloxy)-2,3-dihydro-1H-inden-1-ammonium chloride (4)

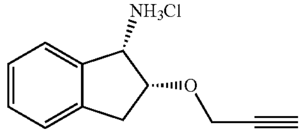

The carbamate 3 (100 mg, 0.348 mmol, 1.00 eq.) was treated with HCl in dioxane (4 M, 2.61 mL, 10.4 mmol, 30.0 eq.) at rt. After 2 h, all volatiles were removed under reduced pressure, the residue was transferred on a fitted funnel and washed with $Et_2O$. The remaining product was dried under reduced pressure. Colorless solid, yield 71 mg (91%). $^1$H NMR (400 MHz, DMSO-$D_6$): δ (ppm)=3.07-3.20 (m, 2H), 3.55 (t, 1H), 4.29-4.39 (m, 2H), 4.51 (q, 1H), 4.71 (s, 1H), 7.25-7.36 (m, 3H), 7.60 (d, 1H), 8.61 (s, 3H). LC-MS: m/z=188.05 (calcd. 188.11 for $C_{12}H_{14}NO^+$[M+H$^+$]).

Example 4. Preparation of tert-Butyl N-[(1S,2R)-2-[(6-{[(1S,2R)-1-{[(tert-butoxy)carbonyl]amino}-2,3-dihydro-1H-inden-2-yl]oxy}hexa-2,4-diyn-1-yl)oxy]-2,3-dihydro-1H-inden-1-yl]carbamate (5a)

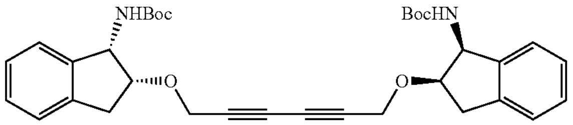

Copper(II) acetate hydrate (216 mg, 1.08 mmol, 1.15 eq.) was added to a solution of the alkyne 4 (270 mg, 0.940 mmol, 1.00 eq.) in acetonitrile (8.5 mL) and pyridine (450 µL, 5.58 mmol, 5.94 eq.). The resulting mixture was placed in an oil bath preheated to 80° C. After 1 h, the reaction mixture was cooled to rt and concentrated in vacuo. A aqueous $NH_4OH$ solution (3%, 10 mL) was added to the residue and extracted with ethyl acetate (3×10 mL). The combined organic layers were washed with water (10 mL) and brine (10 mL). The brine layer was extracted with ethyl acetate (2×10 mL) and the combined organic layers were dried ($Na_2SO_4$) and concentrated in vacuo. The residue was purified by fc (cyclohexane/ethyl acetate). Colorless solid, yield 166 mg (62%). $R_f$=0.55 (hexanes/ethyl acetate 8:2). $^1$H NMR (400 MHz, $CDCl_3$): δ (ppm)=1.51 (s, 18H), 2.98-3.11 (m, 4H), 4.30 (s, 4H), 4.45 (q, 2H), 4.99-5.25 (m, 4H), 7.22 (dd, 6H), 7.30-7.34 (m, 2H). LC-MS: m/z=573.25 (calcd. 573.30 for $C_{34}H_4N_2O_6^+$[M+H$^+$]), 595.25 (calcd. 595.28 for $C_{34}$H40$N_2NaO_6^+$[M+Na$^+$]).

Example 5. Preparation of (1S,2R)-2-[(6-{[(1S,2R)-1-Ammonio-2,3-dihydro-1H-inden-2-yl]oxy}hexa-2,4-diyn-1-yl)oxy]-2,3-dihydro-1H-inden-1-ammonium dichloride (6a)

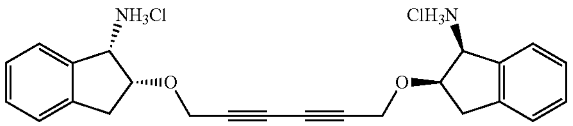

The compound 6a was prepared according to general procedure A. Colorless solid, yield 99 mg (95%). 1H NMR (400 MHz, DMSO-D6): δ (ppm)=3.08-3.19 (m, 4H), 4.47-4.58 (m, 6H), 4.72 (t, 2H), 7.23-7.39 (m, 6H), 7.60 (d, 2H), 8.66 (s, 6H). LC-MS: m/z=373.00 (calcd. 373.19 for $C_{24}H_{25}N_2O_2$+[M+H$^+$]), 187.05 (calcd. 187.10 for $C_{24}H_{26}N_2O_{22}{}^+$[M+2H$^+$]).
Synthetic Scheme for the Preparation of Dimer 18a and Monomer 16
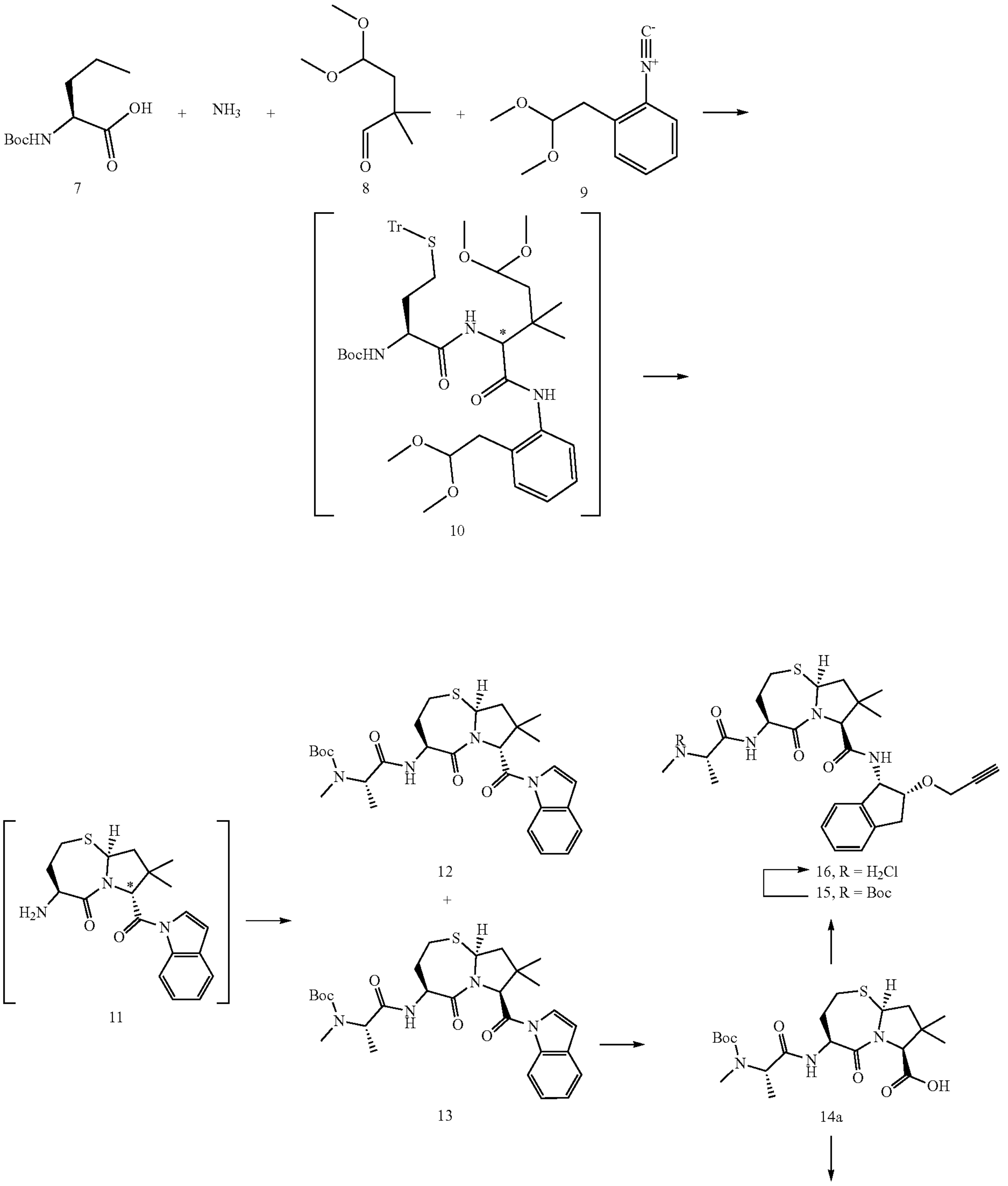
7 8 9
10
11
12
\+
13
14a
16, R = $H_2Cl$
15, R = Boc -continued

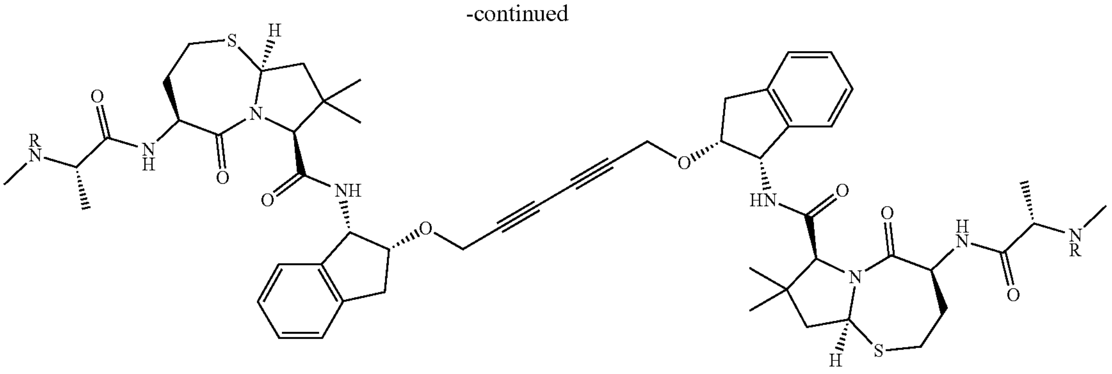

17a, R = Boc
18a, R = $H_2Cl$

Example 6. Preparation of 4,4-Dimethoxy-2,2-dimethylbutanal (8)

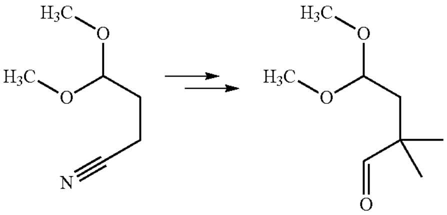

The compound 8 was prepared according to the established literature procedure; see Vamos, M.; Welsh, K.; Finlay, D.; Lee, P. S.; Mace, P. D.; Snipas, S. J.; Gonzalez, M. L.; Ganji, S. R.; Ardecky, R. J.; Riedl, Stefan J.; Salvesen, G. S.; Vuori, K.; Reed, J. C.; Cosford, N. D. P. *ACS Chem. Biol.* 2013, 8, 725-732.

Example 7. Preparation of 1-(2,2-Dimethoxyethyl)-2-isocyanobenzene (9)

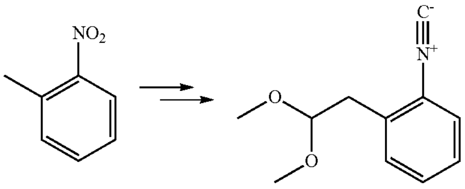

The isocyanide 9 was prepared according to the established literature procedure; see Gilley, Cynthia B.; Buller, M. J.; Kobayashi, Y. *Org. Lett.* 2007, 9 (18), 3631-3634.

Example 8. Preparation of tert-Butyl [(2S)-1-{[(4S, 7S,9aS)-7-(1H-indol-1-carbonyl)-8,8-dimethyl-5-oxooctahydropyrrolo[2,1-b][1,3]thiazepin-4-yl] amino}-1-oxopropan-2-yl](methyl)carbamate (13)

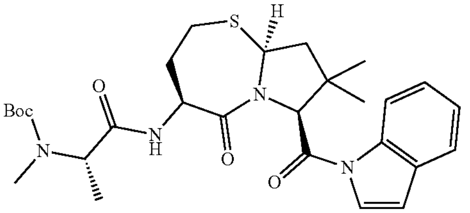 [SMILES: C[C@@H](C(=O)N[C@H]1CCS[C@H]2CC(C)(C)[C@@H](C(=O)n3ccc4ccccc43)N2C1=O)N(C)C(=O)OC(C)(C)C]

A mixture of N-(tert-butoxycarbonyl)-S-trityl-L-homocysteine (1.34 g, 2.80 mmol, 1.00 eq.), 4,4-Dimethoxy-2,2-dimethylbutanal 8 (471 mg, 2.94 mmol, 1.05 eq.), 1-(2,2-Dimethoxyethyl)-2-isocyanobenzene 9 (616 mg, 3.22 mmol, 1.15 eq.) and $NH_3$ in MeOH (7 M, 800 µL, 5.60 mmol, 2.00 eq.) in 2,2,2-trifluoroethanol (2.1 mL) was stirred under microwave irradiation at 80° C. After 20 min, all volatiles were removed under reduced pressure.

The residue was treated with HCl in dioxane (4 M, 7.00 mL, 28.0 mmol, 10.0 eq.) for 2.5 h at 40° C. After removal of all volatiles, the residue was dissolved in ethyl acetate (150 mL) and washed with NaOH (1 M, 30 mL), water (30 mL) and brine (30 mL). The organic solvent was dried ($Na_2SO_4$) and removed under reduced pressure.

The amine, N-(tert-butoxycarbonyl)-N-methyl-L-alanine (683 mg, 3.36 mmol, 1.20 eq.), 1-Hydroxybenzotriazole hydrate (623 mg, 3.64 mmol, 1.30 eq.) and N-Methylmorpholine (926 µL, 8.40 mmol, 3.00 eq.) were dissolved in dry THF (10 mL) and cooled down to 0° C. EDC·HCl (698 mg, 3.64 mmol, 1.30 eq.) was added. After stirring at 0° C. for 30 min, stirring was continued for 16 h at rt. All volatiles were removed in vacuo and the residue was dissolved in ethyl acetate (100 mL). The organic layer was washed with NaOH solution (1 M, 50 mL), HCl solution (1 M, 50 mL), water (50 mL) and brine (20 mL), dried ($Na_2SO_4$) and concentrated in vacuo. The residue was purified by fc (cyclohexane/ethyl acetate).

Isomer 1: Yellow solid, yield 214 mg (14%). $R_f$=0.47 (hexanes/ethyl acetate 5:5).

Isomer 2: Yellow solid, yield 254 mg (17%). $R_f$=0.20 (hexanes/ethyl acetate 5:5). 1H NMR (400 MHz, $CDCl_3$): δ

(ppm)=1.02 (s, 3H), 1.24-1.26 (m, 3H), 1.33 (d, 3H), 1.43 (s, 9H), 1.96 (q, 1H), 2.25-2.33 (m, 3H), 2.75 (s, 3H), 2.90 (ddd, 1H), 3.30 (ddd, 1H), 4.61 (dd, 1H), 4.71 (s, broad, 1H), 5.09 (s, 1H), 5.26 (t, 1H), 6.70 (d, 1H), 7.27-7.37 (m, 3H), 7.55-7.59 (m, 2H), 8.57 (d, 1H). LC-MS: m/z=565.26 (calcd. 565.25 for $C_{28}H_{38}N_4NaO_{5S}^+$[M+Na$^+$]).

Example 9. Preparation of (4S,7S,9aS)-4-({(2S)-2-[(tert-Butoxycarbonyl)(methyl)amino]propanoyl}amino)-8,8-dimethyl-5-oxooctahydropyrrolo[2,1-b][1,3]thiazepine-7-carboxylic acid (14a)

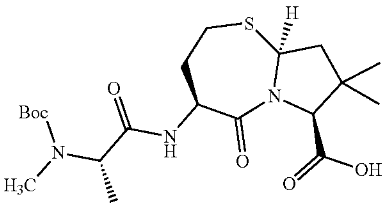

The indole amide 13 (130 mg, 0.240 mmol, 1.00 eq.) was dissolved in methanol (3.0 mL) and aq. NaOH (1 M, 1.20 mL, 1.20 mmol, 5.00 eq.) was added. After the resulting mixture was stirred for 5 h at 32° C., the methanol was removed in vacuo. NaOH solution (1 M, 30 mL) and brine (10 mL) were added and washed with ethyl acetate (3×10 mL). The aqueous layer was acidified with HCl solution (3 M) to pH≤2 and extracted with $CH_2Cl_2$ (2×20 mL, 1×10 mL). The combined $CH_2Cl_2$ layers were dried ($Na_2SO_4$) and concentrated in vacuo. The residue was purified by fc (cyclohexane/ethyl acetate with 1% HCOOH). Colorless solid, yield 56 mg (53%). $R_f$=0.52 (hexanes/ethyl acetate/formic acid 3:7:0.2, Ceric Ammonium Molybdate stain). 1H NMR (400 MHz, $CDCl_3$): δ (ppm)=1.17 (d, 3H), 1.21 (d, 3H), 1.35 (d, 3H), 1.46 (d, 9H), 1.93 (q, 1H), 2.02 (dd, 1H), 2.21-2.35 (m, 2H), 2.77-2.91 (m, 4H), 3.25 (ddd, 1H), 4.23 (d, 1H), 4.60 (q, 1H), 5.19 (t, 1H), 7.38 (s, 1H). $CHCH_3$ and COOH are not seen in the spectrum. LC-MS: m/z=444.10 (calcd. 444.22 for $C_{20}H_{34}N_3O_6S$+[M+H$^+$]).

Example 10. Preparation of tert-Butyl [(2S)-1-{[(4S,7S,9aS)-8,8-dimethyl-5-oxo-7-{[(1S,2R)-2-(prop-2-yn-1-yloxy)-2,3-dihydro-1H-inden-1-yl]carbamoyl}octahydropyrrolo[2,1-b][1,3]thiazepin-4-yl]amino}-1-oxopropan-2-yl](methyl)carbamate (15)

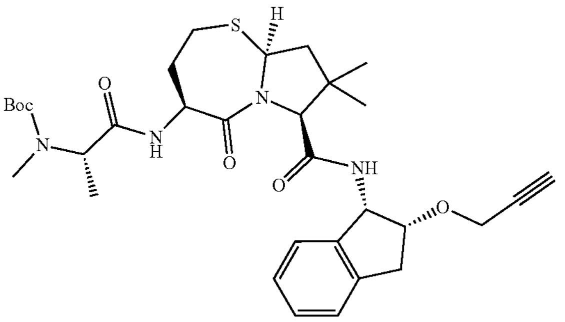 [SMILES: C#CCO[C@@H]1Cc2ccccc2[C@@H]1NC(=O)[C@H]1N2C(=O)[C@@H](NC(=O)[C@H](C)N(C)C(=O)OC(C)(C)C)CCS[C@H]2CC1(C)C]

Under $N_2$ atmosphere, N-Ethyl-N-(propan-2-yl)propan-2-amine (80 μL, 0.460 mmol, 3.00 eq.) and COMU® (85 mg, 0.199 mmol, 1.30 eq.) were added to a solution of carboxylic acid 14 (68 mg, 0.153 mmol, 1.00 eq.) in dry THF (1.5 mL) at 0° C. After the reaction mixture was stirred for 30 min at 0° C., the amine hydrochloride 4 (41 mg, 0.184 mmol, 1.20 eq.) was added and stirring was continued for 16 h at rt. Afterwards, all volatiles were removed under reduced pressure, the residue was dissolved in ethyl acetate (30 mL), washed with NaOH solution (1 M, 2×10 mL), HCl solution (1 M, 2×10 mL), water (2×10 mL) and brine (10 mL), dried ($Na_2SO_4$) and concentrated in vacuo. The residue was purified by fc (hexanes/ethyl acetate). Colorless solid, yield 67 mg (71%). $R_f$=0.41 (hexanes/ethyl acetate 7:3, Cerium (IV) sulfate stain). $^1H$ NMR (400 MHz, $CDCl_3$): δ (ppm)=1.13 (s, 3H), 1.20 (s, 3H), 1.34 (d, 3H), 1.48 (s, 9H), 1.83 (dd, 1H), 1.98-2.10 (m, 1H), 2.24-2.32 (m, 2H), 2.49 (s, 1H), 2.79 (s, 4H), 3.09 (dd, 2H), 3.30 (ddd, 1H), 4.07-4.13 (m, 1H), 4.14-4.19 (m, 1H), 4.31 (s, 1H), 4.48 (q, 1H), 4.54 (dd, 1H), 5.16 (dd, 1H), 5.54 (dd, 1H), 7.19-7.23 (m, 3H), 7.31 (d, 1H), 7.35-7.43 (m, 2H). $CHCH_3$ is not seen in the spectrum. LC-MS: m/z=613.40 (calcd. 613.79 for $C_{32}H_{45}N_4O_6S^+$[M+H$^+$]).

Example 11. Preparation of (2S)-1-{[(4S,7S,9aS)-8,8-Dimethyl-5-oxo-7-{[(1S,2R)-2-(prop-2-yn yloxy)-2,3-dihydro-1H-inden-1-yl]carbamoyl}octahydropyrrolo[2,1-b][1,3]thiazepin-4-yl]amino}-N-methyl-1-oxopropan-2-ammonium chloride (16)

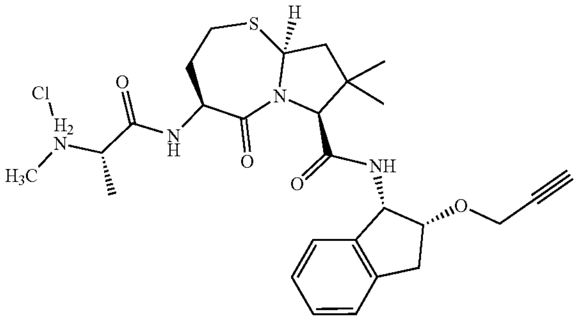

The carbamate 15 (67 mg, 0.109 mmol, 1.00 eq.) was treated with HCl in dioxane (4 M, 820 μL, 3.28 mmol, 30.0 eq.) at rt. After 2 h, all volatiles were removed under reduced pressure, the residue was transferred on a fitted funnel and washed with $Et_2O$ (3×1.5 mL). The remaining product was dried under reduced pressure. Colorless solid, yield 51 mg (85%). $^1H$ NMR (400 MHz, $CD_3OD$): δ (ppm)=1.12-1.19 (m, 6H), 1.55 (d, 3H), 1.81 (dd, 1H), 2.07-2.20 (m, 1H), 2.21-2.30 (m, 1H), 2.34 (dd, 1H), 2.68 (s, 3H), 2.87-2.96 (m, 2H), 3.09 (dd, 1H), 3.16 (dd, 1H), 3.28-3.37 (m, 1H), 3.94 (q, 1H), 4.16 (dd, 1H), 4.21-4.28 (m, 2H), 4.52 (td, 1H), 4.75 (dd, 1H), 5.40-5.52 (m, 2H), 7.17-7.26 (m, 3H), 7.32 (d, 1H), 8.00 (d, 1H). $NH_2$+ and $H_3CNCHC(O)NH$ are not seen in the spectrum. LC-MS: m/z=513.65 (calcd. 513.25 for $C_{27}H_{37}N_4O_4S$+[M+H$^+$]).

Example 12. Preparation of tert-Butyl [(2S)-1-{[(4S,7S,9aS)-7-({(1S,2R)-2-[(6-{[(1S,2R)-1-({[(4S,7S,9aS)-4-amino-8,8-dimethyl-5-oxooctahydropyrrolo[2,1-b][1,3]thiazepin-7-yl]carbonyl}amino)-2,3-dihydro-1H-inden-2-yl]oxy}hexa-2,4-diyn-1-yl)oxy]-2,3-dihydro-1H-inden-1-yl}carbamoyl)-8,8-dimethyl-5-oxooctahydropyrrolo[2,1-b][1,3]thiazepin-4-yl]amino}-1-oxopropan-2-yl](methyl)carbamate (17a)

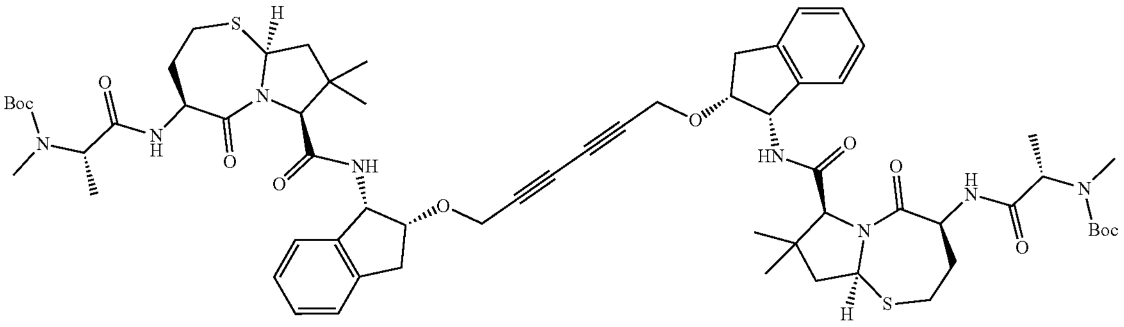

The compound was prepared according to general procedure B. Colorless solid, yield 68 mg (69%). $R_f$=0.59 (ethyl acetate/methanol 10:0.5, Ceric Ammonium Molybdate stain). $^1H$ NMR (400 MHz, $CD_3OD$): δ (ppm)=1.15 (m, 12H), 1.36 (d, 6H), 1.46 (s, 18H), 1.81 (dd, 2H), 1.97 (q, 2H), 2.20-2.28 (m, 2H), 2.31 (dd, 2H), 2.76-2.91 (m, 8H), 3.03-3.16 (m, 4H), 3.22-3.34 (m, 2H), 4.21-4.35 (m, 6H), 4.43 (q, 2H), 4.53 (s, broad, 2H), 4.63 (d, 2H), 5.45 (dt, 4H), 7.15-7.25 (m, 6H), 7.31 (d, 2H), 7.85-8.02 (m, 2H). LC-MS: m/z=1223.70 (calcd. 1223.59 for $C_{64}H_{87}N_8O_{12}S_2^+$[M+H$^+$]).

Example 13. Preparation of (2S)-1-{[(4S,7S,9aS)-74{(1S,2R)-2-[(6-{[(1S,2R)-1-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}hexa-2,4-diyn-1-yl)oxy]-2,3-dihydro-1H-inden-1-yl}carbamoyl)-8,8-dimethyl-5-oxooctahydropyrrolo[2,1-b][1,3]thiazepin yl]amino}-N-methyl-1-oxopropan-2-ammonium dichloride (18a)

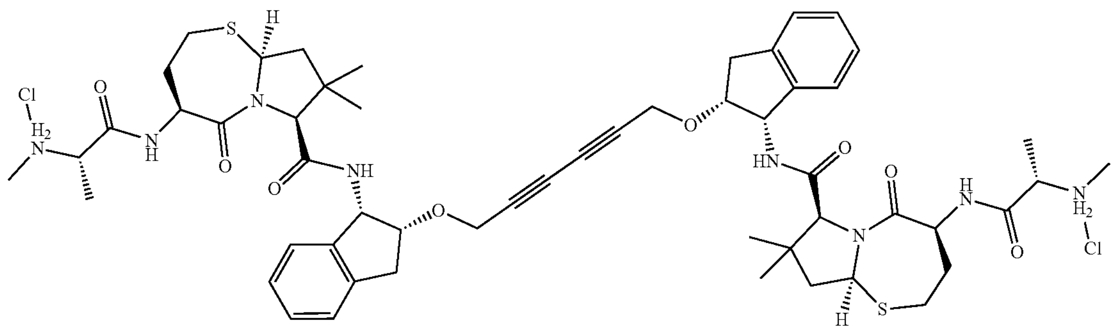

The compound was prepared according to general procedure A. Colorless solid, yield 53 mg (88%). $R_f$=0.53 (ethyl acetate/methanol/$NEt_3$ 8:2:0.2, Ceric Ammonium Molybdate stain). 114 NMR (400 MHz, $CD_3OD$): δ (ppm)=1.15 (s, 12H), 1.55 (d, 6H), 1.81 (dd, 2H), 2.04 (q, 2H), 2.21-2.38 (m, 4H), 2.68 (s, 6H), 2.91 (d, 2H), 3.05-3.17 (m, 4H), 3.30 (dt, 2H), 3.95 (q, 2H), 4.22-4.39 (m, 6H), 4.46 (q, 2H), 4.75 (d, 2H), 5.46 (t, 4H), 7.16-7.26 (m, 6H), 7.32 (d, 2H), 8.02 (d, 2H), 8.73 (d, 2H). $NH_2^+$ is not seen in the spectrum. 13C NMR (101 MHz, $CD_3OD$): δ (ppm)=16.4, 24.2, 28.9, 31.9, 32.4, 33.5, 37.2, 40.8, 47.3, 54.4, 56.8, 58.0, 58.3, 61.8, 71.1, 73.6, 76.9, 81.0, 125.5, 126.2, 128.1, 129.4, 141.0, 142.2, 169.3, 172.2, 172.5. LC-MS: m/z=1223.70 (calcd. 1223.59 for $C_{64}H_{87}N_8O_{12}S_2^+$[M+H$^+$]).

Synthetic Scheme for the Preparation of Diamines 6b-h

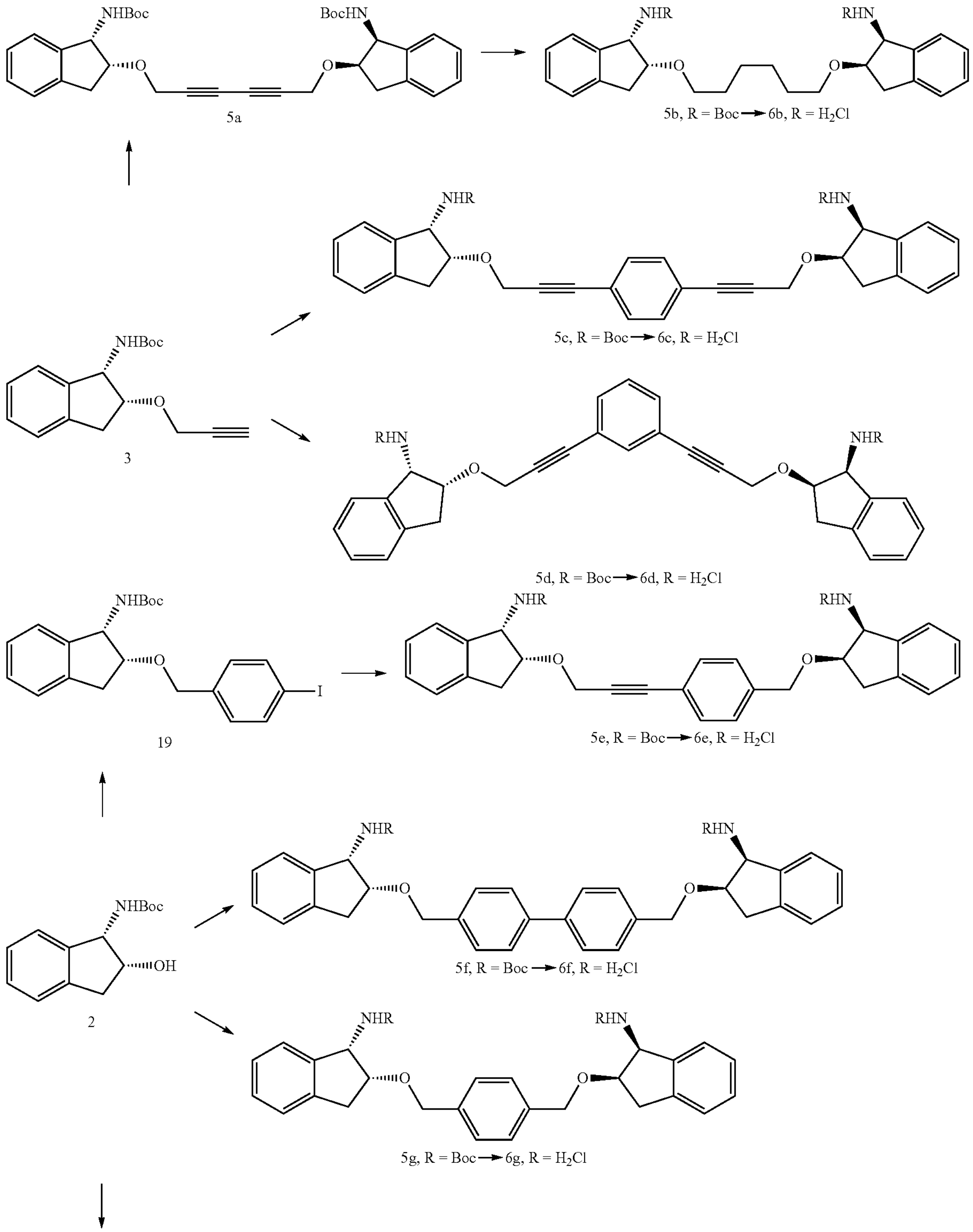

5a

5b, R = Boc → 6b, R = $H_2Cl$

5c, R = Boc → 6c, R = $H_2Cl$

3

5d, R = Boc → 6d, R = $H_2Cl$

19

5e, R = Boc → 6e, R = $H_2Cl$

5f, R = Boc → 6f, R = $H_2Cl$

2

5g, R = Boc → 6g, R = $H_2Cl$

-continued

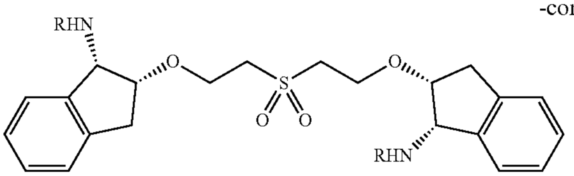

5h, R = Boc → 6h, R = $H_2Cl$

Example 14. Preparation of tert-Butyl N-[(1S,2R)-2-[(6-{[(1S,2R)-1-{[(tert-butoxy)carbonyl]amino}-2,3-dihydro-1H-inden-2-yl]oxy}hexyl)oxy]-2,3-dihydro-1H-inden-1-yl]carbamate (5b)

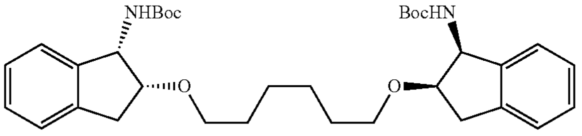 [SMILES: CC(C)(C)OC(=O)N[C@H]1c2ccccc2C[C@H]1OCCCCCCO[C@@H]1Cc2ccccc2[C@@H]1NC(=O)OC(C)(C)C]

Pd/C (10%, 18 mg, 0.05 eq) was added to a solution of alkyne 5a (200 mg, 0.349 mmol, 1.00 eq) in methanol (3 mL) and THF (1 mL). The resulting mixture was stirred for 16 h under $H_2$ atmosphere (balloon). Following Celite® filtration with $CH_2Cl_2$, the solvent was removed in vacuo and the resulting residue was purified by fc (hexanes/ethyl acetate). Colorless solid, yield 182 mg (90%). $R_f$=0.38 (hexane/ethyl acetate 8.5:1.5). NMR (400 MHz, $CDCl_3$): δ (ppm)=1.31 (q, 4H), 1.46-1.55 (m, 22H), 2.91-3.04 (m, 4H), 3.37-3.45 (m, 2H), 3.46-3.56 (m, 2H), 4.15-4.24 (m, 2H), 5.10-5.19 (m, 2H), 5.22-5.32 (m, 2H), 7.16-7.24 (m, 6H), 7.33 (q, 2H). LC-MS: m/z=581.25 (calcd. 581.36 for $C_{34}H_{49}N_2O_6^+$[M+11+]).

Example 15. Preparation of tert-Butyl N-[(1S,2R)-2-({3-[4-(3-{[(1S,2R)-1-{[(tert-butoxy)carbonyl]amino}-2,3-dihydro-1H-inden-2-yl]oxy}prop-1-yn-1-yl)phenyl]prop-2-yn yl}oxy)-2,3-dihydro-1H-inden-1-yl]carbamate (5c)

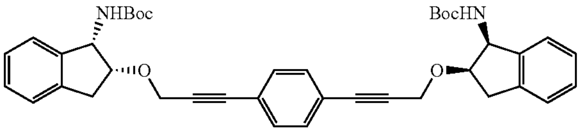 [SMILES: CC(C)(C)OC(=O)N[C@H]1c2ccccc2C[C@H]1OCC#Cc1ccc(C#CCO[C@@H]2Cc3ccccc3[C@@H]2NC(=O)OC(C)(C)C)cc1]

Under $N_2$ atmosphere, 1,4-Diiodobenzene (120 mg, 0.364 mmol, 1.00 eq) was added to a solution of alkyne 3 (418 mg, 1.45 mmol, 4.00 eq) dissolved in $NEt_3$ (3.0 mL, 21.8 mmol, 60.0 eq.). $Pd(PPh_3)_4$ (21 mg, 0.05 eq) and CuI (3 mg, 0.05 eq) were added and the resulting mixture was stirred at 80° C. for 4 h. Upon completion, water (10 mL) was added to the mixture and extracted with $CH_2Cl_2$ (3×10 mL). The combined organic layers were washed with water (10 mL), dried ($Na_2SO_4$) and concentrated in vacuo. The resulting residue was purified by fc (hexanes/ethyl acetate). Colorless solid, yield 188 mg (80%). $R_f$=0.37 (hexanes/ethyl acetate 8:2). $^1$H NMR (400 MHz, $CDCl_3$): δ (ppm)=1.50 (s, 18H), 3.05 (dd, 2H), 3.14 (dd, 2H), 4.45 (s, 4H), 4.54 (td, 2H), 5.18-5.32 (m, 4H), 7.21-7.25 (m, 6H), 7.32-7.37 (m, 2H), 7.39 (s, 4H). LC-MS: m/z=671.30 (calcd. 671.31 for $C_{40}H_{44}N_2NaO_6^+$ [M+Na$^+$]).

Example 16. Preparation of tert-Butyl N-[(1S,2R)-2-({3-[3-(3-{[(1S,2R)-1-{[(tert-butoxy)carbonyl]amino}-2,3-dihydro-1H-inden-2-yl]oxy}prop-1-yn-1-yl)phenyl]prop-2-yn-1-yl}oxy)-2,3-dihydro-1H-inden-1-yl]carbamate (5d)

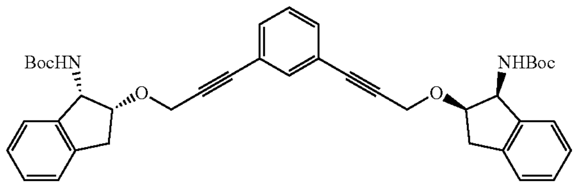 [SMILES: CC(C)(C)OC(=O)N[C@H]1c2ccccc2C[C@H]1OCC#Cc1cccc(C#CCO[C@@H]2Cc3ccccc3[C@@H]2NC(=O)OC(C)(C)C)c1]

Under $N_2$ atmosphere, 1,3-Diiodobenzene (110 mg, 0.333 mmol, 1.00 eq) was added to a solution of alkyne 3 (383 mg, 1.33 mmol, 4.00 eq) dissolved in $NEt_3$ (1.9 mL, 13.3 mmol, 40.0 eq.). $Pd(PPh_3)_4$ (19 mg, 0.05 eq) and CuI (3 mg, 0.05 eq) were added and the resulting mixture was stirred at 80° C. for 4 h. Upon completion, water (15 mL) was added to the mixture and extracted with $CH_2Cl_2$ (3×15 mL). The combined organic layers were washed with water (15 mL), dried ($Na_2SO_4$) and concentrated in vacuo. The resulting residue was purified by fc (hexanes/ethyl acetate). Colorless solid, yield 178 mg (82%). $R_f$=0.40 (hexanes/ethyl acetate 8:2). $^1$H NMR (400 MHz, $CDCl_3$): δ (ppm)=1.49 (s, 18H), 3.05 (dd, 2H), 3.13 (dd, 2H), 4.44 (s, 4H), 4.54 (td, 2H), 5.18-5.34 (m, 4H), 7.23 (d, 6H), 7.28 (d, 1H), 7.34 (dt, 2H), 7.40 (dd, 2H), 7.52 (t, 1H). LC-MS: m/z=671.20 (calcd. 671.31 for $C_{40}H_{44}N_2NaO_6^+$[M+Na$^+$]).

Example 17. Preparation of tert-Butyl {(1S,2R)-2-[(4-iodobenzyl)oxy]-2,3-dihydro-1H-inden-1-yl}carbamate (19)

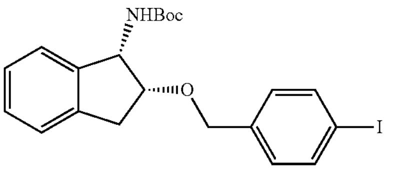 [SMILES: CC(C)(C)OC(=O)N[C@H]1c2ccccc2C[C@H]1OCc1ccc(I)cc1]

Under $N_2$ atmosphere, 1-(Bromomethyl)-4-iodobenzene (357 mg, 1.20 mmol, 1.20 eq) was added to a solution of alcohol 2 (250 mg, 1.00 mmol, 1.00 eq) dissolved in dry DMF (2.0 mL). The resulting mixture was treated with powdered KOH (115 mg, 2.06 mmol, 2.05 eq) and stirred at rt for 1.5 h. Upon completion, water (15 mL) was added to the mixture and extracted with ethyl acetate (3×15 mL). The combined organic layers were washed with water (15 mL), brine (15 mL), dried ($Na_2SO_4$) and concentrated in vacuo. The resulting residue was purified by fc (hexanes/ethyl acetate). Colorless solid, yield 148 mg (32%). $R_f$=0.66 (hexanes/ethyl acetate 8.5:1.5). 1H NMR (400 MHz, $CDCl_3$): δ (ppm)=1.50 (s, 9H), 3.00 (dd, 1H), 3.06 (dd, 1H), 4.34 (dp, 1H), 4.51 (d, 1H), 4.56 (d, 1H), 5.21 (s, 2H), 7.05 (d, 2H), 7.21 (p, 3H), 7.34 (q, 1H), 7.62-7.67 (m, 2H). LC-MS: m/z=487.90 (calcd. 488.07 for $C_{21}H_{24}INNaO_3^+$ [M+Na$^+$]).

Example 18. Preparation of tert-Butyl N-[(1S,2R)-2-({3-[4-({[(1S,2R)-1-{[(tert-butoxy)carbonyl] amino}-2,3-dihydro-1H-inden-2-yl]oxy}methyl) phenyl]prop-2-yn-1-yl}oxy)-2,3-dihydro-1H-inden-1-yl]carbamate (5e)

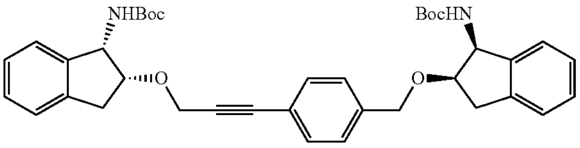 [SMILES: CC(C)(C)OC(=O)N[C@H]1c2ccccc2C[C@H]1OCC#Cc1ccc(CO[C@@H]2Cc3ccccc3[C@@H]2NC(=O)OC(C)(C)C)cc1]

Under $N_2$ atmosphere, alkyne 3 (158 mg, 0.550 mmol, 2.00 eq) was added to a solution of iodobenzene 19 (128 mg, 0.275 mmol, 1.00 eq) dissolved in $NEt_3$ (1.5 mL, 11.0 mmol, 40.0 eq.). $Pd(PPh_3)_4$ (9 mg, 0.03 eq) and CuI (1 mg, 0.03 eq) were added and the resulting mixture was stirred at 70° C. for 4 h. Upon completion, water (10 mL) was added to the mixture and extracted with $CH_2Cl_2$ (3×10 mL). The combined organic layers were washed with water (10 mL), dried ($Na_2SO_4$) and concentrated in vacuo. The resulting residue was purified by fc (hexanes/ethyl acetate). Colorless solid, yield 130 mg (76%). $R_f$=0.51 (hexanes/ethyl acetate 8:2). $^1$H NMR (400 MHz, $CDCl_3$): δ (ppm)=1.48-1.51 (m, 18H), 2.95-3.10 (m, 3H), 3.14 (dd, 1H), 4.32-4.37 (m, 1H), 4.44 (s, 2H), 4.53 (dt, 1H), 4.57 (d, 1H), 4.61 (d, 1H), 5.22 (tt, 4H), 7.19-7.26 (m, 8H), 7.31-7.37 (m, 2H), 7.38-7.43 (m, 2H). LC-MS: m/z=647.25 (calcd. 647.31 for $C_{38}H_{44}N_2NaO_6^+$ [M+Na$^+$]).

Example 19. Preparation of tert-Butyl N-[(1S,2R)-2-{[4'-({[(1S,2R)-1-{[(tert-butoxy)carbonyl]amino}-2,3-dihydro-1H-inden-2-yl]oxy}methyl)-[1,1'-biphenyl]-4-yl]methoxy}-2,3-dihydro-1H-inden-1-yl] carbamate (5f)

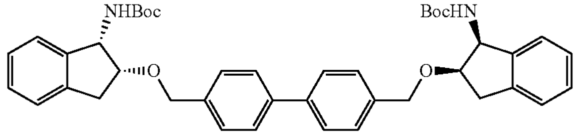

Under $N_2$ atmosphere, 1-(Bromomethyl)-4-(4-(bromomethyl)phenyl)benzene (93 mg, 0.273 mmol, 1.00 eq) was added to a solution of alcohol 2 (150 mg, 0.602 mmol, 2.20 eq) dissolved in dry DMF (1.0 mL) at 0° C. The resulting mixture was treated with powdered KOH (49 mg, 0.875 mmol, 3.20 eq) and stirred for 1 h at 0° C., followed by stirring at rt for 3 h. Upon completion, water (30 mL) was added to the mixture and extracted with ethyl acetate (3×10 mL). The combined organic layers were washed with water (2×10 mL), brine (10 mL), dried ($Na_2SO_4$) and concentrated in vacuo. The resulting residue was purified by fc (hexanes/$CH_2Cl_2$, $CH_2Cl_2$/MeOH). Colorless solid, crude yield 131 mg (71%). $R_f$=0.43 (hexanes/ethyl acetate 8:2).

Example 20. Preparation of tert-Butyl N-[(1S,2R)-2-{[4-({[(1S,2R)-1-{[(tert-butoxy)carbonyl]amino}-2,3-dihydro-1H-inden-2-yl]oxy}methyl)phenyl]methoxy}-2,3-dihydro-1H-inden-1-yl]carbamate (5g)

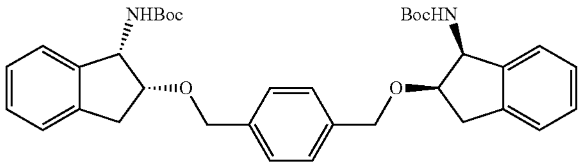 [SMILES: CC(C)(C)OC(=O)N[C@H]1c2ccccc2C[C@H]1OCc1ccc(CO[C@@H]2Cc3ccccc3[C@@H]2NC(=O)OC(C)(C)C)cc1]

Under $N_2$ atmosphere, 1,4-Bis(bromomethyl)benzene (81 mg, 0.310 mmol, 1.00 eq) was added to a solution of the alcohol 2 (170 mg, 0.682 mmol, 2.20 eq) dissolved in dry DMF (1.1 mL) at 0° C. The resulting mixture was treated with powdered KOH (55 mg, 0.992 mmol, 3.20 eq) and stirred for 2 h at 0° C. Upon completion, water (10 mL) was added to the mixture and extracted with ethyl acetate (4×10 mL). The combined organic layers were washed with water (2×10 mL), brine (10 mL), dried ($Na_2SO_4$) and concentrated in vacuo. The resulting residue was purified by fc (hexanes/ethyl acetate). Colorless solid, yield 84 mg (45%). 1H NMR (400 MHz, $CDCl_3$): δ (ppm)=1.50 (s, 18H), 2.99 (dd, 2H), 3.07 (dd, 2H), 4.34 (q, 2H), 4.55 (d, 2H), 4.60 (d, 2H), 5.16-5.23 (m, 2H), 7.17-7.23 (m, 6H), 7.27 (s, 4H), 7.32-7.36 (m, 2H). CHNH are not seen in the spectrum. LC-MS: m/z=623.20 (calcd. 623.31 for $C_{36}H_{44}N_2NaO_6^+$[M+Na$^+$]).

Example 21. Preparation of tert-Butyl N-[(1S,2R)-2-[2-(2-{[(1S,2R)-1-{[(tert-butoxy)carbonyl] amino}-2,3-dihydro-1H-inden-2-yl] oxy}ethanesulfonyl)ethoxy]-2,3-dihydro-1H-inden-1-yl]carbamate (5h)

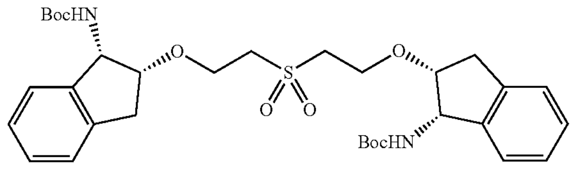 [SMILES: CC(C)(C)OC(=O)N[C@H]1c2ccccc2C[C@H]1OCCS(=O)(=O)CCO[C@@H]1Cc2ccccc2[C@@H]1NC(=O)OC(C)(C)C]

Under $N_2$ atmosphere, triphenylphosphine (9 mg, 0.10 eq) was added to a solution of alcohol 2 (250 mg, 1.00 mmol, 3.00 eq) dissolved in dry $CH_2Cl_2$ (0.70 mL). Divinyl sulfone (33 μL, 0.334 mmol, 1.00 eq) was added and the resulting mixture was stirred at rt for 24 h. Upon completion, all volatiles were removed in vacuo and the resulting residue was purified by fc (hexanes/ethyl acetate). Colorless solid, yield 150 mg (73%). 1H NMR (400 MHz, $CDCl_3$): δ (ppm)=1.46 (s, 18H, $C(CH_3)_3$), 2.90 (dd, 2H), 2.95-3.21 (m, 6H), 3.72-3.81 (m, 2H), 3.90-3.98 (m, 2H), 4.18-4.24 (m, 2H), 5.17 (dd, 2H), 5.40 (d, 2H), 7.01 (d, 2H), 7.17 (dt, 6H). LC-MS: m/z=617.20 (calcd. 617.29 for $C_{32}H_{45}N_2O_8S+[M+H^+]$).

Example 22. Preparation of (1S,2R)-2-[(6-{[(1S,2R)-1-Ammonio-2,3-dihydro-1H-inden-2-yl]oxy}hexyl)oxy]-2,3-dihydro-1H-inden-1-ammonium dichloride (6b)

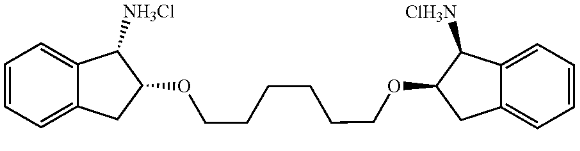

The compound was prepared according to general procedure A. Colorless solid, yield 107 mg (91%). LC-MS: m/z=381.00 (calcd. 381.25 for $C_{24}H_{33}N_2O_2^+[M+H^+]$).

Example 23. Preparation of (1S,2R)-2-({3-[4-(3-{[(1S,2R)-1-Ammonio-2,3-dihydro-1H-inden yl]oxy}prop-1-yn-1-yl)phenyl]prop-2-yn-1-yl}oxy)-2,3-dihydro-1H-inden-1-ammonium dichloride (6c)

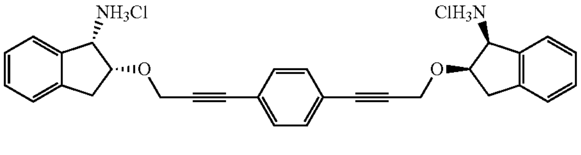

The compound was prepared according to general procedure A. Colorless solid, yield 122 mg (91%). LC-MS: m/z=449.10 (calcd. 449.22 for $C_{30}H_{29}N_2O_2^+[M+H^+]$).

Example 24. Preparation of (1S,2R)-2-({3-[3-(3-{[(1S,2R)-1-Ammonio-2,3-dihydro-1H-inden-2-yl]oxy}prop-1-yn-1-yl)phenyl]prop-2-yn-1-yl}oxy)-2,3-dihydro-1H-inden-1-ammonium dichloride (6d)

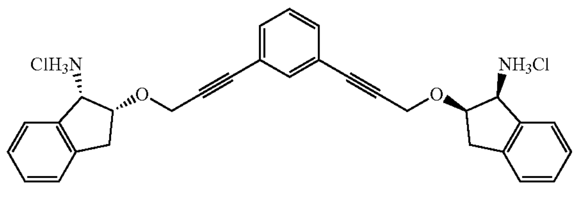

The compound was prepared according to general procedure A. Colorless solid, yield 104 mg (81%). LC-MS: m/z=449.00 (calcd. 449.22 for $C_{30}H_{29}N_2O_2^+[M+H^+]$).

Example 25. Preparation of (1S,2R)-2-({3-[4-({[(1S,2R)-1-Ammonio-2,3-dihydro-1H-inden-2-yl]oxy}methyl)phenyl]prop-2-yn-1-yl}oxy)-2,3-dihydro-1H-inden-1-ammonium dichloride (6e)

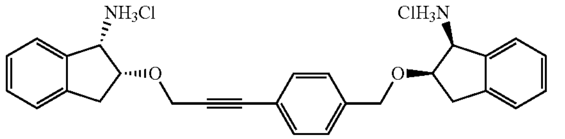

The compound was prepared according to general procedure A. Colorless solid, yield 136 mg (93%). LC-MS: m/z=425.05 (calcd. 425.22 for $C_{28}H_{29}N_2O_2^+[M+H^+]$).

Example 26. Preparation of (1S,2R)-2-({4-[4-({[(1S,2R)-1-Ammonio-2,3-dihydro-1H-inden-2-yl]oxy}methyl)phenyl]benzyl}oxy)-2,3-dihydro-1H-inden-1-ammonium dichloride (6f)

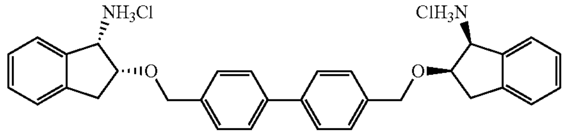

The compound was prepared according to general procedure A. Colorless solid, yield 93 mg (87%). LC-MS: m/z=477.20 (calcd. 477.25 for $C_{32}H_{33}N_2O_2^+[M+H^+]$).

Example 27. Preparation of (1S,2R)-2-{[4-({[(1S,2R)-1-Ammonio-2,3-dihydro-1H-inden-2-yl]oxy}methyl)benzyl]oxy}-2,3-dihydro-1H-inden-1-ammonium dichloride (6g)

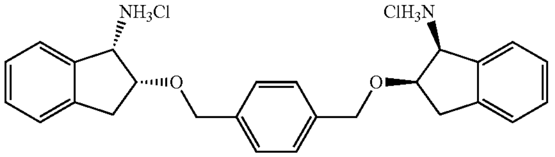

The compound was prepared according to general procedure A. Colorless solid, yield 51 mg (81%). LC-MS: m/z=401.00 (calcd. 401.22 for $C_{26}H_{29}N_2O_2^+[M+H^+]$).

Example 28. Preparation of (1S,2R)-2-{2-[(2-{[(1S,2R)-1-Ammonio-2,3-dihydro-1H-inden yl]oxy}ethyl)sulfonyl]ethoxy}-2,3-dihydro-1H-inden-1-ammonium dichloride (6h)

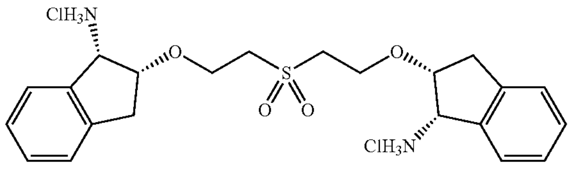

The compound was prepared according to general procedure A. Colorless solid, yield 104 mg (87%). LC-MS: m/z=417.35 (calcd. 417.18 for $C_{22}H_{29}N_2O_4S$+[M+H$^+$]).

Synthetic Scheme for the Preparation of Diamine 6i

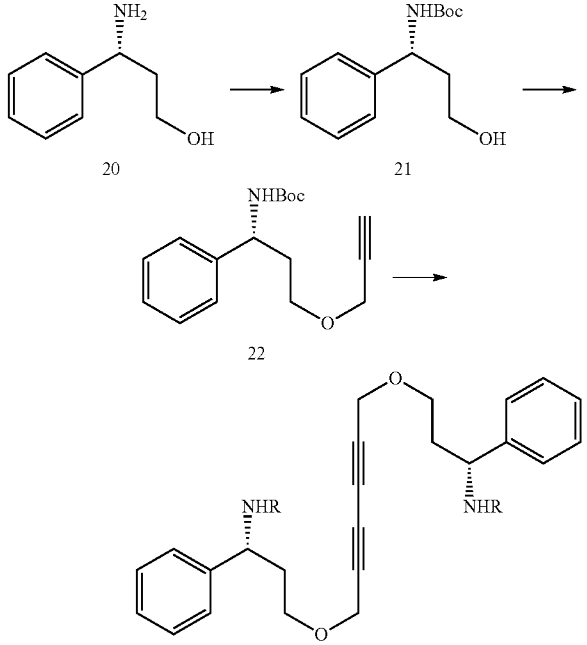

20

21

22

5i, R = Boc → 6i, R = $H_2Cl$

Example 29. Preparation of tert-Butyl [(1R)-3-hydroxy-1-phenylpropyl]carbamate (21)

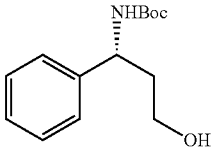 [SMILES: CC(C)(C)OC(=O)N[C@H](CCO)c1ccccc1]

The compound 21 was prepared according to the established literature procedure; see Barnes, D.; Bebernitz, G. R.; Cohen, S. L.; Damon, R. E.; Day, R. F.; Jain, M.; Karki, R. G.; Kirman, L. C.; Patel, T. J.; Raymer, B. K.; Schuster, H. F.; Zhang, W. Application: WO 2011067306 A1

Example 30. Preparation of tert-Butyl [(1R)-1-phenyl-3-(prop-2-yn-1-yloxy)propyl]carbamate (22)

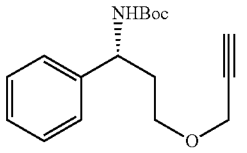 [SMILES: C#CCOCC[C@@H](NC(=O)OC(C)(C)C)c1ccccc1]

Under $N_2$ atmosphere, Propargyl bromide in toluene (80%, 106 μL, 0.955 mmol, 1.20 eq.) was added to a solution of alcohol 21 (200 mg, 0.796 mmol, 1.00 eq) dissolved in dry DMF (1.6 mL) at 0° C. The solution was treated with powdered KOH (92 mg, 1.63 mmol, 2.05 eq) and stirred at 0° C. for 1.5 h. Upon completion, water (10 mL) was added to the mixture and extracted with ethyl acetate (4×10 mL). The combined organic layers were washed with water (2×10 mL), brine (10 mL), dried ($Na_2SO_4$) and concentrated in vacuo. The resulting residue was purified by fc (hexane/ethyl acetate). Colorless solid, yield 147 mg (64%). $R_f$=0.56 (hexanes/ethyl acetate 8:2). $^1$H NMR (400 MHz, $CDCl_3$): δ (ppm)=1.41 (s, 9H), 2.04 (dq, 2H), 2.38-2.41 (m, 1H), 3.49 (q, 2H), 4.11 (s, 1H), 4.11-4.16 (m, 1H), 4.84 (s, 1H), 5.30 (s, 1H), 7.19-7.37 (m, 5H). LC-MS: m/z=289.90 (calcd. 290.18 for $C_{17}H_{24}NO_3^+$[M+H$^+$]).

Example 31. Preparation of tert-Butyl N-[(1R)-3-({6-[(3R)-3-{[(tert-butoxy)carbonyl]amino}phenylpropoxy]hexa-2,4-diyn-1-yl}oxy)-1-phenylpropyl]carbamate (5i)

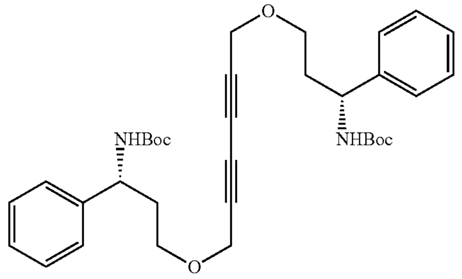 [SMILES: CC(C)(C)OC(=O)N[C@H](CCOCC#CC#CCOCC[C@@H](NC(=O)OC(C)(C)C)c1ccccc1)c1ccccc1]

Copper (II) acetate (96 mg, 0.530 mmol, 1.15 eq.) was added to a solution of alkyne 22 (133 mg, 0.461 mmol, 1.00 eq.) in acetonitrile (4.1 mL) and pyridine (220 μL, 2.74 mmol, 5.94 eq.). The resulting solution was placed in an oil bath preheated to 80° C. and stirred for 1 h. Upon completion, all volatiles were removed under reduced pressure, aqueous $NH_4OH$ solution (3%, 10 mL) was added to the residue and extracted with ethyl acetate (3×10 mL). The combined organic layers were washed with water (10 mL), brine (10 mL), dried ($Na_2SO_4$) and concentrated in vacuo. The resulting residue was purified by fc (hexanes/ethyl acetate). Colorless solid, yield 112 mg (42%). $R_f$=0.33 (hexanes/ethyl acetate 8:2). $^1$H NMR (400 MHz, $CDCl_3$): δ (ppm)=1.40 (s, 18H), 1.91-2.13 (m, 4H), 3.38-3.56 (m, 4H), 4.09-4.26 (m, 4H), 4.83 (s, 2H), 5.27 (s, 2H), 7.31 (td, 10H). LC-MS: m/z=577.20 (calcd. 577.33 for $C_{34}H_{45}N_2O_6^+$[M+H$^+$]).

Example 32. Preparation of (1R)-3-[(6-{[(3R)-3-Ammonio-3-phenylpropyl]oxy}hexa-2,4-diyn-1-yl)oxy]-1-phenylpropan-1-ammonium dichloride (6i)

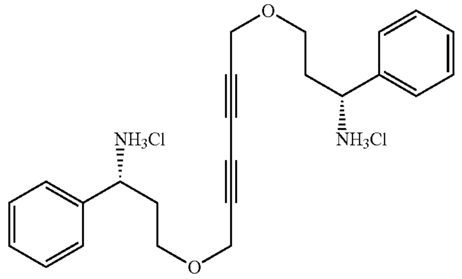

The compound was prepared according to general procedure A. Colorless solid, yield 68 mg (90%). LC-MS: m/z=377.35 (calcd. 377.22 for $C_{24}H_{29}N_2O_2^+[M+H^+]$).

Synthetic Scheme for the Preparation of Diamine 6j

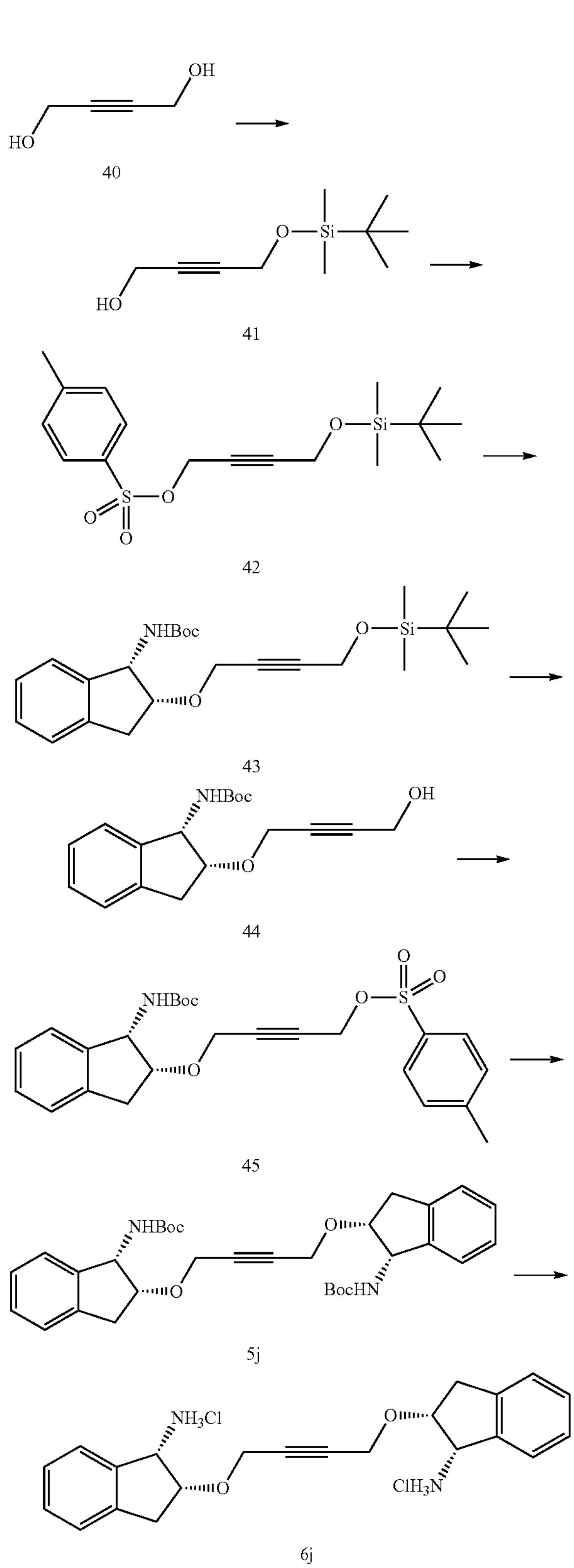

40

41

42

43

44

45

5j

6j

Example 33: Preparation of 4-[(tert-Butyldimethylsilyl)oxy]but-2-yn-1-ol (41)

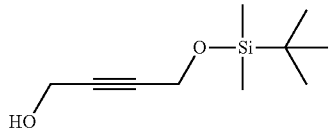

The compound 41 was prepared according to the established literature procedure; see Zbieg, J. R.; McInturff, E. L.; Leung, J. C.; Krische, M. J. *J. Am. Chem. Soc.* 2011, 133 (4), 1141-1144.

Example 34: Preparation of 4-[(tert-Butyldimethylsilyl)oxy]but-2-yn-1-yl 4-methylbenzene-1-sulfonate (42)

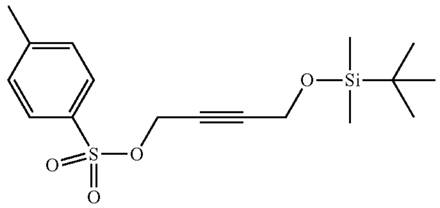 [SMILES: Cc1ccc(S(=O)(=O)OCC#CCO[Si](C)(C)C(C)(C)C)cc1]

The compound 42 was prepared according to the established literature procedure; see Köpfer, A.; Breit, B. *Angew. Chem.* 2015, 54 (23), 6913-6917.

Example 35: Preparation of tert-Butyl [(1S,2R)-2-({4-[(tert-butyldimethylsilyl)oxy]but-2-yn-1-yl}oxy)-2,3-dihydro-1H-inden-1-yl]carbamate (43)

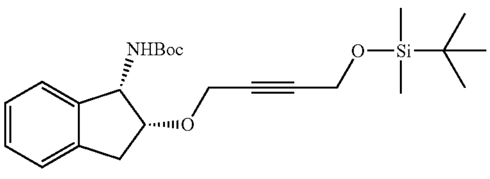 [SMILES: CC(C)(C)OC(=O)N[C@H]1c2ccccc2C[C@H]1OCC#CCO[Si](C)(C)C(C)(C)C]

Under $N_2$ atmosphere, alcohol 2 (70 mg, 0.281 mmol, 1.00 eq.) was dissolved in dry DMF (567 μL) and the solution was cooled down to 0° C. Tosylate 42 (110 mg, 0.309 mmol, 1.10 eq.) was added. The resulting solution was treated with powdered KOH (32 mg, 0.576 mmol, 2.05 eq.) and stirring was continued at 0° C. After 2 h, water (10 mL) was added and the resulting mixture was extracted with ethyl acetate (4×10 mL). The combined organic layers were washed with water (2×10 mL) and brine (10 mL), dried ($Na_2SO_4$) and concentrated in vacuo. The residue was purified by fc (hexanes/ethyl acetate). Yellow resin, yield 61 mg (50%). NMR (400 MHz, $CDCl_3$): δ (ppm)=0.11 (s, 6H), 0.90 (s, 9H), 1.50 (s, 9H), 2.99 (d, 1H), 3.07 (d, 1H), 4.22-4.26 (m, 2H), 4.35 (dd, 2H), 4.42-4.48 (m, 1H), 5.15-5.30 (m, 2H), 7.20 (s, 3H), 7.29-7.36 (m, 1H). LC-MS: m/z=454.20 (calcd. 454.24 for $C_{24}H_{37}NNaO_4Si^+[M+Na^+]$).

Example 36: Preparation of tert-Butyl [(1S,2R)-2-[(4-hydroxybut-2-yn-1-yl)oxy]-2,3-dihydro-1H-inden-1-yl]carbamate (44)

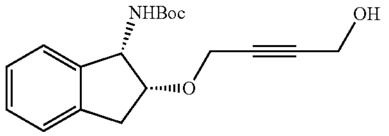 [SMILES: CC(C)(C)OC(=O)N[C@H]1c2ccccc2C[C@H]1OCC#CCO]

Compound 43 (60 mg, 0.139 mmol, 1.00 eq.) was dissolved in THF (153 μL) and TBAF in THF (1.00 M, 153 μL, 0.153 mmol, 1.10 eq.) was added. After the mixture was stirred for 16 h at rt, sat. $NH_4Cl$ solution (10 mL) was added and the resulting mixture was extracted with ethyl acetate (3x10 mL). The combined organic layers were washed with brine (10 mL), dried ($Na_2SO_4$) and concentrated in vacuo. The residue was purified by fc (hexanes/ethyl acetate, Ceric Ammonium Molybdate stain). Yellow resin, yield 32 mg (73%). $R_f$=0.36 (hexanes/ethyl acetate 7:3). 1H NMR (400 MHz, $CDCl_3$): δ (ppm)=1.50 (s, 9H), 3.02 (d, 2H), 4.18-4.30 (m, 4H), 4.45 (q, 1H), 5.16-5.23 (m, 1H), 5.28 (d, 1H), 7.17-7.25 (m, 3H), 7.28-7.36 (m, 1H). OH is not seen in the spectrum. LC-MS: m/z=339.95 (calcd. 340.15 for $C_{18}H_{23}NNaO_4^+$[M+Na$^+$]).

Example 37: Preparation of tert-Butyl [(1S,2R)-2-({4-[(4-methylbenzenesulfonyl)oxy]but-2-yn-1-yl}oxy)-2,3-dihydro-1H-inden-1-yl]carbamate (45)

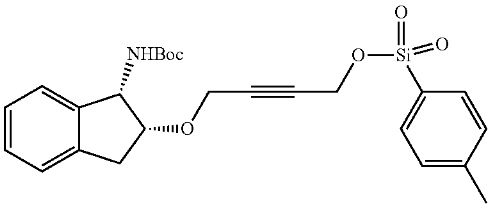

Alcohol 44 (85 mg, 0.267 mmol, 1.00 eq.) was dissolved in diethyl ether (415 μL) and the mixture was cooled down to 0° C. Tosyl chloride (71 mg, 0.373 mmol, 1.40 eq.) and powdered KOH (80 mg, 1.43 mmol, 5.35 eq.) were added. After stirring for 1 h at rt, water (10 mL) was added and the resulting mixture was extracted with $CH_2Cl_2$ (3x10 mL). The combined organic layers were dried ($Na_2SO_4$) and concentrated in vacuo. The residue was purified by fc (hexanes/ethyl acetate, Ceric Ammonium Molybdate stain). Red resin, yield 84 mg (67%). $R_f$=0.33 (hexanes/ethyl acetate 8:2). $^1$H NMR (400 MHz, $CDCl_3$): δ (ppm)=1.50 (s, 9H), 2.43 (s, 3H), 2.91-3.04 (m, 2H), 4.12 (s, 2H), 4.30 (t, 1H), 4.73 (s, 2H), 5.15 (s, 2H), 7.16-7.24 (m, 3H), 7.28-7.36 (m, 3H), 7.74-7.85 (m, 2H). LC-MS: m/z=494.05 (calcd. 494.16 for $C_{25}H_{29}NNaO_6S$+[M+Na$^+$]).

Example 38: Preparation of tert-Butyl [(1S,2R)-2-[(4-{[(1S,2R)-1-{[(tert-butoxy)carbonyl]amino}-2,3-dihydro-1H-inden-2-yl]oxy}but-2-yn-1-yl)oxy]-2,3-dihydro-1H-inden-1-yl]carbamate (5j)

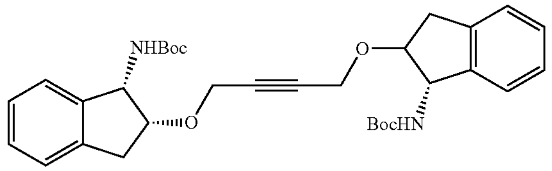 [SMILES: CC(C)(C)OC(=O)N[C@H]1c2ccccc2CC1OCC#CCO[C@@H]1Cc2ccccc2[C@@H]1NC(=O)OC(C)(C)C]

Under $N_2$ atmosphere, alcohol 2 (42 mg, 0.170 mmol, 1.20 eq.) was dissolved in dry DMF (560 μL) and the solution was cooled down to 0° C. Tosylate 45 (67 mg, 0.142 mmol, 1.00 eq.) was added. The resulting solution was treated with powdered KOH (16 mg, 0.291 mmol, 2.05 eq.) and stirring was continued at 0° C. After 2 h, water (10 mL) was added and the resulting mixture was extracted with ethyl acetate (4x10 mL). The combined organic layers were washed with water (10 mL) and brine (10 mL), dried ($Na_2SO_4$) and concentrated in vacuo. The residue was purified by fc (hexanes/ethyl acetate). White solid, yield 41 mg (53%). $R_f$=0.42 (hexanes/ethyl acetate 9:1, Ceric Ammonium Molybdate stain). $^1$H NMR (400 MHz, $CDCl_3$): δ (ppm)=1.50 (s, 18H), 3.01 (dd, 2H), 3.08 (dd, 2H), 4.27 (s, 4H), 4.44 (q, 2H), 5.04-5.28 (m, 4H), 7.18-7.24 (m, 6H), 7.30-7.35 (m, 2H). LC-MS: m/z=549.25 (calcd. 549.30 for $C_{32}H_{41}N_2O_6^+$[M+H$^+$]).

Example 39: Preparation of 1S,2R)-2-[(4-{[(1S, 2R)-1-(chloroamino)-2,3-dihydro-1H-inden-2-yl]oxy}but-2-yn-1-yl)oxy]-2,3-dihydro-1H-inden-1-ammonium dichloride (6j)

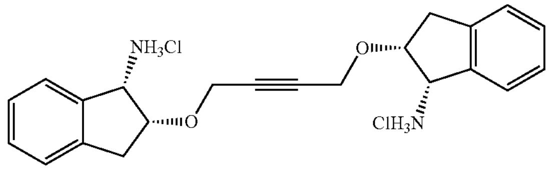

The compound was prepared according to general procedure A. White solid, yield 27 mg (86%). LC-MS: m/z=349.25 (calcd. 349.19 for $C_{22}H_{25}N_2O_2^+$[M+H$^+$]).

Synthetic Scheme for the Highly Stereoselective Preparation of Carboxylic Acids 14

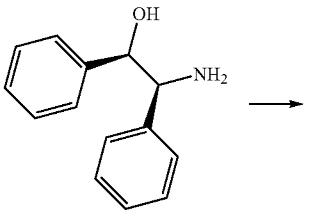

23

-continued
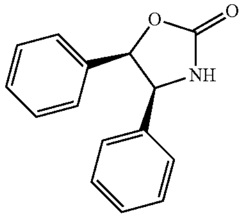
24
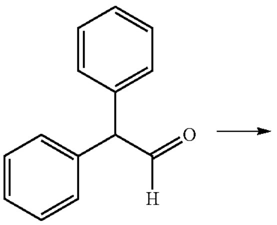
25
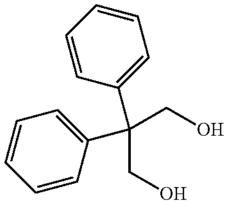
26
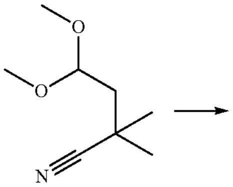
8
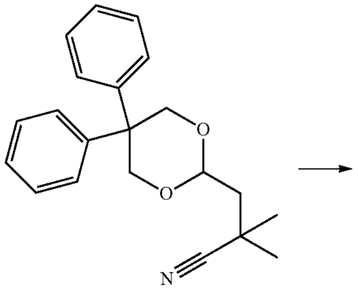
27
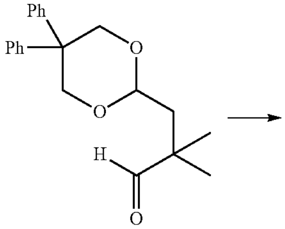
28
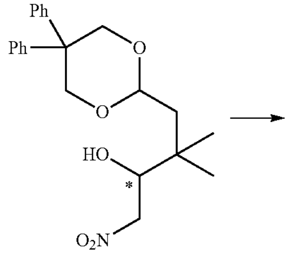
29
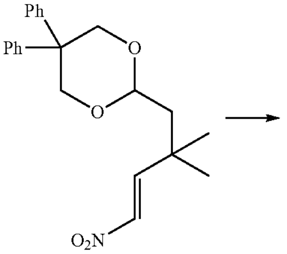
30
-continued
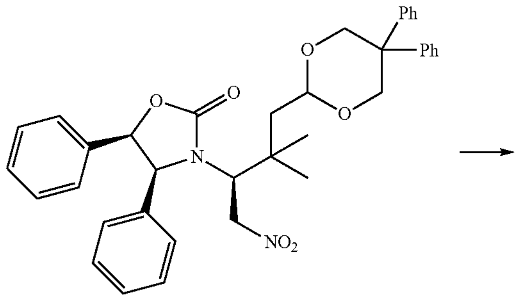
31
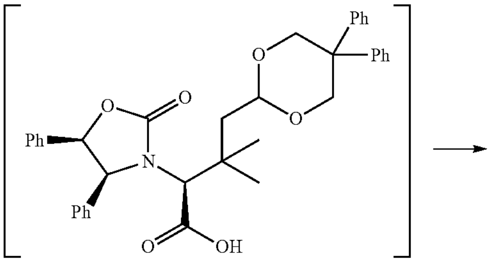
32
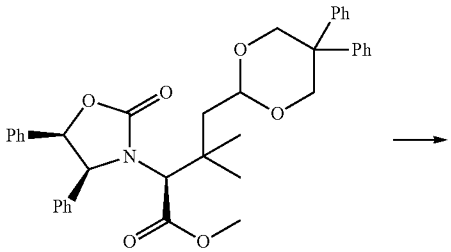
33
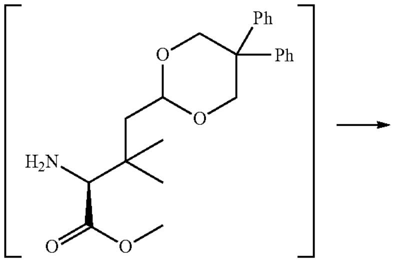
34
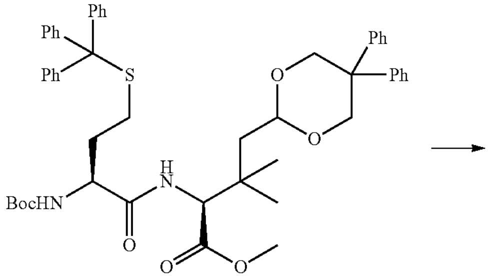
35

-continued

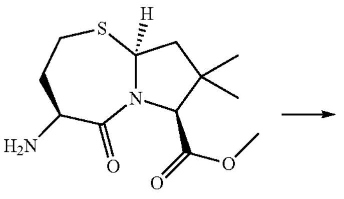

36

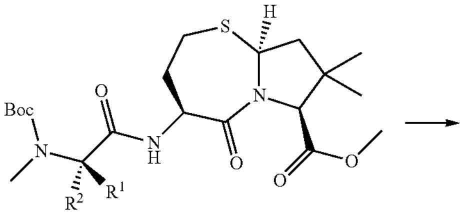

37a-c

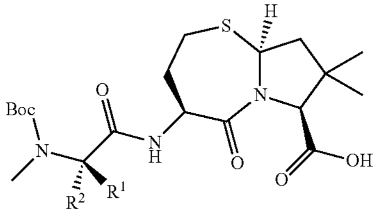

14a-c

| | $R^1$ | $R^2$ |
|---|---|---|
| a | H | $CH_3$ |
| b | $CH_3$ | $CH_3$ |
| c | H | Ethyl |

Example 40. Preparation of (4S,5R)-4,5-Diphenyl-1,3-oxazolidin-2-one (24)

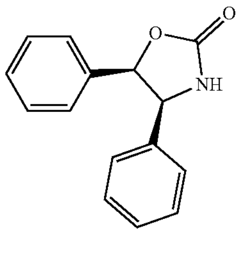 [SMILES: O=C1N[C@@H](c2ccccc2)[C@@H](c2ccccc2)O1]

The compound 24 was prepared according to the established literature procedure; see Akiba T.; Tamura O.; Terashima S. (4R,5S)-4,5-Diphenyl-3-vinyl-2-oxazolidinone, *Org. Synth.* 1998, 75, 45.

Example 41. Preparation of 2,2-Diphenylpropane-1,3-diol (26)

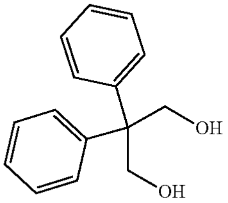 [SMILES: OCC(CO)(c1ccccc1)c1ccccc1]

The compound 26 was prepared according to the established literature procedure; see Sato T.; Onuma T.; Nakamura I.; Terada M. Platinum-Catalyzed Cycloisomerization of 1,4-Enynes via 1,2-Alkenyl Rearrangement, *Org. Lett.* 2011, 13, 4992-4995.

Example 42. Preparation of 3-(5,5-Diphenyl-1,3-dioxan-2-yl)-2,2-dimethylpropanenitrile (27)

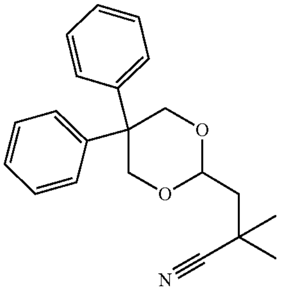 [SMILES: CC(C)(C#N)CC1OCC(c2ccccc2)(c2ccccc2)CO1]

To a mixture of dimethyl acetal 8 (9.08 g, 57.8 mmol, 1.05 eq.) and diol 26 (12.5 g, 55.0 mmol, 1.00 eq.) in $CH_2Cl_2$ (80 mL) was added camphor-10-sulfonic acid (1.28 g, 5.50 mmol, 0.10 eq.) portion wise at 0° C. The resulting mixture was stirred at 60° C. for 18 h. Afterwards, sat. $NaHCO_3$ solution was added (20 mL) and extracted with $CH_2Cl_2$ (3×50 mL). The organic layer was washed with water (50 mL) and brine (50 mL), dried ($Na_2SO_4$) and concentrated in vacuo. The resulting residue was purified by fc (petroleum ether/ethyl acetate). Colorless oil, yield 13.3 g (76%). $^1H$ NMR (400 MHz, $CDCl_3$): δ (ppm)=1.37 (s, 6H), 1.87 (d, 2H), 4.17-4.27 (m, 2H), 4.68-4.79 (m, 2H), 4.93 (t, 1H), 7.00-7.08 (m, 2H), 7.18-7.35 (m, 6H), 7.41-7.48 (m, 2H). LC-MS: m/z=322.20 (calcd. 322.18 for $C_{21}H_{24}NO_2^+$[M+H$^+$]).

Example 43. Preparation of 3-(5,5-Diphenyl-1,3-dioxan-2-yl)-2,2-dimethylpropanal (28)

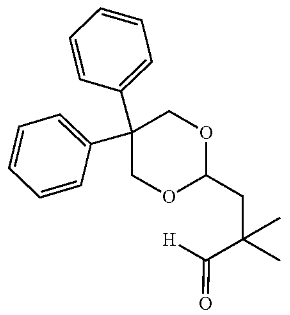 [SMILES: CC(C)(C=O)CC1OCC(c2ccccc2)(c2ccccc2)CO1]

Under $N_2$ atmosphere, DIBAL-H in hexanes (1 M, 123 mL, 124 mmol, 3.00 eq.) was added dropwise to a solution of nitrile 27 (13.2 g, 41.2 mmol, 1.00 eq.) in dry $CH_2Cl_2$ (200 mL) at −78° C. The mixture was stirred at 0° C. for 2 h. Afterwards, sat. potassium sodium tartrate solution (20 mL) was added and the mixture was stirred at rt for 1 h. After filtration through a Celite® pad, the filtrate was concentrated in vacuo. The resulting residue was purified by fc (petroleum ether/ethyl acetate). White solid, yield 8.01 g (60%). $^1H$ NMR (400 MHz, DMSO-D6): δ (ppm)=0.86-1.03 (m, 6H), 1.75 (d, 2H), 4.10 (d, 2H), 4.69-4.82 (m, 3H), 7.08-7.13 (m, 2H), 7.14-7.22 (m, 2H), 7.24-7.33 (m, 4H), 7.38-7.45 (m, 2H), 9.31 (s, 1H). LC-MS: m/z=325.20 (calcd. 325.18 for $C_{21}H_{25}O_3^+[M+H^+]$).

Example 44. Preparation of 4-(5,5-Diphenyl-1,3-dioxan-2-yl)-3,3-dimethyl-1-nitrobutan-2-ol (29)

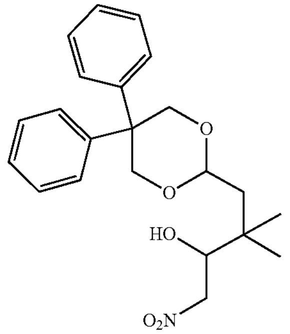 [SMILES: CC(C)(CC1OCC(c2ccccc2)(c2ccccc2)CO1)C(O)C[N+](=O)[O-]]

To a solution of aldehyde 28 (8.01 g, 24.7 mmol, 1.00 eq.) in nitromethane (30 mL, 560 mmol, 22.7 eq.) was added $NEt_3$ (10 mL, 71.7 mmol, 2.90 eq.) slowly at 0° C. The mixture was stirred at rt for 2 days. The reaction mixture was concentrated under reduced pressure. The resulting residue was purified by fc (petroleum ether/ethyl acetate). White solid, yield 9.04 g (95%). $^1H$ NMR (400 MHz, $CDCl_3$): δ (ppm)=0.93 (s, 3H), 1.03 (s, 3H), 1.54 (dd, 1H), 1.86 (dd, 1H), 3.41 (d, 1H), 4.14-4.28 (m, 3H), 4.32-4.47 (m, 2H), 4.75 (ddd, 2H), 4.86 (dd, 1H), 6.99-7.06 (m, 2H), 7.19-7.35 (m, 6H), 7.38-7.44 (m, 2H). LC-MS: m/z=386.20 (calcd. 386.20 for $C_{22}H_{28}NO_5^+[M+H^+]$).

Example 45. Preparation of 2-[(3E)-2,2-Dimethyl-4-nitrobut-3-en-1-yl]-5,5-diphenyl-1,3-dioxane (30)

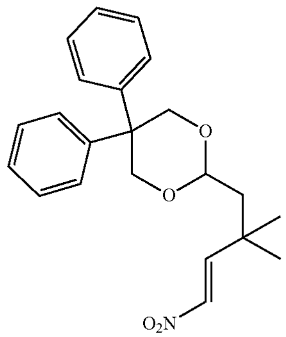 [SMILES: CC(C)(/C=C/[N+](=O)[O-])CC1OCC(c2ccccc2)(c2ccccc2)CO1]

To a solution of nitroaldol 29 (9.02 g, 23.4 mmol, 1.00 eq.) in $CH_2Cl_2$ (100 mL) was added Methanesulfonyl chloride (4.5 mL, 58.4 mmol, 2.50 eq.). The mixture was cooled to 0° C. and $NEt_3$ (14.2 mL, 105 mmol, 4.50 eq.) was added dropwise. The resulting mixture was stirred at rt for 2 h. Afterwards, water (40 mL) was added and extracted with $CH_2Cl_2$ (3×50 mL). The organic layer was washed with water (50 mL) and brine (50 mL), dried ($Na_2SO_4$) and concentrated in vacuo. The resulting residue was purified by fc (petroleum ether/ethyl acetate). White solid, yield 6.75 g (75%). $^1H$ NMR (400 MHz, $CDCl_3$): δ (ppm)=1.16 (s, 6H), 1.81 (d, 2H), 4.10-4.16 (m, 3H), 4.60-4.73 (m, 3H), 6.84 (d, 1H), 6.97-7.05 (m, 2H), 7.20-7.23 (m, 1H), 7.27-7.36 (m, 4H), 7.38-7.45 (m, 2H). LC-MS: m/z=368.20 (calcd. 368.19 for $C_{22}H_{26}NO_4^+[M+H^+]$).

Example 46. Preparation of (4S,5R)-3-[(2S)-4-(5,5-Diphenyl-1,3-dioxan-2-yl)-3,3-dimethyl-1-nitrobutan-2-yl]-4,5-diphenyl-1,3-oxazolidin-2-one (31)

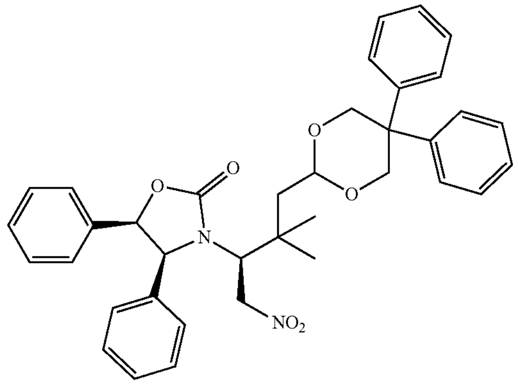 [SMILES: CC(C)(CC1OCC(c2ccccc2)(c2ccccc2)CO1)[C@@H](C[N+](=O)[O-])N1C(=O)O[C@H](c2ccccc2)[C@@H]1c1ccccc1]

Under $N_2$ atmosphere, KOtBu (3.05 g, 27.2 mmol, 1.60 eq.) was added portion wise to a suspension of oxazolidone 24 (6.51 g, 27.2 mmol, 1.60 eq.) and 18-crown-6 (7.18 g, 27.2 mmol, 1.60 eq.) in THF (240 mL) at 0° C. The mixture was stirred at 0° C. for 1 h. Afterwards, the mixture was cooled to −78° C. and nitroalkene 30 (6.24 g, 17.0 mmol, 1.00 eq.) in THF (50 mL) was added dropwise. The resulting mixture was stirred at −78° C. for 30 min before sat. $NH_4Cl$ solution (50 mL) was added. After the reaction mixture was warmed up to rt, the aqueous layer was extracted with ethyl acetate (3×100 mL). The combined organic layers were washed with water (50 mL) and brine (50 mL), dried ($Na_2SO_4$) and concentrated in vacuo. The resulting residue was purified by fc ($CH_2Cl_2$/ethyl acetate). White solid, yield 7.22 g (70%). $^1$H NMR (400 MHz, $CDCl_3$): δ (ppm)=1.00 (s, 3H), 1.14 (s, 3H), 1.64 (dd, 1H), 2.08 (dd, 1H), 3.97 (d, 1H), 4.23 (t, 1H), 4.41 (d, 1H), 4.63 (dd, 1H), 4.73 (dd, 1H), 4.76-4.85 (m, 2H), 4.92 (d, 1H), 5.23 (dd, 1H), 5.81 (d, 1H), 6.39 (d, 2H), 6.86-6.92 (m, 2H), 6.94-7.00 (m, 2H), 7.01-7.11 (m, 6H), 7.21-7.33 (m, 4H), 7.37-7.43 (m, 2H), 7.54-7.59 (m, 2H). LC-MS: m/z=607.25 (calcd. 607.28 for $C_{37}H_{39}N_2O_6^+[M+H^+]$).

Example 47. Preparation of (2S)-4-(5,5-Diphenyl-1,3-dioxan-2-yl)-3,3-dimethyl-2-((4S,5R)-2-oxo-4,5-diphenyl-1,3-oxazolidin-3-yl)butanoate (33)

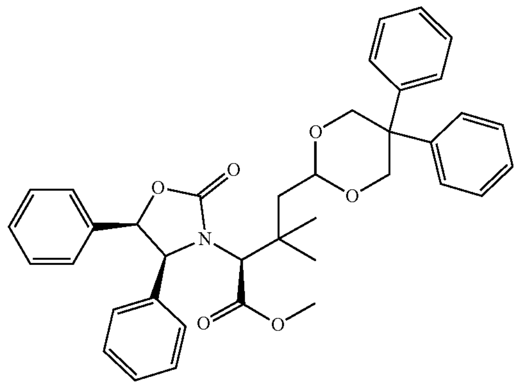 [SMILES: COC(=O)[C@@H](N1C(=O)O[C@H](c2ccccc2)[C@@H]1c1ccccc1)C(C)(C)CC1OCC(c2ccccc2)(c2ccccc2)CO1]

Under $N_2$ atmosphere, sodium nitrite (5.00 g, 72.5 mmol, 3.00 eq) and dry acetic acid (13.8 mL, 242 mmol, 10.0 eq) were added to a solution of nitro derivative 31 (14.6 g, 24.2 mmol, 1.00 eq) suspended in dry DMSO (60 mL). The resulting mixture was stirred at 35° C. for 7 h. Upon completion, citric acid solution (5%, 200 mL) was added and extracted with ethyl acetate (3×200 mL). The combined organic layers were washed with water (200 mL) and brine (150 mL), dried ($Na_2SO_4$) and concentrated in vacuo.

The crude carboxylic acid 32 was dissolved in dry DMF (28 mL) and cooled to 0° C. $K_2CO_3$ (3.68 g, 26.6 mmol, 1.10 eq) was added and stirred for 10 minutes. After $CH_3I$ (3.02 mL, 48.3 mmol, 2.00 eq) addition, stirring was continued at 0° C. for 30 min. Afterwards, the solution was stirred at rt for 12 h, at which point additional $K_2CO_3$ (3.68 g, 26.6 mmol, 1.10 eq) and $CH_3I$ (3.02 mL, 48.3 mmol, 2.00 eq) were added. After stirring for an additional 7 h, water (200 mL) was added and extracted with $CH_2Cl_2$ (3×200 mL). The combined organic layers were washed with water (200 mL), dried ($Na_2SO_4$) and concentrated in vacuo. The resulting residue was purified by fc (hexanes/ethyl acetate). Colorless solid, yield 13.3 g (89%). $R_f$=0.38 (hexanes/ethyl acetate 8:2). $^1$H NMR (400 MHz, $CDCl_3$): δ (ppm)=1.21 (s, 3H), 1.22 (s, 3H), 1.72 (dd, 1H), 1.94 (dd, 1H), 3.63 (s, 3H), 3.96 (d, 1H), 4.00 (s, 1H), 4.30 (d, 1H), 4.57 (dd, 1H), 4.72 (dd, 1H), 4.78 (dd, 1H), 5.08 (d, 1H), 5.83 (d, 1H), 6.91-7.09 (m, 11H), 7.20-7.31 (m, 5H), 7.37 (t, 2H), 7.52 (dt, 2H). LC-MS: m/z=606.15 (calcd. 606.29 for $C_{38}H_{40}NO_6^+[M+H^+]$).

Example 48. Preparation of Methyl (2S)-2-({(2S)-2-[(tert-butoxycarbonyl)amino]-4-(tritylsulfanyl)butanoyl}amino)-4-(5,5-diphenyl-1,3-dioxan-2-yl)-3,3-dimethylbutanoate (35)

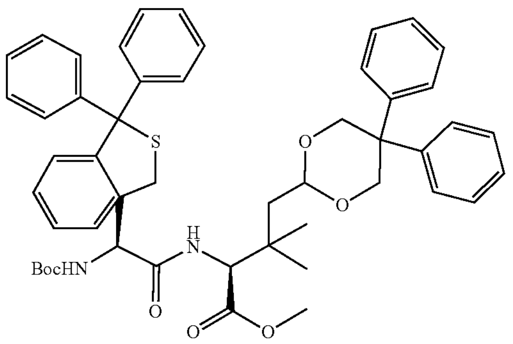

Pd/C (10%, matrix activated carbon support, Sigma Aldrich, 439 mg, 0.25 eq) was added to a solution of carbamate 33 (1.00 g, 1.65 mmol, 1.00 eq) in methanol (20 mL). Under $H_2$ atmosphere, the resulting mixture was stirred at 45° C. for 4 h. After Celite® filtration with methanol, all volatiles were removed in vacuo.

Under $N_2$ atmosphere, amine 34, carboxylic acid 7 (788 mg, 1.65 mmol, 1.00 eq), 1-Hydroxybenzotriazole hydrate (303 mg, 1.98 mmol, 1.20 eq.) and N-Methylmorpholine (546 μL, 4.95 mmol, 3.00 eq.) were dissolved in dry THF (5.9 mL) and cooled to 0° C. EDC·HCl (380 mg, 1.98 mmol, 1.20 eq) was added and the resulting mixture was stirred for 30 min at 0° C. followed by 14 h at rt. Upon completion, water (30 mL) was added and extracted with ethyl acetate (3×30 mL). The combined organic layers were washed with saturated $NaHCO_3$ solution (30 mL), citric acid solution (5%, 30 mL), water (30 mL) and brine (30 mL), dried ($Na_2SO_4$) and concentrated in vacuo. The resulting residue was purified by fc (hexanes/ethyl acetate). Colorless solid, yield 994 mg (71%). $R_f$=0.36 (hexanes/ethyl acetate 8:2). $^1$H NMR (400 MHz, $CDCl_3$): δ (ppm)=0.97 (s, 3H), 1.00 (s, 3H), 1.40 (s, 10H), 1.59 (dd, 1H), 1.69 (dd, 1H), 1.72-1.83 (m, 1H), 2.16-2.32 (m, 2H), 3.64 (s, 3H), 3.89-3.99 (m, 1H), 4.18 (d, 1H), 4.22 (d, 1H), 4.46 (d, 1H), 4.57 (d, 1H), 4.69 (d, 2H), 4.78 (t, 1H), 6.88 (d, 1H), 7.02 (d, 2H), 7.19 (dd, 5H), 7.27 (q, 10H), 7.39 (d, 6H), 7.43 (d, 2H). LC-MS: m/z=865.40 (calcd. 865.39 for $C_{51}H_{58}N_2NaO_7S+[M+Na^+]$).

Example 49. Preparation of Methyl (4S,7S,9aS)-4-({(2S)-2-[(tert-butoxycarbonyl)(methyl)amino]propanoyl}amino)-8,8-dimethyl-5-oxooctahydropyrrolo[2,1-b][1,3]thiazepine-7-carboxylate (37a)

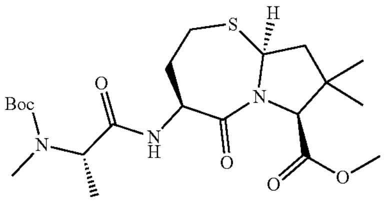

Compound 35 (1.21 g, 1.43 mmol, 1.00 eq.) was treated with HCl in dioxane (4 M, 7.2 mL, 28.7 mmol, 20.0 eq.) and stirred at 40° C. for 2 h. Upon completion, all volatiles were removed under reduced pressure.

Under $N_2$ atmosphere, the resulting amine 36, N-(tert-Butoxycarbonyl)-N-methyl-L-alanine (349 mg, 1.72 mmol, 1.20 eq.), 1-Hydroxybenzotriazole hydrate (263 mg, 1.72 mmol, 1.20 eq.) and 4-Methylmorpholine (473 µL, 3.00 eq.) were dissolved in dry DMF (6.7 mL) and cooled to 0° C. EDC·HCl (329 mg, 1.72 mmol, 1.20 eq.) was added and the resulting mixture was stirred for 30 minutes at 0° C. followed by 17 h at rt. Upon completion, water (30 mL) was added and extracted with ethyl acetate (3×30 mL). The combined organic layers were washed with NaOH solution (1M, 30 mL), citric acid solution (5%, 30 mL), water (30 mL) and brine (30 mL), dried ($Na_2SO_4$) and concentrated in vacuo. The resulting residue was purified by fc (hexanes/ethyl acetate). Colorless solid, yield 506 mg (77%). $R_f$=0.22 (hexanes/ethyl acetate 6:4, Ceric Ammonium Molybdate stain). $^1$H NMR (400 MHz, $CDCl_3$): δ (ppm)=1.09 (s, 3H), 1.13 (s, 3H), 1.33 (d, 3H), 1.45 (s, 9H), 1.84-1.95 (m, 1H), 2.00 (dd, 1H), 2.22-2.31 (m, 2H), 2.77 (s, 3H), 2.84 (ddd, 1H), 3.24 (ddd, 1H), 3.75 (s, 3H), 4.24 (s, 1H), 4.53 (dd, 1H), 4.70 (s, 1H, broad), 5.15 (t, 1H), 7.30 (s, 1H). LC-MS: m/z=458.10 (calcd. 458.23 for $C_{21}H_{36}N_3O_6S^+$[M+H$^+$]).

Example 50. Preparation of (4S,7S,9aS)-4-({(2S)-2-[(tert-Butoxycarbonyl)(methyl)amino]propanoyl}amino)-8,8-dimethyl-5-oxooctahydropyrrolo[2,1-b][1,3]thiazepine-7-carboxylic acid (14a)

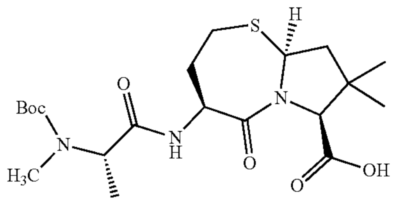

Lithium hydroxide solution (1 M, 2.21 mL, 2.21 mmol, 2.00 eq.) was added to a solution of the methyl ester 37a (506 mg, 1.11 mmol, 1.00 eq.) dissolved in THF (2.2 mL) at rt. The resulting emulsion was stirred at 40° C. for 15 h. Upon completion, $Et_2O$ (10 mL) was added and washed with a mixture of NaOH solution 1 M and brine (7:1, 3×8 mL). The combined aq. layers were extracted with ethyl acetate (10 mL) and the ethyl acetate layer was washed with a mixture of NaOH solution 1 M and brine (7:1, 2×8 mL). After acidification of the combined aq. layers with conc. HCl to pH 1, the aq. layer was extracted with $CH_2Cl_2$ (3×10 mL) and ethyl acetate (2×10 mL). The combined organic layers were dried ($Na_2SO_4$) and concentrated in vacuo. The resulting residue was purified by fc (hexanes/ethyl acetate/formic acid 0.2%). Colorless solid, yield 337 mg (69%). $R_f$=0.60 (hexanes/ethyl acetate/formic acid 3:7:0.1, Ceric Ammonium Molybdate stain).

Example 51. Preparation of Methyl (4S,7S,9aS)-4-({2-[(tert-butoxycarbonyl)(methyl)amino]-2-methylpropanoyl}amino)-8,8-dimethyl-5-oxooctahydropyrrolo[2,1-b][1,3]thiazepine-7-carboxylate (37b)

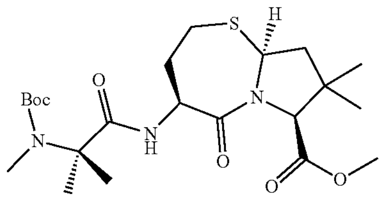

Compound 35 (250 mg, 0.297 mmol, 1.00 eq.) was treated with HCl in dioxane (4 M, 1.5 mL, 5.93 mmol, 20.0 eq.) and stirred at 40° C. for 2 h. Upon completion, all volatiles were removed under reduced pressure.

Under $N_2$ atmosphere, the resulting amine 36, N-(tert-Butoxycarbonyl)-N,2-dimethylalanine (77 mg, 0.356 mmol, 1.20 eq.), 1-Hydroxybenzotriazole hydrate (54 mg, 0.356 mmol, 1.20 eq.) and 4-Methylmorpholine (98 µL, 0.890 mmol, 3.00 eq.) were dissolved in dry DMF (1.4 mL) and cooled to 0° C. EDC·HCl (68 mg, 0.356 mmol, 1.20 eq.) was added and the resulting mixture was stirred for 30 minutes at 0° C. followed by 16 h at rt. Upon completion, water (10 mL) was added and extracted with ethyl acetate (3×10 mL). The combined organic layers were washed with sat. $NaHCO_3$ solution (10 mL), citric acid solution (5%, 10 mL), water (10 mL) and brine (10 mL), dried ($Na_2SO_4$) and concentrated in vacuo. The resulting residue was purified by fc (hexanes/ethyl acetate). Colorless solid, yield 57 mg (41%). Rf=0.42 (hexanes/ethyl acetate 6:4, Ceric Ammonium Molybdate stain). 1H NMR (400 MHz, CDCl3): δ (ppm)=1.09-1.13 (m, 6H, CHC(CH3)2), 1.36-1.42 (m, 15H), 1.79-1.91 (m, 1H), 2.03 (dd, 1H), 2.27 (dd, 1H), 2.34-2.42 (m, 1H), 2.83 (ddd, 1H), 2.89 (s, 3H), 3.28 (ddd, 1H), 3.76 (s, 3H), 4.23 (s, 1H), 4.52 (ddd, 1H), 5.18 (t, 1H), 7.13 (d, 1H). LC-MS: m/z=472.05 (calcd. 472.25 for $C_{22}H_{38}N_3O_6S^+$[M+H$^+$]).

Example 52. Preparation of (4S,7S,9aS)-4-({2-[(tert-Butoxycarbonyl)(methyl)amino]-2-methylpropanoyl}amino)-8,8-dimethyl-5-oxooctahydropyrrolo[2,1-b][1,3]thiazepine-7-carboxylic acid (14b)

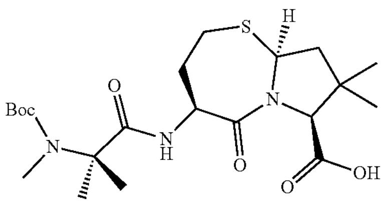

Lithium hydroxide solution (1 M, 375 µL, 0.375 mmol, 2.00 eq.) was added to a solution of the methyl ester 37b (88 mg, 0.187 mmol, 1.00 eq.) dissolved in THF (375 µL) at rt. The resulting emulsion was stirred at 40° C. for 17 h. Upon completion, $Et_2O$ (10 mL) was added and washed with a mixture of NaOH solution 1 M and brine (7:1, 3×8 mL). The combined aq. layers were extracted with ethyl acetate (10 mL) and the ethyl acetate layer was washed with a mixture of NaOH solution 1 M and brine (7:1, 2×8 mL). After acidification of the combined aq. layers with conc. HCl to pH 1, the aq. layer was extracted with $CH_2Cl_2$ (3×10 mL) and ethyl acetate (2×10 mL). The combined organic layers were dried ($Na_2SO_4$) and concentrated in vacuo. The resulting residue was purified by fc (hexanes/ethyl acetate/formic acid 0.2%). Colorless solid, yield 41 mg (48%). $R_f$=0.42 (hexanes/ethyl acetate/formic acid 6:4:0.1, Ceric Ammonium Molybdate stain). $^1H$ NMR (400 MHz, $CDCl_3$): δ (ppm)=1.14 (s, 3H), 1.19 (s, 3H), 1.35-1.41 (m, 15H), 1.84 (q, 1H), 2.00 (dd, 1H), 2.27 (dd, 1H), 2.32-2.40 (m, 1H), 2.77-2.84 (m, 1H), 2.89 (s, 3H), 3.27 (t, 1H), 4.20 (s, 1H), 4.59 (dd, 1H), 5.22 (t, 1H), 7.18 (d, 1H). COOH is not seen in the spectrum. LC-MS: m/z=458.10 (calcd. 458.23 for $C_{21}H_{36}N_3O_6S^+$[M+H$^+$]).

Example 53: Methyl (4S,7S,9aS)-4-[(2S)-2-{[(tert-butoxy)carbonyl](methyl)amino}butanamido]-8,8-dimethyl-5-oxo-octahydropyrrolo[2,1-b][1,3]thiazepine-7-carboxylate (37c)

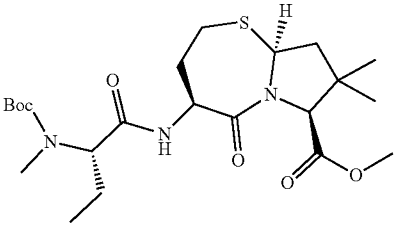

Compound 35 (406 mg, 0.481 mmol, 1.10 eq.) was treated with HCl in dioxane (4 M, 2.4 mL, 9.62 mmol, 20.0 eq.) and stirred at 40° C. for 2 h. Upon completion, all volatiles were removed under reduced pressure.

Under $N_2$ atmosphere, the resulting amine 36, (25)-2-{[(tert-Butoxy)carbonyl](methyl)amino}butanoic acid (95 mg, 0.437 mmol, 1.00 eq.), 1-Hydroxybenzotriazole hydrate (80 mg, 0.524 mmol, 1.20 eq.) and 4-Methylmorpholine (144 μL, 3.00 eq.) were dissolved in dry DMF (2.0 mL) and cooled to 0° C. EDC·HCl (101 mg, 0.524 mmol, 1.20 eq.) was added and the resulting mixture was stirred for 30 minutes at 0° C. followed by 20 h at rt. Upon completion, water (10 mL) was added and extracted with ethyl acetate (3×10 mL). The combined organic layers were washed with sat. $NaHCO_3$ solution (2×10 mL), citric acid solution (5%, 2×10 mL), water (10 mL) and brine (10 mL), dried ($Na_2SO_4$) and concentrated in vacuo. The resulting residue was purified by fc (hexanes/ethyl acetate). Colorless resin, quantitative yield. $^1H$ NMR (400 MHz, $CDCl_3$): δ (ppm)=0.89 (t, 3H), 1.09-1.16 (m, 6H), 1.47 (s, 9H), 1.66 (s, 1H), 1.86-2.04 (m, 3H), 2.27 (dd, 2H), 2.76 (s, 3H), 2.84 (d, 1H), 3.21-3.30 (m, 1H), 3.77 (s, 3H), 4.26 (s, 1H), 4.55 (dd, 1H), 5.16 (d, 1H), 7.34 (d, 1H). $CHCH_3$ is not seen in the spectrum. LC-MS: m/z=472.15 (calcd. 472.25 for $C_{22}H_{38}N_3O_6S^+$[M+H$^+$]).

Example 54: (4S,7S,9aS)-4-[(2S)-2-{[(tert-Butoxy)carbonyl](methyl)amino}butanamido]-8,8-dimethyl-5-oxo-octahydropyrrolo[2,1-b][1,3]thiazepine-7-carboxylic acid (14c)

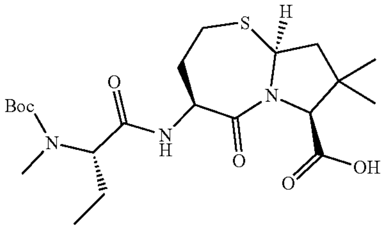

Lithium hydroxide solution (1 M, 848 μL, 0.848 mmol, 2.00 eq.) was added to a solution of the methyl ester 37c (200 mg, 0.424 mmol, 1.00 eq.) dissolved in THF (848 μL) at rt. The resulting emulsion was stirred at 40° C. for 39 h. After 16 h and 22 h, lithium hydroxide monohydrate (18 mg, 0.424 mmol, 1.00 eq.) was added, respectively. Upon completion, $Et_2O$ (12 mL) was added and washed with a mixture of NaOH solution 1 M and brine (10:2, 3×12 mL). The combined aq. layers were extracted with $Et_2O$ (12 mL) and the $Et_2O$ layer was washed with a mixture of NaOH solution 1 M and brine (10:2, 2×12 mL). After acidification of the combined aq. layers with conc. HCl to pH 1, the aq. layer was extracted with $CH_2Cl_2$ (3×10 mL) and ethyl acetate (2×10 mL). The combined organic layers were dried ($Na_2SO_4$) and concentrated in vacuo. The resulting residue was purified by fc (hexanes/ethyl acetate/formic acid 0.2%). Colorless resin, yield 134 mg (69%). $^1H$ NMR (400 MHz, $CDCl_3$): δ (ppm)=0.88 (t, 3H), 1.17 (s, 3H), 1.20 (s, 3H), 1.47 (s, 9H), 1.66 (s, 1H), 1.87-2.03 (m, 3H), 2.21-2.32 (m, 2H), 2.77 (s, 3H), 2.79-2.87 (m, 1H), 3.24 (t, 1H), 4.25 (s, 1H), 4.49-4.67 (m, 2H), 5.21 (t, 1H), 7.38 (d, 1H). COOH is not seen in the spectrum. LC-MS: m/z=458.20 (calcd. 458.23 for $C_{21}H_{36}N_3O_6S^+$[M+H$^+$]).

Synthetic Scheme for the Preparation of Aldehyde 47

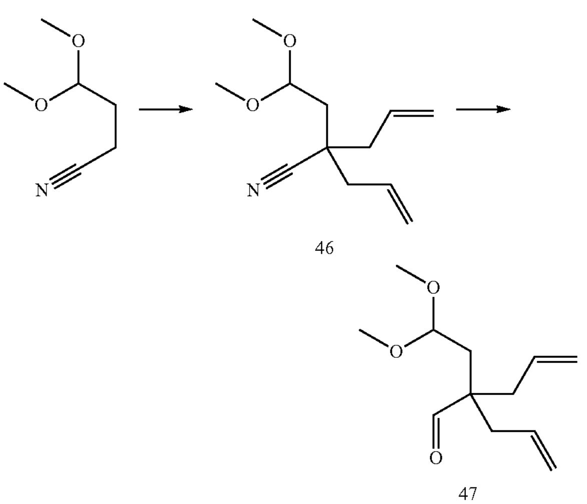

46

47

Example 55: 2-(2,2-Dimethoxyethyl)-2-(prop-2-en-1-yl)pent-4-enenitrile (46)

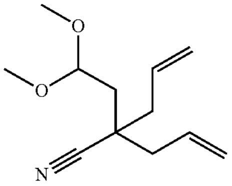

Under $N_2$ atmosphere, LDA in THF/heptane/ethylbenzene (2 M, 34.1 mL, 68.1 mmol, 2.20 eq.) was added dropwise to a solution of 4,4-Dimethoxybutanenitrile at −78° C. After 30 min, allyl bromide (6.70 mL, 77.4 mmol, 2.50 eq.) was slowly added at −78° C. After stirring at −78° C. for 1 h, stirring was continued for 16 h at rt. The mixture was carefully poured in a sat. solution of $NH_4Cl$ (300 mL) and extracted with $CH_2Cl_2$ (3×200 mL). The organic layer was dried ($Na_2SO_4$) and concentrated in vacuo. The residue was purified by fc (hexanes/ethyl acetate). Colorless liquid, yield 3.41 mg (53%). $R_f$=0.65 (hexane/ethyl acetate 8:2, $KMnO_4$ stain). $^1H$ NMR (400 MHz, $CDCl_3$): δ (ppm)=1.85 (d, 2H), 2.36-2.42 (m, 4H), 3.37 (s, 6H), 4.63 (t, 1H), 5.20 (dq, 2H), 5.25 (ddt, 2H), 5.78-5.90 (m, 2H, —CH═$CH_2$). LC-MS: m/z=210.10 (calcd. 210.15 for $C_{12}H_{20}NO_2^+$[M+$H^+$]).

Example 56: 2-(2,2-Dimethoxyethyl)-2-(prop-2-en-1-yl)pent-4-enal (47)

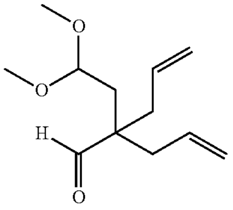

Under $N_2$ atmosphere, DIBAL-H in hexanes (1 M, 6.21 mL, 6.21 mmol, 1.30 eq.) was added dropwise to a solution of nitrile 46 (1.00 g, 4.78 mmol, 1.00 eq.) in dry $CH_2Cl_2$ (1.00 mL) at −78° C. over 45 min. After stirring at −78° C. for 2 h, stirring was continued for 2 h at 0° C. Afterwards, sat. $NH_4Cl$ solution (7.5 mL), sat. potassium sodium tartrate solution (11 mL) and $Et_2O$ (35 mL) were added and the mixture was stirred at rt for 1 h. After filtration through a Celite® pad, the organic solvents were removed in vacuo. The aqueous phase was extracted with $CH_2Cl_2$ (3×30 mL). The combined organic layers were washed with brine (30 mL), dried ($Na_2SO_4$) and concentrated in vacuo. The resulting residue was purified by fc (cyclohexane/ethyl acetate). Colorless liquid, yield 0.766 g (76%). $R_f$=0.65 (hexane/ethyl acetate 8.5:1.5, $KMnO_4$ stain). 1H NMR (400 MHz, $CDCl_3$): δ (ppm)=1.87 (d, 2H), 2.20 (ddt, 2H), 2.35 (ddt, 2H), 3.30 (s, 6H), 4.39 (t, 1H), 5.07-5.12 (m, 2H), 5.13 (tq, 2H), 5.70 (dddd, 2H), 9.42 (s, 1H). LC-MS: m/z=181.00 (calcd. 181.12 for $C_{11}H_{17}O_2^+$[M−$H_3$C−$O^-$]).

Synthetic Scheme for the Preparation of Carboxylic Acid 14d

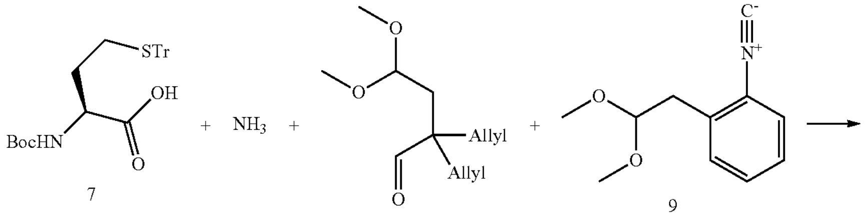

7

47

9

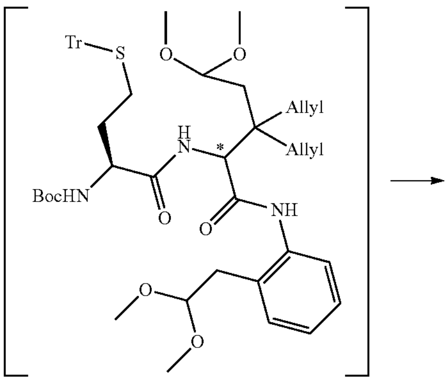

48

-continued

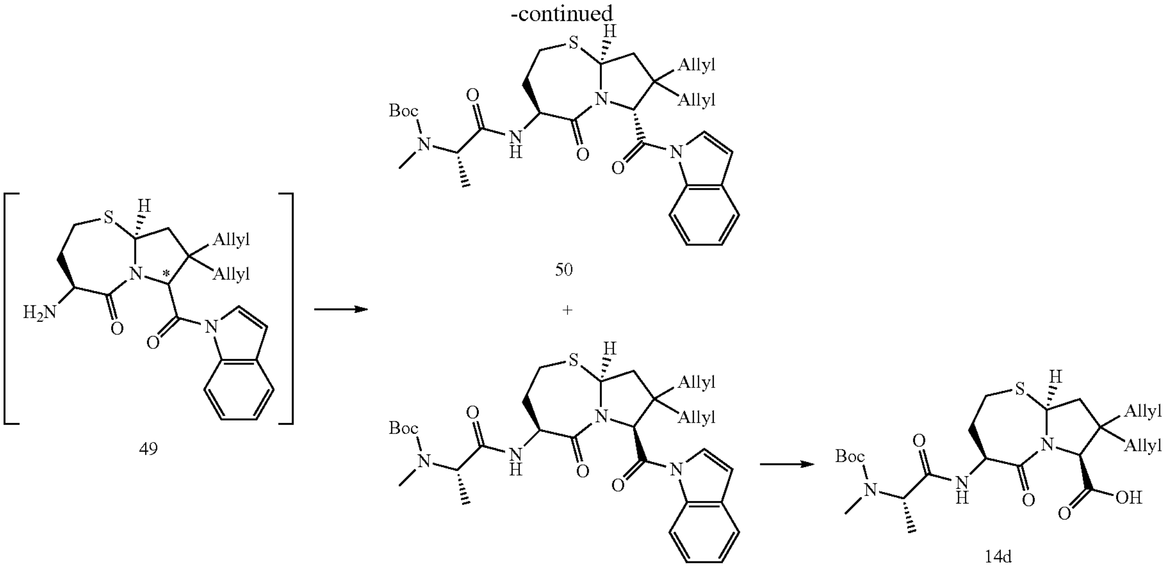

49 50 + 51 14d

Example 57: tert-Butyl N-[(1S)-1-{[(4S,7S,9aS)-7-(1H-indole-1-carbonyl)-5-oxo-8,8-bis(prop-2-en-1-yl)-octahydropyrrolo[2,1-b][1,3]thiazepin-4-yl] carbamoyl}ethyl]-N-methylcarbamate (51)

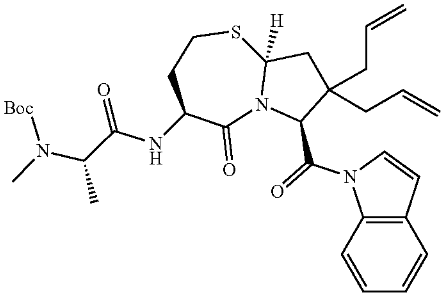 [SMILES: C=CCC1(CC=C)C[C@@H]2SCC[C@H](NC(=O)[C@H](C)N(C)C(=O)OC(C)(C)C)C(=O)N2[C@@H]1C(=O)n1ccc2ccccc21]

A mixture of N-(tert-butoxycarbonyl)-S-trityl-L-homocysteine (2.00 g, 4.19 mmol, 1.00 eq.), aldehyde 47 (888 mg, 4.19 mmol, 1.00 eq.), 1-(2,2-Dimethoxyethyl)-2-isocyanobenzene 9 (800 mg, 4.19 mmol, 1.00 eq.) and $NH_3$ in MeOH (7 M, 1.20 mL, 8.37 mmol, 2.00 eq.) in 2,2,2-trifluoroethanol (3.4 mL) was stirred under microwave irradiation at 80° C. After 30 min, all volatiles were removed under reduced pressure.

The residue was treated with HCl in dioxane (4 M, 10.5 mL, 41.8 mmol, 10.0 eq.) for 2 h at 40° C. Afterwards, all volatiles were removed under reduced pressure.

The amine 49, N-(tert-butoxycarbonyl)-N-methyl-L-alanine (1.02 g, 5.02 mmol, 1.20 eq.), 1-Hydroxybenzotriazole hydrate (931 mg, 5.44 mmol, 1.30 eq.) and N-Methylmorpholine (1.38 mL, 12.6 mmol, 3.00 eq.) were dissolved in dry THF (20 mL) and cooled down to 0° C. EDC·HCl (1.04 g, 5.44 mmol, 1.30 eq.) was added. After stirring at 0° C. for 30 min, stirring was continued for 16 h at rt. All volatiles were removed in vacuo and the residue was dissolved in ethyl acetate (150 mL). The organic layer was washed with NaOH solution (1 M, 50 mL), HCl solution (1 M, 50 mL), water (50 mL) and brine (25 mL), dried ($Na_2SO_4$) and concentrated in vacuo. The residue was purified by fc (hexanes/ethyl acetate).

Isomer 1: Yellowish solid, yield 617 mg (25%). $R_f$=0.63 (hexanes/ethyl acetate 6:4).

Isomer 2: Brown solid, yield 868 mg (35%). $R_f$=0.49 (hexanes/ethyl acetate 6:4). $^1$H NMR (400 MHz, $CDCl_3$): δ (ppm)=1.33 (d, 3H), 1.42 (s, 9H), 1.91-2.01 (m, 2H), 2.08-2.21 (m, 2H), 2.24-2.36 (m, 3H), 2.43 (dd, 1H), 2.70-2.92 (m, 4H), 3.29 (ddd, 1H), 4.61 (ddd, 1H), 4.92 (dd, 1H), 4.98 (dd, 1H), 5.18-5.25 (m, 2H), 5.31-5.36 (m, 2H), 5.53-5.65 (m, 1H), 5.82-5.95 (m, 1H), 6.68 (d, 1H), 7.27-7.36 (m, 3H), 7.56 (d, 1H), 7.62 (d, 1H), 8.57 (d, 1H). $CHCH_3$ is not seen in the spectrum. LC-MS: m/z=595.20 (calcd. 595.25 for $C_{32}H_{43}N_4O_5S^+$[M+H$^+$]).

Example 58: (4S,7S,9aS)-4-[(2S)-2-{[(tert-Butoxy) carbonyl](methyl)amino}propanamido]-5-oxo-8,8-bis(prop-2-en-1-yl)-octahydropyrrolo[2,1-b][1,3] thiazepine-7-carboxylic acid (14d)

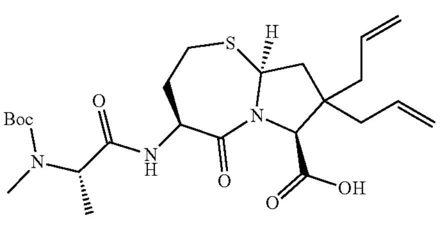 [SMILES: C=CCC1(CC=C)C[C@@H]2SCC[C@H](NC(=O)[C@H](C)N(C)C(=O)OC(C)(C)C)C(=O)N2[C@@H]1C(=O)O]

The indole amide 51 (250 mg, 0.420 mmol, 1.00 eq.) was dissolved in methanol (5.0 mL) and aq. NaOH (1 M, 1.26 mL, 1.26 mmol, 3.00 eq.) was added. After the resulting mixture was stirred for 3 h at 30° C., the methanol was removed in vacuo. $Et_2O$ (10 mL) was added and washed with NaOH solution (1 M, 3x15 mL). After the combined NaOH layers were extracted with $Et_2O$ (2x10 mL), the aqueous layer was acidified with conc. HCl to pH 1. and extracted with $CH_2Cl_2$ (2x10 mL, 1x20 mL) and EtOAc (1×20 mL). The combined org. layers were dried ($Na_2SO_4$) and concentrated in vacuo. The residue was purified by fc (hexanes/ethyl acetate with 0.2% HCOOH). Colorless solid, yield 81 mg (39%). $^1H$ NMR (400 MHz, $CDCl_3$): δ (ppm)= 1.35 (d, 3H), 1.46 (s, 9H), 1.92 (q, 1H), 2.01 (dd, 1H), 2.15 (dd, 3H), 2.23-2.31 (m, 1H), 2.37 (dd, 2H), 2.75-2.87 (m, 4H), 3.18-3.31 (m, 1H), 3.71 (s, 1H), 4.49 (s, 1H), 4.58 (dd, 1H), 5.05-5.22 (m, 5H), 5.67-5.86 (m, 2H), 7.37 (s, 1H). LC-MS: m/z=496.20 (calcd. 496.25 for $C_{24}H_{38}N_3O_6S^+$[M+$H^+$]).

Synthetic Scheme for the Preparation of Carboxylic Acid 14e

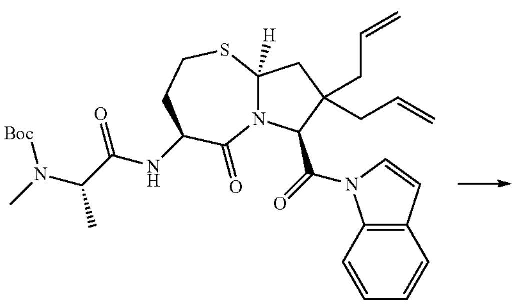

51

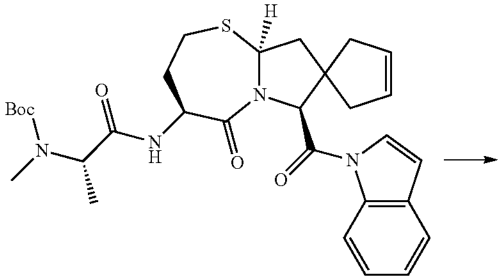

52

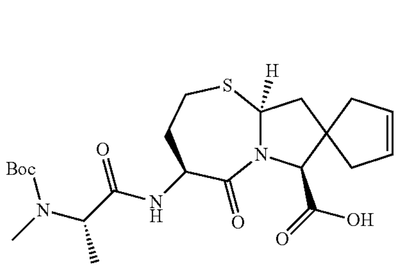

14e

Example 59: tert-Butyl N-[(1S)-1-{[(4'S,7'S,9'aS)-7'-(1H-indole-1-carbonyl)-5'-oxo-3',4',5',7',9',9'a-hexahydro-2'H-spiro[cyclopentane-1,8'-pyrrolo[2,1-b][1,3]thiazepin]-3-en-4'-yl]carbamoyl}ethyl]-N-methylcarbamate (52)

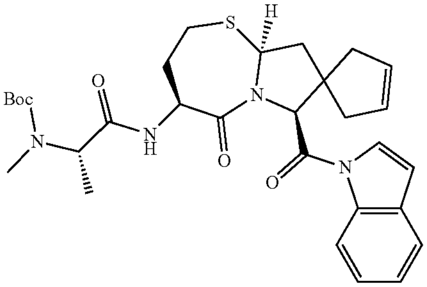 [SMILES: C[C@@H](C(=O)N[C@H]1CCS[C@H]2CC3(CC=CC3)[C@@H](C(=O)n3ccc4ccccc43)N2C1=O)N(C)C(=O)OC(C)(C)C]

Under $N_2$ atmosphere, Grubbs Catalyst® 1st Generation (71 mg, 0.086 mmol, 0.125 eq.) was added to a solution of indole 51 in dry 1,2-dichloroethane (5.78 mL) and the resulting mixture was stirred for 4 days at reflux. After 4 h, 8 h, 23 h, 27 h, 39 h, 51 h, 63 h, 75 h and 87 h Grubbs Catalyst® 1st Generation (71 mg, 0.086 mmol, 0.125 eq.) was added, respectively. All volatiles were removed in vacuo and the resulting residue was purified by fc (hexanes/ethyl acetate).

Isomer 1: Brown solid, yield 37 mg (10%). $R_f$=0.33 (hexanes/ethyl acetate 6:4).

Isomer 2: Brown solid, yield 86 mg (22%). $R_f$=0.21 (hexanes/ethyl acetate 6:4). $^1H$ NMR (400 MHz, $CDCl_3$): δ (ppm)=1.34 (d, 3H), 1.44 (s, 9H), 1.68 (s, 2H), 1.95 (q, 1H), 2.18-2.29 (m, 2H), 2.42 (s, 2H), 2.50-2.63 (m, 2H), 2.76 (s, 3H), 2.85-2.93 (m, 1H), 3.30 (dd, 1H), 4.61 (d, 1H), 5.20-5.26 (m, 2H), 5.60-5.65 (m, 1H), 5.69-5.75 (m, 1H), 6.66 (t, 1H), 7.32 (ddtd, 3H), 7.57 (d, 1H), 7.61 (d, 1H), 8.56 (d, 1H). LC-MS: m/z=567.25 (calcd. 567.26 for $C_{30}H_{39}N_4O_5S^+$ [M+$H^+$]).

Example 60: (4'S,7'S,9'aS)-4'-(2-{[(tert-Butoxy)carbonyl](methyl)amino}acetamido)-5'-oxo-3',4',5',7',9',9'a-hexahydro-2'H-spiro[cyclopentane-1,8'-pyrrolo[2,1-b][1,3]thiazepin]-3-ene-7'-carboxylic acid (14e)

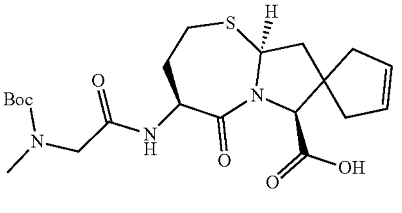 [SMILES: CN(CC(=O)N[C@H]1CCS[C@H]2CC3(CC=CC3)[C@@H](C(=O)O)N2C1=O)C(=O)OC(C)(C)C]

The indole amide 52 (86 mg, 0.152 mmol, 1.00 eq.) was dissolved in methanol (1.84 mL) and aq. NaOH (1 M, 456 μL, 0.456 mmol, 3.00 eq.) was added. After the resulting mixture was stirred for 2 days at 40° C., the methanol was removed in vacuo. $Et_2O$ (10 mL) was added and washed with NaOH solution (1 M, 3x10 mL). After the combined NaOH layers were extracted with $Et_2O$ (2x10 mL), the aqueous layer was acidified with conc. HCl to pH 1. and extracted with $CH_2Cl_2$ (3x10 mL) and EtOAc (2x10 mL).

The combined org. layers were dried ($Na_2SO_4$) and concentrated in vacuo. The residue was purified by fc (hexanes/ethyl acetate with 0.2% HCOOH). Colorless solid, yield 48 mg (68%). $^1$H NMR (400 MHz, $CDCl_3$): δ (ppm)=1.34 (d, 3H), 1.45 (s, 9H), 1.93 (t, 1H), 2.15 (ddd, 1H), 2.22-2.36 (m, 4H), 2.46 (ddd, 1H), 2.73 (d, 1H), 2.79 (s, 3H), 3.25 (t, 1H), 4.46 (s, 1H), 4.63 (t, 1H), 5.18 (td, 1H), 5.60-5.66 (m, 1H), 5.68-5.74 (m, 1H), 7.40 (s, 1H).
Synthetic Scheme for the Preparation of Carboxylic Acid 14f
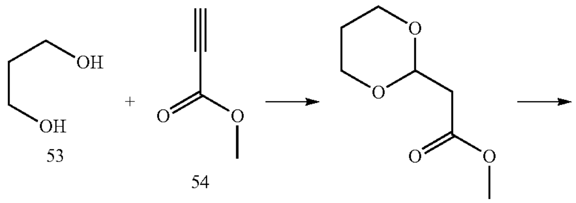
53 54 55
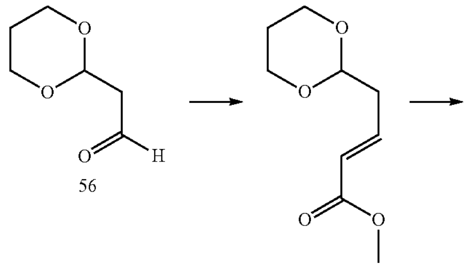
56 57
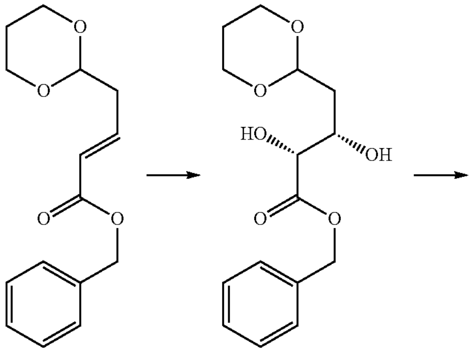
58 59
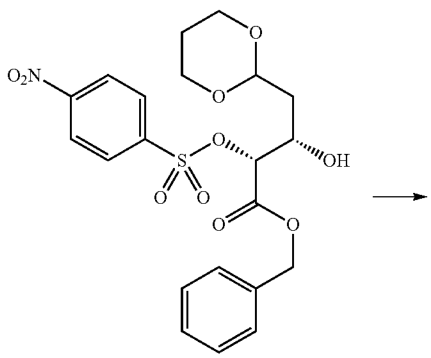
60
-continued
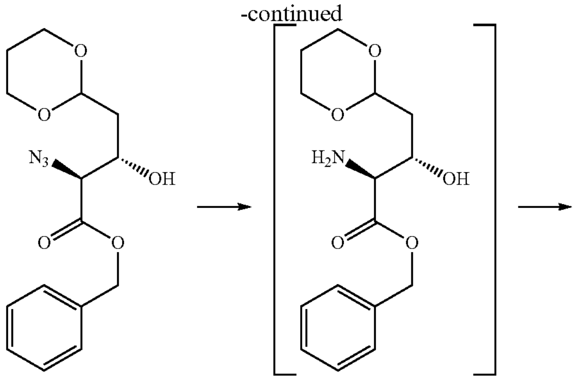
61 62
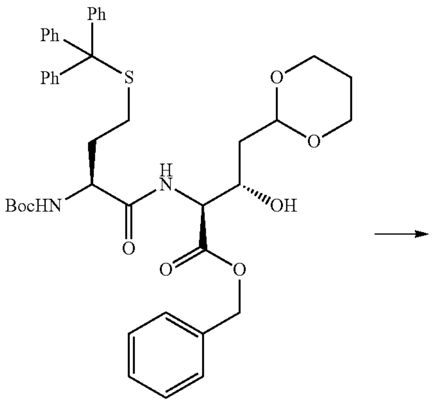
63
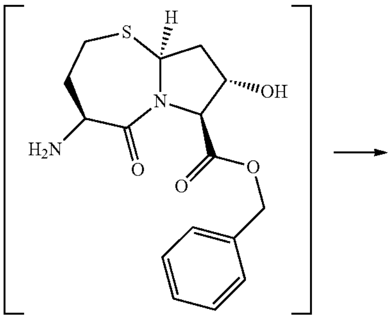
64
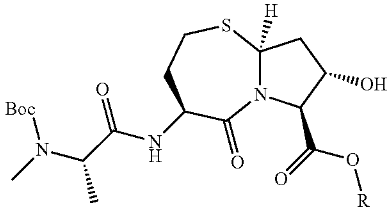
65, R = Bn
14f, R = H Example 61: Methyl 2-(1,3-dioxan-2-yl)acetate (55)

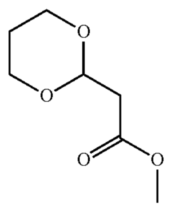

The compound 55 was prepared according to the established literature procedure; see Gobbi, L.; Jaeschke, G.; Rodriguez S., Rosa M.; Steward, L. Application: WO 2010031735 A1

Example 61: 2-(1,3-Dioxan-2-yl)acetaldehyde (56)

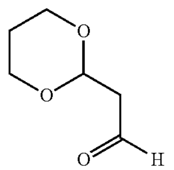

Under $N_2$ atmosphere, DIBAL-H in hexanes (1 M, 5.91 mL, 5.91 mmol, 1.10 eq.) was added dropwise to a solution of ester 55 (860 mg, 4.78 mmol, 5.37 eq.) in dry $CH_2Cl_2$ (11.2 mL) at −78° C. over 30 min. After stirring at −78° C. for 1.5 h, sat. potassium sodium tartrate solution (12.5 mL) was added and the mixture was stirred at rt for 2 h. The two layers were separated, and the aqueous phase was extracted with $CH_2Cl_2$ (3×20 mL). The combined organic layers were washed with brine (20 mL), dried ($Na_2SO_4$) and concentrated in vacuo. The resulting residue was purified by fc (hexanes/ethyl acetate). Colorless liquid, yield 356 mg (50%). The analytical data corresponds to the literature.

Example 62: Benzyl (2S,3S)-2-amino-4-(1,3-dioxan-2-yl)-3-hydroxybutanoate (62)

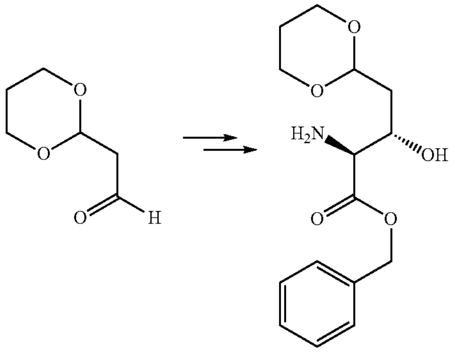 [SMILES: O=CCC1OCCCO1 ; N[C@H](C(=O)OCc1ccccc1)[C@@H](O)CC1OCCCO1]

The compound 62 was prepared according to the established literature procedure; see Boger, D. L.; Schüle G. *J. org. Chem.* 1998, 63, 6421-6424.

Example 63: Benzyl (2S,3S)-2-[(2S)-2-{[(tert-butoxy)carbonyl]amino}-4-[(triphenylmethyl)sulfanyl]butanamido]-4-(1,3-dioxan-2-yl)-3-hydroxybutanoate (63)

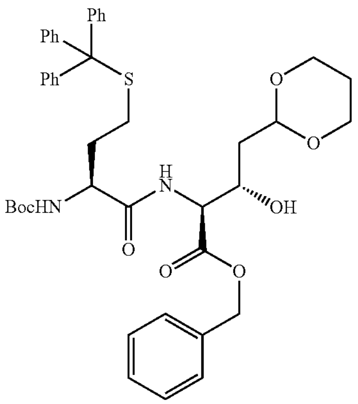 [SMILES: CC(C)(C)OC(=O)N[C@@H](CCSC(c1ccccc1)(c1ccccc1)c1ccccc1)C(=O)N[C@H](C(=O)OCc1ccccc1)[C@@H](O)CC1OCCCO1]

$PPh_3$ (270 mg, 1.03 mmol, 2.00 eq.) was added to azide 61 (166 mg, 0.515 mmol, 1.00 eq.) dissolved in THF (1.80 mL) and water (93 μL). After the resulting mixture was stirred for 16 h at 50° C., all volatiles were removed in vacuo.

Under $N_2$ atmosphere, amine 62, carboxylic acid 7 (246 mg, 0.515 mmol, 1.00 eq), 1-Hydroxybenzotriazole hydrate (95 mg, 0.618 mmol, 1.20 eq.) and N-Methylmorpholine (170 μL, 1.55 mmol, 3.00 eq.) were dissolved in dry THF (1.84 mL) and cooled to 0° C. EDC·HCl (119 mg, 0.618 mmol, 1.20 eq) was added and the resulting mixture was stirred for 30 min at 0° C. followed by 16 h at rt. Upon completion, ethyl acetate (30 mL) was added and was washed with saturated $NaHCO_3$ solution (2×10 mL), citric acid solution (5%, 2×10 mL), water (10 mL) and brine (10 mL), dried ($Na_2SO_4$) and concentrated in vacuo. The resulting residue was purified by fc (hexanes/ethyl acetate). Colorless solid, yield 235 mg (60%). 1H NMR (400 MHz, $CDCl_3$): δ (ppm)=1.40 (s, 9H), 1.69-1.88 (m, 4H), 1.98-2.11 (m, 2H), 2.16-2.32 (m, 2H), 3.67-3.78 (m, 2H), 3.98 (s, 1H), 4.03-4.10 (m, 2H), 4.18-4.24 (m, 1H), 4.51-4.58 (m, 1H), 4.66-4.75 (m, 2H), 5.14 (d, 1H), 5.19 (d, 1H), 6.86 (d, 1H), 7.16-7.22 (m, 3H), 7.23-7.30 (m, 7H), 7.31-7.35 (m, 4H), 7.37-7.41 (m, 6H). LC-MS: m/z=777.30 (calcd. 777.32 for $C_{43}H_{50}N_2NaO_8S^+$[M+Na$^+$]).

Example 64: Benzyl (4S,7S,8S,9aS)-4-[(2S)-2-{[(tert-butoxy)carbonyl](methyl) amino}propanamido]-8-hydroxy-5-oxo-octahydro-pyrrolo[2,1-b][1,3]thiazepine-7-carboxylate (65)

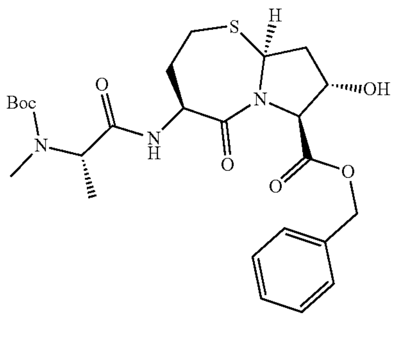 [SMILES: C[C@@H](C(=O)N[C@H]1CCS[C@H]2C[C@H](O)[C@@H](C(=O)OCc3ccccc3)N2C1=O)N(C)C(=O)OC(C)(C)C]

Compound 63 (222 mg, 0.294 mmol, 1.00 eq.) dissolved in 1,4-dioxane (1.47 mL) was treated with HCl in dioxane (4 M, 1.47 mL, 5.88 mmol, 20.0 eq.) and stirred at 40° C. for 2 h. Upon completion, all volatiles were removed under reduced pressure.

Under $N_2$ atmosphere, the resulting amine 64, N-(tert-Butoxycarbonyl)-N-methyl-L-alanine (60 mg, 0.294 mmol, 1.00 eq.), 1-Hydroxybenzotriazole hydrate (54 mg, 0.353 mmol, 1.20 eq.) and 4-Methylmorpholine (97 μL, 0.882 mmol, 3.00 eq.) were dissolved in dry DMF (1.37 mL) and cooled to 0° C. EDC·HCl (68 mg, 0.353 mmol, 1.20 eq.) was added and the resulting mixture was stirred for 30 minutes at 0° C. followed by 15 h at rt. Upon completion, water (30 mL) was added and extracted with ethyl acetate (3×10 mL). The combined organic layers were washed with sat. $NaHCO_3$ solution (2×10 mL), citric acid solution (5%, 2×10 mL), water (10 mL) and brine (10 mL), dried ($Na_2SO_4$) and concentrated in vacuo. The resulting residue was purified by fc (hexanes/ethyl acetate). Yellow resin, yield 67 mg (43%). 1H NMR (400 MHz, $CDCl_3$): δ (ppm)=1.32 (d, 3H), 1.46 (s, 9H), 1.84-1.91 (m, 1H), 2.05-2.14 (m, 1H), 2.19-2.28 (m, 1H), 2.48-2.57 (m, 1H), 2.77 (s, 3H), 2.79-2.85 (m, 1H), 3.21-3.39 (m, 2H), 4.51-4.59 (m, 2H), 4.68 (s, 1H), 5.14-5.23 (m, 2H), 5.30-5.35 (m, 1H), 7.29-7.38 (m, 6H). LC-MS: m/z=522.25 (calcd. 522.23 for $C_{25}H_{36}N_3O_7S^+$[M+$H^+$]).

Example 65: (4S,7S,8S,9aS)-4-[(2S)-2-{[(tert-Butoxy)carbonyl](methyl)amino}propanamido]-8-hydroxy-5-oxo-octahydropyrrolo[2,1-b][1,3]thiazepine-7-carboxylic acid (140

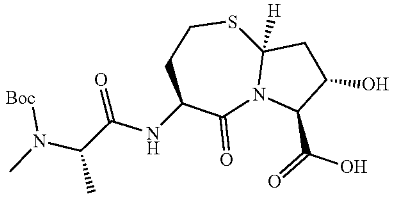 [SMILES: C[C@@H](C(=O)N[C@H]1CCS[C@H]2C[C@H](O)[C@@H](C(=O)O)N2C1=O)N(C)C(=O)OC(C)(C)C]

Lithium hydroxide solution (1 M, 255 μL, 0.255 mmol, 2.00 eq.) was added to a solution of the ester 65 (67 mg, 0.127 mmol, 1.00 eq.) dissolved in TI-1F (255 μL) at rt. The resulting emulsion was stirred at 40° C. for 15 h. Upon completion, $Et_2O$ (10 mL) was added and washed with a mixture of NaOH solution 1 M and brine (8:2, 3×10 mL). The combined aq. layers were extracted with $Et_2O$ (10 mL) and the $Et_2O$ layer was washed with a mixture of NaOH solution 1 M and brine (8:2, 2×10 mL). After acidification of the combined aq. layers with conc. HCl to pH 1, the aq. layer was extracted with $CH_2Cl_2$ (3×10 mL) and ethyl acetate (2×10 mL). The combined organic layers were dried ($Na_2SO_4$) and concentrated in vacuo. The resulting residue was purified by fc (hexanes/ethyl acetate/formic acid 0.2%). Yellow resin, yield 32 mg (59%).

Synthetic Scheme for the Preparation of Dimers 18b-k

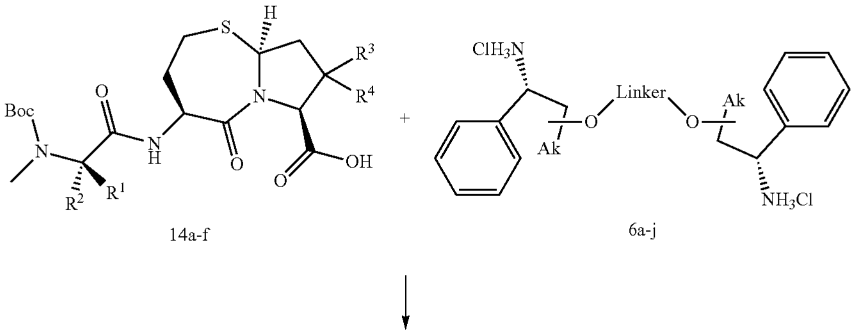

14a-f 6a-j

-continued
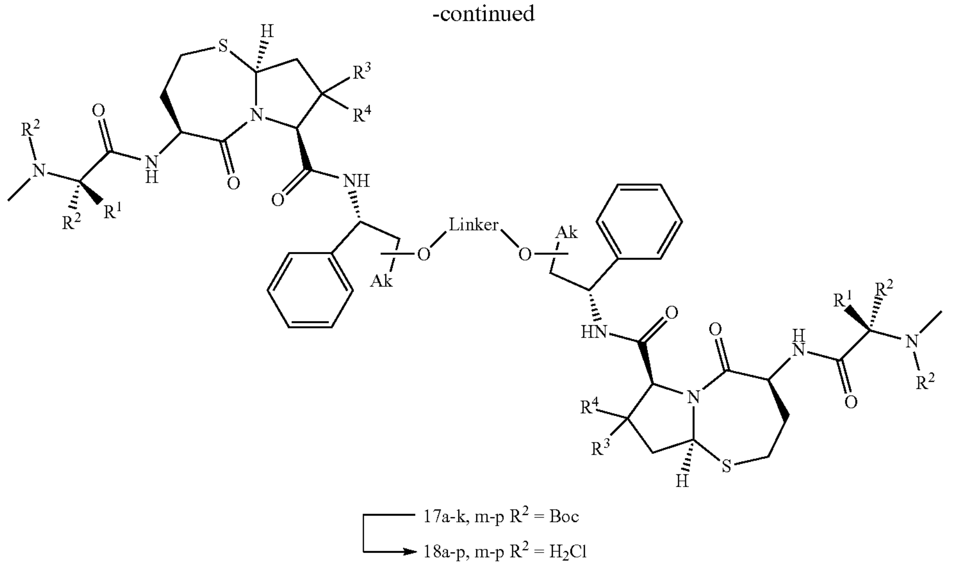
Example 66: Preparation of tert-Butyl [(2S)-1-{[(4S,7S,9aS)-7-({(1S,2R)-2-[(6-{[(1S,2R)-1-({[(4S,7S,9aS)-4-amino-8,8-dimethyl-5-oxooctahydropyrrolo[2,1-b][1,3]thiazepin-7-yl]carbonyl}amino)-2,3-dihydro-1H-inden-2-yl]oxy}hexyl)oxy]-2,3-dihydro-1H-inden-1-yl}carbamoyl)-8,8-dimethyl-5-oxooctahydropyrrolo[2,1-b][1,3]thiazepin-4-yl]amino}-1-oxopropan-2-yl](methyl)carbamate (17b)
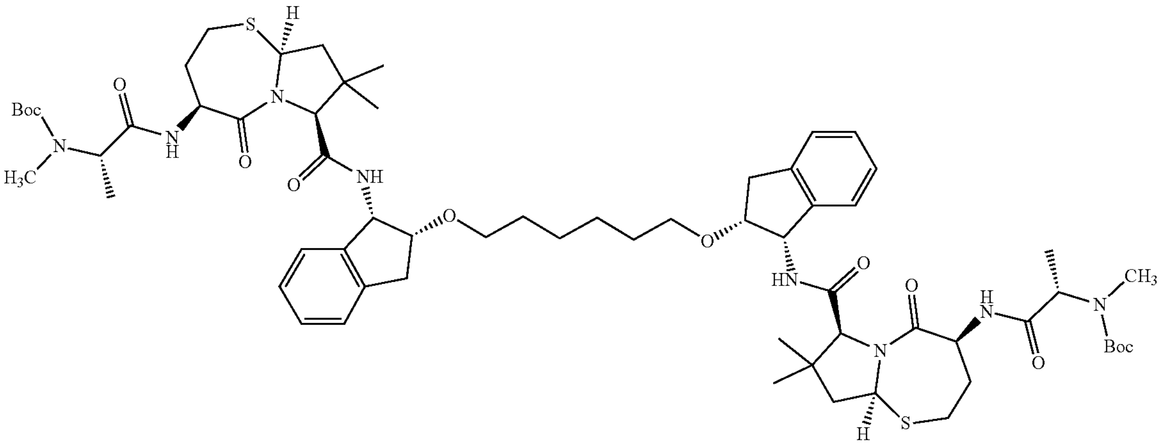

The compound was prepared according to general procedure B. White solid, yield 49 mg (62%). $R_f$=0.64 (ethyl acetate/methanol 10:0.5, Ceric Ammonium Molybdate stain). 1H NMR (400 MHz, $CD_3OD$): δ (ppm)=1.14 (s, 12H), 1.31 (d, 4H), 1.36 (d, 6H), 1.47 (s, 18H), 1.49-1.56 (m, 4H), 1.80 (dd, 2H), 1.89-2.00 (m, 2H), 2.19-2.27 (m, 2H), 2.30 (dd, 2H), 2.81-2.86 (m, 8H), 3.05 (d, 4H), 3.27 (d, 2H), 3.40-3.52 (m, 4H), 4.22 (q, 2H), 4.27 (s, 2H), 4.64 (d, 4H), 5.38-5.48 (m, 4H), 7.15-7.25 (m, 6H), 7.30-7.35 (m, 2H), 7.92 (d, 2H). C(O)NH are not seen in the spectrum. LC-MS: m/z=1231.65 (calcd. 1231.65 for $C_{64}H_{95}H_8O_{12}S_2^+[M+H^+]$).

Example 67. Preparation of tert-Butyl [(2S)-1-{[(4S,7S,9aS)-7-{[(1S,2R)-2-({3-[4-(3-{[(1S,2R)({[(4S,7S,9aS)-4-amino-8,8-dimethyl-5-oxooctahydropyrrolo[2,1-b][1,3]thiazepin yl]carbonyl}amino)-2,3-dihydro-1H-inden-2-yl]oxy}prop-1-yn-1-yl)phenyl]prop-2-yn-1-yl}oxy)-2,3-dihydro-1H-inden-1-yl]carbamoyl}-8,8-dimethyl-5-oxooctahydropyrrolo[2,1-b][1,3]thiazepin yl]amino}-1-oxopropan-2-yl](methyl)carbamate (17c)

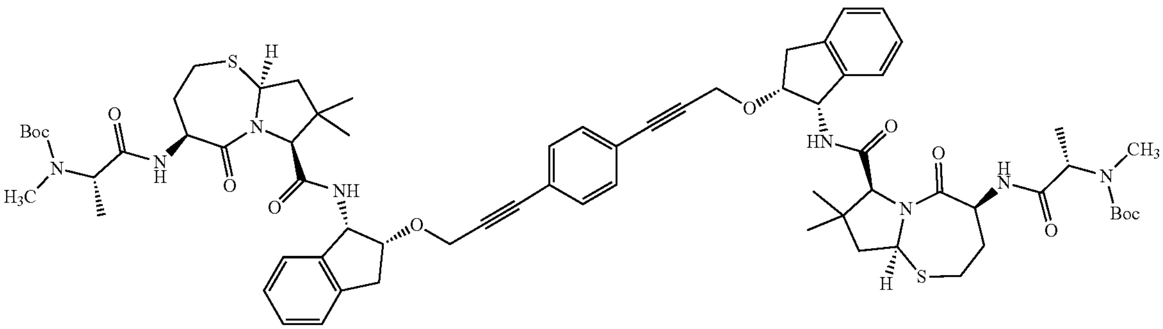

The compound was prepared according to general procedure B. White solid, yield 57 mg (66%). Rf=0.56 (ethyl acetate/methanol 10:0.5, Ceric Ammonium Molybdate stain). 1H NMR (400 MHz, CD3OD): δ (ppm)=1.16 (d, 12H), 1.33 (d, 6H), 1.46 (s, 18H), 1.81 (dd, 2H), 1.98-2.10 (m, 2H), 2.23 (dd, 2H), 2.32 (dd, 2H), 2.78-2.89 (m, 8H), 3.11 (dd, 2H), 3.20 (dd, 2H), 3.26-3.31 (m, 2H), 4.29 (s, 2H), 4.40 (d, 2H), 4.47 (d, 2H), 4.56 (q, 2H), 4.65 (dd, 2H), 5.42-5.52 (m, 4H), 7.22 (ddt, 6H), 7.33 (d, 2H), 7.43 (s, 4H), 7.86 (d, 2H), 8.07 (d, 2H). $CHCH_3$ is not seen in the spectrum. LC-MS: m/z=1299.45 (calcd. 1299.62 for $C_{70}H_{91}N_8O_{12}S_2^+$[M+H$^+$]).

Example 68. Preparation of tert-Butyl [(2S)-1-{[(4S,7S,9aS)-7-{[(1S,2R)-2-({3-[3-(3-{[(1S,2R)-1-({[(4S,7S,9aS)-4-amino-8,8-dimethyl-5-oxooctahydropyrrolo[2,1-b][1,3]thiazepin-7-yl]carbonyl}amino)-2,3-dihydro-1H-inden-2-yl]oxy}prop-1-yn-1-yl)phenyl]prop-2-yn-1-yl}oxy)-2,3-dihydro-1H-inden-1-yl]carbamoyl}-8,8-dimethyl-5-oxooctahydropyrrolo[2,1-b][1,3]thiazepin-4-yl]amino}-1-oxopropan-2-yl](methyl)carbamate (17d)

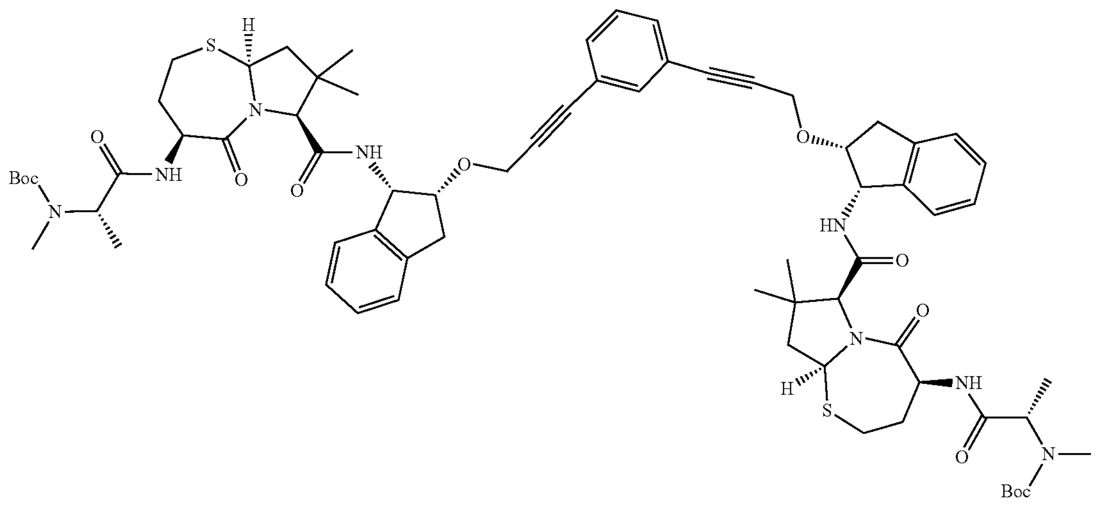

The compound was prepared according to general procedure B. White solid, yield 57 mg (68%). Rf=0.54 (ethyl acetate/methanol 10:0.5, Ceric Ammonium Molybdate stain). 1H NMR (400 MHz, CD3OD): δ (ppm)=1.14 (s, 6H), 1.16 (s, 6H), 1.33 (d, 6H), 1.45 (s, 18H), 1.81 (dd, 2H), 1.98-2.10 (m, 2H), 2.19-2.26 (m, 2H), 2.31 (dd, 2H), 2.77-2.88 (m, 8H), 3.12 (dd, 2H), 3.19 (dd, 2H), 3.26-3.30 (m, 2H), 4.29 (s, 2H), 4.39 (d, 2H), 4.46 (d, 2H), 4.53-4.58 (m, 2H), 4.64 (dd, 2H), 5.41-5.52 (m, 4H), 7.22 (dt, 6H), 7.31-7.37 (m, 3H), 7.44 (d, 2H), 7.51 (s, 1H), 7.86 (d, 2H), 8.07 (d, 2H). $CHCH_3$ is not seen in the spectrum. LC-MS: m/z=1299.60 (calcd. 1299.62 for $C_{70}H_{91}N_8O_{12}S_2^+[M+H^+]$).

Example 69. Preparation of tert-Butyl [(2S)-1-{[(4S,7S,9aS)-7-{[(1S,2R)-2-{[4-(3-{[(1S,2R) ({[(4S,7S,9aS)-4-amino-8,8-dimethyl-5-oxooctahydropyrrolo[2,1-b][1,3]thiazepin yl]carbonyl}amino)-2,3-dihydro-1H-inden-2-yl]oxy}prop-1-yn-1-yl)benzyl]oxy}-2,3-dihydro-1H-inden-1-yl]carbamoyl}-8,8-dimethyl-5-oxooctahydropyrrolo[2,1-b][1,3]thiazepin-4-yl]amino}-1-oxopropan-2-yl](methyl) carbamate (17e)

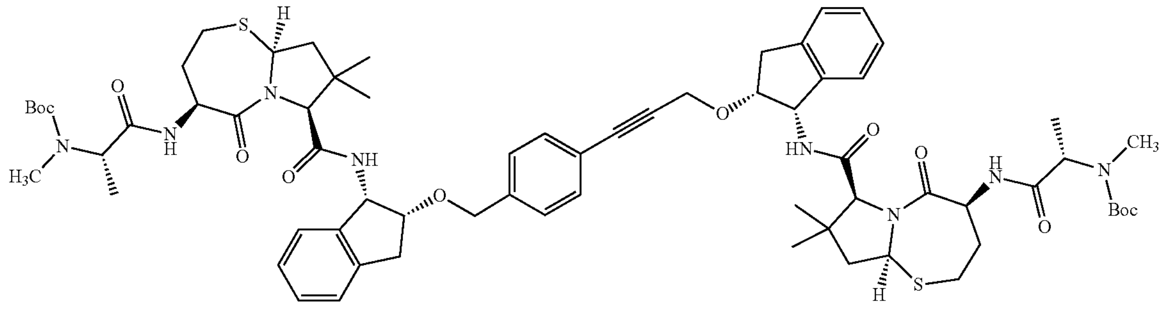

The compound was prepared according to general procedure B. White solid, yield 53 mg (65%). $R_f$=0.43 (ethyl acetate/methanol 10:0.5, Ceric Ammonium Molybdate stain). 1H NMR (400 MHz, $CD_3OD$): δ (ppm)=1.09-1.17 (m, 12H, $C(CH_3)_2$), 1.28-1.35 (m, 6H), 1.42-1.48 (m, 18H), 1.58-1.68 (m, 1H), 1.72-1.85 (m, 2H), 1.94-2.11 (m, 2H), 2.18-2.26 (m, 1H), 2.31 (dt, 2H), 2.48-2.57 (m, 1H), 2.76-2.86 (m, 8H), 3.04-3.23 (m, 5H), 4.24-4.30 (m, 2H), 4.34-4.47 (m, 3H), 4.52-4.67 (m, 5H), 5.38-5.51 (m, 4H), 7.19-7.34 (m, 10H), 7.39 (d, 2H), 7.73 (d, 1H), 7.87 (d, 1H), 8.01 (d, 1H), 8.06 (d, 1H). $CHCH_3$ are not seen in the spectrum. LC-MS: m/z=1275.55 (calcd. 1275.62 for $C_{68}H_{91}H_8O_{12}S_2^+$ [M+H$^+$]).

Example 70. Preparation of tert-Butyl [(2S)-1-{[(4S,7S,9aS)-7-{[(1S,2R)-2-({4-[4-({[(1S,2R)-1-({[(4S,7S,9aS)-4-amino-8,8-dimethyl-5-oxooctahydropyrrolo[2,1-b][1,3]thiazepin-7-yl]carbonyl}amino)-2,3-dihydro-1H-inden-2-yl]oxy}methyl)phenyl]benzyl}oxy)-2,3-dihydro-1H-inden-1-yl]carbamoyl}-8,8-dimethyl-5-oxooctahydropyrrolo[2,1-b][1,3]thiazepin-4-yl]amino}-1-oxopropan-2-yl](methyl)carbamate (17f)

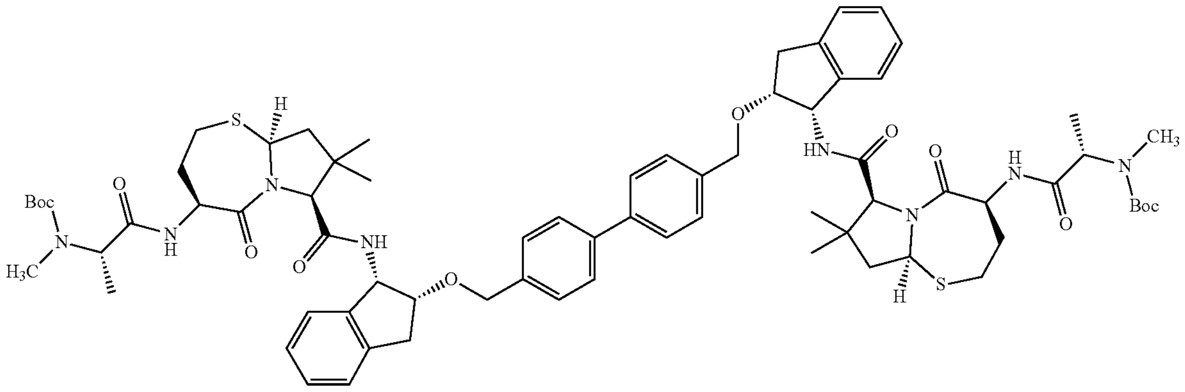

The compound was prepared according to general procedure B. White solid, yield 42 mg (49%). $R_f$=0.63 (ethyl acetate/methanol 10:0.5, Ceric Ammonium Molybdate stain). 1H NMR (400 MHz, $CD_3OD$): δ (ppm)=1.13 (s, 12H), 1.30 (d, 6H), 1.43 (s, 18H), 1.58-1.70 (m, 2H), 1.76 (dd, 2H), 1.93-2.00 (m, 2H), 2.30 (dd, 2H), 2.46-2.54 (m, 2H), 2.77 (s, 6H), 3.07 (dd, 2H), 3.14-3.23 (m, 4H), 4.28 (s, 2H), 4.36-4.41 (m, 2H), 4.46-4.67 (m, 8H), 5.41 (t, 2H), 5.48 (dd, 2H), 7.18-7.27 (m, 6H), 7.33 (d, 2H), 7.37 (d, 4H), 7.56 (d, 4H), 7.74 (d, 2H), 8.03 (d, 2H). LC-MS: m/z=1327.85 (calcd. 1327.65 for $C_{72}H_{95}N_8O_{12}S_2^+[M+H^+]$).

Example 71. Preparation of tert-Butyl [(2S)-1-{[(4S,7S,9aS)-7-{[(1S,2R)-2-{[4-({[(1S,2R)-1-({[(4S,7S,9aS)-4-amino-8,8-dimethyl-5-oxooctahydropyrrolo[2,1-b][1,3]thiazepin yl]carbonyl}amino)-2,3-dihydro-1H-inden-2-yl]oxy}methyl)benzyl]oxy}-2,3-dihydro-1H-inden yl]carbamoyl}-8,8-dimethyl-5-oxooctahydropyrrolo[2,1-b][1,3]thiazepin-4-yl]amino}-1-oxopropan-2-yl](methyl)carbamate (17g)

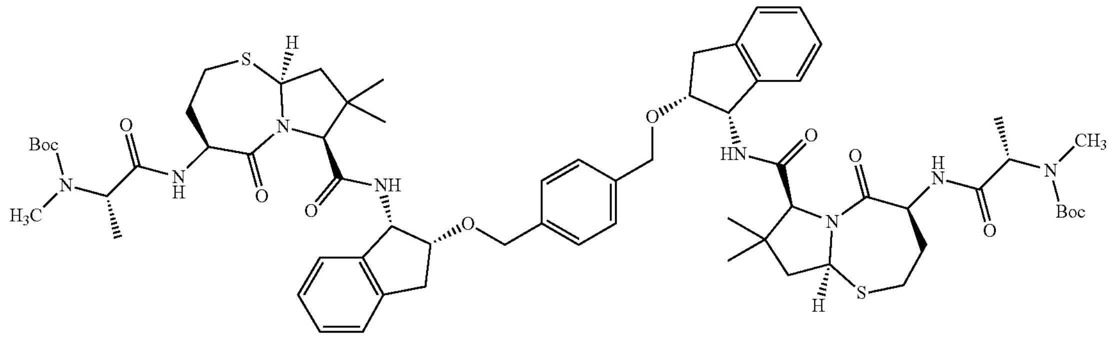

The compound was prepared according to general procedure B. White solid, yield 39 mg (49%). $R_f$=0.63 (ethyl acetate/methanol 10:0.5, Ceric Ammonium Molybdate stain). 1H NMR (400 MHz, $CD_3OD$): δ (ppm)=1.13 (s, 12H), 1.35 (d, 6H), 1.45 (s, 18H), 1.61-1.84 (m, 4H), 1.98-2.04 (m, 2H), 2.26-2.34 (m, 2H), 2.45-2.56 (m, 2H), 2.82 (s, 6H), 3.04 (dd, 2H), 3.15 (dd, 4H), 4.27 (s, 2H), 4.31-4.37 (m, 2H), 4.58 (s, 6H), 5.37-5.50 (m, 4H), 7.17-7.35 (m, 12H), 7.81 (d, 2H), 8.01 (d, 2H). $CHCH_3$ are not seen in the spectrum. LC-MS: m/z=1251.65 (calcd. 1251.62 for $C_{66}H_{91}N_8O_{12}S_2{}^+[M+H^+]$).

Example 72. Preparation of tert-Butyl [(2S)-1-{[(4S,7S,9aS)-7-{[(1S,2R)-2-{2-[(2-{[(1S,2R)-1-({[(4S,7S,9aS)-4-amino-8,8-dimethyl-5-oxooctahydro-pyrrolo[2,1-b][1,3]thiazepin-7-yl]carbonyl}amino)-2,3-dihydro-1H-inden-2-yl]oxy}ethyl)sulfonyl]ethoxy}-2,3-dihydro-1H-inden-1-yl]carbamoyl}-8,8-dimethyl-5-oxooctahydropyrrolo[2,1-b][1,3]thiazepin-4-yl]amino}-1-oxopropan-2-yl](methyl)carbamate (17h)

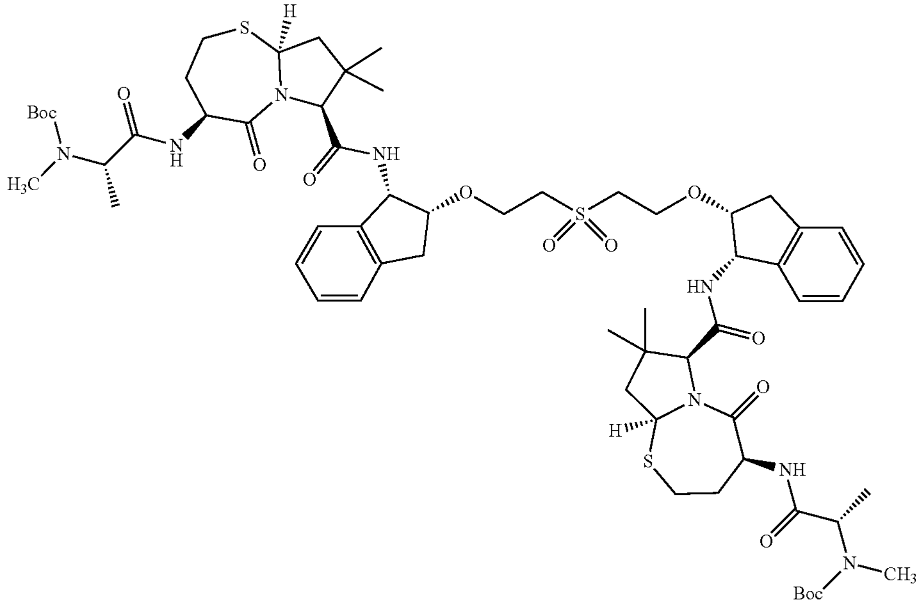

The compound was prepared according to general procedure B. White solid, yield 41 mg (50%). Rf=0.72 (ethyl acetate/methanol 10:1, Ceric Ammonium Molybdate stain). 1H NMR (400 MHz, CD3OD): δ (ppm)=1.16 (d, 12H), 1.37 (d, 6H), 1.46 (s, 18H), 1.87 (dd, 2H), 1.98 (dd, 2H), 2.19-2.26 (m, 2H), 2.30 (dd, 2H), 2.81-2.92 (m, 8H), 3.03 (d, 4H), 3.14 (dt, 2H), 3.24-3.30 (m, 4H), 3.76-3.90 (m, 4H), 4.05 (q, 2H), 4.41 (s, 2H), 4.67 (dd, 4H), 5.31 (dd, 2H), 5.45 (t, 2H), 7.04-7.22 (m, 6H), 7.36 (d, 2H), 7.90 (d, 1H), 7.96 (d, 2H). LC-MS: m/z=1267.60 (calcd. 1267.58 for $C_{62}H_{91}N_8O_{14}S_3{}^+$[M+H$^+$]).

Example 73. Preparation of tert-Butyl [(2S)-1-{[(4S,7S,9aS)-7-({(1R)-3-[(6-{[(3R)-3-({[(4S,7S,9aS)-4-amino- 8,8-dimethyl-5-oxooctahydropyrrolo[2,1-b][1,3]thiazepin-7-yl]carbonyl}amino) phenylpropyl]oxy}hexa-2,4-diyn-1-yl)oxy]-1-phenylpropyl}carbamoyl)-8,8-dim ethyl oxooctahydropyrrolo[2,1-b][1,3]thiazepin-4-yl]amino}-1-oxopropan-2-yl](methyl)carbamate (17i)

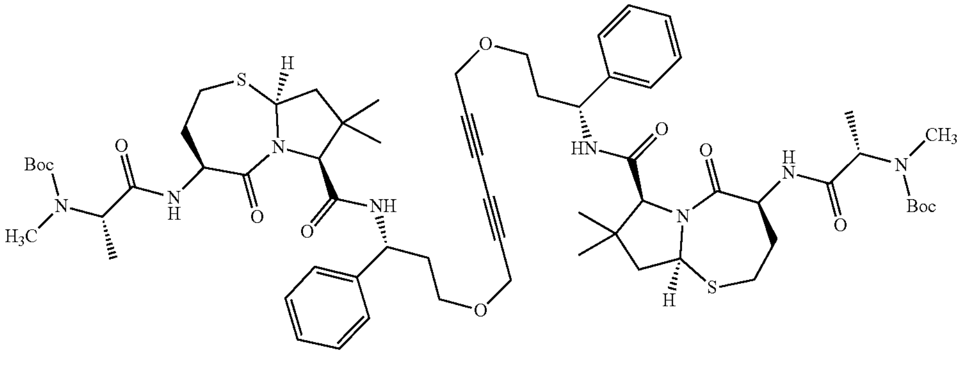

The compound was prepared according to general procedure B. White solid, yield 48 mg (61%). Rf=0.58 (ethyl acetate/methanol 10:0.5, Ceric Ammonium Molybdate stain). 1H NMR (400 MHz, CD3OD): δ (ppm)=1.02 (s, 6H), 1.14 (s, 6H), 1.37 (d, 6H), 1.47 (s, 18H), 1.85-1.96 (m, 4H), 2.02-2.08 (m, 4H), 2.21-2.34 (m, 4H), 2.86 (s, 6H), 2.88-2.95 (m, 2H), 3.32-3.36 (m, 2H), 3.46-3.56 (m, 4H), 4.17-4.23 (m, 4H), 4.26 (d, 2H), 4.47-4.71 (m, 4H), 5.07 (q, 2H), 5.46 (t 2H), 7.21-7.27 (m, 2H), 7.31-7.40 (m, 8H), 7.94 (d, 2H), 8.18 (d, 2H). LC-MS: m/z=1227.65 (calcd. 1227.62 for $C_{64}H_{91}N_8O_{12}S_2^+$[M+H$^+$]).

Example 74: Preparation of tert-Butyl [(1S)-1-{[(4S,7S,9aS)-7-{[(1S,2R)-2-[(4-{[(1S,2R)-1-[(4S,7S,9aS)-4-[(2S)-2-{[(tert-butoxy)carbonyl](methyl)amino}propanamido]-8,8-dimethyl-5-oxo-octahydropyrrolo[2,1-b][1,3]thiazepine-7-amido]-2,3-dihydro-1H-inden-2-yl]oxy}but-2-yn-1-yl)oxy]-2,3-dihydro-1H-inden-1-yl]carbamoyl}-8,8-dimethyl-5-oxo-octahydropyrrolo[2,1-b][1,3]thiazepin-4-yl]amino}-1-oxopropan-2-yl](methyl)carbamate (17j)

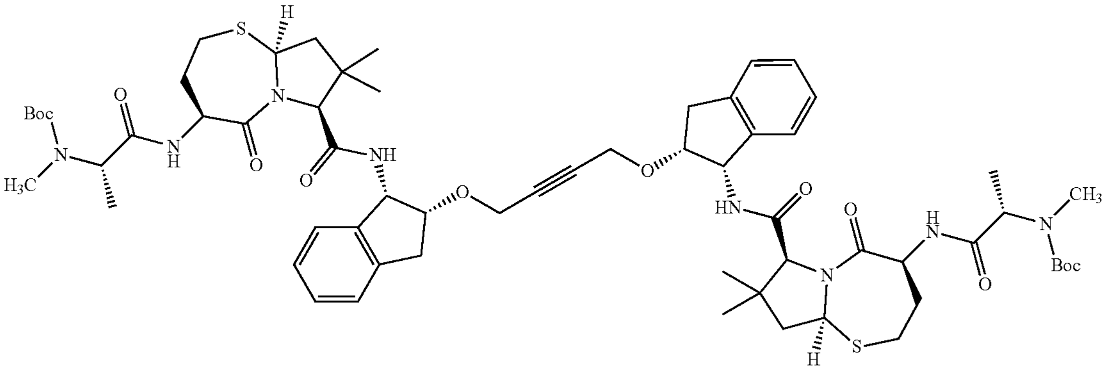

The compound was prepared according to general procedure B. White solid, yield 51 mg (66%). $R_f$=0.80 (ethyl acetate/methanol 10:0.5, Ceric Ammonium Molybdate stain). 1H NMR (400 MHz, $CD_3OD$): δ (ppm)=1.15 (s, 6H), 1.18 (s, 6H), 1.39 (d, 6H), 1.48 (s, 18H), 1.81 (dd, 2H), 1.93-2.05 (m, 2H), 2.07-2.18 (m, 2H), 2.35 (dd, 2H), 2.66 (d, 2H), 2.86 (s, 6H), 3.11 (d, 6H), 4.15-4.32 (m, 6H), 4.43 (d, 2H), 4.55-4.70 (m, 4H), 5.38-5.47 (m, 2H), 5.55 (dd, 2H), 7.18-7.30 (m, 8H), 7.81-7.88 (m, 2H), 7.95 (d, 2H). LC-MS: m/z=1199.60 (calcd. 1199.59 for $C_{62}H_{87}N_8O_{12}S_2^+$[M+H$^+$]).

Example 75. Preparation of tert-Butyl (1-{[(4S,7S,9aS)-74{(1S,2R)-2-[(6-{[(1S,2R)-1-({[(4S,7S,9aS)-4-amino-8,8-dimethyl-5-oxooctahydropyrrolo[2,1-b][1,3]thiazepin-7-yl]carbonyl}amino)-2,3-dihydro-1H-inden-2-yl]oxy}hexa-2,4-diyn-1-yl)oxy]-2,3-dihydro-1H-inden-1-yl}carbamoyl)-8,8-dimethyl-5-oxooctahydropyrrolo[2,1-b][1,3]thiazepin-4-yl]amino}-2-methyl-1-oxopropan yl)(methyl) carbamate (17k)

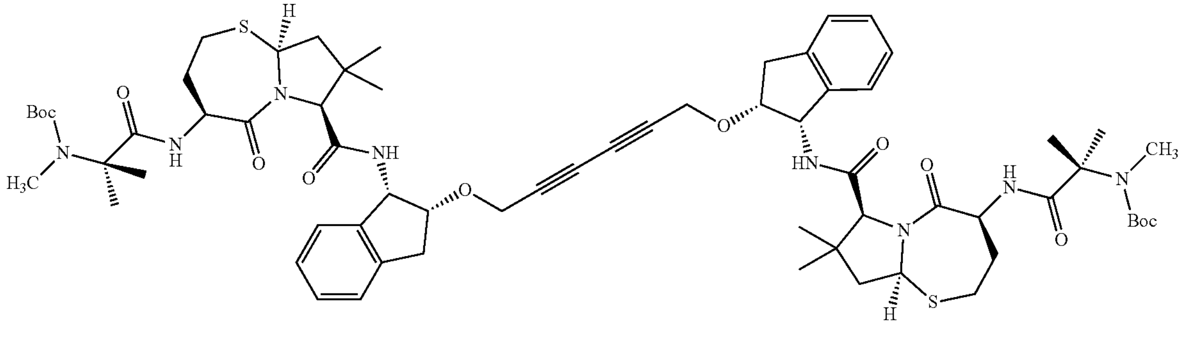

The compound was prepared according to general procedure B. White solid, yield 34 mg (65%). $R_f$=0.58 (ethyl acetate/methanol 10:0.5, Ceric Ammonium Molybdate stain). 114 NMR (400 MHz, $CD_3OD$): δ (ppm)=1.09-1.19 (m, 12H), 1.40 (d, 30H), 1.80 (dd, 2H), 1.89-2.00 (m, 2H), 2.22-2.29 (m, 2H), 2.33 (dd, 2H), 2.81-2.89 (m, 2H), 2.94 (s, 6H), 3.06-3.17 (m, 4H), 3.35 (s, 2H), 4.21-4.28 (m, 4H), 4.33 (d, 2H), 4.43 (q, 2H), 4.59 (dd, 2H), 5.42-5.50 (m, 4H), 7.18-7.34 (m, 8H), 7.56 (d, 2H), 7.99 (d, 2H). LC-MS: m/z=1251.70 (calcd. 1251.62 for $C_{66}H_{91}N_8O_{12}S_2^+$[M+H$^+$]).

Example 76: Preparation of tert-Butyl N-[(1S)-1-{[(4S,7S,9aS)-7-{[(1S,2R)-2-[(6-{[(1S,2R)-1-[(4S,7S,9aS)-4-[(2S)-2-{[(tert-butoxy)carbonyl](methyl)amino}butanamido]-8,8-dimethyl-5-oxo-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-8,8-dimethyl-5-oxo-octahydropyrrolo[2,1-b][1,3]thiazepin-4-yl]carbamoyl}propyl]-N-methylcarbamate (17m)

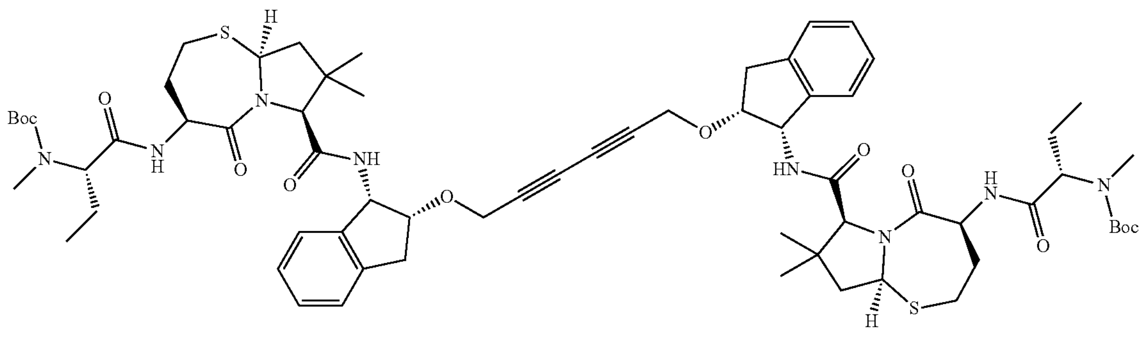

The compound was prepared according to general procedure B. Modification: Ethyl acetate (30 mL) was added to the reaction mixture and washed with sat. $NaHCO_3$ solution (3×10 mL), citric acid solution (5%, 2×10 mL), water (10 mL) and brine (10 mL), dried ($Na_2SO_4$) and concentrated in vacuo. White solid, yield 117 mg (75%). 114 NMR (400 MHz, $CDCl_3$): δ (ppm)=0.89 (t, 6H), 1.12 (s, 6H), 1.19 (s, 6H), 1.48 (s, 18H), 1.67 (s, 2H), 1.79-1.93 (m, 6H), 2.23-2.34 (m, 4H), 2.75-2.83 (m, 8H), 3.10 (d, 4H), 3.21-3.32 (m, 2H), 4.14-4.28 (m, 6H), 4.47 (q, 2H), 4.53 (s, 2H), 5.16 (t, 2H), 5.52 (dd, 2H), 7.18-7.34 (m, 8H), 7.42 (s, 2H). Boc-NCH and C(=O)NH are not seen in the spectrum. LC-MS: m/z=1251.65 (calcd. 1251.62 for $C_{66}H_{91}N_8O_{12}S_2^+$[M+H$^+$]).

Example 78: Preparation of tert-Butyl N-[(1S)-1-{[(4S,7S,9aS)-7-{[(1S,2R)-2-[(6-{[(1S,2R)-1-[(4S,7S,9aS)-4-[(2S)-2-{[(tert-butoxy)carbonyl](methyl)amino}propanamido]-5-oxo-8,8-bis(prop-2-en-1-yl)-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-5-oxo-8,8-bis(prop-2-en-1-yl)-octahydropyrrolo[2,1-b][1,3]thiazepin-4-yl]carbamoyl}ethyl]-N-methylcarbamate (17n)

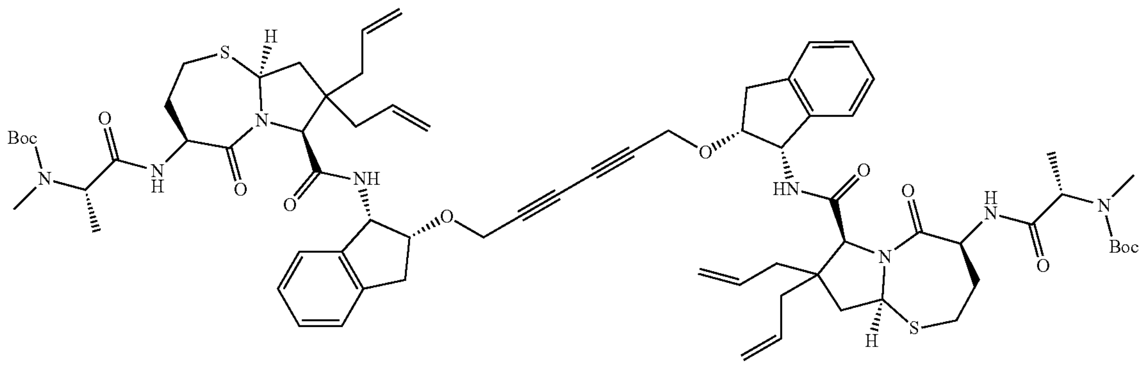

The compound was prepared according to general procedure B. Colorless solid, yield 60 mg (63%).

$^1$H NMR (400 MHz, $CDCl_3$): δ (ppm)=1.35 (d, 6H), 1.48 (s, 18H), 1.79-1.94 (m, 6H), 2.00-2.10 (m, 6H), 2.31 (d, 2H), 2.39 (dd, 2H), 2.43-2.50 (m, 2H), 2.76-2.83 (m, 8H), 3.10 (d, 4H), 3.21-3.31 (m, 2H), 4.16 (d, 2H), 4.25 (d, 2H), 4.48 (d, 6H), 5.02-5.19 (m, 11H), 5.47-5.54 (m, 2H), 5.68-5.88 (m, 4H), 7.17-7.25 (m, 6H), 7.34 (t, 6H). LC-MS: m/z=1327.60 (calcd. 1327.65 for $C_{72}H_{95}N_8O_{12}S_2^+$[M+H$^+$]).

Example 79: Preparation of tert-Butyl N-[(1S)-1-{[(4'S,7'S,9'aS)-7'-{[(1S,2R)-2-[(6-{[(1S,2R)-1-{[(4'S,7'S,9'aS)-4'-[(2S)-2-{[(tert-butoxy)carbonyl](methyl)amino}propanamido]-5'-oxo-3',4',5',7',9',9'a-hexahydro-2'H-spiro[cyclopentane-1,8'-pyrrolo[2,1-b][1,3]thiazepin]-3-en-7'-yl]amido}-2,3-dihydro-1H-inden-2-yl]oxy}hexa-2,4-diyn-1-yl)oxy]-2,3-dihydro-1H-inden-1-yl]carbamoyl}-5'-oxo-3',4',5',7',9',9'a-hexahydro-2'H-spiro[cyclopentane-1,8'-pyrrolo[2,1-b][1,3]thiazepin]-3-en-4'-yl]carbamoyl}ethyl]-N-methylcarbamate (17o)

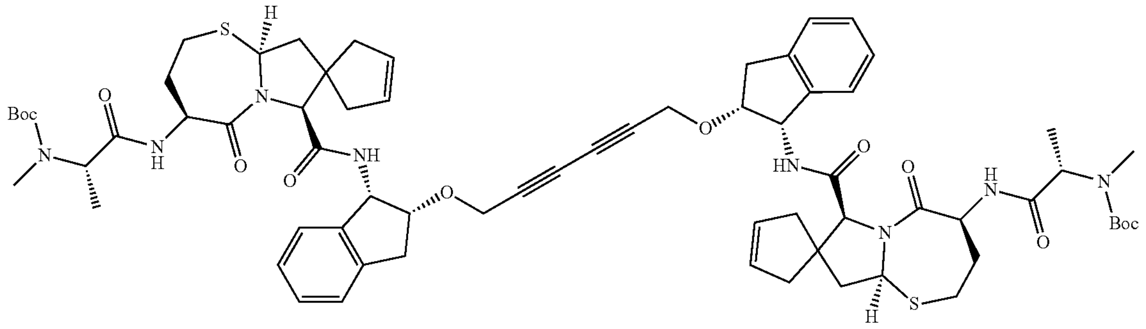

The compound was prepared according to general procedure B. Modification: Ethyl acetate (30 mL) was added to the reaction mixture and washed with sat. $NaHCO_3$ solution (2×10 mL), citric acid solution (5%, 2×10 mL), water (10 mL) and brine (10 mL), dried ($Na_2SO_4$) and concentrated in vacuo. Colorless solid, yield 37 mg (60%). $^1$H NMR (400 MHz, $CDCl_3$): δ (ppm)=1.35 (d, 6H), 1.47 (s, 18H), 1.85 (t, 4H), 2.09 (d, 2H), 2.23 (d, 8H), 2.51 (dd, 2H), 2.77-2.85 (m, 8H), 2.95 (d, 2H), 3.10 (d, 4H), 3.31 (dd, 2H), 4.21 (d, 2H), 4.28 (d, 2H), 4.45-4.50 (m, 4H), 4.54 (t, 2H), 5.14 (d, 2H), 5.53 (dd, 2H), 5.59-5.64 (m, 2H), 5.76 (d, 2H), 7.17-7.25 (m, 6H), 7.30 (t, 6H). LC-MS: m/z=1271.70 (calcd. 1271.59 for $C_{68}H_{87}N_8O_{12}S_2^+$[M+H$^+$]).

Example 80: Preparation of tert-Butyl N-[(1S)-1-{[(4S,7S,8S,9aS)-7-{[(1S,2R)-2-[(6-{[(1S,2R)-1-[(4S,7S,8S,9aS)-4-[(2S)-2-{[(tert-butoxy)carbonyl](methyl)amino}propanamido]-8-hydroxy-5-oxo-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-8-hydroxy-5-oxo-octahydropyrrolo[2,1-b][1,3]thiazepin-4-yl]carbamoyl}ethyl]-N-methylcarbamate (17p)

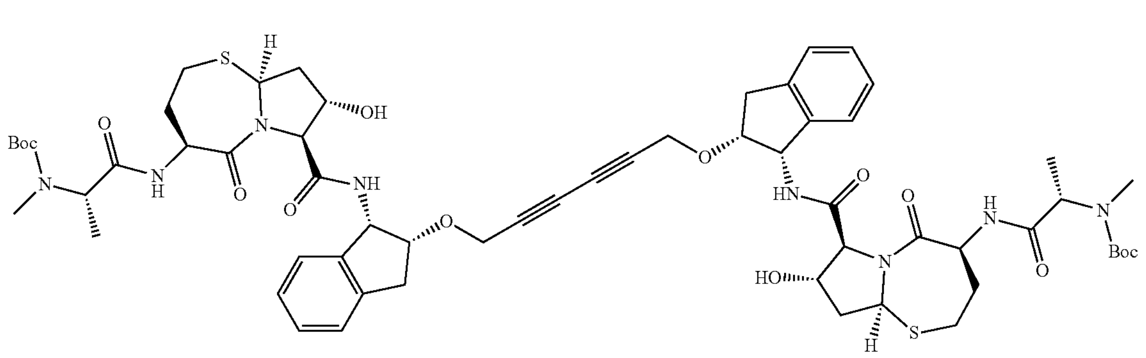

The compound was prepared according to general procedure B. Modification: The reaction was performed in a 4:1 mixture of THF and DMF. Moreover, water (10 mL) was added to the reaction mixture and extracted with EtOAc (3×10 mL). The combined org. layers were washed with sat. $NaHCO_3$ solution (2×10 mL), citric acid solution (5%, 2×10 mL), water (10 mL) and brine (10 mL), dried ($Na_2SO_4$) and concentrated in vacuo. Colorless solid, yield 31 mg (69%). 114 NMR (400 MHz, $CD_3OD$): δ (ppm)=1.36 (d, 6H), 1.45 (s, 18H), 1.93 (q, 2H), 2.11 (ddd, 2H), 2.26 (dd, 2H), 2.55 (dd, 2H), 2.84 (s, 6H), 3.05-3.16 (m, 4H), 3.21-3.31 (m, 2H), 4.27-4.36 (m, 4H), 4.39-4.46 (m, 2H), 4.56 (d, 2H), 4.64-4.71 (m, 4H), 5.40-5.52 (m, 4H), 7.17-7.29 (m, 9H), 7.88 (d, 2H). LC-MS: m/z=1199.60 (calcd. 1199.52 for $C_{60}H_{79}N_8O_{14}S_2^+[M+H^+]$).

Example 81. Preparation of (2S)-1-{[(4S,7S,9aS)-7-({(1S,2R)-2-[(6-{[(1S,2R)-1-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}hexyl)oxy]-2,3-dihydro-1H-inden-1-yl}carbamoyl)-8,8-dimethyl-5-oxooctahydropyrrolo[2,1-b][1,3]thiazepin-4-yl]amino}-N-methyl-1-oxopropan-2-ammonium dichloride (18b)

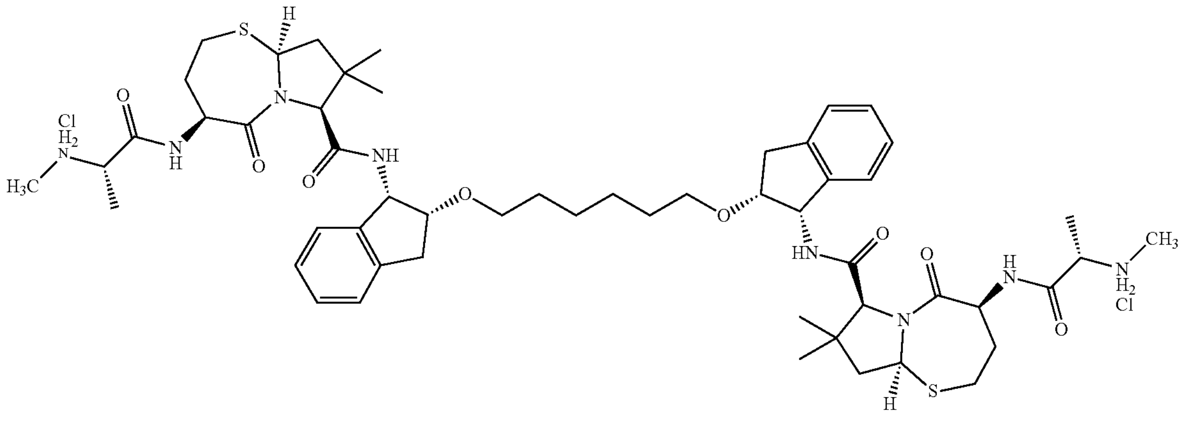

The compound 18b was prepared according to general procedure A. White solid, yield 34 mg (82%). 1H NMR (400 MHz, $CD_3OD$): δ (ppm)=1.14 (s, 12H), 1.31 (d, 4H), 1.36 (d, 6H), 1.47 (s, 18H), 1.49-1.56 (m, 4H), 1.80 (dd, 2H), 1.89-2.00 (m, 2H), 2.19-2.27 (m, 2H), 2.30 (dd, 2H), 2.81-2.86 (m, 8H), 3.05 (d, 4H), 3.27 (d, 2H), 3.40-3.52 (m, 4H), 4.22 (q, 2H), 4.27 (s, 2H), 4.64 (d, 4H), 5.38-5.48 (m, 4H), 7.15-7.25 (m, 6H), 7.30-7.35 (m, 2H), 7.92 (d, 2H). C(O)NH are not seen in the spectrum. 13C NMR (101 MHz, $CD_3OD$): δ (ppm)=14.5, 24.1, 27.0, 28.7, 28.8, 30.9, 31.2, 32.4, 33.9, 37.5, 40.9, 47.1, 54.2, 56.9, 61.9, 70.7, 73.4, 81.6-81.7, 125.5, 126.1, 127.9, 129.2, 141.3, 142.7, 172.0, 172.8, 173.2. $CHCH_3$ and $C{=}O_{cathamate}$ are not seen in the spectrum. LC-MS: m/z=1231.65 (calcd. 1231.65 for $C_{64}H_{95}N_8O_{12}S_2^+$[M+H$^+$]).

Example 82. Preparation of (2S)-1-{[(4S,7S,9aS)-7-{[(1S,2R)-2-({3-[4-(3-{[(1S,2R)-1-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}prop-1-yn-1-yl)phenyl]prop-2-yn-1-yl}oxy)-2,3-dihydro-1H-inden-1-yl]carbamoyl}-8,8-dim ethyl-5-oxooctahydropyrrolo[2,1-b][1,3]thiazepin-4-yl]amino}-N-methyl-1-oxopropan-2-ammonium dichloride (18c)

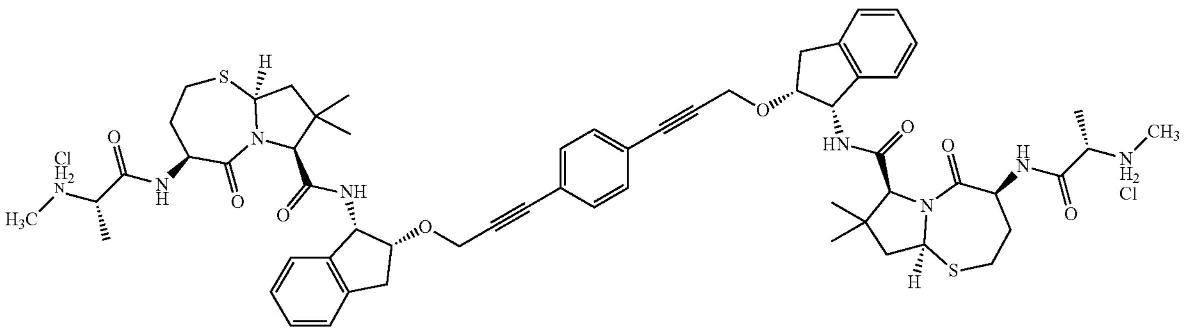

The compound 18c was prepared according to general procedure A. White solid, yield 40 mg (81%). 1H NMR (400 MHz, $CD_3OD$): δ (ppm)=1.16 (s, 12H), 1.53 (d, 6H), 1.82 (dd, 2H), 2.11 (q, 2H), 2.25 (d, 2H), 2.33 (dd, 2H), 2.65 (s, 6H), 2.90 (q, 2H), 3.12 (dd, 2H), 3.16-3.23 (m, 2H), 3.25-3.30 (m, 2H), 3.89 (q, 2H), 4.26 (s, 2H), 4.40 (d, 2H), 4.49 (d, 2H), 4.54-4.60 (m, 2H), 4.75 (d, 2H), 5.48 (q, 4H), 7.17-7.36 (m, 8H), 7.43 (s, 4H), 8.07 (d, 2H), 8.71 (d, 2H). $NH_2^+$ are not seen in the spectrum. 13C NMR (101 MHz, $CD_3OD$): δ (ppm)=16.4, 24.2, 28.9, 31.8, 32.4, 33.5, 37.3, 40.8, 47.3, 54.4, 56.9, 58.2, 58.3, 61.7, 73.6, 80.7, 86.6, 88.4, 124.1, 125.5, 126.1, 128.0, 129.4, 132.8, 141.1, 142.3, 169.3, 172.2, 172.4. LC-MS: m/z=1099.50 (calcd. 1099.51 for $C_{60}H_{75}N_8O_8S_2^+$[M+H+]).

Example 83. Preparation of (2S)-1-{[(4S,7S,9aS)-7-{[(1S,2R)-2-({3-[3-(3-{[(1S,2R)-1-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}prop-1-yn-1-yl)phenyl]prop-2-yn-1-yl}oxy)-2,3-dihydro-1H-inden-1-yl]carbamoyl}-8,8-dim ethyl-5-oxooctahydropyrrolo[2,1-b][1,3]thiazepin-4-yl]amino}-N-methyl-1-oxopropan-2-ammonium dichloride (18d)

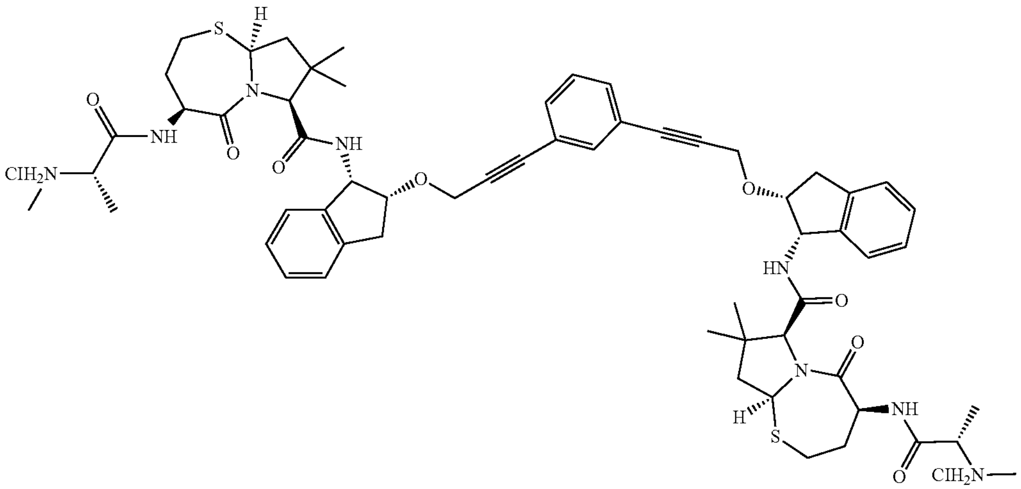

The compound 18d was prepared according to general procedure A. White solid, yield 41 mg (86%). 1H NMR (400 MHz, $CD_3OD$): δ (ppm)=1.12-1.18 (m, 12H), 1.53 (d, 6H), 1.82 (dd, 2H), 2.10 (q, 2H), 2.21-2.36 (m, 4H), 2.65 (s, 6H), 2.90 (d, 2H), 3.13 (dd, 2H), 3.20 (dd, 2H), 3.26 (s, 2H), 3.88 (q, 2H), 4.26 (s, 2H), 4.40 (d, 2H), 4.49 (d, 2H), 4.58 (q, 2H), 4.74 (dt, 2H), 5.42-5.52 (m, 4H), 7.17-7.27 (m, 6H), 7.31-7.38 (m, 3H), 7.44 (d, 2H), 7.51 (s, 1H), 8.07 (d, 2H), 8.70 (d, 2H). $NH_2^+$ are not seen in the spectrum. 13C NMR (101 MHz, $CD_3OD$): δ (ppm)=16.4, 24.2, 28.9, 31.9, 32.4, 33.5, 37.3, 40.8, 47.3, 54.4, 56.8, 58.2, 58.3, 61.8, 73.5, 80.7, 86.2, 87.3, 124.4, 125.5, 126.2, 128.0, 129.4, 130.0, 132.8, 135.5, 141.1, 142.3, 169.2, 172.2, 172.4. LC-MS: m/z=1099.50 (calcd. 1099.51 for $C_{60}H_{75}N_8O_8S_2^+$[M+$H^+$]).

Example 84. Preparation of (2S)-1-{[(4S,7S,9aS)-7-{[(1S,2R)-2-({3-[4-({[(1S,2R)-1-({[(4S,7S,9aS)-8,8-Dimethyl-4-{[(2S)-2-(methylammonio)propanoyl] amino}-5-oxooctahydropyrrolo[2,1-b][1,3]thiazepin-7-yl]carbonyl}amino)-2,3-dihydro-1H-inden-2-yl] oxy}methyl)phenyl]prop-2-yn yl}oxy)-2,3-dihydro-1H-inden-1-yl]carbamoyl}-8,8-dimethyl-5-oxooctahydropyrrolo[2,1-b][1,3]thiazepin-4-yl] amino}-N-methyl-1-oxopropan-2-ammonium dichloride (18e)

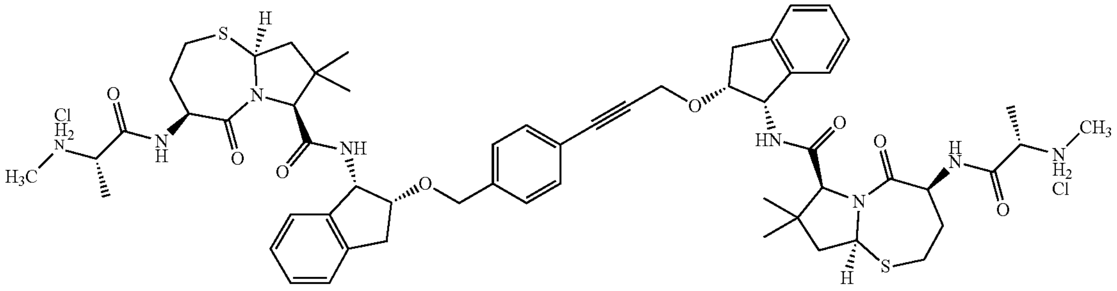

The compound 18e was prepared according to general procedure A. White solid, yield 36 mg (89%). 1H NMR (400 MHz, $CD_3OD$): δ (ppm)=1.09-1.17 (m, 12H), 1.49-1.57 (m, 6H), 1.72-1.87 (m, 3H), 2.00-2.08 (m, 1H), 2.08-2.17 (m, 1H), 2.20-2.38 (m, 3H), 2.56 (dd, 1H), 2.60-2.67 (m, 6H), 2.83-2.94 (m, 1H), 3.02-3.29 (m, 6H), 3.86-3.96 (m, 2H), 4.22-4.29 (m, 2H), 4.30-4.41 (m, 2H), 4.47 (d, 1H), 4.53-4.59 (m, 1H), 4.61 (s, 2H), 4.68 (d, 1H), 4.75 (d, 1H), 5.40-5.51 (m, 4H), 7.17-7.27 (m, 6H), 7.28-7.35 (m, 4H), 7.40 (d, 2H), 8.02 (d, 1H), 8.07 (d, 1H). C(O)NH and $NH_2^+$ are not seen in the spectrum. 13C NMR (101 MHz, $CD_3OD$): δ (ppm)=15.1-15.2, 22.7-22.9, 27.6, 30.5-30.7, 31.0-31.1, 32.0-32.2, 35.9-36.0, 39.5-39.6, 45.8-46.0, 53.0-53.2, 55.4-55.6, 56.9, 57.0-57.1, 60.4-60.5, 70.3, 72.2, 79.2, 79.9, 85.1, 85.8, 121.7, 124.1-124.2, 124.8, 126.7-126.8, 127.5, 128.0-128.1, 131.4, 139.2, 139.8-139.8, 141.0, 141.2, 167.9, 168.0, 170.7, 170.8, 171.1. LC-MS: m/z=1075.60 (calcd. 1075.51 for $C_{58}H_{75}N_8O_8S_2^+$[M+H$^+$]).

Example 85. Preparation of (2S)-1-{[(4S,7S,9aS)-7-{[(1S,2R)-2-({4-[4-({[(1S,2R)-1-({[(4S,7S,9aS)-8,8-Dimethyl-4-{[(2S)-2-(methylammonio)propanoyl] amino}-5-oxooctahydropyrrolo[2,1-b][1,3]thiazepin-7-yl]carbonyl}amino)-2,3-dihydro-1H-inden-2-yl] oxy}methyl)phenyl]benzyl}oxy)-2,3-dihydro-1H-inden-1-yl]carbamoyl}-8,8-dimethyl-5-oxooctahydropyrrolo[2,1-b][1,3]thiazepin-4-yl] amino}-N-methyl-1-oxopropan-2-ammonium dichloride (180

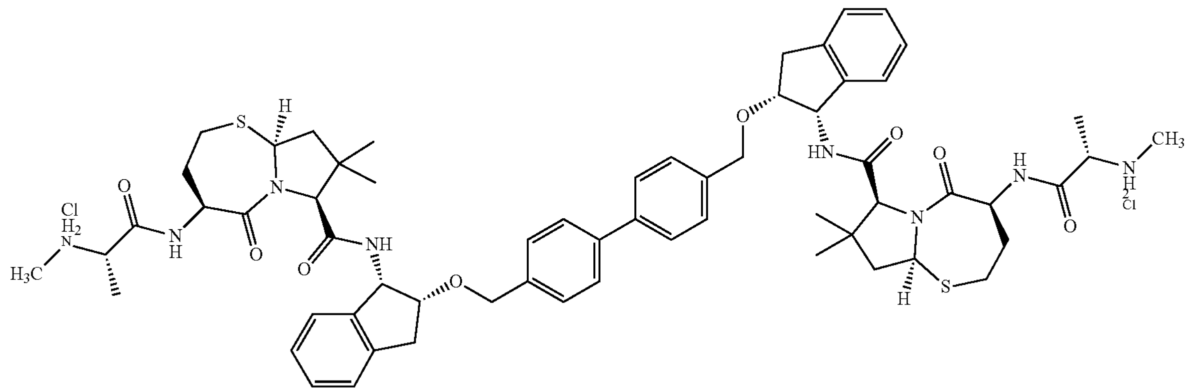

The compound 18f was prepared according to general procedure A. White solid, yield 34 mg (89%). 1H NMR (400 MHz, $CD_3OD$): δ (ppm)=1.05-1.16 (m, 12H), 1.53 (d, 6H), 1.74-1.88 (m, 4H), 2.05 (d, 2H), 2.27-2.37 (m, 2H), 2.62 (d, 8H), 3.08 (dd, 2H), 3.14-3.24 (m, 4H), 3.88 (q, 2H), 4.26 (s, 2H), 4.35-4.42 (m, 2H), 4.60-4.73 (m, 6H), 5.39-5.51 (m, 4H), 7.18-7.28 (m, 6H), 7.34 (d, 2H), 7.40 (d, 4H), 7.59 (d, 4H), 8.05 (d, 2H), 8.63 (d, 2H). $NH_2^+$ are not seen in the spectrum. 13C NMR (101 MHz, $CD_3OD$): δ (ppm)=16.4, 24.1, 28.9, 31.8, 32.3, 33.3, 37.3, 40.9, 47.2, 54.4, 56.8, 58.3, 61.7, 71.8, 73.5, 80.9, 125.5, 126.2, 127.8, 128.0, 129.4, 129.5, 138.9, 141.2-141.3, 142.6, 169.2, 172.1, 172.5. LC-MS: m/z=1127.60 (calcd. 1127.55 for $C_{62}H_{79}H_8O_8S_2^+$[M+$H^+$]).

Example 86. Preparation of (2S)-1-{[(4S,7S,9aS)-7-{[(1S,2R)-2-{[4-({[(1S,2R)-1-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}methyl)benzyl]oxy}-2,3-dihydro-1H-inden-1-yl]carbamoyl}-8,8-dimethyl-5-oxooctahydropyrrolo[2,1-b][1,3]thiazepin-4-yl]amino}-N-methyl-1-oxopropan-2-ammonium dichloride (18g)

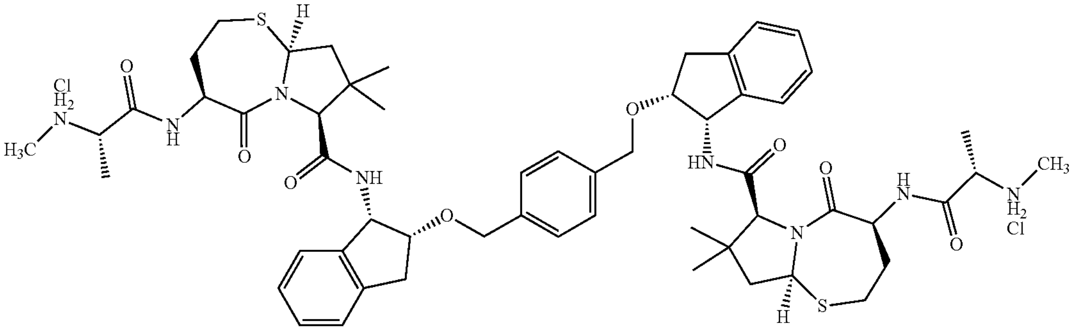

The compound 18g was prepared according to general procedure A. White solid, yield 25 mg (71%). 1H NMR (400 MHz, $CD_3OD$): δ (ppm)=1.10 (d, 12H), 1.55 (d, 6H), 1.62-1.83 (m, 4H), 2.00 (d, 2H), 2.29 (dd, 2H), 2.56 (d, 2H), 2.62-2.73 (m, 6H), 3.00-3.25 (m, 6H), 4.02 (q, 1H), 4.20 (s, 2H), 4.29-4.41 (m, 2H), 4.53 (s, 4H), 4.74 (d, 2H), 5.33-5.52 (m, 4H), 7.14-7.37 (m, 12H), 7.96 (d, 2H), 8.65 (d, 2H). $NH_2^+$ are not seen in the spectrum. 13C NMR (101 MHz, $CD_3OD$): δ (ppm)=16.9, 24.0, 28.9, 32.0, 32.4, 33.6, 37.3, 41.0, 47.0, 54.5, 56.6, 58.3, 61.8, 72.1, 73.8, 80.8, 125.7, 126.2, 128.1, 129.3, 129.6, 139.1, 141.1, 142.5, 169.3, 172.0, 172.9. LC-MS: m/z=1051.60 (calcd. 1051.51 for $C_{56}H_{75}N_8O_8S_2^+$[M+H$^+$]).

Example 87. Preparation of (2S)-1-{[(4S,7S,9aS)-7-{[(1S,2R)-2-{2-[(2-{[(1S,2R)-1-({[(4S,7S,9aS)-8,8-Dimethyl-4-{[(2S)-2-(methylammonio)propanoyl] amino}-5-oxooctahydropyrrolo[2,1-b][1,3]thiazepin-7-yl]carbonyl}amino)-2,3-dihydro-1H-inden-2-yl] oxy}ethyl)sulfonyl]ethoxy}-2,3-dihydro-1H-inden-1-yl]carbamoyl}-8,8-dimethyl-5-oxooctahydropyrrolo[2,1-b][1,3]thiazepin-4-yl] amino}-N-methyl-1-oxopropan-2-ammonium dichloride (18h)

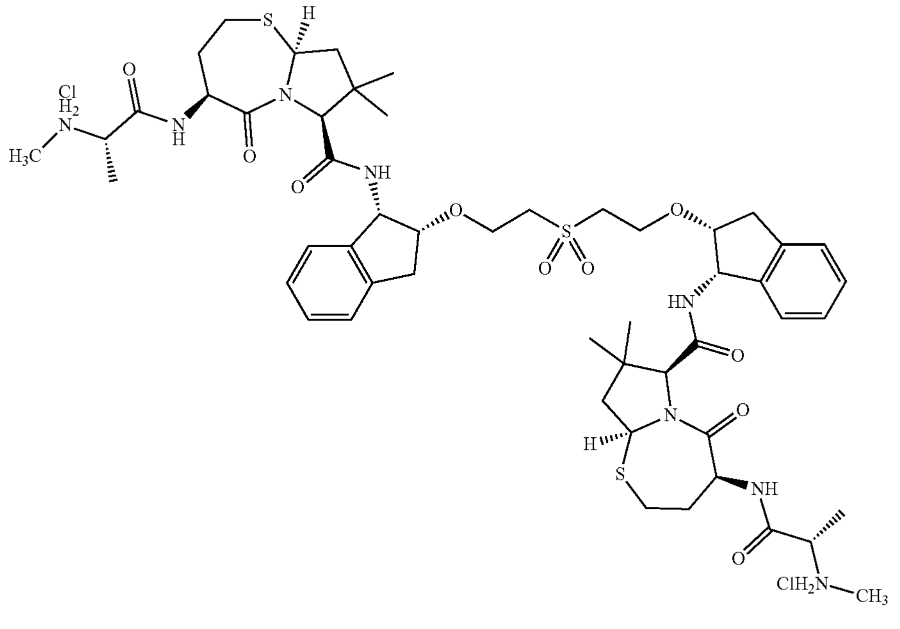

The compound 18h was prepared according to general procedure A. White solid, yield 28 mg (76%). 1H NMR (400 MHz, $CD_3OD$): δ (ppm)=1.10-1.23 (m, 12H), 1.55 (d, 6H), 1.83-1.94 (m, 2H), 2.03 (q, 2H), 2.23-2.37 (m, 4H), 2.68 (s, 6H), 2.92 (d, 2H), 2.97-3.07 (m, 4H), 3.14-3.30 (m, 6H), 3.84 (s, 4H), 3.95 (q, 2H), 4.02-4.09 (m, 2H), 4.38 (s, 2H), 4.75 (d, 2H), 5.28-5.38 (m, 2H), 5.46 (t, 2H), 7.02-7.23 (m, 6H), 7.35 (d, 2H), 7.95 (d, 2H), 8.68 (d, 2H). $NH_2^+$ are not seen in the spectrum. 13C NMR (101 MHz, $CD_3OD$): δ (ppm)=16.4, 24.0, 28.8, 31.9, 32.2, 33.6, 37.3, 40.9, 47.4, 54.5, 55.7, 57.2, 58.4, 61.8, 64.0, 73.5, 82.3, 125.7, 126.2, 128.1, 129.3, 141.1, 142.4, 169.2, 172.3, 172.4. LC-MS: m/z=1067.55 (calcd. 1067.48 for $C_{52}H_{75}N_8O_{10}S_3^+$[M+H$^+$]).

Example 88. Preparation of (2S)-1-{[(4S,7S,9aS)-74{(1R)-3-[(6-{[(3R)-3-({[(4S,7S,9aS)-8,8-Dimethyl-4-{[(2S)-2-(methylammonio)propanoyl] amino}-5-oxooctahydropyrrolo[2,1-b][1,3]thiazepin-7-yl]carbonyl}amino)-3-phenylpropyl]oxy}hexa-2,4-diyn-1-yl)oxy]-1-phenylpropyl}carbamoyl)-8,8-dimethyl-5-oxooctahydropyrrolo[2,1-b][1,3]thiazepin-4-yl]amino}-N-methyl-1-oxopropan-2-ammonium dichloride (18i)

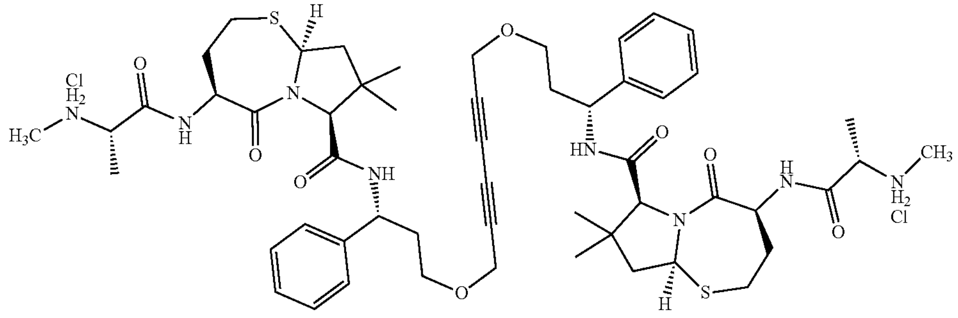

The compound 18i was prepared according to general procedure A. White solid, yield 27 mg (61%). 1H NMR (400 MHz, $CD_3OD$): δ (ppm)=1.03 (s, 6H), 1.15 (s, 6H), 1.55 (d, 6H), 1.87-1.95 (m, 2H), 1.99 (d, 2H), 2.03-2.09 (m, 4H), 2.23-2.37 (m, 4H), 2.67 (s, 6H), 2.95 (d, 2H), 3.32-3.36 (m, 2H), 3.44-3.54 (m, 4H), 3.92 (q, 2H), 4.17-4.29 (m, 6H), 4.72-4.79 (m, 2H), 5.07 (q, 2H), 5.47 (t, 2H), 7.18-7.47 (m, 10H), 8.20 (d, 2H), 8.73 (d, 2H). $NH_2^+$ are not seen in the spectrum. 13C NMR (101 MHz, $CD_3OD$): δ (ppm)=16.3, 23.9, 28.8, 31.8, 32.3, 33.6, 37.6, 40.9, 47.2, 52.2, 54.4, 58.3, 59.4, 61.8, 68.0, 70.9, 73.5, 76.8, 127.7, 128.3, 129.6, 143.4, 169.3, 171.6, 172.3. LC-MS: m/z=1027.55 (calcd. 1027.51 for $C_{54}H_{75}N_8O_8S_2^+[M+H^+]$).

Example 89: Preparation of (1R)-1-{[(4S,7S,9aS)-7-{[(1S,2R)-2-[(6-{[(1S,2R)-1-[(4S,7S,9aS)-4-[(1R)-1-formamido-1-methylpropan-2-ylium]-8,8-dimethyl-5-oxo-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-8,8-dimethyl-5-oxo-octahydropyrrolo[2,1-b][1,3]thiazepin-4-yl]carbamoyl}-1-methylpropan-2-ylium dichloride (18j)

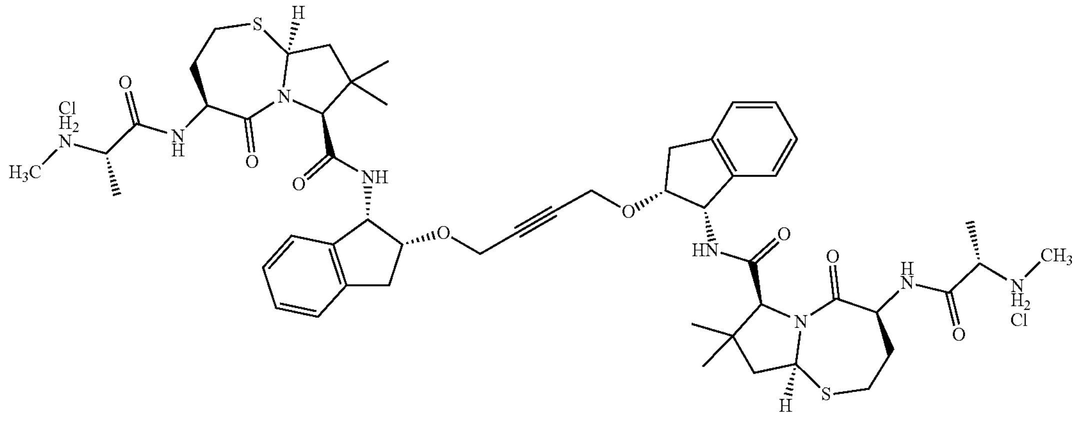

The compound 18j was prepared according to general procedure A. White solid, yield 33 mg (72%). 1H NMR (400 MHz, $CD_3OD$): δ (ppm)=1.08-1.19 (m, 12H), 1.45-1.60 (m, 6H), 1.77 (t, 2H), 2.15 (d, 4H), 2.38 (dd, 2H), 2.65-2.87 (m, 8H), 3.02-3.15 (m, 4H), 3.17-3.27 (m, 2H), 4.06 (d, 2H), 4.19 (d, 6H), 4.42 (dd, 2H), 4.76-4.83 (m, 2H), 5.34-5.57 (m, 4H), 7.08-7.35 (m, 8H), 7.93 (t, 2H), 8.66 (d, 2H). $NH_2^+$ are not seen in the spectrum. 13C NMR (101 MHz, $CD_3OD$): δ (ppm)=16.8, 24.1, 29.0, 31.9, 32.4, 33.9, 37.6, 40.9, 47.1, 54.4, 56.6, 58.1, 58.2, 61.9, 74.1, 80.9, 83.7, 125.5, 126.2, 128.1, 129.5, 141.1, 142.2, 169.2, 172.0, 173.0. LC-MS: m/z=999.50 (calcd. 999.48 for $C_{52}H_{71}N_8O_8S_2^+$[M+H$^+$]).

Example 90. Preparation of 1-{[(4S,7S,9aS)-7-({(1S,2R)-2-[(6-{[(1S,2R)-1-({[(4S,7S,9aS)-8,8-Dimethyl-4-{[2-methyl-2-(methylammonio)propanoyl]amino}-5-oxooctahydropyrrolo[2,1-b][1,3]thiazepin-7-yl]carbonyl}amino)-2,3-dihydro-1H-inden-2-yl]oxy}hexa-2,4-diyn-1-yl)oxy]-2,3-dihydro-1H-inden-1-yl}carbamoyl)-8,8-dimethyl-5-oxooctahydropyrrolo[2,1-b][1,3]thiazepin-4-yl]amino}-N,2-dimethyl-1-oxopropan-2-ammonium dichloride (18k)

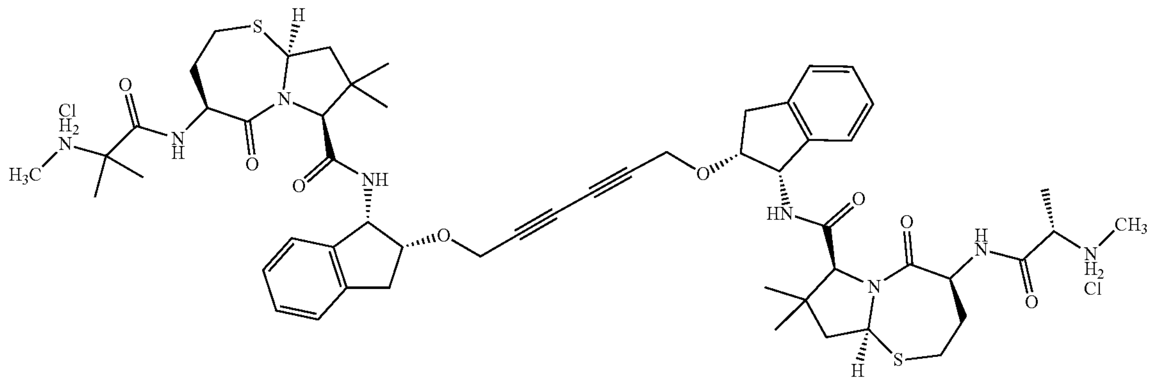

The compound 18k was prepared according to general procedure A. White solid, yield 23 mg (75%). 1H NMR (400 MHz, $CD_3OD$): δ (ppm)=1.12-1.20 (m, 12H), 1.58-1.68 (m, 12H), 1.77-1.86 (m, 2H), 2.09 (q, 2H), 2.26 (d, 2H), 2.32 (dd, 2H), 2.62 (s, 6H), 2.91 (d, 2H), 3.06-3.17 (m, 4H), 3.25 (d, 2H), 4.20-4.32 (m, 4H), 4.37 (d, 2H), 4.42-4.50 (m, 2H), 4.73 (d, 2H), 5.47 (dd, 4H), 7.16-7.38 (m, 8H), 8.02 (d, 2H). C(O)NH and $NH_2^+$ are not seen in the spectrum. 13C NMR (101 MHz, $CD_3OD$): δ (ppm)=20.4, 20.9, 22.9, 27.1, 27.5, 31.1, 31.6, 35.8, 39.5, 45.9, 53.5, 55.5, 56.7, 60.5, 61.8, 69.7, 72.2, 75.6, 79.7, 124.2, 124.8, 126.8, 128.1, 139.7, 140.85, 170.3, 170.8, 171.4. LC-MS: m/z=1051.60 (calcd. 1051.51 for $C_{56}H_{75}N_8O_8S_2{}^+$[M+H$^+$]).

Example 91: [(1S)-1-{[(4S,7S,9aS)-7-{[(1S,2R)-2-[(6-{[(1S,2R)-1-[(4S,7S,9aS)-8,8-Dimethyl-4-[(2S)-2-(methylazaniumyl)butanamido]-5-oxo-octahydro-pyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-8,8-dimethyl-5-oxo-octahydropyrrolo[2,1-b][1,3]thiazepin-4-yl]carbamoyl}propyl](methyl)azanium dichloride (18m)

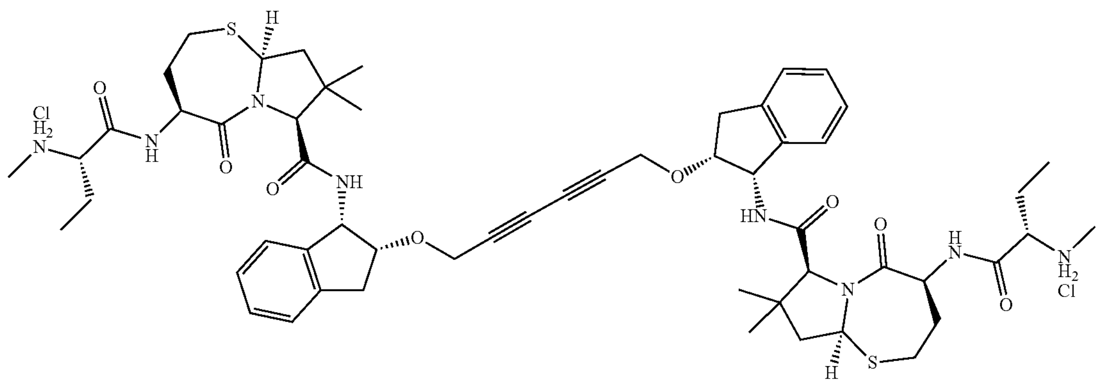

The compound 18m was prepared according to general procedure A. White solid, yield 83 mg (92%). 1H NMR (400 MHz, $CD_3OD$): δ (ppm)=1.07 (t, 6H), 1.17 (s, 12H), 1.82 (dd, 2H), 1.96 (tt, 4H), 2.09 (q, 2H), 2.26-2.39 (m, 4H), 2.68 (s, 6H), 2.92 (d, 2H), 3.06-3.17 (m, 4H), 3.25-3.31 (m, 2H), 3.87 (t, 2H), 4.22-4.31 (m, 4H), 4.38 (d, 2H), 4.47 (d, 2H), 4.79 (d, 2H), 5.43-5.51 (m, 4H), 7.18-7.27 (m, 6H), 7.33 (d, 2H), 8.01 (d, 2H). $NH_2^+$ and C(O)NH are not seen in the spectrum. 13C NMR (101 MHz, $CD_3OD$): δ (ppm)=9.2, 24.2, 24.9, 28.9, 32.3-32.5, 33.5, 37.2, 40.8, 47.4, 54.5, 56.7, 58.1, 61.7, 63.7, 71.1, 73.5, 76.9, 81.0, 125.5, 126.1, 128.1, 129.4, 141.0, 142.2, 168.0, 172.1, 172.3. LC-MS: m/z=1051.50 (calcd. 1051.51 for $C_{56}H_{75}N_8O_8S_2^+[M+H^+]$).

Example 92: (2S)-2-{[(4S,7S,9aS)-7-{[(1S,2R)-2-[(6-{[(1S,2R)-1-[(4S,7S,9aS)-4-[(2S)-2-(Methylamino)propanamido]-5-oxo-8,8-bis(prop-2-en-1-yl)-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-5-oxo-8,8-bis(prop-2-en-1-yl)-octahydropyrrolo[2,1-b][1,3]thiazepin-4-yl]carbamoyl}-2-(methylazaniumyl)ethanide dichloride (18n)

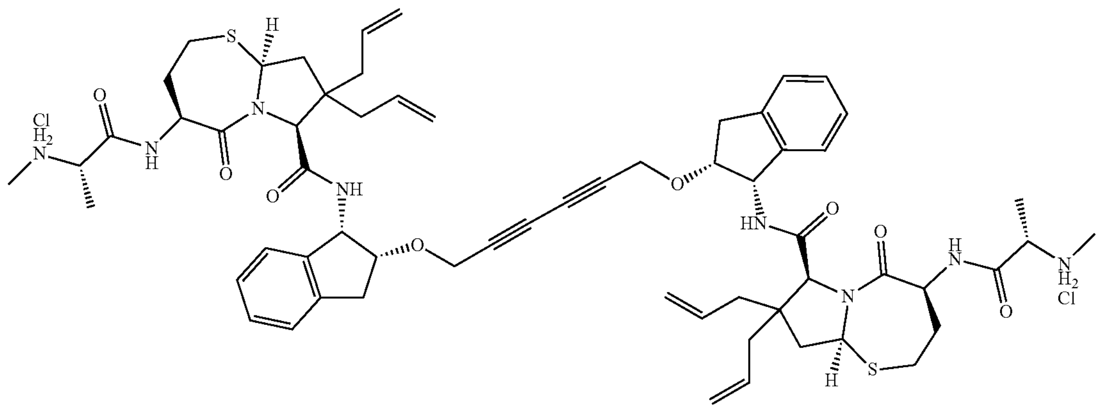

The compound 18n was prepared according to general procedure A. Colorless solid, yield 45 mg (83%). 1H NMR (400 MHz, $CD_3OD$): δ (ppm)=1.59 (d, 6H), 1.83 (dd, 2H), 2.00-2.14 (m, 4H), 2.19 (d, 4H), 2.31 (d, 2H), 2.45 (dd, 4H), 2.70 (s, 6H), 2.93 (d, 2H), 3.16 (d, 4H), 3.98 (q, 2H), 4.28 (d, 2H), 4.39 (d, 2H), 4.50 (s, 4H), 4.75 (d, 2H), 5.13 (dt, 8H), 5.47 (d, 4H), 5.81-5.96 (m, 4H), 7.19-7.31 (m, 6H), 7.35 (d, 2H), 8.05 (d, 2H). LC-MS: m/z=1127.55 (calcd. 1127.55 for $C_{62}H_{79}N_8O_8S_2^+$[M+H$^+$]).

Example 93: [(1S)-1-{[(4'S,7'S,9'aS)-7'-{[(1S,2R)-2-[(6-{[(1S,2R)-1-{[(4'S,7'S,9'aS)-4'-[(2S)-2-(Methylazaniumyl)propanamido]-5'-oxo-3',4',5',7',9',9'a-hexahydro-2'H-spiro[cyclopentane-1,8'-pyrrolo[2,1-b][1,3]thiazepin]-3-en-7'-yl]amido}-2,3-dihydro-1H-inden-2-yl]oxy}hexa-2,4-diyn-1-yl)oxy]-2,3-dihydro-1H-inden-1-yl]carbamoyl}-5'-oxo-3',4',5',7',9',9'a-hexahydro-2'H-spiro[cyclopentane-1,8'-pyrrolo[2,1-b][1,3]thiazepin]-3-en-4'-yl]carbamoyl}ethyl](methyl)azanium dichloride (18o)

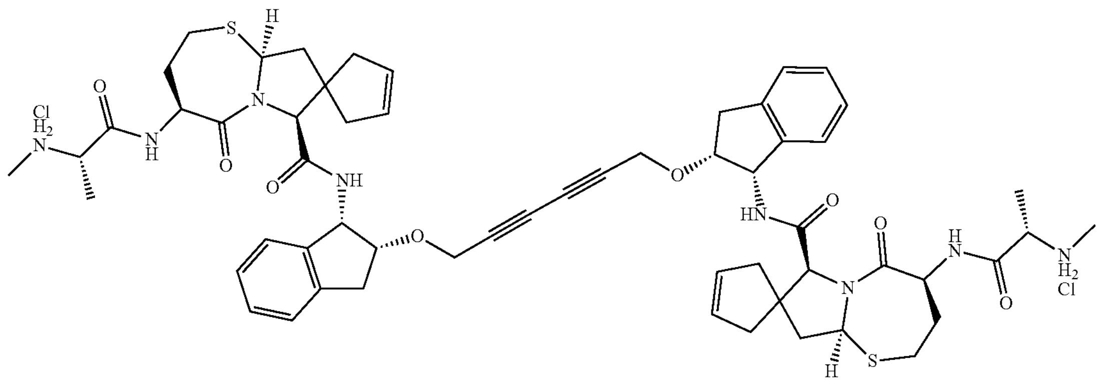

The compound 18o was prepared according to general procedure A. Colorless solid, yield 26 mg (78%). 1H NMR (400 MHz, $CD_3OD$): δ (ppm)=1.54 (d, 6H), 2.02 (t, 4H), 2.24 (dd, 6H), 2.42 (d, 2H), 2.52 (dd, 2H), 2.68 (s, 6H), 2.82-2.94 (m, 4H), 3.09 (q, 4H), 3.95 (q, 2H), 4.29 (d, 2H), 4.36 (d, 2H), 4.46 (d, 4H), 4.74 (d, 2H), 5.45 (t, 4H), 5.65 (s, 2H), 5.76 (s, 2H), 7.16-7.27 (m, 6H), 7.30 (d, 2H), 8.07 (d, 1H). LC-MS: m/z=1071.50 (calcd. 1071.48 for $C_{58}H_{71}N_8O_8S_2^+$[M+H$^+$]).

Example 94: [(1S)-1-{[(4S,7S,8S,9aS)-7-{[(1S,2R)-2-[(6-{[(1S,2R)-1-[(4S,7S,8S,9aS)-8-Hydroxy-4-[(2S)-2-(methylazaniumyl)propanamido]-5-oxo-octahydropyrrolo[2,1-b][1,3]thiazepine-7-amido]-2,3-dihydro-1H-inden-2-yl]oxy}hexa-2,4-diyn-1-yl)oxy]-2,3-dihydro-1H-inden-1-yl]carbamoyl}-8-hydroxy-5-oxo-octahydropyrrolo[2,1-b][1,3]thiazepin-4-yl]carbamoyl}ethyl](methyl)azanium dichloride (18p)

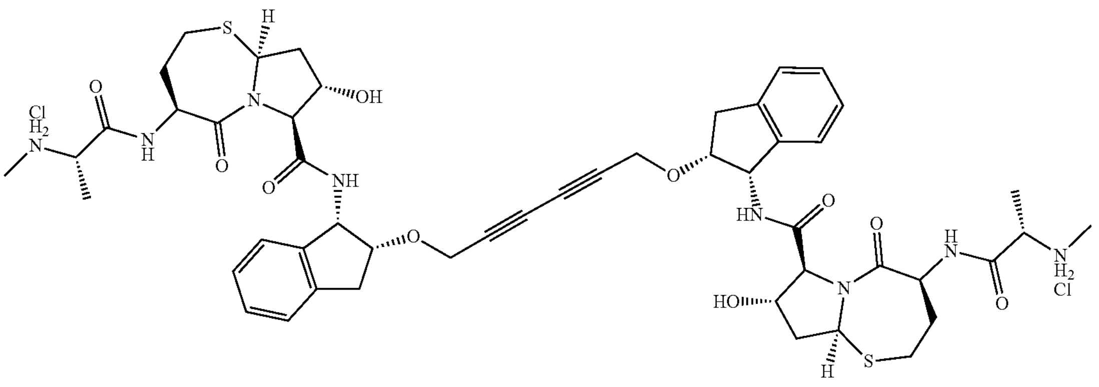

The compound 18p was prepared according to general procedure A. Colorless solid, yield 24 mg (87%). 1H NMR (400 MHz, $CD_3OD$): δ (ppm)=1.54 (d, 6H), 1.96-2.06 (m, 2H), 2.13 (ddd, 2H), 2.29 (d, 2H), 2.56 (dd, 2H), 2.67 (d, 6H), 2.93 (d, 2H), 3.06-3.13 (m, 4H), 3.32-3.35 (m, 2H), 3.90-4.00 (m, 2H), 4.35 (d, 4H), 4.42-4.48 (m, 2H), 4.56 (d, 2H), 4.65 (s, 2H), 4.79 (d, 2H), 5.44 (d, 2H), 5.50 (t, 2H), 7.16-7.27 (m, 8H), 7.30 (d, 2H). —$NH_2^+$, C(O)NH and OH are not seen in the spectrum. 13C NMR (101 MHz, $CD_3OD$): δ (ppm)=15.1, 30.7, 31.2, 32.6, 36.0, 40.9, 53.0, 55.7, 57.0, 60.6, 69.6, 70.6, 71.3, 75.7, 80.1, 124.1, 124.8, 126.7, 128.0, 139.7, 140.7, 168.0, 169.8, 171.6. LC-MS: m/z=999.45 (calcd. 999.41 for $C_{50}H_{63}N_8O_{10}S_2^+$[M+H$^+$]).

Synthetic Scheme for the Preparation of Dimer 181

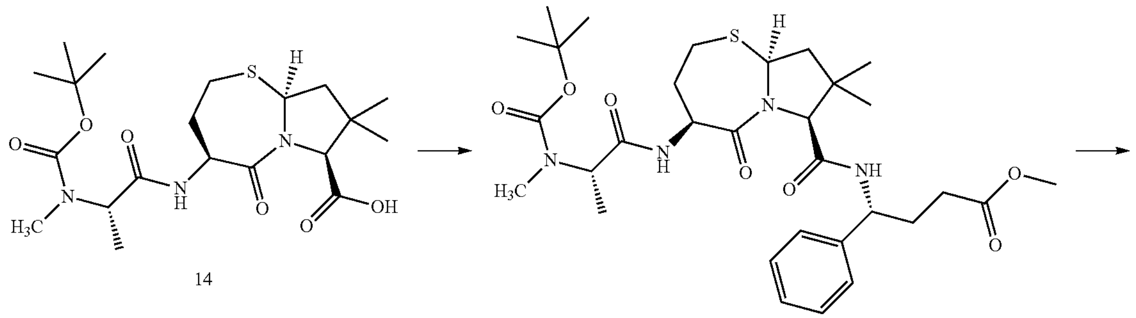

14

38

-continued

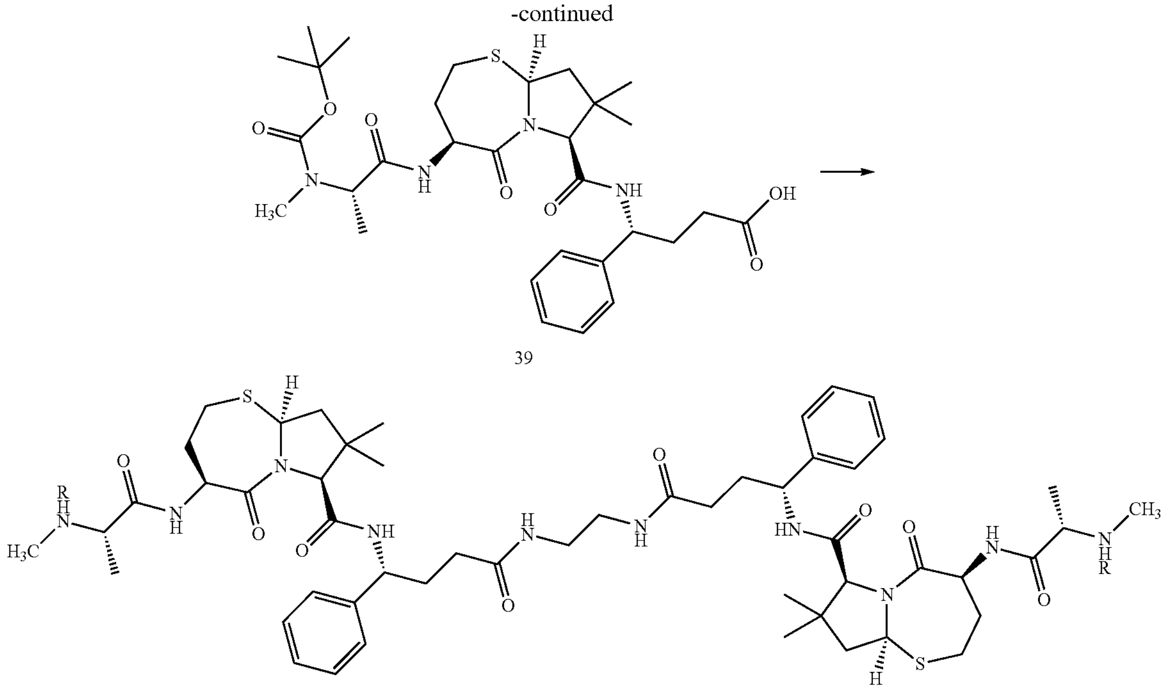

39

171, $R^2$ = Boc
181, $R^2$ = $H_2Cl$

Example 95. Preparation of Methyl (4R)-4-{[(4S,7S,9aS)-4-[(2S)-2-{[(tert-butoxy)carbonyl](methyl)amino}propanamido]-8,8-dimethyl-5-oxo-octahydropyrrolo[2,1-b][1,3]thiazepin-7-yl]formamido}-4-phenylbutanoate (38)

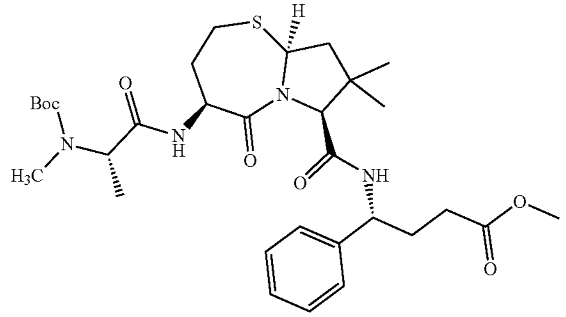

Under $N_2$ atmosphere, N-Ethyl-N-(propan-2-yl)propan-2-amine (153 μL, 0.879 mmol, 3.00 eq.) and COMU® (157 mg, 0.366 mmol, 1.25 eq.) were added to a solution of carboxylic acid 14 (130 mg, 0.293 mmol, 1.00 eq.) dissolved in dry THF (2.4 mL) and stirred at rt. After 45 minutes, the (1R)-4-Methoxy-4-oxo-1-phenylbutan-1-ammonium chloride (80 mg, 0.352 mmol, 1.20 eq.) was added and stirring was continued for 22 h. Upon completion, ethyl acetate (30 mL) was added and washed with NaOH solution (1 M, 2×10 mL), HCl solution (1 M, 2×10 mL), water (10 mL) and brine (10 mL), dried ($Na_2SO_4$) and concentrated in vacuo. The resulting residue was purified by fc (hexanes/ethyl acetate). Colorless solid, yield 123 mg (68%). $R_f$=0.30 (hexanes/ethyl acetate 3:7, Ceric Ammonium Molybdate stain). $^1H$ NMR (400 MHz, $CD_3OD$): δ (ppm)=1.00 (s, 3H, $C(CH_3)_2$), 1.13 (s, 3H), 1.37 (d, 3H), 1.47 (s, 9H), 1.82-1.98 (m, 2H), 2.02-2.15 (m, 2H), 2.20-2.33 (m, 2H), 2.37 (td, 2H), 2.85 (s, 3H), 2.91 (ddd, 1H), 3.31-3.35 (m, 1H), 3.65 (s, 3H), 4.20 (s, 1H), 4.61-4.67 (m, 1H), 4.89-4.95 (m, 1H), 5.46 (d, 1H), 7.22-7.28 (m, 1H), 7.31-7.39 (m, 4H), 8.15 (d, 1H). $CHCH_3$ and C(O)NH are not seen in the spectrum. LC-MS: m/z=619.30 (calcd. 619.32 for $C_{31}H_{47}N_4O_7S^+[M+H^+]$).

Example 96. Preparation of (4R)-4-{[(4S,7S,9aS)-4-[(2S)-2-{[(tert-Butoxy)carbonyl](methyl)amino}propanamido]-8,8-dimethyl-5-oxo-octahydropyrrolo[2,1-b][1,3]thiazepin-7-yl]formamido}-4-phenylbutanoic Acid (39)

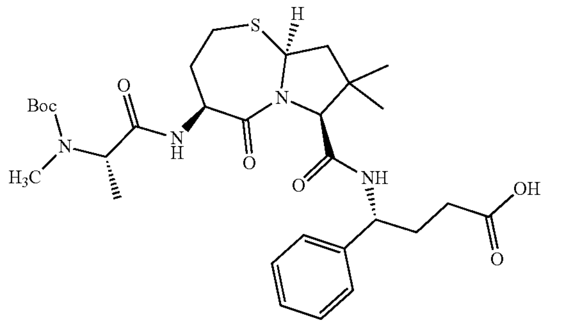 [SMILES: C[C@@H](C(=O)N[C@H]1CCS[C@H]2CC(C)(C)[C@@H](C(=O)N[C@H](CCC(=O)O)c3ccccc3)N2C1=O)N(C)C(=O)OC(C)(C)C]

Lithium hydroxide solution (1 M, 250 μL, 0.250 mmol, 2.00 eq.) was added to a solution of the methyl ester 38 (77 mg, 0.125 mmol, 1.00 eq.) dissolved in THF (250 μL) at rt. The resulting emulsion was stirred at 40° C. for 16 h. Upon completion, ethyl acetate (30 mL) was added and washed with HCl solution (1 M, 10 mL), water (10 mL) and brine (10 mL), dried ($Na_2SO_4$) and concentrated in vacuo. The resulting residue was purified by fc (hexane/ethyl acetate/formic acid 0.2%). Colorless oil, yield 53 mg (70%). $R_f$=0.56 (hexanes/ethyl acetate/formic acid 1:9:0.1, Ceric Ammonium Molybdate stain). 1H NMR (400 MHz, $CD_3OD$): δ (ppm)=0.99 (s, 3H), 1.11 (s, 3H), 1.35 (d, 3H), 1.45 (s, 9H), 1.81-1.94 (m, 2H), 2.00-2.12 (m, 2H), 2.19-2.25 (m, 1H), 2.25-2.29 (m, 1H), 2.32 (td, 2H), 2.83 (s, 3H), 2.85-2.92 (m, 1H), 3.29-3.34 (m, 1H), 4.18 (s, 1H), 4.63 (d, 1H), 4.89-4.93 (m, 1H), 5.44 (t, 1H), 7.20-7.26 (m, 1H), 7.28-7.38 (m, 4H), 8.14 (d, 1H). $CHCH_3$, C(O)NH and COOH are not seen in the spectrum. LC-MS: m/z=605.25 (calcd. 605.30 for $C_{30}H_{45}N_4O_7S^+[M+H^+]$).

Example 97. Preparation of tert-Butyl [(2S)-1-{[(4S,7S,9aS)-7-({(1R)-4-[(2-{[(4R)-4-({[(4S,7S,9aS)-4-amino-8,8-dimethyl-5-oxooctahydropyrrolo[2,1-b][1,3]thiazepin-7-yl]carbonyl}amino)-4-phenylbutanoyl]amino}ethyl)amino]-4-oxo-1-phenylbutyl}carbamoyl)-8,8-dimethyl-5-oxooctahydropyrrolo[2,1-b][1,3]thiazepin-4-yl]amino}-1-oxopropan-2-yl](methyl)carbamate (171)

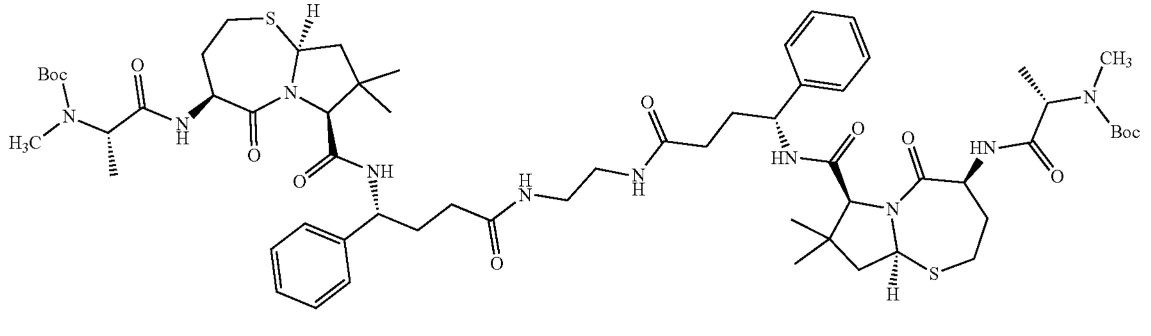 [SMILES: C[C@@H](C(=O)N[C@H]1CCS[C@H]2CC(C)(C)[C@@H](C(=O)N[C@H](CCC(=O)NCCNC(=O)CC[C@@H](NC(=O)[C@H]3N4C(=O)[C@@H](NC(=O)[C@H](C)N(C)C(=O)OC(C)(C)C)CCS[C@H]4CC3(C)C)c3ccccc3)c3ccccc3)N2C1=O)N(C)C(=O)OC(C)(C)C]

Under $N_2$ atmosphere, ethane-1,2-diamine (3 μL, 0.0495 mmol, 1.00 eq.), carboxylic acid 39 (63 mg, 0.104 mmol, 2.10 eq.), 1-Hydroxybenzotriazole hydrate (21 mg, 0.139 mmol, 2.80 eq.) and $NEt_3$ (21 μL, 0.149 mmol, 3.00 eq.) were dissolved in dry THF (0.8 mL). EDC*HCl (24 mg, 0.124 mmol, 2.50 eq.) was added and stirred for 23 h. Upon completion, ethyl acetate (30 mL) was added to the residue and washed with NaOH solution (1 M, 2×10 mL), HCl solution (1 M, 2×10 mL), water (10 mL) and brine (10 mL), dried ($Na_2SO_4$) and concentrated in vacuo. The resulting residue was purified by fc (hexane/ethyl acetate). Colorless solid, yield 35 mg (57%). $R_f$=0.35 (ethyl acetate/methanol 9:1, Ceric Ammonium Molybdate stain). 1H NMR (400 MHz, $CD_3OD$): δ (ppm)=0.97 (s, 6H), 1.13 (s, 6H), 1.35 (d, 6H), 1.46 (s, 18H), 1.83 (dd, 2H), 1.88-1.98 (m, 2H), 2.01-2.28 (m, 10H), 2.33 (dd, 2H), 2.85 (s, 6H), 2.90-2.97 (m, 2H), 3.20-3.31 (m, 4H), 3.34-3.39 (m, 2H), 4.18 (s, 2H), 4.44-4.73 (m, 4H), 4.82-4.86 (m, 2H), 5.51 (t, 2H), 7.22-7.28 (m, 2H), 7.30-7.37 (m, 8H), 8.05 (d, 2H). C(O)$NHCH_2CH_2HN$(O)C and C(O)NH are not seen in the spectrum. LC-MS: m/z=1233.70 (calcd. 1233.64 for $C_{62}H_{93}N_{10}O_{12}S_2{}^+$[M+H$^+$]).

Example 98. Preparation of (2S)-1-{[(4S,7S,9aS)-74{(1R)-4-[(2-{[(4R)-4-({[(4S,7S,9aS)-8,8-Dimethyl-4-{[(2S)-2-(methylammonio)propanoyl]amino}-5-oxooctahydropyrrolo[2,1-b][1,3]thiazepin-7-yl]carbonyl}amino)-4-phenylbutanoyl]amino}ethyl)amino]-4-oxo-1-phenylbutyl}carbamoyl)-8,8-dimethyl-5-oxooctahydropyrrolo[2,1-b][1,3]thiazepin-4-yl]amino}-N-methyl-1-oxopropan-2-ammonium dichloride (181)

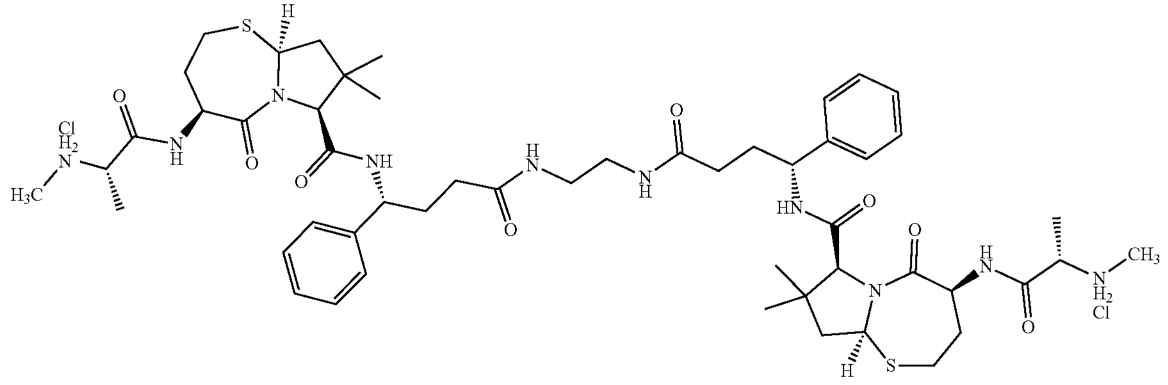

The compound 181 was prepared according to general procedure A. White solid, yield 29 mg (92%). 1H NMR (400 MHz, $CD_3OD$): δ (ppm)=0.95 (s, 6H), 1.12 (s, 6H), 1.52 (s, 6H), 1.77-1.87 (m, 2H), 1.96-2.37 (m, 14H), 2.65 (s, 6H), 2.96 (d, 2H), 3.28-3.37 (m, 6H), 3.95 (s, 2H), 4.15 (s, 2H), 4.78 (d, 4H), 5.50 (s, 2H), 7.21-7.36 (m, 10H). $NH_2{}^+$ are not seen in the spectrum. 13C NMR (101 MHz, $CD_3OD$): δ (ppm)=16.5, 23.9, 28.9, 32.2, 32.4, 33.4, 33.7, 34.0, 40.1, 40.8, 47.2, 54.3, 54.4, 58.3, 61.8, 73.7, 127.6, 128.5, 129.7, 143.3, 169.3, 171.6, 172.7. LC-MS: m/z=1033.55 (calcd. 1033.54 for $C_{52}H_{77}N_{10}O_8S_2{}^+$[M+H$^+$]).

Synthetic Scheme for the Preparation of Dimer 18q

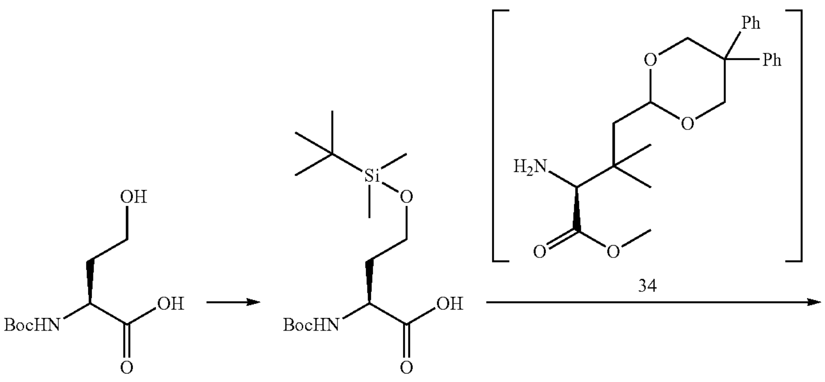

66 67

-continued

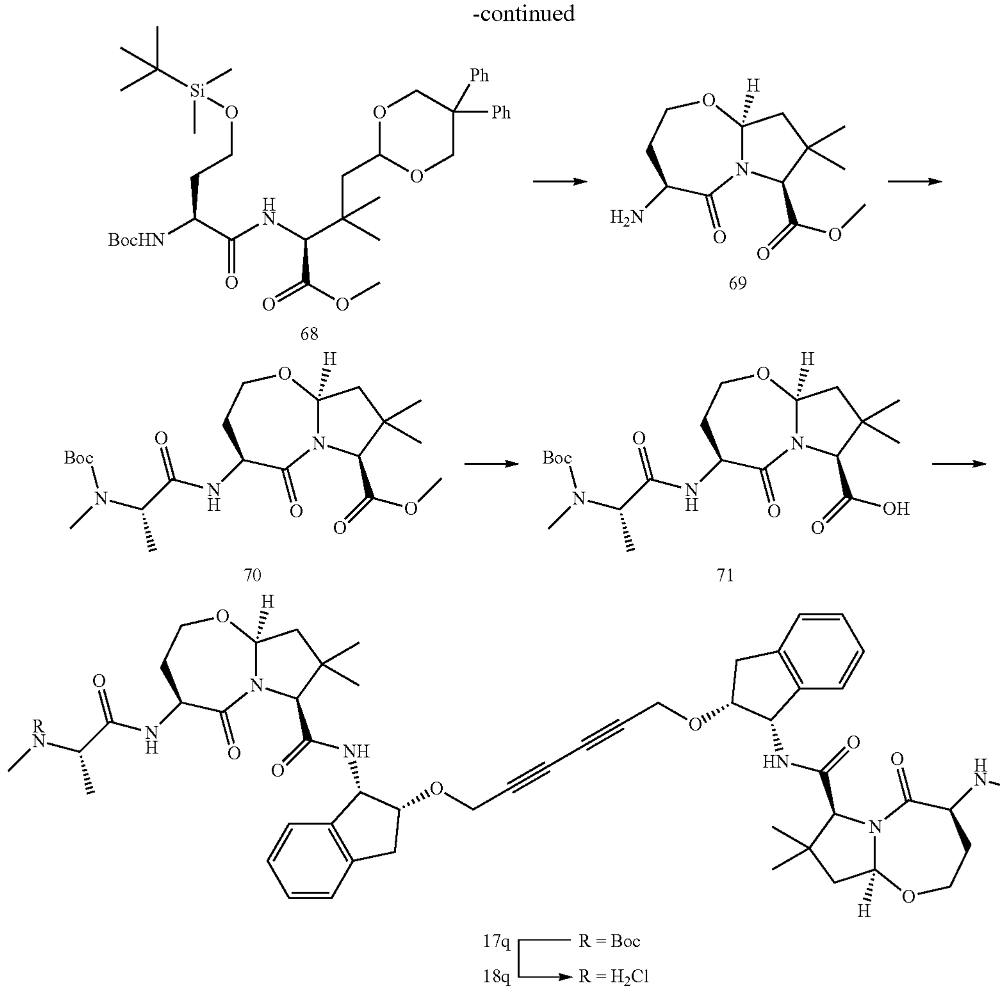

Example 99: Preparation of (2S)-2-{[(tert-Butoxy)carbonyl]amino}-4-[(tert-butyldimethylsilyl)oxy]butanoic acid (67)

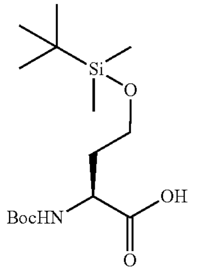 [SMILES: CC(C)(C)OC(=O)N[C@@H](CCO[Si](C)(C)C(C)(C)C)C(=O)O]

N-(tert-Butoxycarbonyl)-L-homoserine 66 (1.00 g, 4.56 mmol, 1.00 eq.) was dissolved in dry $CH_2Cl_2$ (10 mL) and tert-butyl(chloro)dimethylsilane (1.72 g, 11.4 mmol, 2.50 eq.) was added. The solution was cooled down to 0° C., N-Ethyl-N-(propan-2-yl)propan-2-amine (1.99 mL, 11.4 mmol, 2.50 eq.) was added and stirring was continued at rt for 17 h. Upon completion, all volatiles were removed in vacuo. Citric acid solution (5%, 20 mL) was added to the residue and extracted with ethyl acetate (3×20 mL). The combined organic layers were washed with brine (20 mL), dried ($Na_2SO_4$) and concentrated in vacuo. The crude material 67 (2.02 g) was used without any further purification. LC-MS: m/z=334.55 (calcd. 334.51 for $C_{15}H_{32}NO_5Si^+$[M+$H^+$]).

Example 100: Preparation of Methyl (2S)-2-[(2S)-2-{[(tert-butoxylcarbonyl]amino}-4-[(tert-butyldimethylsilyl)oxy]butanamido]-4-(5,5-diphenyl-1,3-dioxan-2-yl)-3,3-dimethylbutanoate (68)

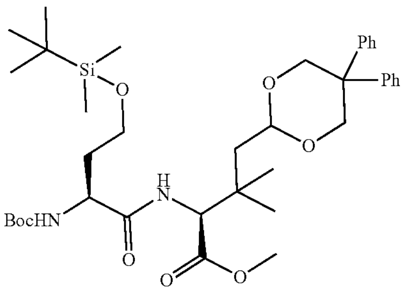 [SMILES: COC(=O)[C@@H](NC(=O)[C@H](CCO[Si](C)(C)C(C)(C)C)NC(=O)OC(C)(C)C)C(C)(C)CC1OCC(c2ccccc2)(c2ccccc2)CO1]

Under $N_2$ atmosphere, amine 34, crude carboxylic acid 67 (1.10 g, 3.30 mmol, 2.00 eq), 1-hydroxybenzotriazole hydrate (506 mg, 3.30 mmol, 2.00 eq.) and N-methylmorpholine (1.09 mL, 9.91 mmol, 6.00 eq.) were dissolved in dry THF (5.89 mL) and cooled to 0° C. EDC·HCl (633 mg, 3.30 mmol, 2.00 eq) was added and the resulting mixture was stirred for 30 min at 0° C. followed by 18 h at rt. Upon completion, ethyl acetate (30 mL) was added and washed with saturated $NaHCO_3$ solution (2×10 mL), citric acid solution (5%, 2×10 mL), water (10 mL) and brine (10 mL), dried ($Na_2SO_4$) and concentrated in vacuo. The resulting residue was purified by fc (hexanes/ethyl acetate). Colorless oil, yield 727 mg (63%). $R_f$=0.25 (hexanes/ethyl acetate 2:8, Ceric Ammonium Molybdate stain). 1H NMR (400 MHz, $CDCl_3$): δ (ppm)=0.05 (d, 6H), 0.90 (s, 9H), 1.01 (s, 3H), 1.03 (s, 3H), 1.43 (s, 9H), 1.63 (dd, 1H), 1.70 (dd, 1H), 1.95 (q, 2H), 3.67 (s, 3H), 3.72 (t, 1H), 3.76-3.83 (m, 1H), 4.16-4.27 (m, 3H), 4.56 (d, 1H), 4.68 (d, 2H), 4.81 (t, 1H), 5.95 (dd, 1H), 7.02-7.06 (m, 2H), 7.17-7.23 (m, 3H), 7.24-7.32 (m, 4H), 7.42-7.47 (m, 2H). LC-MS: m/z=699.40 (calcd. 699.40 for $C_{38}H_{59}N_2O_8Si^+$[M+H$^+$]).

Example 101: Preparation of methyl (4S,7S,9aS)-4-amino-8,8-dimethyl-5-oxooctahydropyrrolo[2,1-b][1,3]oxazepine-7-carboxylate (69)

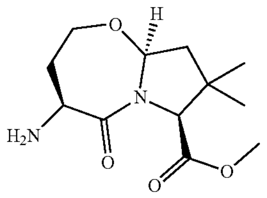 [SMILES: COC(=O)[C@H]1N2C(=O)[C@@H](N)CCO[C@H]2CC1(C)C]

Compound 68 (590 mg, 0.844 mmol, 1.00 eq.) was treated with HCl in dioxane (4 M, 4.22 mL, 16.8 mmol, 20.0 eq.) and stirred at 40° C. for 2 h. Upon completion, all volatiles were removed under reduced pressure.

Example 102: Preparation of Methyl (4S,7S,9aS)-4-[(2S)-2-{[(tert-butoxy)carbonyl](methyl)amino}propanamido]-8,8-dimethyl-5-oxo-octahydropyrrolo[2,1-b][1,3]oxazepine-7-carboxylate (70)

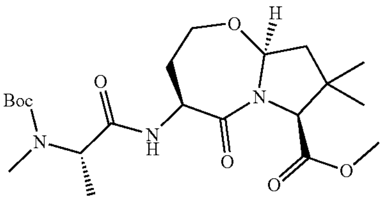

Under $N_2$ atmosphere, the amine 69, N-(tert-butoxycarbonyl)-N-methyl-L-alanine (349 mg, 1.72 mmol, 1.20 eq.), 1-hydroxybenzotriazole hydrate (206 mg, 1.01 mmol, 1.20 eq.) and 4-methylmorpholine (279 μL, 2.53 mmol, 3.00 eq.) were dissolved in dry DMF (3.9 mL) and cooled to 0° C. EDC·HCl (194 mg, 1.01 mmol, 1.20 eq.) was added and the resulting mixture was stirred for 30 minutes at 0° C. followed by 18 h at rt. Upon completion, water (30 mL) was added and extracted with ethyl acetate (3×30 mL). The combined organic layers were washed with NaOH solution (1 M, 30 mL), citric acid solution (5%, 30 mL), water (30 mL) and brine (30 mL), dried ($Na_2SO_4$) and concentrated in vacuo. The resulting residue was purified by fc (hexanes/ethyl acetate). Colorless solid 70, yield 254 mg (68%). $R_f$=0.36 (hexanes/ethyl acetate 4:6, Ceric Ammonium Molybdate stain). $^1H$ NMR (400 MHz, $CDCl_3$): δ (ppm)=1.05 (s, 3H), 1.11 (s, 3H), 1.31 (d, 3H), 1.44 (s, 9H), 1.81-1.99 (m, 3H), 2.12 (dd, 1H), 2.75 (s, 3H), 3.73 (s, 3H), 3.92 (t, 1H), 4.12-4.20 (m, 2H), 4.63-4.70 (m, 1H), 5.18-5.22 (m, 1H), 7.15 (s, 1H). $CHCH_3$ is not seen in the spectrum. LC-MS: m/z=442.40 (calcd. 442.53 for $C_{21}H_{36}N_3O_7^+$[M+H$^+$]).

Example 103: Preparation of (4S,7S,9aS)-4-[(2S)-2-{[(tert-Butoxy)carbonyl](methyl)amino}propanamido]-8,8-dimethyl-5-oxo-octahydropyrrolo[2,1-b][1,3]oxazepine-7-carboxylic acid (71)

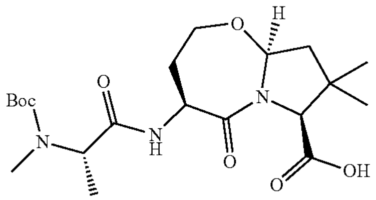

Lithium hydroxide solution (1 M, 1.15 mL, 1.15 mmol, 2.00 eq.) was added to a solution of the methyl ester 70 (254 mg, 0.574 mmol, 1.00 eq.) dissolved in THF (1.15 mL) at rt. The resulting emulsion was stirred at 40° C. for 17 h. Upon completion, $Et_2O$ (10 mL) was added and washed with a mixture of NaOH solution 1 M and brine (8:1, 3×9 mL). The combined aq. layers were extracted with ethyl acetate (10 mL) and the ethyl acetate layer was washed with a mixture of NaOH solution 1 M and brine (8:1, 2×9 mL). After acidification of the combined aq. layers with conc. HCl to pH 1, the aq. layer was extracted with $CH_2Cl_2$ (3×15 mL) and ethyl acetate (2×15 mL). The combined organic layers were dried ($Na_2SO_4$) and concentrated in vacuo. The resulting residue was purified by fc (hexanes/ethyl acetate/formic acid 0.2%). Colorless solid, yield 186 mg (76%). $^1H$ NMR (400 MHz, $CDCl_3$): δ (ppm)=1.09-1.19 (m, 6H), 1.35 (d, 3H), 1.46 (s, 9H), 1.83-2.03 (m, 3H), 2.15 (dd, 1H), 2.79 (s, 3H), 3.88-3.98 (m, 1H), 4.17 (d, 2H), 4.69-4.76 (m, 1H), 5.21-5.25 (m, 1H), 7.29 (s, 1H). $CHCH_3$ and COOH are not seen in the spectrum. LC-MS: m/z=442.50 (calcd. 442.53 for $C_{21}H_{36}N_3O_7^+$[M+H$^+$]).

Example 104: Preparation of tert-Butyl N-[(1S)-1-{[(4S,7S,9aS)-7-{[(1S,2R)-2-[(6-{[(1S,2R)-1-[(4S,7S,9aS)-4-[(2S)-2-{[(tert-butoxy)carbonyl](methyl)amino}propanamido]-8,8-dimethyl-5-oxo-octahydropyrrolo[2,1-b][1,3]oxazepine-7-amido]-2,3-dihydro-1H-inden-2-yl]oxy}hexa-2,4-diyn-1-yl)oxy]-2,3-dihydro-1H-inden-1-yl]carbamoyl}-8,8-dimethyl-5-oxo-octahydropyrrolo[2,1-b][1,3]oxazepin-4-yl]carbamoyl}ethyl]-N-methylcarbamate (17q)

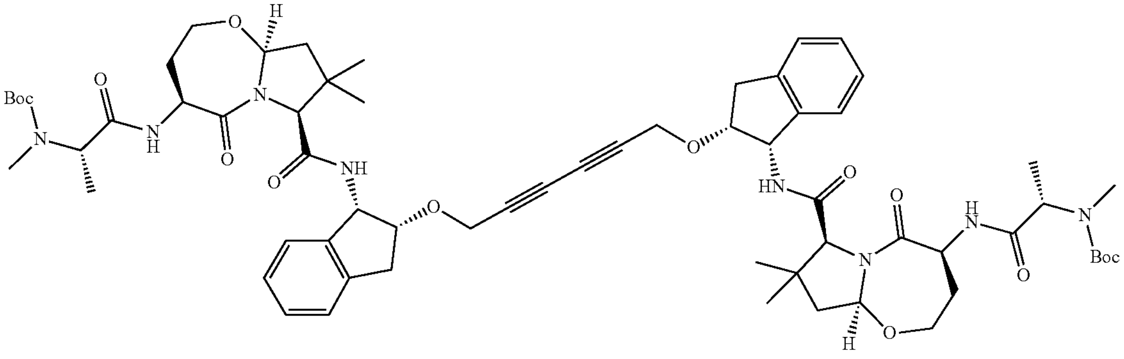

The compound 17q was prepared according to general procedure B. Colorless solid, yield 51 mg (59%). $R_f$=0.48 (ethyl acetate/methanol 10:0.5, Ceric Ammonium Molybdate stain). 1H NMR (400 MHz, $CD_3OD$): δ (ppm)=1.12 (s, 12H), 1.38 (d, 6H), 1.44-1.50 (m, 18H), 1.83-1.93 (m, 4H), 1.98-2.08 (m, 2H), 2.18-2.28 (m, 2H), 2.85 (s, 6H), 3.04-3.13 (m, 4H), 3.97 (t, 2H), 4.10-4.16 (m, 2H), 4.19 (s, 2H), 4.27 (d, 2H), 4.35 (d, 2H), 4.41-4.48 (m, 2H), 4.64 (s, 2H), 4.82 (d, 2H), 5.42-5.52 (m, 4H), 7.17-7.26 (m, 6H), 7.29-7.35 (m, 2H), 7.80-7.91 (m, 4H). LC-MS: m/z=1192.65 (calcd. 1192.44 for $C_{64}H_{87}N_8O_{14}^+$[M+H$^+$]).

Example 105: Preparation of [(1S)-1-{[(4S,7S,9aS)-7-{[(1S,2R)-2-[(6-{[(1S,2R)-1-[(4S,7S,9aS)-8,8-Dimethyl-4-[(2S)-2-(methylazaniumyl)propanamido]-5-oxo-octahydropyrrolo[2,1-b][1,3]oxazepine-7-amido]-2,3-dihydro-1H-inden-2-yl]oxy}hexa-2,4-diyn-1-yl)oxy]-2,3-dihydro-1H-inden-1-yl]carbamoyl}-8,8-dimethyl-5-oxo-octahydropyrrolo[2,1-b][1,3]oxazepin-4-yl]carbamoyl}ethyl](methyl)azanium dichloride (18q)

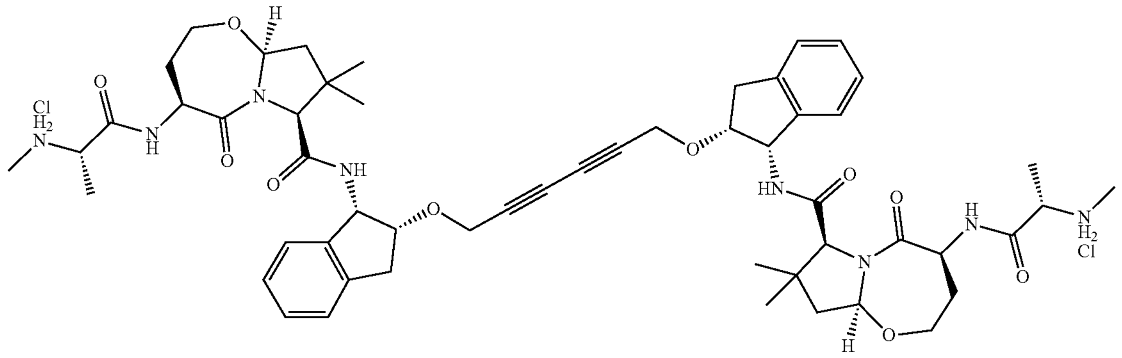

The compound 18q was prepared according to general procedure A. Colorless solid, yield 35 mg (78%). 1H NMR (400 MHz, $CD_3OD$): δ (ppm)=1.05-1.16 (m, 12H), 1.59 (d, 6H), 1.80-1.94 (m, 4H), 2.06-2.18 (m, 2H), 2.24 (dd, 2H), 2.69 (s, 6H), 3.10 (d, 4H), 3.93-4.03 (m, 4H), 4.13-4.22 (m, 4H), 4.29 (d, 2H), 4.40 (d, 2H), 4.48 (q, 2H), 4.91-4.97 (m, 2H), 5.41-5.55 (m, 4H), 7.17-7.27 (m, 6H), 7.33 (d, 2H), 7.91 (d, 2H), 8.70 (d, 2H). —$NH_2^+$ are not seen in the spectrum. 13C NMR (101 MHz, $CD_3OD$): δ (ppm)=16.5, 24.3, 29.4, 31.9, 33.0, 37.0, 40.3, 47.0, 54.0, 56.7, 58.0, 58.4, 71.1, 71.4, 71.9, 76.9, 80.9, 90.4, 125.5, 126.1, 128.1, 129.4, 140.9, 142.2, 169.6, 172.2, 172.4. LC-MS: m/z=992.50 (calcd. 992.21 for $C_{54}H_{71}N_8O_{10}^+$[M+H$^+$]).
Synthetic Scheme for the Preparation of Dimer 18r
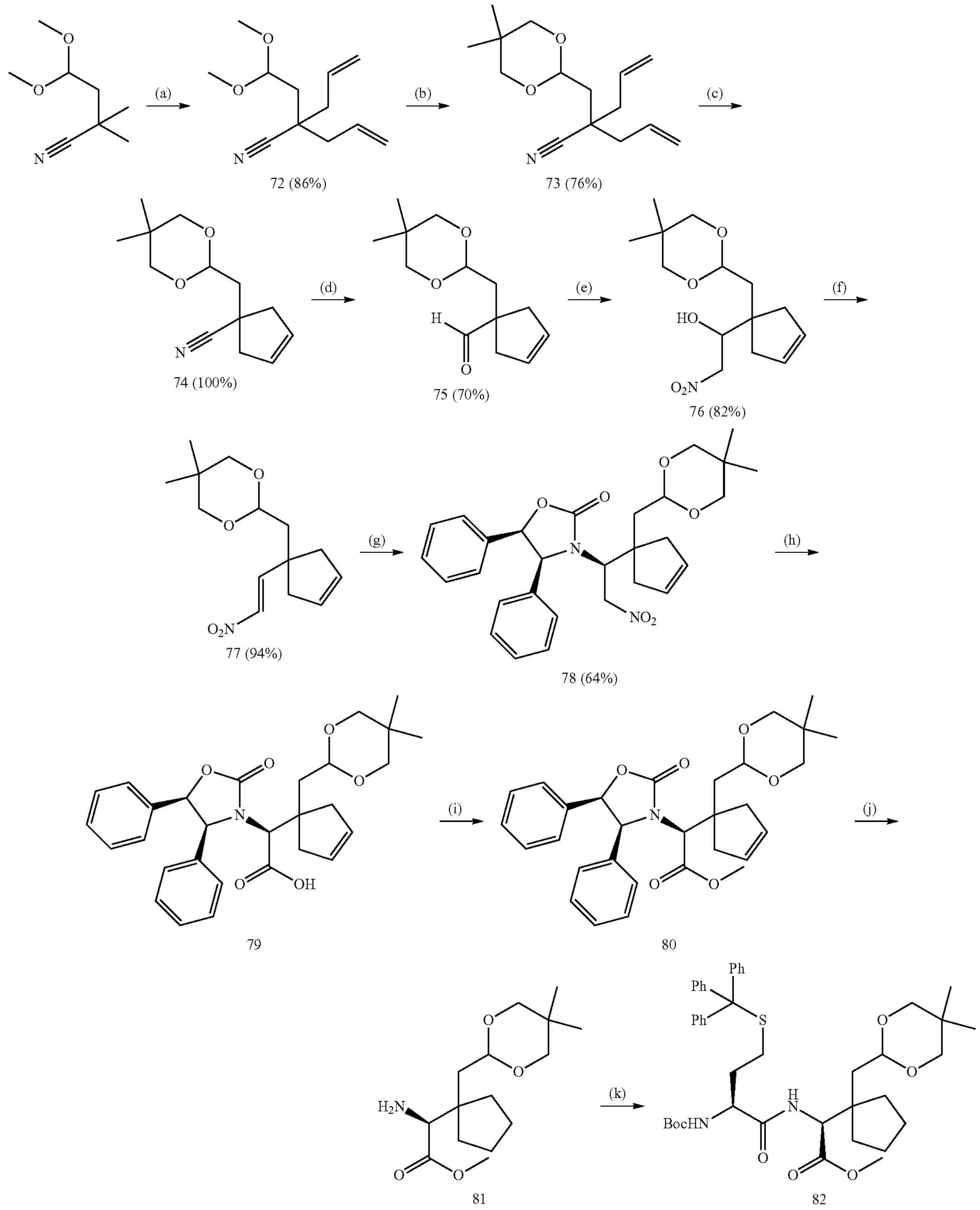

-continued

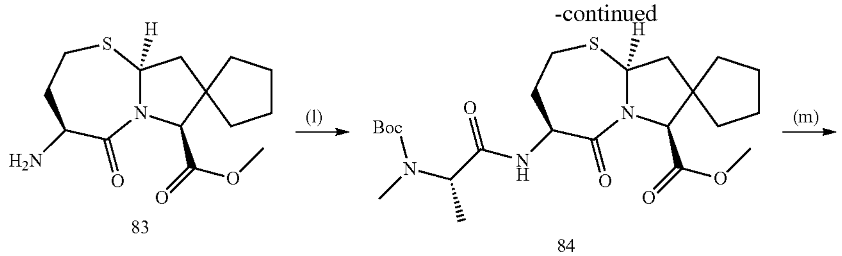

83 84

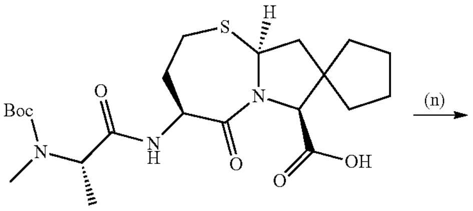

85

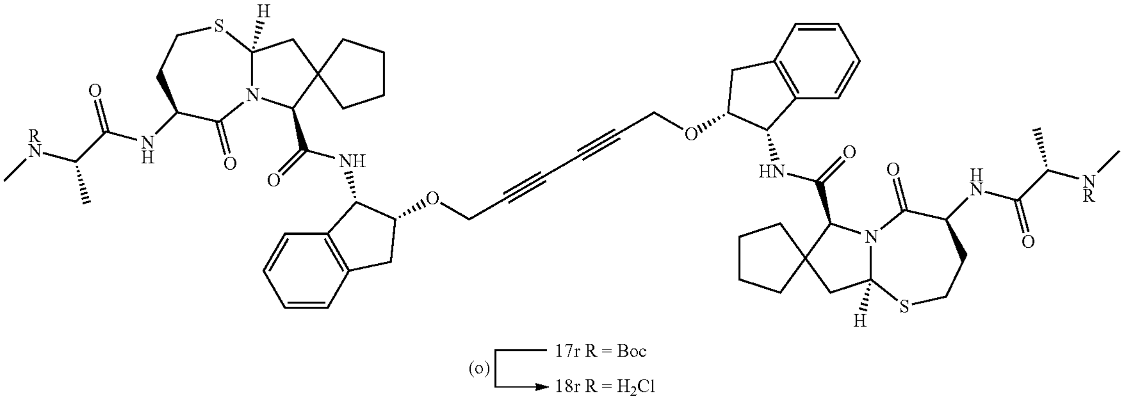

Example 107: Preparation of 2-[(5,5-Dimethyl-1,3-dioxan-2-yl)methyl]-2-(prop-2-en-1-yl)pent-4-enenitrile (73)

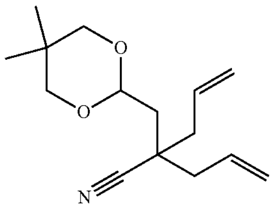 [SMILES: C=CCC(C#N)(CC=C)CC1OCC(C)(C)CO1]

The compound 73 was prepared according to Example 42 from dimethyl acetal 55 and the appropriate 2,2-dimethyl-propane-1,3-diol. Yield (76%).

Example 108: Preparation of 1-[(5,5-Dimethyl-1,3-dioxan-2-yl)methyl]cyclopent-3-ene-1-carbonitrile (74)

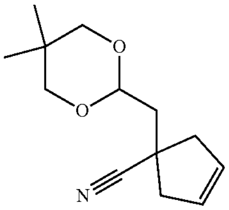 [SMILES: CC1(C)COC(CC2(C#N)CC=CC2)OC1]

The compound 74 was prepared according to Example 59 from intermediate 73. Yield (100%).

Example 109: Preparation of 1-[(5,5-Dimethyl-1,3-dioxan-2-yl)methyl]cyclopent-3-ene-1-carbaldehyde (75)

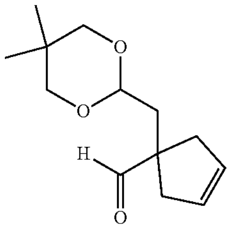 [SMILES: CC1(C)COC(CC2(C=O)CC=CC2)OC1]

The compound 75 was prepared from nitrile 74 and DIBAL-H in hexanes, according to Example 43. Yield (70%).

Example 110: Preparation of 1-{1-[(5,5-Dimethyl-1,3-dioxan-2-yl)methyl]cyclopent-3-en-1-yl}-2-nitro-ethan-1-ol (76)

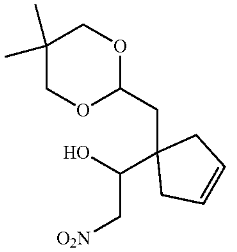 [SMILES: CC1(C)COC(CC2(C(O)C[N+](=O)[O-])CC=CC2)OC1]

The compound 76 was prepared from aldehyde 75, nitromethane and $NEt_3$, according to Example 44. Yield (82%).

Example 111: Preparation of 5,5-Dimethyl-2-({1-[(E)-2-nitroethenyl]cyclopent-3-en-1-yl}methyl)-1,3-dioxane (77)

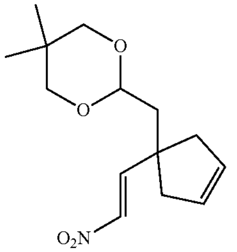 [SMILES: CC1(C)COC(CC2(/C=C/[N+](=O)[O-])CC=CC2)OC1]

The compound 77 was prepared from nitroaldol 76, nitromethane and $NEt_3$, according to Example 45. Yield (94%).

Example 112: Preparation of (4S,5R)-3-[(1S)-1-{1-[(5,5-Dimethyl-1,3-dioxan-2-yl)methyl]cyclopent-3-en-1-yl}-2-nitroethyl]-4,5-diphenyl-1,3-oxazolidin-2-one (78)

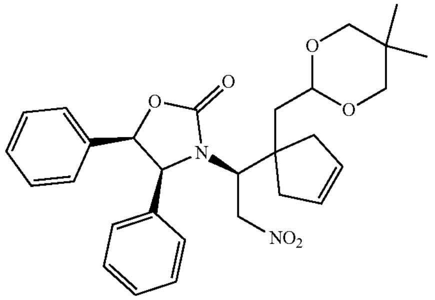 [SMILES: CC1(C)COC(CC2([C@@H](C[N+](=O)[O-])N3C(=O)O[C@H](c4ccccc4)[C@@H]3c3ccccc3)CC=CC2)OC1]

The compound 78 was prepared from nitroalkene 77, according to Example 46. Yield (64%). NMR (400 MHz, $CDCl_3$): δ (ppm)=0.74 (s, 3H), 1.24 (s, 3H), 1.91 (dd, 1H), 2.03 (dd, 1H), 2.22-2.33 (m, 2H), 2.49 (d, 1H), 2.86 (d, 1H), 3.42 (d, 2H), 3.57-3.66 (m, 2H), 4.14 (dd, 1H), 4.45-4.54 (m, 2H), 5.16 (d, 1H), 5.54 (dd, 2H), 5.59-5.65 (m, 1H), 5.93 (d, 1H), 6.83-6.89 (m, 2H), 6.99-7.03 (m, 2H), 7.05-7.13 (m, 6H). LC-MS: m/z=507.15 (calcd. 507.25 for $C_{29}H_{35}N_2O_6^+$ $[M+H^+]$).

Example 113: Preparation of (S)-2-(1-((5,5-dimethyl-1,3-dioxan-2-yl)methyl)cyclopent-3-en-1-yl)-2-((4S,5R)-2-oxo-4,5-diphenyloxazolidin-3-yl)acetic acid (79)

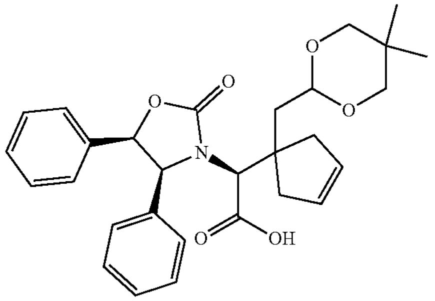 [SMILES: CC1(C)COC(CC2([C@@H](C(=O)O)N3C(=O)O[C@H](c4ccccc4)[C@@H]3c3ccccc3)CC=CC2)OC1]

Under $N_2$ atmosphere, sodium nitrite (2.08 g, 30.2 mmol, 3.00 eq) and dry acetic acid (5.76 mL, 101 mmol, 10.0 eq) were added to a solution of nitro derivative 78 (5.10 g, 10.1 mmol, 1.00 eq) suspended in dry DMSO (25 mL). The resulting mixture was stirred at 35° C. for 6 h. Upon completion, citric acid solution (5%, 80 mL) was added and extracted with ethyl acetate (3×50 mL). The combined organic layers were washed with water (2×50 mL) and brine (50 mL), dried ($Na_2SO_4$) and concentrated in vacuo.

Example 114: Preparation of Methyl (2S)-2-{1-[(5,5-dimethyl-1,3-dioxan-2-yl)methyl]cyclopent-3-en-1-yl}-2-[(4S,5R)-2-oxo-4,5-diphenyl-1,3-oxazolidin-3-yl]acetate (80)

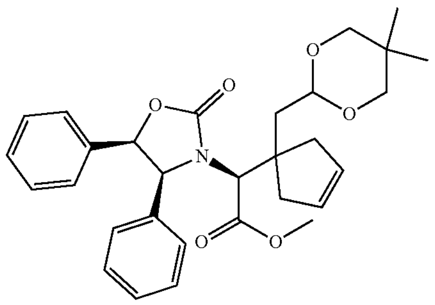 [SMILES: COC(=O)[C@@H](N1C(=O)O[C@H](c2ccccc2)[C@@H]1c1ccccc1)C1(CC2OCC(C)(C)CO2)CC=CC1]

The crude carboxylic acid 79 was dissolved in dry DMF (20 mL) and cooled to 0° C. $K_2CO_3$ (1.53 g, 11.1 mmol, 1.10 eq) was added and stirred for 10 minutes. After $CH_3I$ (1.26 mL, 20.1 mmol, 2.00 eq) addition, stirring was continued at 0° C. for 30 min. Afterwards, the solution was stirred at rt for 12 h. Water (50 mL) was added and extracted with $CH_2Cl_2$ (3×50 mL). The combined organic layers were washed with water (50 mL) and brine (50 mL), dried ($Na_2SO_4$) and concentrated in vacuo. The resulting residue was purified by fc (hexanes/$CH_2Cl_2$). Beige solid 80, yield 2.18 g (43%). $R_f$=0.72 (hexanes/ethyl acetate 7:3). 1H NMR (400 MHz, $CDCl_3$): δ (ppm)=0.68 (s, 3H), 1.13 (s, 3H), 1.61-1.68 (m, 1H), 1.81 (dd, 1H), 2.15 (d, 1H), 2.31 (d, 1H), 2.60 (dp, 1H), 2.71 (dp, 1H), 3.29 (dd, 2H), 3.48 (ddd, 2H), 3.76 (s, 3H), 4.39 (dd, 1H), 4.41 (s, 1H), 5.31 (d, 1H), 5.47-5.51 (m, 1H), 5.52-5.56 (m, 1H), 5.94 (d, 1H), 6.98-7.03 (m, 3H), 7.07 (m, 7H). LC-MS: m/z=506.15 (calcd. 506.25 for $C_{30}H_{36}NO_6^+$[M+H$^+$]).

Example 115: Preparation of methyl (S)-2-amino-2-(1-((5,5-dimethyl-1,3-dioxan yl)methyl)cyclopentyl) acetate (81)

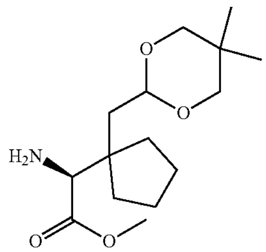 [SMILES: COC(=O)[C@@H](N)C1(CC2OCC(C)(C)CO2)CCCC1]

Pd/C (10%, matrix activated carbon support, Sigma Aldrich, 526 mg, 0.25 eq) was added to a solution of carbamate 80 (1.00 g, 1.97 mmol, 1.00 eq) in methanol (24 mL). Under $H_2$ atmosphere, the resulting mixture was stirred at 45° C. for 5 h. After Celite® filtration with methanol, all volatiles were removed in vacuo.

Example 116: Preparation of Methyl (2S)-2-[(2S)-2-{[(tert-butoxy)carbonyl]amino}-4-[(triphenylmethyl)sulfanyl]butanamido]-2-{1-[(5,5-dimethyl-1,3-dioxan-2-yl)methyl]cyclopentyl}acetate (82)

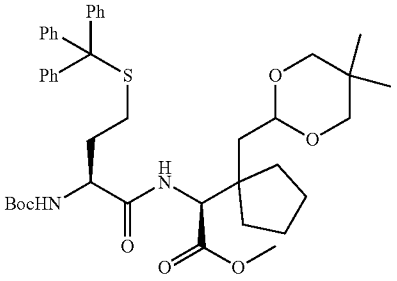 [SMILES: COC(=O)[C@@H](NC(=O)[C@H](CCSC(c1ccccc1)(c1ccccc1)c1ccccc1)NC(=O)OC(C)(C)C)C1(CC2OCC(C)(C)CO2)CCCC1]

Under $N_2$ atmosphere, amine 81, carboxylic acid 7 (945 mg, 1.98 mmol, 1.00 eq), 1-hydroxybenzotriazole hydrate (363 mg, 2.37 mmol, 1.20 eq.) and N-methylmorpholine (654 μL, 5.93 mmol, 3.00 eq.) were dissolved in a mixture of dry THF (7.1 mL)/DMF (1.0 mL) and cooled to 0° C. EDC·HCl (455 mg, 2.37 mmol, 1.20 eq) was added and the resulting mixture was stirred for 30 min at 0° C. followed by 14 h at rt. Upon completion, NaOH solution (1 M, 30 mL) was added to the residue and extracted with ethyl acetate (3×30 mL). The combined organic layers were washed with NaOH solution (1 M, 30 mL), citric acid solution (5%, 30 mL), HCl solution (1 M, 30 mL), water (30 mL) and brine (30 mL), dried ($Na_2SO_4$) and concentrated in vacuo. The resulting residue was purified by fc (hexanes/ethyl acetate). Colorless solid, yield 1.07 g (73%). $R_f$=0.66 (hexanes/ethyl acetate 8:2).

$^1$H NMR (400 MHz, $CDCl_3$): δ (ppm)=0.68 (s, 3H), 1.16 (s, 3H), 1.41 (s, 9H), 1.46-1.88 (m, 12H), 2.17-2.37 (m, 2H), 3.40 (d, 1H), 3.50 (d, 1H), 3.56 (dd, 1H), 3.62-3.67 (m, 4H), 3.95-4.04 (m, 1H), 4.43 (d, 1H), 4.52 (dd, 1H), 4.73 (d, 1H), 7.18-7.23 (m, 3H), 7.25-7.30 (m, 6H), 7.37-7.42 (m, 7H). LC-MS: m/z=767.35 (calcd. 767.37 for $C_{43}H_{56}N_2NaO_7S^+$ [M+H$^+$]).

Example 117: Preparation of methyl (4'S,7'S,9a'S)-4'-amino-5'-oxohexahydro-7'H-spiro[cyclopentane-1,8'-pyrrolo[2,1-b][1,3]thiazepine]-7'-carboxylate (83)

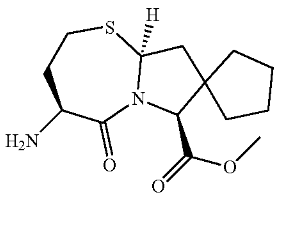 [SMILES: COC(=O)[C@H]1N2C(=O)[C@@H](N)CCS[C@H]2CC12CCCC2]

Compound 82 (1.00 g, 1.34 mmol, 1.00 eq.) was treated with HCl in dioxane (4 M, 6.7 mL, 26.9 mmol, 20.0 eq.) and stirred at 40° C. for 2 h. Upon completion, all volatiles were removed under reduced pressure.

Example 118: Preparation of Methyl (4'S,7'S,9'aS)-4'-[(2S)-2-{[(tert-butoxy)carbonyl](methyl)amino}propanamido]-5'-oxo-hexahydro-2'H-spiro[cyclopentane-1,8'-pyrrolo[2,1-b][1,3]thiazepine]-7'-carboxylate (84)

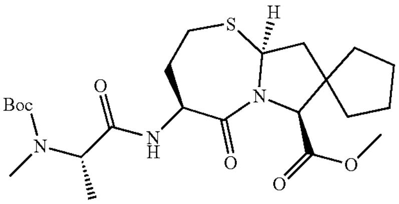 [SMILES: COC(=O)[C@H]1N2C(=O)[C@@H](NC(=O)[C@H](C)N(C)C(=O)OC(C)(C)C)CCS[C@H]2CC12CCCC2]

Under $N_2$ atmosphere, the amine 83, N-(tert-butoxycarbonyl)-N-methyl-L-alanine (327 mg, 1.61 mmol, 1.20 eq.), 1-hydroxybenzotriazole hydrate (247 mg, 1.61 mmol, 1.20 eq.) and 4-methylmorpholine (444 μL, 4.00 mmol, 3.00 eq.) were dissolved in dry DMF (6.2 mL) and cooled to 0° C. EDC·HCl (308 mg, 1.61 mmol, 1.20 eq.) was added and the resulting mixture was stirred for 30 minutes at 0° C. followed by 14 h at rt. Upon completion, water (20 mL) was added and extracted with ethyl acetate (3×20 mL). The combined organic layers were washed with NaOH solution (1 M, 20 mL), HCl solution (1 M, 2×20 mL), water (20 mL) and brine (10 mL), dried ($Na_2SO_4$) and concentrated in vacuo. The resulting residue was purified by fc (hexanes/ethyl acetate). Colorless solid 84, quantitative yield. $R_f$=0.51 (hexanes/ethyl acetate 5:5, Ceric Ammonium Molybdate stain). $^1H$ NMR (400 MHz, $CDCl_3$): δ (ppm)=1.33 (d, 3H), 1.46 (s, 9H), 1.52-1.77 (m, 8H), 1.83-1.95 (m, 1H), 2.09-2.17 (m, 1H), 2.23-2.34 (m, 2H), 2.77 (s, 3H), 2.83 (ddd, 1H), 3.19-3.29 (m, 1H), 3.75 (s, 3H), 4.34 (s, 1H), 4.53 (dd, 1H), 5.10 (t, 1H), 7.30 (s, 1H). $CHCH_3$ is not seen in the spectrum. LC-MS: m/z=484.20 (calcd. 484.25 for $C_{23}H_{38}N_3O_6S^+[M+H^+]$).

Example 119: Preparation of (4'S,7'S,9'aS)-4'-[(2S)-2-{[(tert-Butoxy)carbonyl](methyl)amino}propanamido]-5'-oxo-hexahydro-2'H-spiro[cyclopentane-1,8'-pyrrolo[2,1-b][1,3]thiazepine]-7'-carboxylic acid (85)

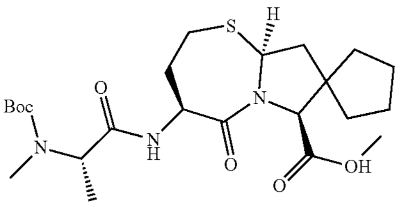 [SMILES: COC(=O)[C@H]1N2C(=O)[C@@H](NC(=O)[C@H](C)N(C)C(=O)OC(C)(C)C)CCS[C@H]2CC12CCCC2]

Lithium hydroxide solution (1 M, 2.68 mL, 2.68 mmol, 2.00 eq.) was added to a solution of the methyl ester 84 (649 mg, 1.34 mmol, 1.00 eq.) dissolved in THF (2.7 mL) at rt. The resulting emulsion was stirred at 40° C. for 19 h. Upon completion, $Et_2O$ (15 mL) was added and washed with a mixture of NaOH solution 1 M and brine (8:1, 3×9 mL). The combined aq. layers were extracted with $Et_2O$ (15 mL) and the $Et_2O$ layer was washed with a mixture of NaOH solution 1 M and brine (8:1, 2×8 mL). After acidification of the combined aq. layers with conc. HCl to pH 1, the aq. layer was extracted with $CH_2Cl_2$ (2×10 mL) and ethyl acetate (3×10 mL). The combined organic layers were dried ($Na_2SO_4$) and concentrated in vacuo. The resulting residue was purified by fc (hexanes/ethyl acetate/formic acid 0.2%). Colorless solid 85, yield 428 mg (68%). $R_f$=0.45 (hexanes/ethyl acetate/formic acid 4:6:0.1, Ceric Ammonium Molybdate stain). $^1H$ NMR (400 MHz, $CDCl_3$): δ (ppm)=1.34 (d, 3H), 1.46 (s, 9H), 1.53-1.84 (m, 8H), 1.91 (q, 1H), 2.12 (dd, 1H), 2.22-2.34 (m, 2H), 2.77-2.84 (m, 4H), 3.24 (ddd, 1H), 4.34 (s, 1H), 4.62 (dd, 1H), 5.15 (dd, 1H), 7.41 (s, 1H). COOH and $CHCH_3$ are not seen in the spectrum. LC-MS: m/z=470.15 (calcd. 470.23 for $C_{22}H_{36}N_3O_6S^+[M+H^+]$).

Example 120: Preparation of tert-Butyl N-[(1S)-1-{[(4'S,7'S,9'aS)-7'-{[(1S,2R)-2-[(6-{[(1S,2R)-1-{[(4'S,7'S,9'aS)-4'-[(2S)-2-{[(tert-butoxy)carbonyl](methyl)amino}propanamido]-5'-oxo-hexahydro-2'H-spiro[cyclopentane-1,8'-pyrrolo[2,1-b][1,3]thiazepin]-7'-yl]amido}-2,3-dihydro-1H-inden-2-yl]oxy}hexa-2,4-diyn-1-yl)oxy]-2,3-dihydro-1H-inden-1-yl]carbamoyl}-5'-oxo-hexahydro-2'H-Spiro[cyclopentane-1,8'-pyrrolo[2,1-b][1,3]thiazepin]-4'-yl]carbamoyl}ethyl]-N-methylcarbamate (17r)

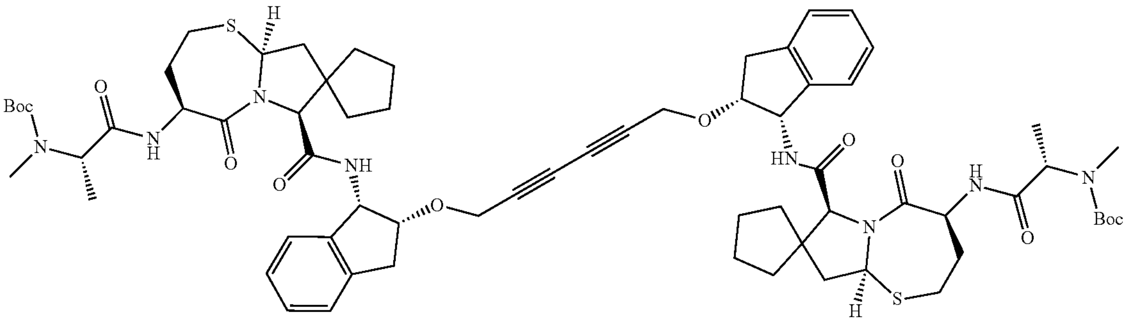

The compound 17r was prepared according to general procedure B. Modification: Ethyl acetate (30 mL) was added to the reaction mixture and washed with sat. $NaHCO_3$ solution (2×10 mL), citric acid solution (5%, 2×10 mL), water (10 mL) and brine (10 mL), dried ($Na_2SO_4$) and concentrated in vacuo. White solid, yield 23 mg (22%). $R_f$=0.82 (ethyl acetate/methanol 10:0.5, Ceric Ammonium Molybdate stain). $^1H$ NMR (400 MHz, $CDCl_3$): δ (ppm)=1.34 (d, 6H), 1.45-1.49 (m, 18H), 1.49-1.92 (m, 18H), 1.98-2.02 (m, 2H), 2.24-2.39 (m, 4H), 2.74-2.83 (m, 8H), 3.03-3.14 (m, 4H), 3.29 (d, 2H), 4.18 (d, 2H), 4.26 (d, 2H), 4.35 (s, 2H), 4.49 (dt, 4H), 5.06-5.15 (m, 2H), 5.52 (dd, 2H), 7.18-7.42 (m, 12H). $CHCH_3$ are not seen in the spectrum. LC-MS: m/z=1275.65 (calcd. 1275.62 for $C_{68}H_{91}N_8O_{12}S_2^+$ [M+H$^+$]).

Example 121: Preparation of [(1S)-1-{[(4'S,7'S,9'aS)-7'-{[(1S,2R)-2-[(6-{[(1S,2R)-1-{[(4'S,7'S,9'aS)-4'-[(2S)-2-(Methylazaniumyl)propanamido]-5'-oxo-hexahydro-2'H-spiro[cyclopentane-1,8'-pyrrolo[2,1-b][1,3]thiazepin]-7'-yl]amido}-2,3-dihydro-1H-inden-2-yl]oxy}hexa-2,4-diyn-1-yl)oxy]-2,3-dihydro-1H-inden-1-yl]carbamoyl}-5'-oxo-hexahydro-2'H-spiro[cyclopentane-1,8'-pyrrolo[2,1-b][1,3]thiazepin]-4'-yl]carbamoyl}ethyl](methyl)azanium dichloride (18r)

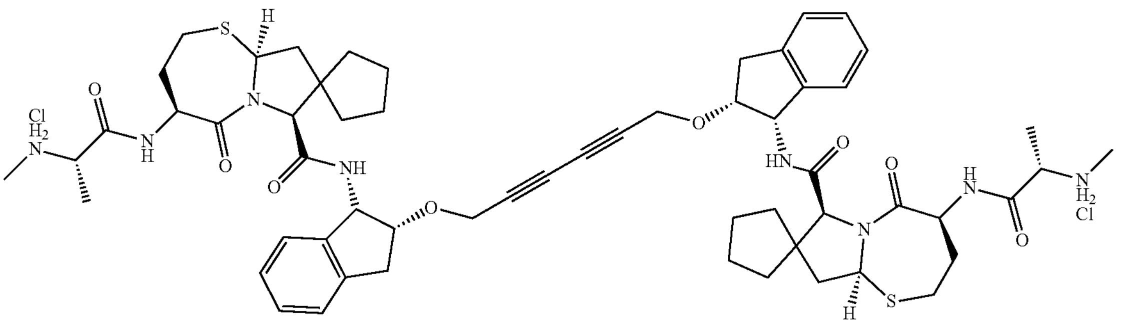

The compound 18r was prepared according to general procedure A. Colorless solid, yield 13 mg (61%). 1H NMR (400 MHz, $CD_3OD$): δ (ppm)=1.45-2.08 (m, 26H), 2.27 (d, 2H), 2.34-2.46 (m, 2H), 2.68 (s, 6H), 2.91 (d, 2H), 3.03-3.17 (m, 4H), 3.18-3.27 (m, 2H), 3.94 (d, 2H), 4.22-4.40 (m, 6H), 4.46 (s, 2H), 4.73 (d, 2H), 5.35-5.52 (m, 4H), 7.15-7.35 (m, 8H), 8.02-8.09 (m, 2H), 8.73 (s, 2H). —$NH_2^+$ are not seen in the spectrum. 13C NMR (101 MHz, $CD_3OD$): δ (ppm)=16.4, 24.6, 25.0, 31.8, 32.3, 33.9, 37.1, 40.3, 45.2, 52.3, 54.5, 56.8, 57.9, 58.3, 61.8, 71.0, 72.0, 76.9, 81.0, 125.4, 126.1, 128.1, 129.4, 141.0, 142.2, 169.3, 172.3. LC-MS: m/z=1075.55 (calcd. 1075.51 for $C_{58}H_{75}N_8O_8S_2^+$[M+H$^+$]).

Example A

The compound 18a was tested in 16 different cell lines. For 6-day compound treatment 1700 cells per well were plated in a 384-well plate (Corning #781098) and incubated overnight at 37° C./5% $CO_2$. The following day, compounds in 10-fold dilutions were added to the plates and the plates were incubated for 6 days. Afterwards, 20 µL CellTiter-Glo reagent (Promega, #G7570) was added to each well outside of the incubator and the plates were read for luminescence on a Spark® multimode microplate reader (Tecan). Data was fit in GraphPad Prism 8 to a nonlinear regression curve to determine the $IC_{50}$ of the compounds.

TABLE 1

Cell viability measurements for a panel of cancer cell lines treated with bivalent 18a for 6 d.

| Human tumor type | Cell lines | 18c<br>$IC_{50}$ [µM] 6 d | 18c<br>Cell viability at max. concentration [%] |
|---|---|---|---|
| Small cell lung cancer | H69AR | D | I |
| | SHP-77 | E | IV |
| | NCI-H510A | E | IV |
| | SW-1271 | C | I |
| Pancreatic cancer | BxPC3 | D | III |
| | MiaPaCa2 | D | I |
| | PANC1 | E | IV |
| Malignant melanoma | MALME 3M | B | I |
| Acute progranulocytic leukemia (APL) | HL-60 | B | I |
| | NB-4 | A | I |
| Acute myeloid leukemia (AML) | MV411 | C | I |
| | MOLM 13 | B | I |
| Triple negative breast cancer (TNBC) | MDA-MB-231 | C | I |
| | MDA-MB-468 | C | I |

TABLE 1-continued

Cell viability measurements for a panel of cancer cell lines treated with bivalent 18a for 6 d.

| | | 18c | |
|---|---|---|---|
| Human tumor type | Cell lines | $IC_{50}$ [μM] 6 d | Cell viability at max. concentration [%] |
| | BT549 | B | I |
| Foreskin fibroblasts | HFF | E | IV |

Cell IC50: A is ≤10 nM;
10 nM <B≤100 nM;
100 nM<C≤1000 nM;
1000 nM<D≤10 uM;
<100 uM = E;
Cell viability at max. concentration: I<10%, 10%<II<50%, 50%<III<100%; IV<100%.

Example B

One thousand seven hundred cells per well were plated in a 384 well plate and incubated overnight at 37° C./5% $CO_2$. The following day, compounds in 10-fold dilutions were added to the plates and the plates returned to the incubator for 48 hrs. 48 hrs later, plates were removed to the bench and 20 μL CellTiter-Glo reagent was added to each well and the plates were read for luminescence on a Spark® multimode microplate reader (Tecan). Data were fit using PRISM to a nonlinear regression curve to determine the $IC_{50}$ of the compounds.

Table 2. below shows assay data for the compounds described herein.

| Compound # | SKOV-3 Viability 48 h $IC_{50}$ | MOLM 13 Viability 6 d $IC_{50}$ | NB-4 Viability 72 h $IC_{50}$ |
|---|---|---|---|
| 18a | A | B | A |
| 18b | A | C | A |
| 18c | A | B | A |
| 18d | A | C | A |
| 18e | A | C | B |
| 18f | A | C | A |
| 18g | A | B | A |
| 18h | B | E | A |
| 18i | A | C | A |
| 18j | B | D | A |
| 18k | C | D | B |
| 18l | C | E | B |
| 18m | A | B | |
| 18n | B | C | |
| 18o | A | B | |
| 18q | A | B | |

Cell IC50: A is ≤10 nM;
10 nM <B≤100 nM;
100 nM<C≤1000 nM;
1000 nM<D≤10 uM;
<100 uM = E;

Example C

Binding of compounds to ML-IAP and BIR3 domain of cIAP1, cIAP2 and XIAP was determined by fluorescence polarization. Assay buffer was 100 mM $KH_2PO_4$ at pH 7.5, 50 μM $ZnSO_4$, 1 mM TCEP (Tris(2-carboxyethyl)phosphine hydrochloride) and 50 nM SMAC-FITC probe (AbuRPF-K (5-Fam)-$NH_2$) as described by Z. Nikolovska-Coleska et al.[9]. cIAP1 and XIAP were present at 800 nM while cIAP2 and MLIAP were present at 1.5 μM. Compounds in 3-fold dilutions were added to the plates ranging from 30 μM to 1.5 nM. Assays were run in 384-well black plates read (Greiner Bio-One #784076) in an Analyst in fluorescence polarization mode with excitation at 485 nm and emission at 535 nm. Data was fit to a nonlinear regression curve in GraphPad Prism 8 to determine the $IC_{50}$ values of the compounds. Ki's were then calculated from the $IC_{50}$ values using equation: $K_i=[I]_{50}/([L]_{50}/K_d+[P]_0/K_d+1)$ formulated by Z. Nikolovska-Coleska et al.

TABLE 3

Fluorescence polarization assay.

| | Fluorescence Polarization | | | |
|---|---|---|---|---|
| Compound # | cIAP1 Ki [nM] | cIAP2 Ki [nM] | XIAP Ki [nM] | ML-IAP Ki [nM] |
| 18a | I | II | I | II |
| 18b | I | II | I | II |
| 18c | I | II | I | II |
| 18d | I | | | |
| 18e | II | III | I | III |
| 18f | II | | | |
| 18g | I | II | I | II |
| 18h | I | | | |
| 18i | I | II | II | II |
| 18j | I | | | |
| 18k | II | | | |
| 18l | I | | | |
| 18m | I | II | I | II |
| 18n | II | | | |
| 18o | I | II | I | III |
| 18q | II | II | I | II |

Fluorescence Polarization: I ≤ 50 nM;
50 nM < II ≤ 100 nM;
100 nM <III ≤ 200 nM;
IV >200 nM

Example D

Patient AML samples were gathered (under IRB 13-6180) from Scripps MD Anderson, La Jolla, CA Fresh blood samples were subjected to gradient density centrifugation with Ficoll-Paque™ PLUS (17-1440-02, GE Healthcare) and peripheral blood mononuclear cells purified as per manufacturer's protocol.

Figure 6:
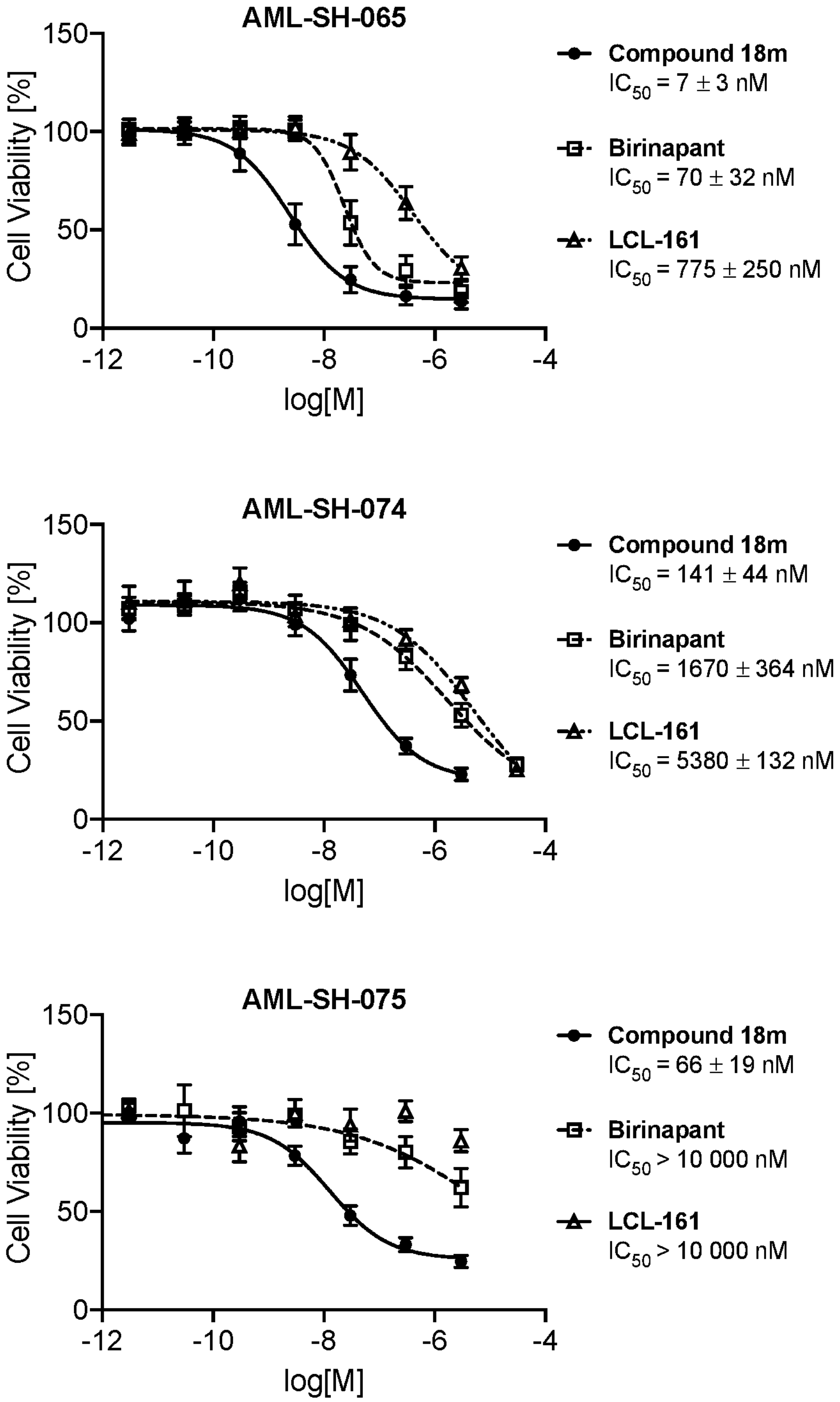
FIG. 6 shows the effect of Compound 18m compared with other IAP antagonists in their potency and efficacy in patient derived AML samples.

75 nL of 1000× serially diluted IAP inhibitors were spotted in triplicate onto 384-well tissue culture treated plates (Greiner) using a Labcyte Echo acoustic dispensing device. Patient-derived AML cells were maintained in mTeSR1$^+$1× supplements (Stemcell Technologies) and penicillin/streptomycin/L-glutamine (Omega Scientific Inc.) and Fungizone (HyClone). 25 μL of cell dilution were plated into 384-well plate containing the drugs and incubated for 72 h. Cell viability was assessed by adding 25 μL CellTiterGlo (Promega Corp.) on a Synergy 2 plate reader with Gen5 software (Biotek). % viability was calculated by normalizing luminescence to vehicle only controls (DMSO) in Microsoft Excel and plotted using GraphPad Prism 8. The $IC_{50}$ values were calculated using log(inhibitor) vs. response—Variable slope (four parameters) equation. (FIG. 6)

TABLE 4

| Cell viability $IC_{50}$ in patient derived AML samples tested with 6 selected compounds | | | | | | |
|---|---|---|---|---|---|---|
| | AML-SH-065 | | AML-SH-074 | | AML-SH-075 | |
| | $IC_{50}$ [nM] | Efficacy [%] | $IC_{50}$ [nM] | Efficacy [%] | $IC_{50}$ [nM] | Efficacy [%] |
| 18a | A | I | C | I | B | I |
| 18c | B | I | C | I | D | I |
| 18e | B | I | C | I | D | I |
| 18g | B | I | C | I | B | I |
| 18m | A | I | C | I | B | I |
| 18q | B | I | C | I | B | I |

Cell IC50: A is ≤10 nM; 10 nM < B ≤ 100 nM; 100 nM < C ≤ 1000 nM; 1000 nM < D ≤ 10 μM; <100 uM = E;
Cell viability at max. concentration: I < 10%, 10% < II < 50%, 50% < III < 100%.

Example E

Several compounds (Table 5) were tested for their efficacy in the reversal of HIV latency in the latently infected cell line Jurkat 2D10. Jurkat 2D10 cells were treated with different doses of the compounds, or one of the following compounds: BV-6, SM-164, Birinapant, LCL-161, GDC-0152, AT-406 for 48 hours. Reversal of HW latency was evaluated by analyzing GFP expression using flow cytometry. Induction of GFP expression was compared to baseline GFP levels detected in the absence of treatment. The results are shown in Table 5 and FIG. 1. Compound 18a has higher efficacy in activating the latently infected cell line than many known compounds (FIG. 1).

TABLE 5

| HIV Jurkat 2D10 cells GFP+ assay | |
|---|---|
| | Jurkat 2D10 GFP+ |
| Compound # | $EC_{50}$ [nM] |
| 18a | A |
| 18b | A |
| 18c | A |
| 18d | AA |
| 18e | AA |
| 18f | A |
| 18g | A |
| 18h | B |
| 18i | B |
| 18j | D |
| 18k | E |
| 18l | C |
| 18m | A |
| 18n | B |
| 18o | A |
| 18p | C |
| 18q | C |
| 18r | B |

Cell EC50: AA is ≤ 1 nM;
1 nM < A ≤ 10 nM;
10 nM < B ≤ 100 nM;
100 nM < C ≤ 1000 nM;
1000 nM < D ≤ 10 μM;
E is > 10 μM.

Figure 2:
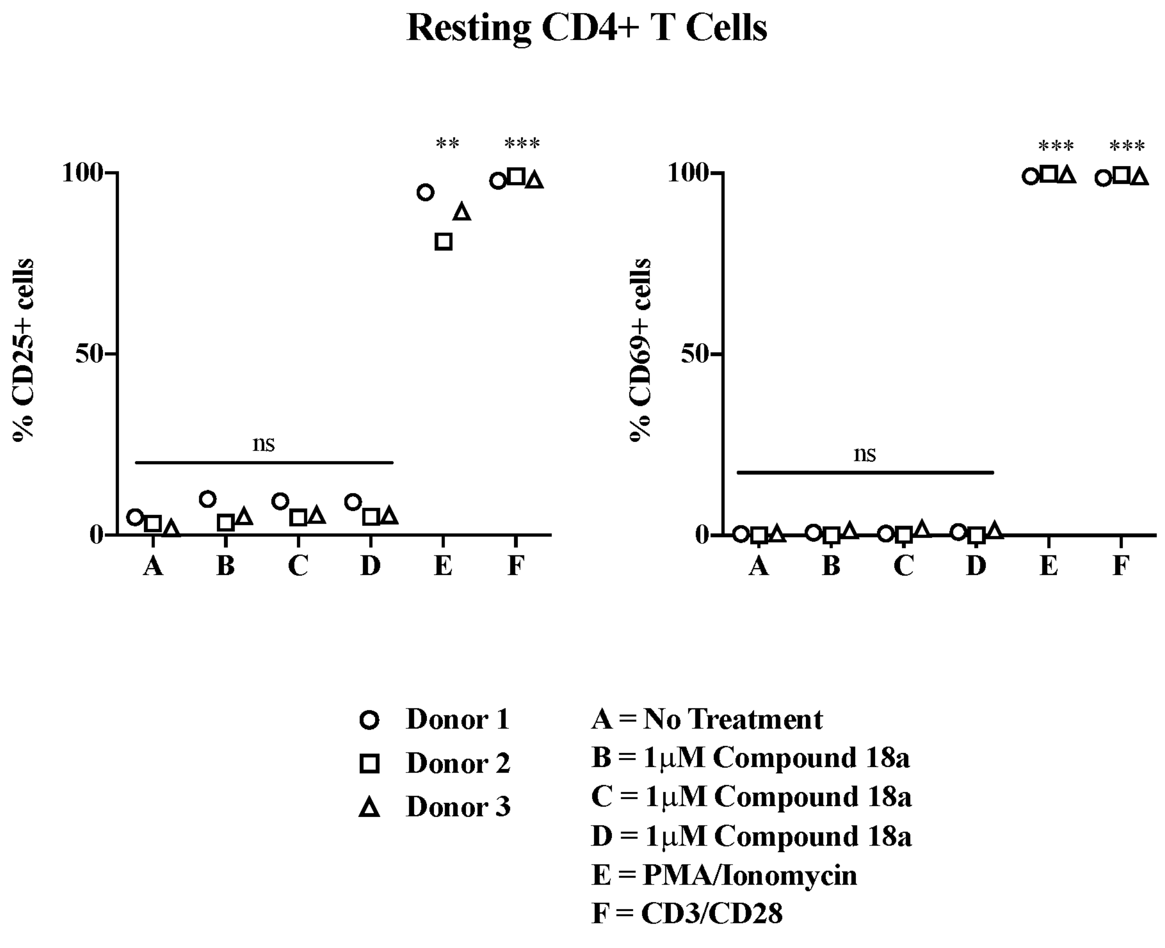
FIG. 2 shows the effect of Compound 18a and various control conditions on the activation of resting CD4+ T cells isolated from a healthy donor, assessed by measuring CD69 expression.
Figure 3:
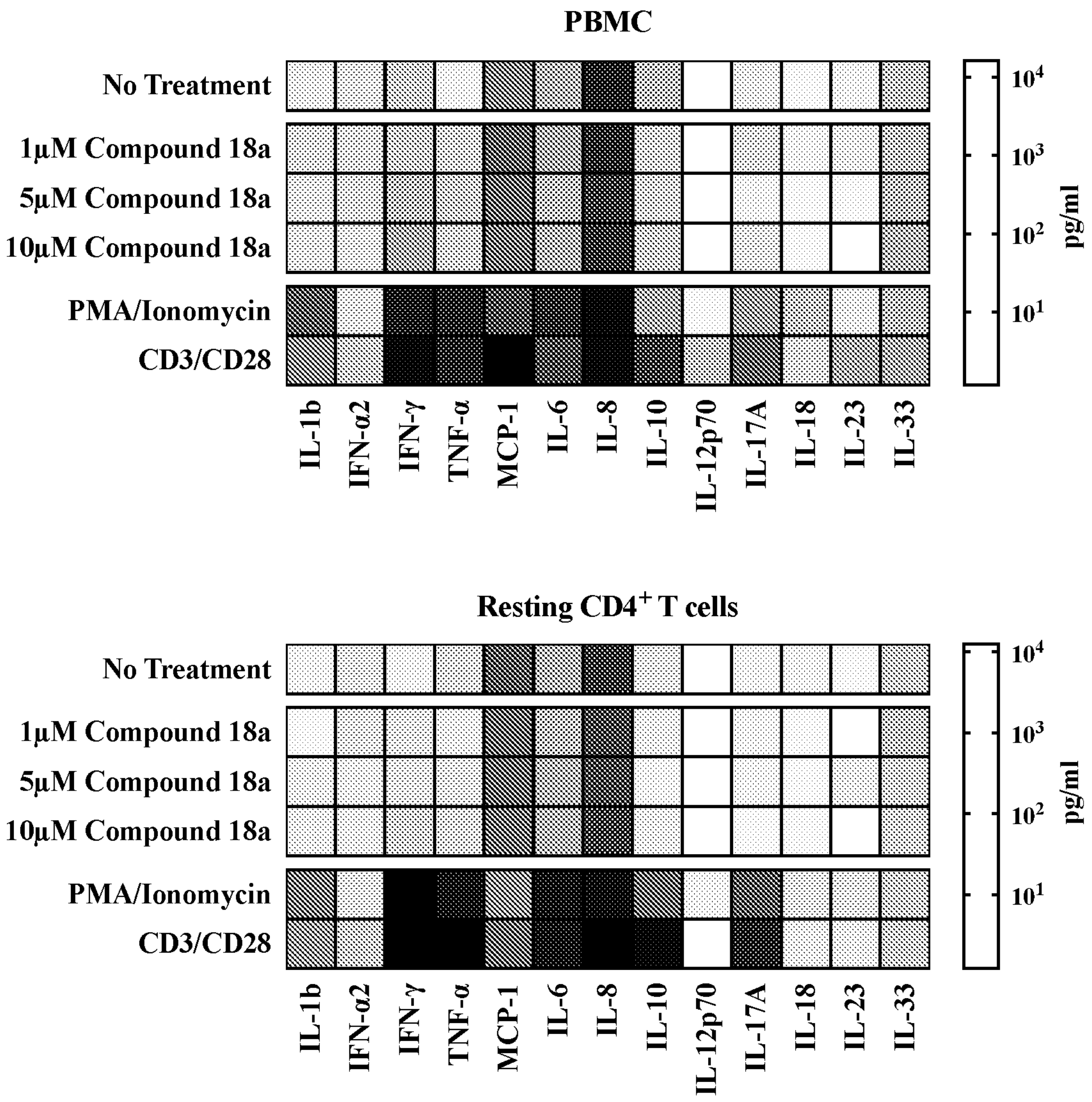
FIG. 3 shows the effect of Compound 18a and various control conditions on cytokine release in peripheral blood mononuclear cell and resting CD4+ T cells isolated from healthy donors.

Compound 18a was also tested for its impact on T cell activation and cytokine release. Peripheral blood mononuclear cells (PBMC) were isolated by Ficoll density gradient centrifugation (Histopaque, Sigma Aldrich) from buffy coats of three healthy human donors (San Diego Blood Bank). Resting $CD4^+$ T cells were subsequently isolated by negative selection using magnetic beads (Miltenyi Biotec). Cells were treated with compound 18a, or 50 ng/ml Phorbol myristate acetate (PMA) and 1 μM lonomycin, or Dynabeads Human T-Activator CD3/CD28 (ThermoFisher Scientific) at a bead-to-cell ratio of 1:1, or left untreated. Expression of the early and late activation markers CD69 and CD25 on CD4+ T cells was assessed by flow cytometry using a Phycoerythrin-labeled anti-CD69 antibody (BioLegend; Cat #310906) and an Allophycocyanin-labeled anti-CD25 antibody (BioLegend; Cat #302610). Cytokine expression levels in cultures of PBMC or resting CD4+ T cells were analyzed using the LEGENDplex Human Inflammation Panel 13-plex (BioLegend). As shown in FIG. 2 and FIG. 3, treatment using compound 18a did not induce activation of resting CD4+ T cells or cytokine release in PBMC or resting CD4+ T cells.

Figure 4:
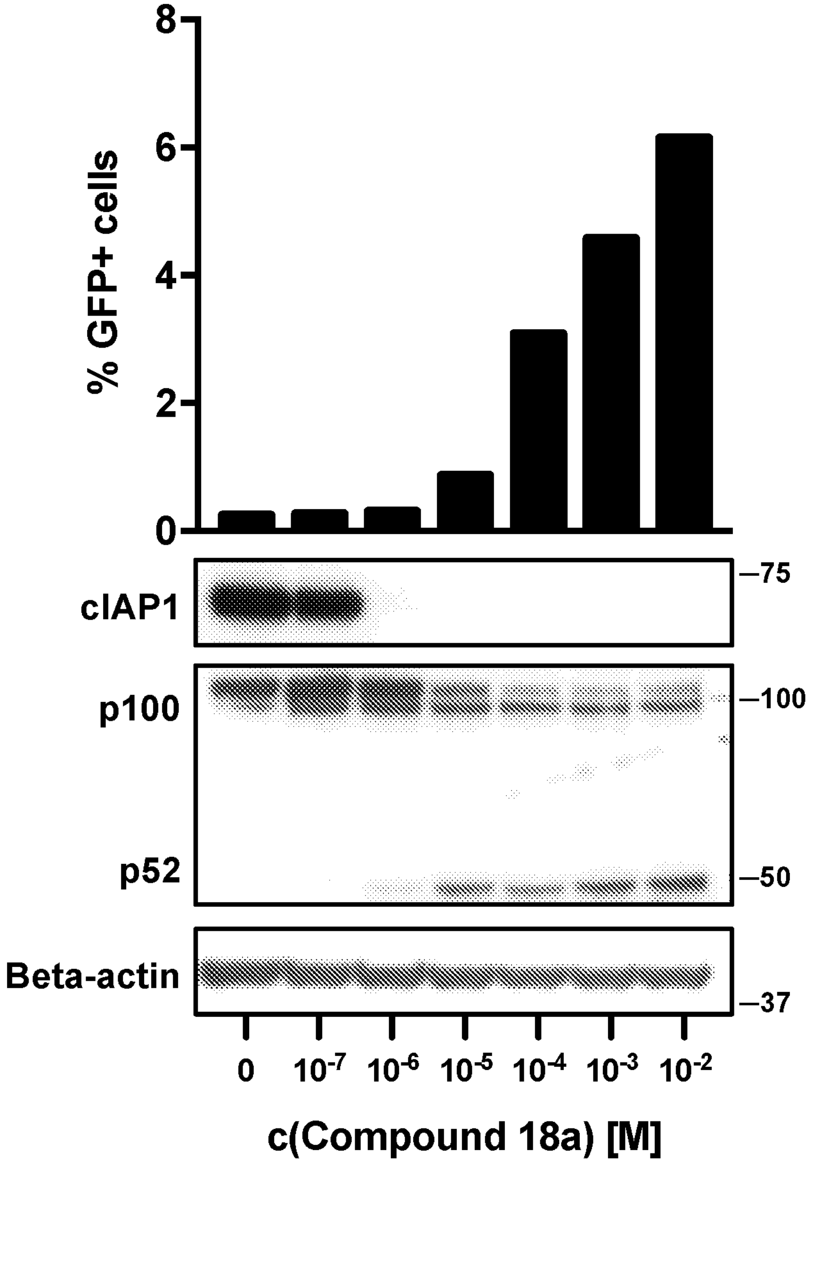

FIG. 4 shows the cIAP1degradation and NFκB pathway activation by the compound. JLat 10.6 cells were treated with different concentrations of compound 18a for 24 hours. GFP expression indicating latency reversal was measured by flow cytometry. cIAP1 degradation and p100 cleavage were assessed by western blot using the antibodies AF8181 (R&D Systems) and #4882 (Cell Signaling Technology), respectively. As shown, cIAP1 degradation and p100 cleavage upon treatment with compound 18a of JLat 10.6 cells correlated with HW latency reversal.

Figure 5:
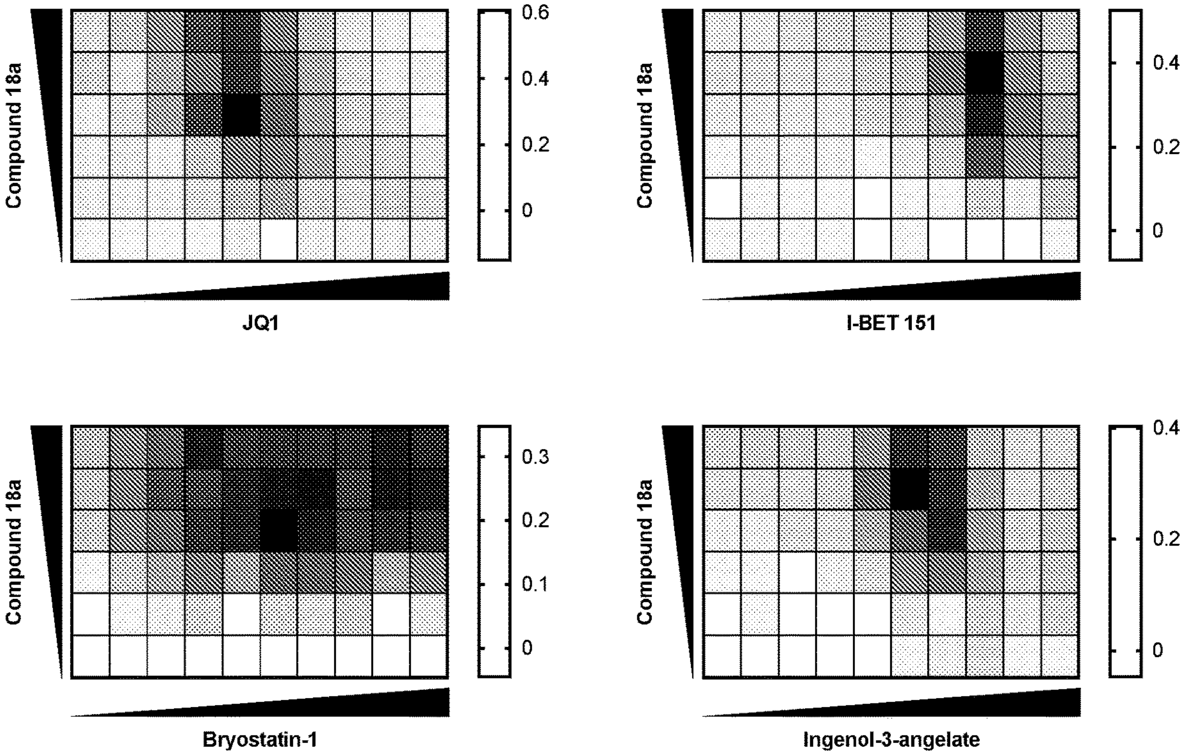
FIG. 5 shows the effects of Compound 18a in combination with other latency reversing agents on activating HIV transcription in latently infected Jurkat 2D10 cells. Heatmaps indicate excess over Bliss (EOB) score where a score greater than zero indicates synergy between compounds.

Compound 18a was also tested in combination with other LRA reagents for synergistic activation of the latently infected cell line Jurkat 2D10. Jurkat 2D10 cells were treated with combinations of compound 18a and BET inhibitors (JQ1, I-BET 151) or PKC agonists (Bryostatin, Ingenol-3-angelate) for 48 hours. Reversal of HW latency was evaluated by analyzing GFP expression using flow cytometry. Synergy was assessed with the Bliss Independence model where the observed effect of a combination of compounds f12 is compared to the expected effect E(f12) that is calculated based on the observed effects of the individual compounds f1 and f2 using the formula E(f12)=f1+J2−(f1*f2). The difference between the observed effect of the combined compounds (f12) and the expected combined effect of the two compounds E(f12) is given as the excess over Bliss score (EOB). An EOB value greater than 0 indicates synergy between the compounds. As shown in Table 6 and FIG. 5, compound 18a synergizes with the tested LRA compounds to reverse HW latency.

TABLE 6

| | | | Compound 18a [M] | | | | | |
|---|---|---|---|---|---|---|---|---|
| | | | 1.00E−05 | 1.00E−06 | 1.00E−07 | 1.00E−08 | 1.00E−09 | 1.00E−10 |
| Bromodomain and extra terminal domain inhibitors (BETi) | JQ1 [M] | 1.00E−05 | A | A | A | B | B | A |
| | | 3.33E−06 | A | A | B | B | B | B |
| | | 1.11E−06 | B | B | B | C | B | A |
| | | 3.70E−07 | C | C | C | C | B | A |
| | | 1.23E−07 | E | E | E | E | C | A |
| | | 4.12E−08 | G | G | G | E | C | A |
| | | 1.37E−08 | F | E | F | C | B | A |
| | | 4.57E−09 | C | C | C | B | A | A |
| | | 1.52E−09 | C | B | B | B | A | A |
| | | 5.08E−10 | B | B | B | A | A | A |
| | I-BET151 [M] | 1.00E−05 | B | C | C | C | B | A |
| | | 3.33E−06 | C | C | E | C | A | A |
| | | 1.11E−06 | F | G | F | E | B | A |
| | | 3.70E−07 | C | E | C | B | A | A |
| | | 1.23E−07 | B | C | B | B | A | A |
| | | 4.12E−08 | B | B | B | A | A | A |
| | | 1.37E−08 | B | B | B | A | A | A |
| | | 4.57E−09 | B | B | B | A | A | A |
| | | 1.52E−09 | B | B | B | A | A | A |
| | | 5.08E−10 | B | B | B | A | A | A |
| Protein Kinase C (PKC) agonists | Bryostatin [M] | 5.00E−07 | E | E | C | C | B | A |
| | | 1.67E−07 | E | E | E | C | A | A |
| | | 5.56E−08 | C | C | C | C | B | A |
| | | 1.85E−08 | C | E | E | C | B | A |
| | | 6.17E−09 | C | E | E | C | B | A |
| | | 2.06E−09 | C | E | E | C | A | A |
| | | 6.86E−10 | E | C | C | C | B | A |
| | | 2.29E−10 | C | C | C | C | A | A |
| | | 7.62E−11 | C | C | C | B | A | A |
| | | 2.54E−11 | B | B | B | A | A | A |
| | Ingenol-3-angelate [M] | 2.00E−07 | B | B | B | B | B | A |
| | | 6.67E−08 | B | B | B | B | B | A |
| | | 2.22E−08 | B | C | C | C | B | B |
| | | 7.41E−09 | E | E | E | C | A | A |
| | | 2.47E−09 | E | F | C | C | B | A |
| | | 8.23E−10 | C | C | C | B | A | A |
| | | 2.74E−10 | B | B | B | A | A | A |
| | | 9.14E−11 | B | B | B | A | A | A |
| | | 3.05E−11 | B | B | A | A | A | A |
| | | 1.02E−11 | B | B | B | A | A | A |

Example F. Pharmacokinetic Study of Compounds in Mice

All animal procedures were approved by the Sanford Burnham Prebys Medical Discovery Institute Institutional Animal Care and Use Committee and were performed according to the NIH guidelines for the Care and Use of Laboratory Animals. Adult female $C_{57}$BL/6J were purchased from JAX laboratories and housed with free access to food and water on a 12 h light/dark cycle. Compounds were formulated in 5% DMSO, 10% Tween-80, and 85% $dH_2O$ and injected intraperitoneally (i.p.) into mice at doses of 10 mg/kg. For snapshot PK analysis, blood samples were collected retro-orbitally one hour after injection and for the time course PK study, blood samples were collected at 15 min, 30 min, 1 h, 2 h, 4 h, 6 h, 24 h time points. For the blood samples plasma was separated by centrifugation. Plasma samples were extracted with acetonitrile:water 4:1 with 0.1% formic acid containing indometacin as an internal standard. Samples were centrifuged and supernatants were diluted with acetonitrile:water and analyzed via LC-MS/MS on a Shimadzu Nexera X2 HPLC coupled to an AB Sciex 6500 QTRAP.

TABLE 7

| Compound | IP dose [mg/kg][a] | $C_{max}$ [μM][a] | $T_{max}$ [h][a] | $AUC_{0-t}$ [μmol/L*h][a] | $t_{1/2}$ [h][a] |
|---|---|---|---|---|---|
| 18 m | 10 | 6.6 | 1.0 | 18.1 | 3.0 |

$C_{max}$: maximum concentration of the compound detected in plasma.
$T_{max}$: time at $C_{max}$.
AUC: area under the curve.
$t_{1/2}$: terminal half-life.

In vivo pharmacokinetic data for compound 18m in mice. Compound was formulated in 5% DMSO, 10% Tween 80 and water and administered by intraperitoneal injection.

TABLE 8

| Comp. | plasma concentration [nM] |
|---|---|
| 18a | 3521 |
| 18g | 2685 |
| 18e | 6200 |
| 18c | 1310 |
| 18b | 714 |
| 18i | 1237 |
| 18m | 6587 |
| 18q | 1867 |
| 18o | 5183 |

Plasma exposure of selected compounds at 1 h compared.

Plasma levels of parent compound determined one hour after i.p. injection of 10 mg/kg While preferred embodiments of the present technology have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound having the structure of Formula II, or pharmaceutically acceptable salt thereof:

Formula (II)

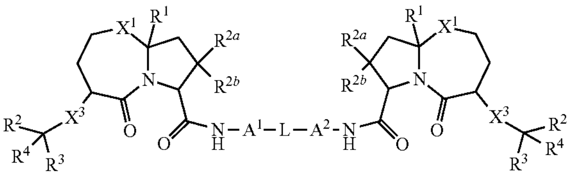

wherein, each $X^1$ is independently O (oxygen), or S (sulfur);

each $R^1$, $R^3$ and $R^4$ is independently H, halogen, or $C_1$-$C_6$alkyl;

each $R^2$ is independently —$NR^5R^6$;

each $R^5$ and $R^6$ is independently H, $C_1$-$C_6$alkyl, or —$C_1$-$C_6$alkyl-($C_3$-$C_6$cycloalkyl);

each $X^3$ is independently —NHC(=O)—, or —C(=O)NH—;

$A^1$ and $A^2$ are each

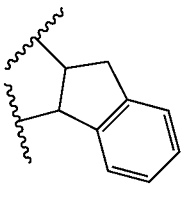

;

L is —$X^5$—$(CH_2)_{n1}$-$Q^1$-$(CH_2)_{n2}$—$X^5$—;

each $X^5$ is independently O or S;

each $n^1$ and $n^2$ is independently 1-3;

$Q^1$ is

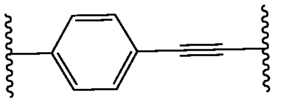

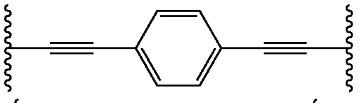

,

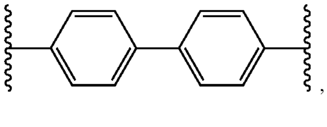

, or

-continued

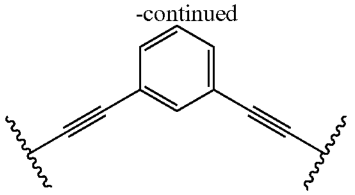

;

and each $R^{2a}$ and $R^{2b}$ is independently $C_1$-$C_6$alkyl or $C_2$-$C_6$alkenyl; or $R^{2a}$ and $R^{2b}$ taken together form a $C_3$-$C_6$cycloalkyl.

2. The compound of claim 1, or pharmaceutically acceptable salt thereof, wherein each $R^{2a}$ and $R^{2b}$ is independently $C_2$-$C_6$ alkenyl.

3. The compound of claim 1, or pharmaceutically acceptable salt thereof, wherein each $X^1$ is S (sulfur).

4. The compound of claim 1, or pharmaceutically acceptable salt thereof, wherein $R^{2a}$ and $R^{2b}$ taken together form a $C_3$-$C_6$cycloalkyl.

5. The compound of claim 1, or pharmaceutically acceptable salt thereof, wherein each $R^{2a}$ and $R^{2b}$ is independently $C_1$-$C_6$alkyl.

6. The compound of claim 1, or pharmaceutically acceptable salt thereof, wherein $X^3$ is —NHC(=O)—.

7. The compound of claim 1, or pharmaceutically acceptable salt thereof, wherein each $R^1$ is independently H or $C_1$-$C_3$alkyl.

8. The compound of claim 1, or pharmaceutically acceptable salt thereof, wherein each $R^2$ is independently —$NH_2$ or $NHCH_3$.

9. The compound of claim 1, or pharmaceutically acceptable salt thereof, wherein each $R^3$ is independently H, $CH_3$, or ethyl.

10. The compound of claim 1, or pharmaceutically acceptable salt thereof, wherein each $R^4$ is independently H or $CH_3$.

11. The compound of claim 1, or pharmaceutically acceptable salt thereof, wherein

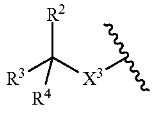

is

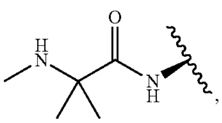

,

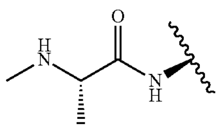

or

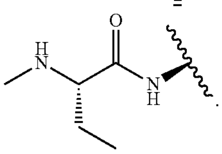

.

12. The compound of claim 1, or pharmaceutically acceptable salt thereof, wherein $Q^1$ is
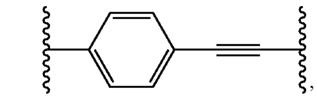
,
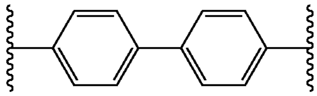
, or
-continued
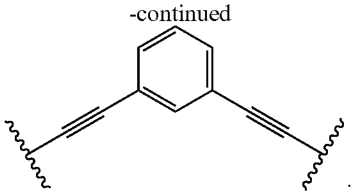
.
13. A compound, or pharmaceutically acceptable salt thereof, wherein the compound is:
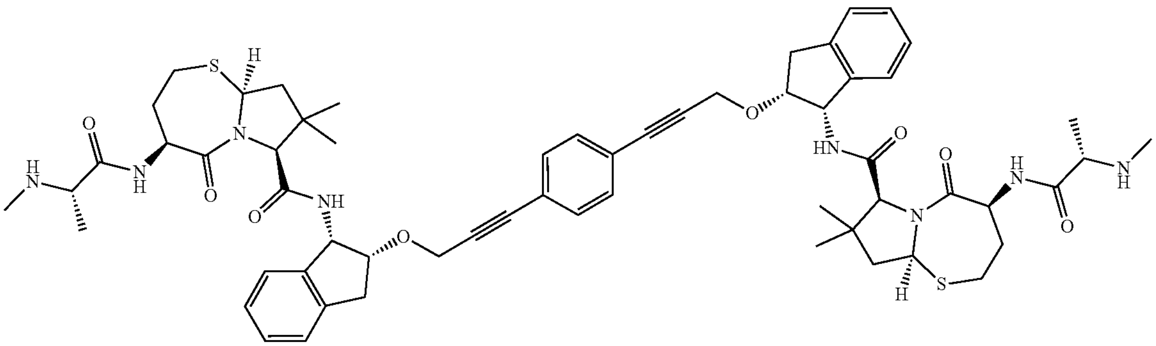
,
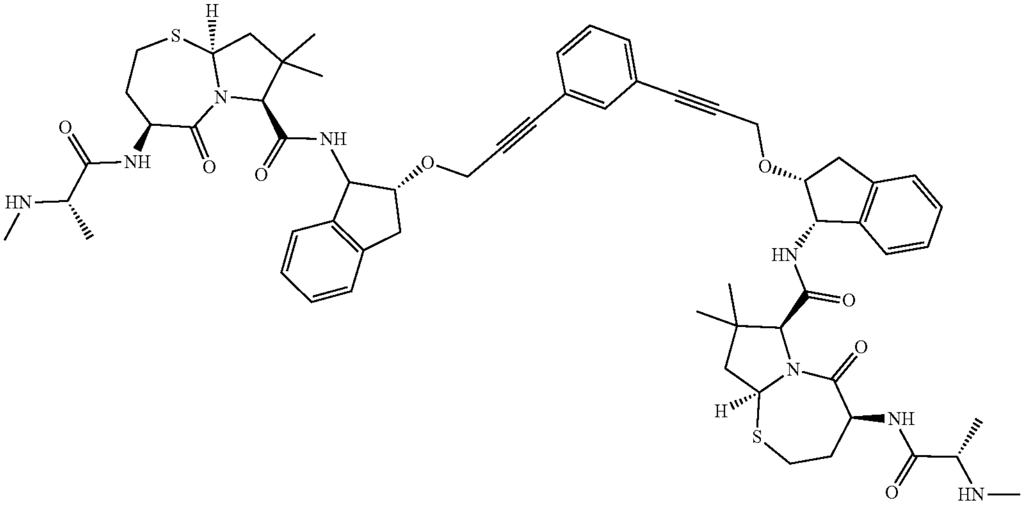
,
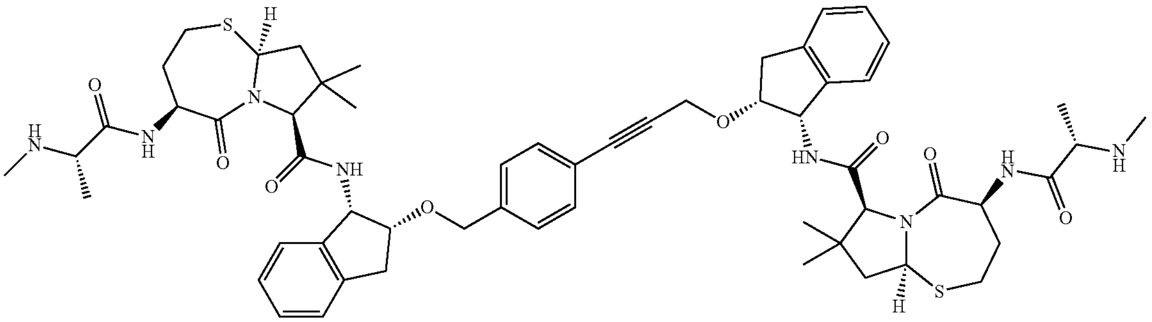
, -continued
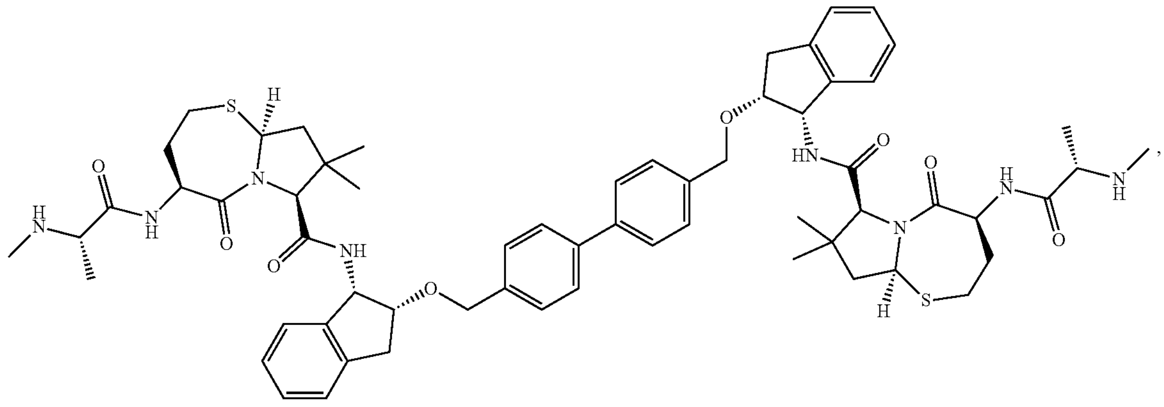
,
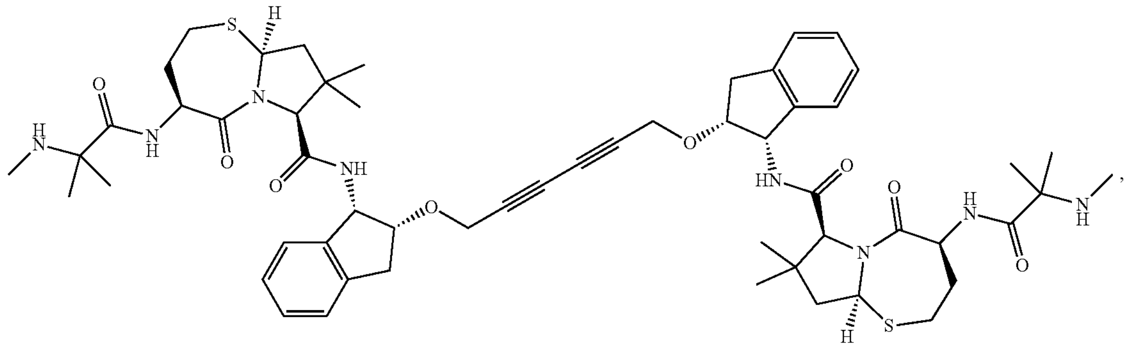
,
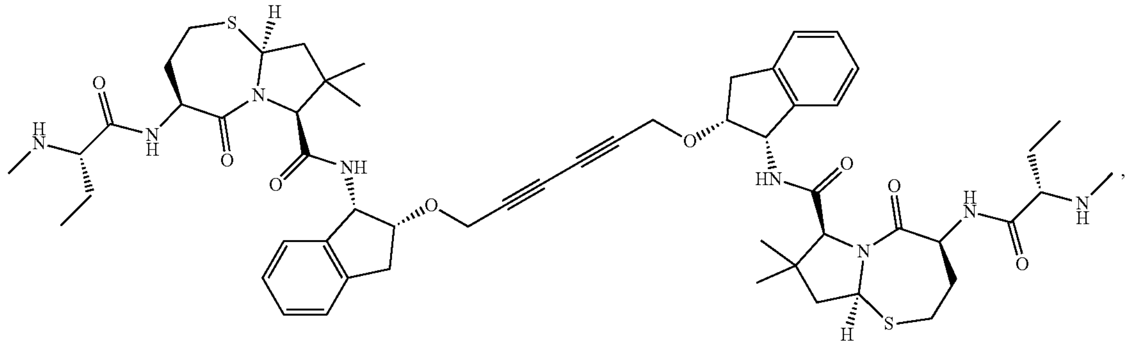
,
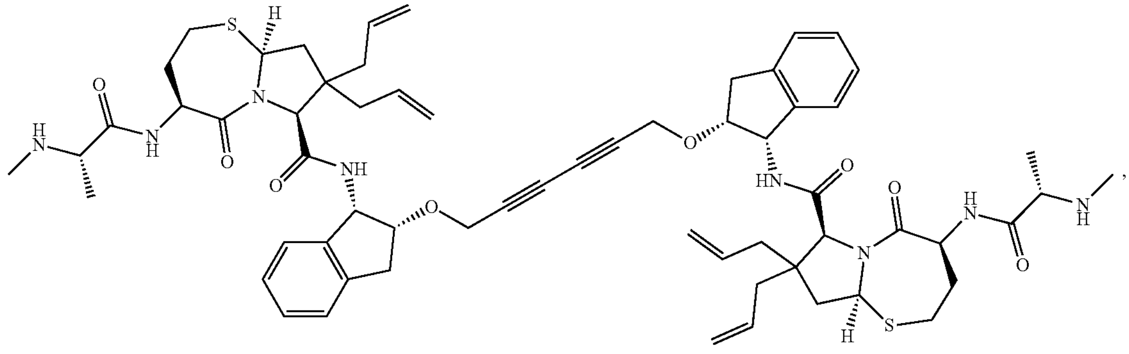
, -continued

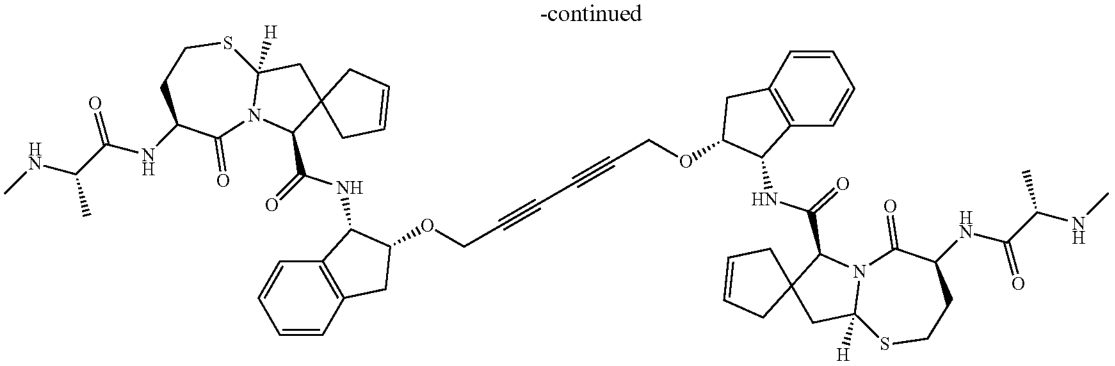
,

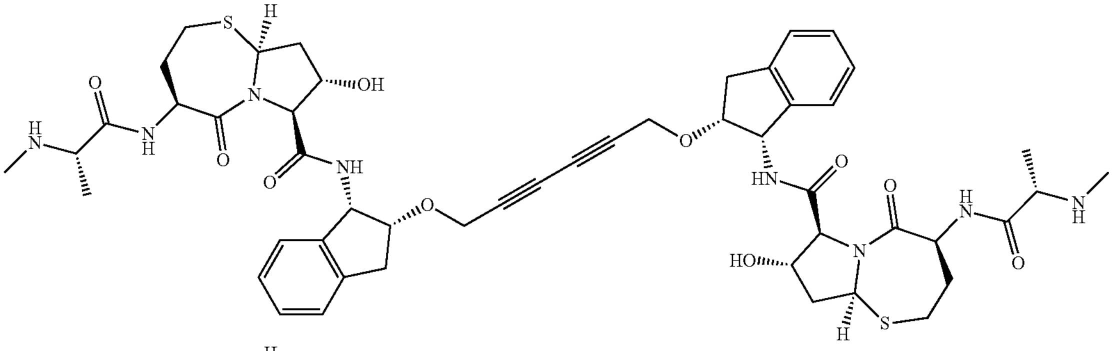
,

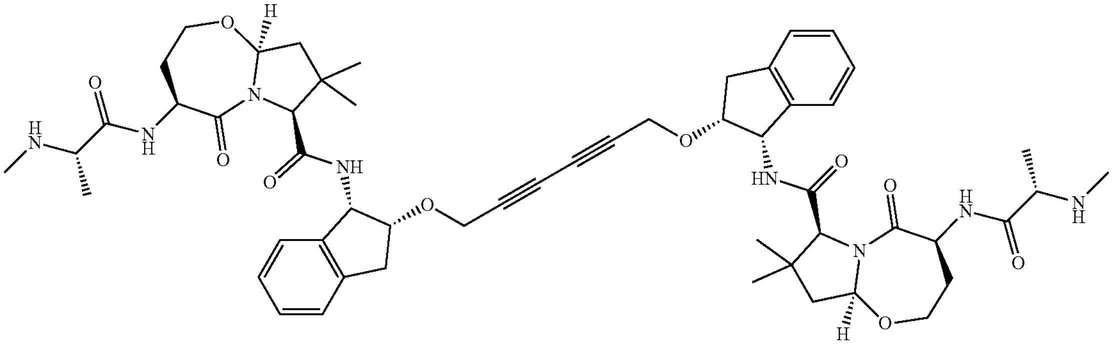
,

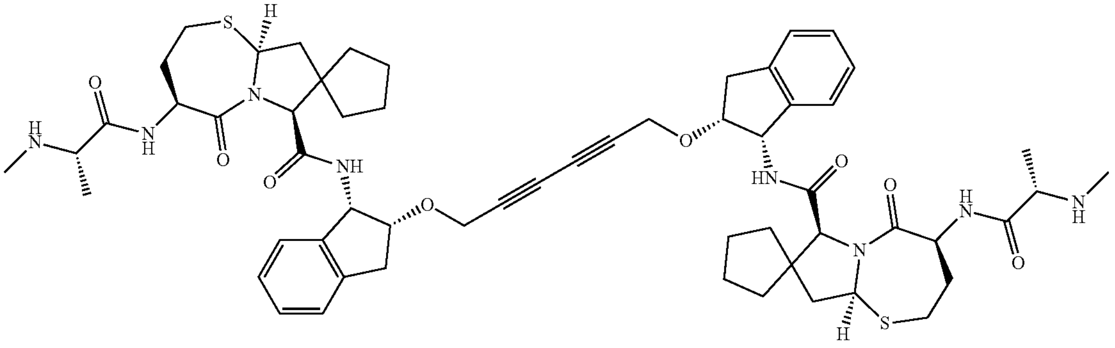

or pharmaceutically acceptable salt thereof.

14. A pharmaceutical composition comprising a compound of claim 1, or pharmaceutically acceptable salt thereof, and a pharmaceutically acceptable carrier.

15. A method of treating a hyperproliferative disorder in an individual in need thereof comprising administering a therapeutically effective amount of a compound of claim 1, or pharmaceutically acceptable salt thereof, to the individual, wherein the hyperproliferative disorder is associated with an upregulation of inhibitor of apoptosis (IAP) proteins in the individual.

* * * * *